(12) United States Patent
Neshat et al.

(10) Patent No.: US 12,324,858 B2
(45) Date of Patent: Jun. 10, 2025

(54) PHARMACEUTICAL FORMULATION AND SYSTEM AND METHOD FOR DELIVERY

(71) Applicant: Rilento Pharma, LLC, Raleigh, NC (US)

(72) Inventors: Khashayar Kevin Neshat, Raleigh, NC (US); William Andrew Daunch, Cary, NC (US); Anthony A. Parker, Newtown, PA (US); Mark Franklin Hanna, Raleigh, NC (US); Raymond A. Dionne, New Bern, NC (US)

(73) Assignee: Rilento Pharma, LLC, Raleigh, NC (US)

(*) Notice: Subject to any disclaimer, the term of this patent is extended or adjusted under 35 U.S.C. 154(b) by 0 days.

(21) Appl. No.: 16/555,669

(22) Filed: Aug. 29, 2019

(65) Prior Publication Data
US 2020/0069595 A1 Mar. 5, 2020

Related U.S. Application Data

(60) Provisional application No. 62/893,413, filed on Aug. 29, 2019, provisional application No. 62/725,694, filed on Aug. 31, 2018.

(51) Int. Cl.
*A61K 9/50* (2006.01)
*A61K 31/445* (2006.01)

(52) U.S. Cl.
CPC .......... *A61K 9/5031* (2013.01); *A61K 9/5052* (2013.01); *A61K 9/5089* (2013.01); *A61K 31/445* (2013.01)

(58) Field of Classification Search
None
See application file for complete search history.

(56) References Cited

U.S. PATENT DOCUMENTS

| | | | |
|---|---|---|---|
| 3,029,188 A * | 4/1962 | Cyr | A61K 6/35 514/788.1 |
| 3,157,524 A | 11/1964 | Artandi | |
| 4,600,533 A | 7/1986 | Chu | |
| 4,622,219 A | 11/1986 | Haynes | |
| 4,725,442 A | 2/1988 | Haynes | |
| 4,938,763 A | 7/1990 | Dunn et al. | |
| 5,061,492 A | 10/1991 | Okada et al. | |
| 5,188,837 A | 2/1993 | Domb | |
| 5,789,465 A | 8/1998 | Harvey et al. | |
| 5,922,340 A | 7/1999 | Berde | |
| 5,972,366 A | 10/1999 | Haynes et al. | |
| 6,217,911 B1 | 4/2001 | Vaugn et al. | |
| 6,261,582 B1 | 7/2001 | Needham et al. | |
| 8,481,074 B2 | 7/2013 | Shalaby et al. | |
| 8,523,569 B2 | 9/2013 | Neshat | |
| 9,943,466 B1 * | 4/2018 | Johnson | A61K 9/06 |
| 11,992,482 B2 | 5/2024 | Neshat | |
| 2005/0123588 A1 | 6/2005 | Zhu et al. | |
| 2007/0110804 A1 | 5/2007 | Royer | |
| 2008/0241245 A1 | 10/2008 | Myers et al. | |
| 2009/0192429 A1 * | 7/2009 | Daniels | A61F 13/00034 602/43 |
| 2009/0202642 A1 | 8/2009 | Huang et al. | |
| 2009/0264472 A1 | 10/2009 | Wohabrebbi et al. | |
| 2011/0301131 A1 | 12/2011 | Fitzpatrick | |
| 2013/0108671 A1 * | 5/2013 | McCoy | A61M 5/19 424/400 |
| 2015/0283286 A1 | 10/2015 | Eastwood et al. | |
| 2018/0169080 A1 | 6/2018 | Neshat | |
| 2024/0285601 A1 | 8/2024 | Neshat | |

FOREIGN PATENT DOCUMENTS

| | | |
|---|---|---|
| EP | 0562864 | 9/1993 |
| WO | 9405265 | 3/1994 |
| WO | 2020047277 | 3/2020 |

OTHER PUBLICATIONS

Neshat, Kevin; Advisory Action for U.S. Appl. No. 15/405,453, filed Jan. 13, 2017, mailed Dec. 28, 2020, 4 pages.
Neshat, Kevin; International Preliminary Report on Patentability and Written Opinion issued for PCT Application No. PCT/US2019/048846, filed Aug. 29, 2019, mailed Mar. 11, 2021, 11 pages.
Neshat, Khashayar Kevin; Final Office Action for U.S. Appl. No. 15/405,453, filed Jan. 13, 2017; mailed Jul. 15, 2020; 13 pages.
Neshat, Khashaya Kevin; Advisory Action for U.S. Appl. No. 15/405,453, filed Jan. 13, 2017, mailed Feb. 7, 2020, 3 pages.
Neshat, Khashayar Kevin; Non-Final Office Action for U.S. Appl. No. 15/405,453, filed Jan. 13, 2017; mailed Mar. 23, 2020; 17 pages.
Neshat, Kevin; International Search Report and Written Opinion issued for PCT Application No. PCT/US2019/048846, filed Aug. 29, 2019; mailed Nov. 25, 2019; 18 pages.
Shepherd, Sarah D., et al., "A Moldable Sustained Release Bupivacaine Formulation for Tailored Treatment for Postoperative Dental Pain", Scientific Reports, vol. 8, No. 1, pp. 1-9, Aug. 15, 2018.
Krill, David et al.; Topical Thrombin and Powdered Gel foam: An Efficient Hemostatic Treatment for Surgery, Journal of Tenn Dent Assoc. 66(2): 26-27 (Year: 1986).
Neshat, Khashayar Kevin; Non-Final Office Action for U.S. Appl. No. 15/405,453, filed Jan. 13, 2017, mailed Aug. 30, 2021, 22 pgs.
Neshat, Khashayar Kevin; Final Office Action for U.S. Appl. No. 15/405,453, filed Jan. 13, 2017, mailed Jun. 7, 2022, 22 pgs.

(Continued)

*Primary Examiner* — Tigabu Kassa
(74) *Attorney, Agent, or Firm* — Taylor English Duma LLP

(57) ABSTRACT

A sustained release pharmaceutical formulation for pain management comprises an active ingredient, and a water-miscible and hygroscopic network-forming material, the active ingredient being dispersed within the water-miscible and hygroscopic network-forming material. The pharmaceutical may comprise a hydrophobic component, wherein the active ingredient dispersed within the water-miscible and hygroscopic network-forming material are together dispersed in hydrophobic component. Optionally, the pharmaceutical formulation may be combined with a reinforcing member for providing a system for sustained release of the pharmaceutical formulation for pain management.

10 Claims, 19 Drawing Sheets

(56) References Cited

OTHER PUBLICATIONS

Neshat, Khashayar Kevin; Applicant-Initiated Interview Summary for U.S. Appl. No. 15/405,453, filed Jan. 13, 2017, mailed Jan. 26, 2023, 7 pgs.
Neshat, Khashayar Kevin; Non-Final Office Action for U.S. Appl. No. 15/405,453, filed Jan. 13, 2017, mailed Mar. 30, 2023, 22 pgs.
Neshat, Kevin; Examination Report for Australia Patent Application No. 2019328276, filed Aug. 29, 2019, mailed Jul. 9, 2024, 5 pgs.
Neshat, Khashayar Kevin; Issue Notification for U.S. Appl. No. 15/405,453, filed Jan. 13, 2017, mailed May 8, 2024, 2 pgs.
Neshat, Kevin; Office Action pursuant to Article 94(3) EPC for Application No. 19768952.4, filed Aug. 29, 2019, mailed Apr. 29, 2024, 7pgs.
Sarah D. Shepherd et al: "A moldable sustained release bupivacaine formulation for tailored treatment of postoperative dental pain", Scientific Reports, vol. 8, No. 1, Aug. 15, 2018 (Aug. 15, 2018), pp. 1-9, XP055640818, DOI: 10.1038/s41598-018-29696-w.
Neshat, Khashayar Kevin; Notice of Allowance for U.S. Appl. No. 15/405,453, filed Jan. 13, 2017, mailed Jan. 23, 2024, 16 pgs.
Neshat, Khashaya Kevin; Non-Final Office Action for U.S. Appl. No. 18/652,317, filed May 1, 2024, mailed Nov. 19, 2024, 22 pages.

\* cited by examiner

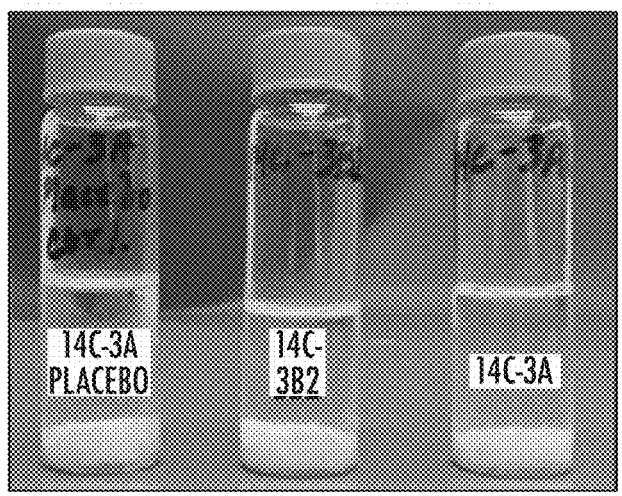
FIG. 10A  t = 0 HRS.
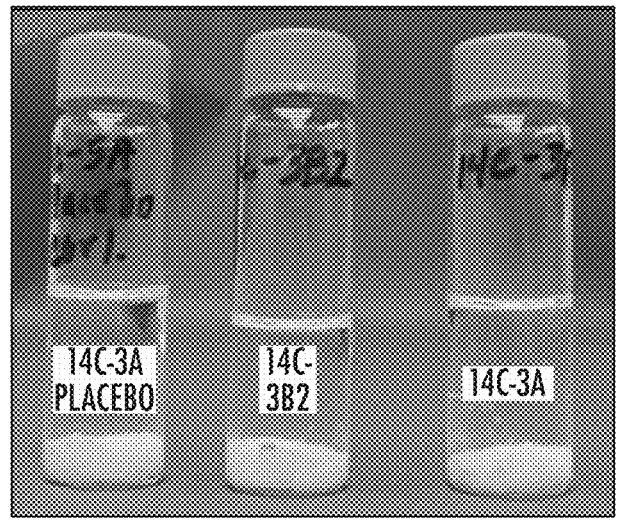
FIG. 10B  t = 1.5 HRS.
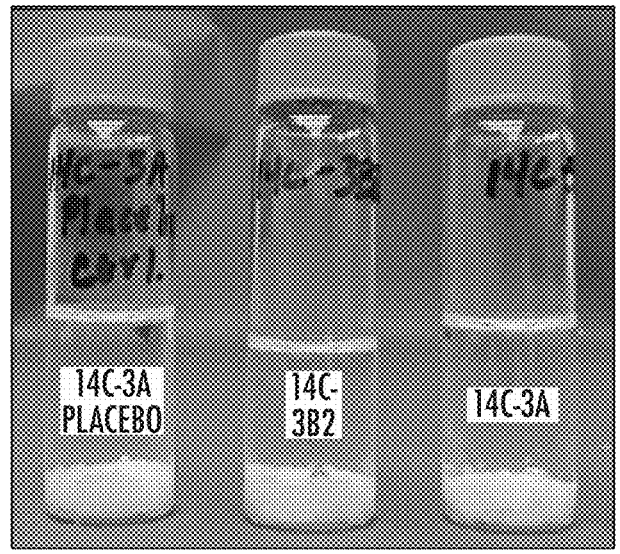
FIG. 10C  t = 4.0 HRS.

t = 24 HRS.

t = 4 DAYS

PHARMACEUTICAL FORMULATION AND SYSTEM AND METHOD FOR DELIVERY

CROSS-REFERENCES

This application is related to U.S. provisional application No. 62/725,694, filed Aug. 31, 2018, and U.S. provisional application No. 62/893,413, filed Aug. 29, 2019. The contents of the provisional applications are incorporated herein by reference in their entirety, and the benefit of the filing dates of the provisional applications are hereby claimed for all purposes that are legally served by such claim for the benefit of the filing dates.

BACKGROUND

A pharmaceutical formulation is described and, more particularly, a sustained release pharmaceutical formulation and a system and method for delivery of the pharmaceutical formulation for use, for example, for pain management in wounds such as dental extractions.

There is currently no sustained delivery system commercially available for the specific indication of post-surgical pain after dental extractions. Ideally, such a product would require minimal preparation and preferably no preparation by the clinician, it would be easily placed into the tooth extraction socket or wound cavity by a clinician, it would have rheological properties that allow the formulation to be molded to fill the extraction socket or wound void, it would preferably remain adhered and resist erosion throughout the treatment duration, it would have no adverse interactions with blood and would preferably function as a hemostat, it would have no local (acute or long-term) tissue or nerve toxicity, it would preferably be comprised of biocompatible ingredients, it would deliver pain medication both acutely after surgery and during healing while preferably addressing acute and sub-acute pain without delaying or adversely affecting wound healing, and it would preferably enhance wound healing.

Products that are current benchmarks for rheological performance in dental surgery and tooth extraction applications include SURGIFOAM® Absorbable Gelatin Sponge and SURGIFOAM® Absorbable Gelatin Powder, each being examples of sterile porcine gelatin absorbable sponges or powders intended for hemostatic use by applying to a bleeding surface ("Surgifoam"). GELFOAM® Dental Sponges (absorbable gelatin sponge, USP) is a medical device also intended for application to bleeding surfaces as a hemostatic. It is a water-insoluble, off-white, nonelastic, porous, pliable product prepared from purified pork skin gelatin USP granules and water for injection, and is able to absorb and hold within its interstices many times its weight of blood and other fluids. Gelfoam® absorbable gelatin powder (absorbable gelatin powder from absorbable gelatin sponge, USP) is a fine, dry, heat-sterilized light powder prepared by milling absorbable gelatin sponge ("Gelfoam"). Soluble collagen powders are another option. However, compared to Surgifoam and Gelfoam, soluble collagen powder exhibits a slower rate of gelation since its rate of network entanglement leads to slower achievement of solidification and final equilibrium properties. Surgifoam and Gelfoam also have a significantly higher rate of water adsorption while simultaneously retaining their solid character; a high overall capacity for water adsorption; and higher overall compliance with negligible elasticity at equal water levels in their final equilibrium state. Commercial collagens generally lead to lower-compliance, rubbery networks.

Presently, the pharmaceutical industry is focusing on the development of sustained release formulations designed to release a drug at a predetermined rate and to maintain a constant drug level for a specific period of time with minimal side effects. The basic rationale behind a sustained release drug delivery system is to optimize the biopharmaceutical, pharmacokinetic and pharmacodynamics properties of a drug in such a way that the utility of the drug is maximized, its side-effects are reduced, and the disease management goals are achieved. There are several advantages of sustained release drug delivery over conventional dosage forms including improved patient compliance due to less frequent drug administration, reduction of fluctuation in steady-state drug levels, maximum utilization of the drug, increased safety margins of potent drugs, and reduction in healthcare costs through improved therapy and shorter treatment periods. One of the basic goals of sustained release is to provide a promising way to decrease the side effects of a drug, first by preventing the fluctuation of the therapeutic concentration of the drug in the body, and secondly by reducing the frequency of dose administration to increase the probability of patient compliance.

According to the Centers for Disease Control and Prevention, drug overdose deaths, including those involving opioids, continue to increase in the United States. Deaths from drug overdose are up among both men and women, among all races, and among adults of nearly all ages. Two out of three drug overdose deaths involve an opioid. Opioids are substances that work in the nervous system of the body or in specific receptors in the brain to reduce the intensity of pain. Overdose deaths from opioids, including prescription opioids, heroin, and synthetic opioids like fentanyl have increased almost six times since 1999. In 2017, drug overdoses of all types averaged 21.7 per 100,000 with opioids alone killing more than 47,000 people, and with opioids representing 67.8% of all drug overdose deaths. According to the NIH HEAL Initiative (Helping to End Addiction Long-term$^{SM}$), more than 25 million Americans suffer from daily chronic pain. New treatment options for pain are needed to reduce the number of people exposed to the risks of opioids. Through the HEAL Initiative, NIH is supporting research to understand how chronic pain develops, making patients susceptible to risks associated with opioid use. HEAL is developing a data sharing collaborative, new biomarkers for pain, and a clinical trials network for testing new pain therapies. Research efforts are also focusing on treatments for opioid misuse and addiction.

According to the American Dental Association's official policies and statements on substance use disorders including the opioid crisis, specifically the Statement on the Use of Opioids in the Treatment of Dental Pain, dentists should follow and continually review Centers for Disease Control and state licensing board recommendations for safe opioid prescribing, dentists should consider treatment options that utilize best practices to prevent exacerbation of or relapse of opioid misuse, Dentists should consider nonsteroidal anti-inflammatory analgesics as the first-line therapy for acute pain management, and dentists should recognize multimodal pain strategies for management for acute postoperative pain as a means for sparing the need for opioid analgesics.

U.S. Pat. Nos. 8,253,569 and 9,943,466 and U.S. Patent Application Pub. No. 2018/0169080 describe sustained release formulations for dental applications. The contents of U.S. Pat. Nos. 8,253,569 and 9,943,466 and U.S. Patent Application Pub. No. 2018/0169080 are incorporated herein by reference in their entirety.

For the foregoing reasons, there is a need for a sustained release pharmaceutical formulation having rheological behavior similar to Surgifoam or Gelfoam, and comprising a matrix for simultaneously achieving and sustaining hemostasis and delivering active ingredients, such as analgesic or anesthetic drugs to manage the acute and sub-acute pain during the transition from the hemostasis phase to the inflammatory phase of wound healing. The pharmaceutical formulation can be combined with resorbable powders, fibers or textiles to reinforce the matrix thereby providing a system for delivering the formulation and for modifying the rheology so that the formulation adheres to the wound and stays in place during drug delivery. A reinforcing textile can be foldable and compressible and have scaffolding and bactericidal properties as well. Uses of the pharmaceutical formulation and the delivery system would provide for controlled release of local anesthetic and anti-inflammatory agents, for example, in a tooth extraction socket for sustained pain relief from multiple sources of pain and should promote wound healing. The pharmaceutical formulation should also satisfy a need to simultaneously address any limits on the restricted volumes of treatment areas like tooth extraction sockets while insuring that the formulation has enough mechanical integrity and cohesive strength to mitigate erosion or detachment from the wound so that the formulation can deliver the required drug dosage over time. Ideally, the functional performance and efficacy of the pharmaceutical formulation and the delivery system with a variety of drugs should be extendable from the oral surgery model to wounds or other forms of tissue injury and post-surgical pain.

SUMMARY

A sustained release pharmaceutical formulation for pain management is provided. The pharmaceutical formulation comprises an active ingredient, and a water-miscible and hygroscopic network-forming material, the active ingredient being dispersed within the water-miscible and hygroscopic network-forming material. The pharmaceutical may comprise a hydrophobic component, wherein the active ingredient dispersed within the water-miscible and hygroscopic network-forming material are together dispersed in hydrophobic component. Optionally, the pharmaceutical formulation may be combined with a reinforcing member for providing a system for sustained release of the pharmaceutical formulation for pain management.

In one aspect, the active ingredient has a weight percent of less than 60% of the pharmaceutical formulation. The active ingredient may be present in an acidic form or a basic form. The active ingredient may comprise an anesthetic. The anesthetic may be bupivacaine, including an acidic form, a basic form, or a mixture of acidic and basic forms. Alternatively, the active ingredient is selected from an analgesic like acetaminophen. Alternatively, the active ingredient is selected from non-steroidal anti-inflammatory drugs (NSAID) analgesics. The NSAID may be ibuprofen, naproxen, meloxicam, ketoprofen, or mixtures thereof. Alternatively, the active ingredient is a mixture of anesthetics and analgesics.

The sustained release pharmaceutical formulation and system may further comprise an encapsulating material encapsulating the active ingredient. In one embodiment, the encapsulating material is a polymer, such as PLGA. The PLGA encapsulating material may have an average particle size of 1 micron to 80 microns, an inherent viscosity of 0.16 to 1.7 dL/g, a Tg of greater than 37 degrees Celsius, or a ratio of lactic acid to glycolic acid of 50/50 w/w to 85/15 w/w. The encapsulating material may also comprise an oligomeric material. The encapsulated particles can be prepared using a spinning disc spray dry process or an emulsion process.

In one aspect, the network-forming material has a weight percent of 5% to 25% of the pharmaceutical formulation. The network-forming material may comprise a polymer, including either collagen or gelatin. The gelatin may have a Bloom value of 50 to 325, a viscosity of 1.5 to 7.5 mPa-s, and a mesh value of between 8 and 400.

In one embodiment, the reinforcing member has a weight percent of up to 15% of the system. The reinforcing member may comprise knitted, woven or non-woven fibers, wherein the interstitial spaces between the fibers are impregnated with the pharmaceutical formulation. In one aspect, the reinforcing member comprises a textile, wherein the textile has a bulk fiber mass per topical unit area of 0.005 $g/cm^2$ to 0.05 $g/cm^2$. In another aspect, the reinforcing member may comprise a cellulose hemostat material.

The sustained release pharmaceutical formulation and system may further comprise a pH modulator. The pH modulator can be an acid, such as citric acid. The acid has a weight percent of up to 5% of the pharmaceutical formulation. The pH modulator may also be a base, such as di-sodium citrate. The base has a weight percent of up to 5%.

The sustained release pharmaceutical formulation and system may further comprise a surfactant, an antiemetic, anti-infective, or chemotherapeutic agent.

In one aspect, the hydrophobic component is an oil, a wax, or mixtures thereof. In particular, the hydrophobic component is selected from mineral oil, isopropyl palmitate, caprylic triglyceride, coconut oil, carnauba wax, beeswax, paraffin wax or mixtures thereof.

In yet another aspect, the water-miscible and hygroscopic network-forming material does not gel for at least a time period of 24 hours after being suspended within the hydrophobic component.

Another embodiment of a sustained release pharmaceutical formulation for pain management comprises 5% to 60% by weight of an active ingredient, 10% to 65% by weight of an encapsulating material in combination with an active ingredient, the encapsulating material encapsulating the active ingredient, 5% to 25% by weight of a water-miscible and hygroscopic network-forming material, and 15% to 35% by weight of a hydrophobic component.

Another embodiment of a system for sustained release of a pharmaceutical formulation for pain management comprises a pharmaceutical formulation, including 5% to 60% by weight of an active ingredient, 10% to 65% by weight of an encapsulating material in combination with an active ingredient, the encapsulating material encapsulating the active ingredient, 5% to 25% by weight of a water-miscible and hygroscopic network-forming material, 20% to 60% by weight of a hydrophilic component, and up to 15% by weight of a reinforcing member. The hydrophilic component may comprise glycerin, water, or a mixture thereof.

A method is also provided for delivering a sustained release pharmaceutical formulation for pain management at a target site of a patient. The delivery method comprises the steps of providing a pharmaceutical formulation, including an active ingredient, a water-miscible and hygroscopic network-forming material, the active ingredient dispersed in the water-miscible and hygroscopic network-forming polymer, and a hydrophobic liquid mixed with the water-miscible and hygroscopic network-forming polymer including the dispersed encapsulated active ingredient. The pharmaceutical formulation is deployed at the target site. The target site may be a tooth extraction socket.

Another embodiment of a method of delivering a sustained release pharmaceutical formulation for pain management at a target site of a patient comprises the steps of providing a pharmaceutical formulation, including an active ingredient, and a water-miscible and hygroscopic network-forming material, the active ingredient dispersed in the water-miscible and hygroscopic network-forming polymer, an active ingredient encapsulated in a polymer, blending water with the water-miscible and hygroscopic network-forming polymer including the dispersed encapsulated active ingredient, and deploying the blend at the target site, such as a tooth extraction socket.

BRIEF DESCRIPTION OF THE DRAWINGS

For a more complete understanding of the present formulation, reference should now be had to the embodiments shown in the accompanying drawings and described below. In the drawings:

FIG. 10a is a photograph showing the hydrophobic textile-impregnated formulations 14C-3A Placebo, 14C-3B2, and 14C-3A (from left to right) at time=0 hours during the pH-2 soak experiment at 37 degrees C.

FIG. 10b is a photograph showing the hydrophobic textile-impregnated formulations 14C-3A Placebo, 14C-3B2, and 14C-3A (from left to right) at t=1.5 hours during the pH-2 soak experiment at 37 degrees C.

FIG. 10c is a photograph showing the hydrophobic textile-impregnated formulations 14C-3A Placebo, 14C-3B2, and 14C-3A (from left to right) at t=4.0 hours during the pH-2 soak experiment at 37 degrees C.

Figure 12A:
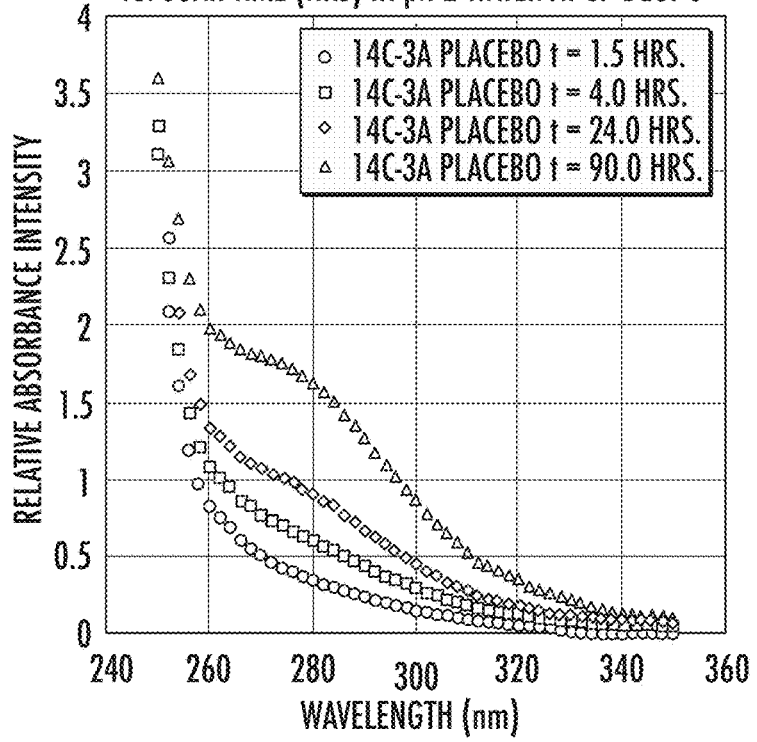
FIG. 12a depicts the relative absorbance vs. wavelength for the supernatant of a delivery system created with formulation 14C-3A Placebo, illustrating the progression of the absorbance curves as a function of time at t=1.5 hours, t=4 hours, t=24 hrs., and t=96 hrs. after the onset of the water soaking experiments in pH-2 water.
Figure 12B:
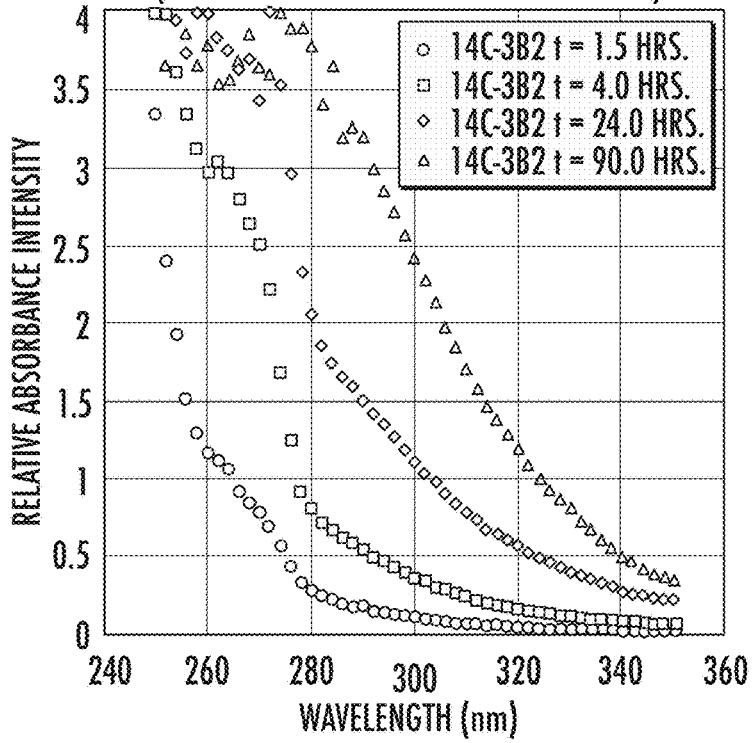

FIG. 12b depicts the relative absorbance vs. wavelength for the supernatant of a delivery system created with formulation 14C-3B2, illustrating the progression of the absorbance curves as a function of time at t=1.5 hours, t=4 hours, t=24 hrs., and t=96 hrs. after the onset of the water soaking experiments in pH-2 water.

Figure 12C:
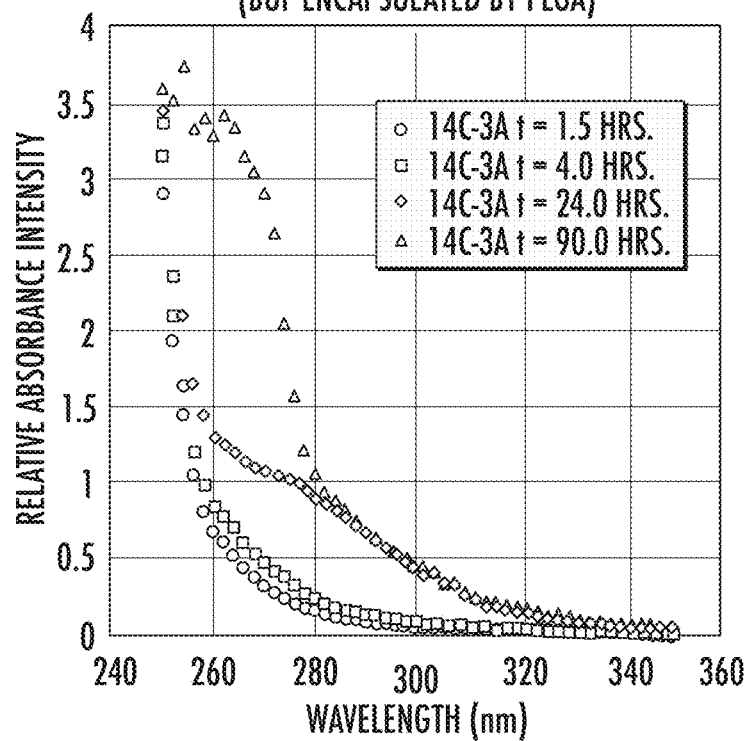

FIG. 12c depicts the relative absorbance vs. wavelength for the supernatant of a delivery system created with formulation 14C-3A, illustrating the progression of the absorbance curves as a function of time at t=1.5 hours, t=4 hours, t=24 hrs., and t=96 hrs. after the onset of the water soaking experiments in pH-2 water.

Figure 13:
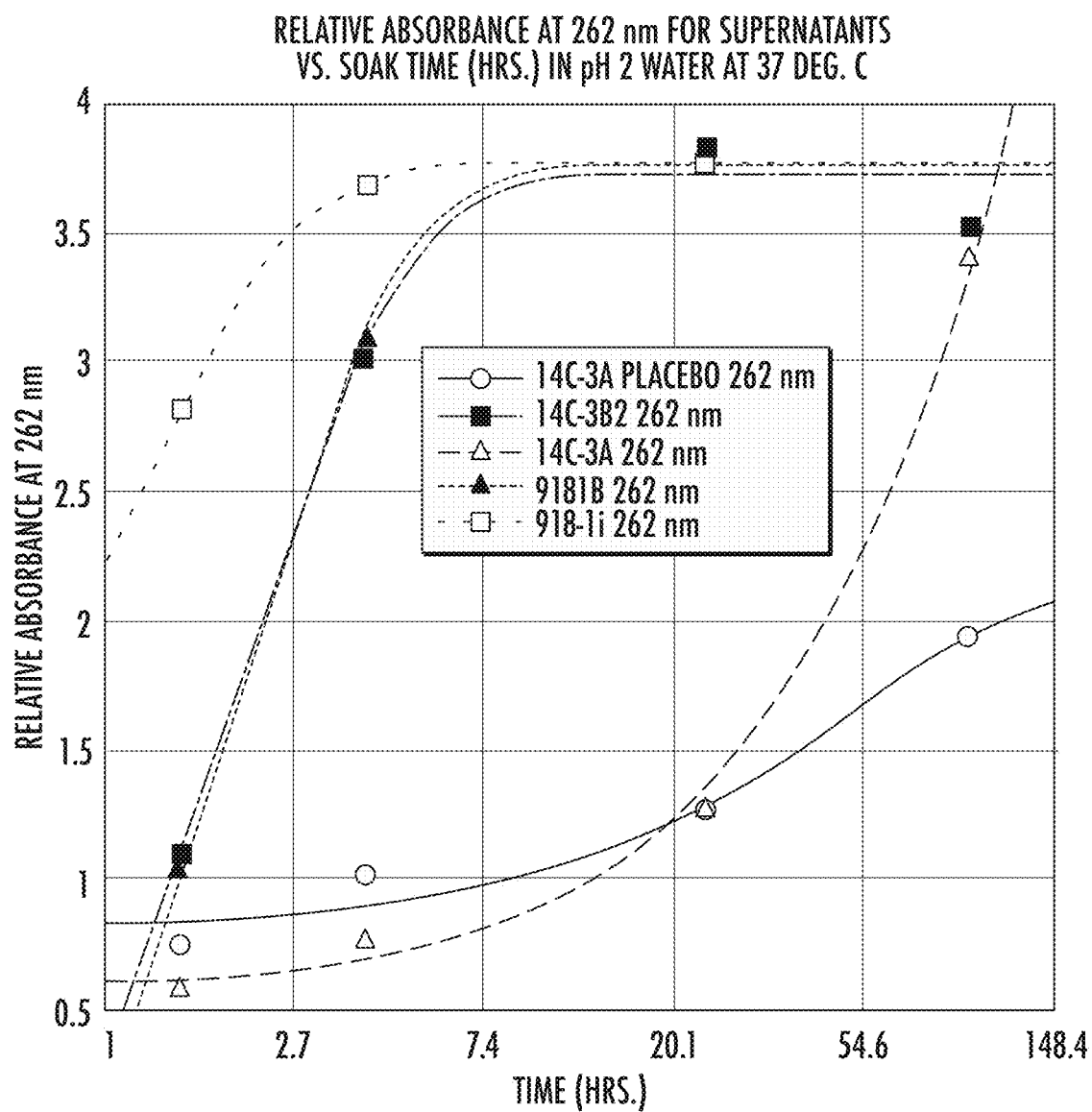
Figure 14:
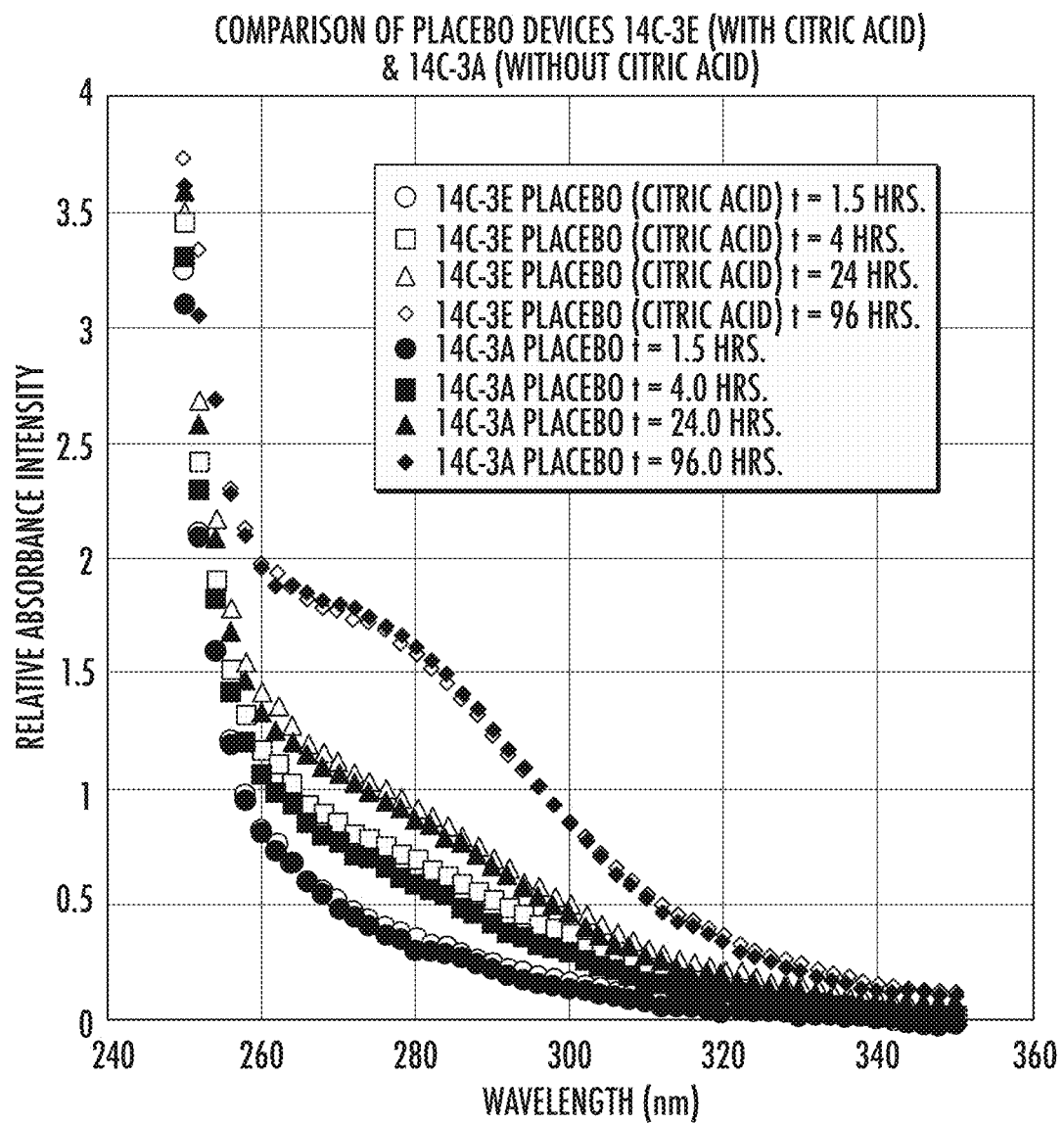

FIG. 13 depicts the time evolution of the absorbance intensity at 262 nm (i.e., the absorbance maximum for BUP-HCl) for each of the hydrophilic and hydrophobic formulation delivery systems FIG. 14 displays a relative absorbance vs. time comparison of placebo devices 14C-3E (with citric acid) and 14C-3A (without citric acid).

Figure 15:
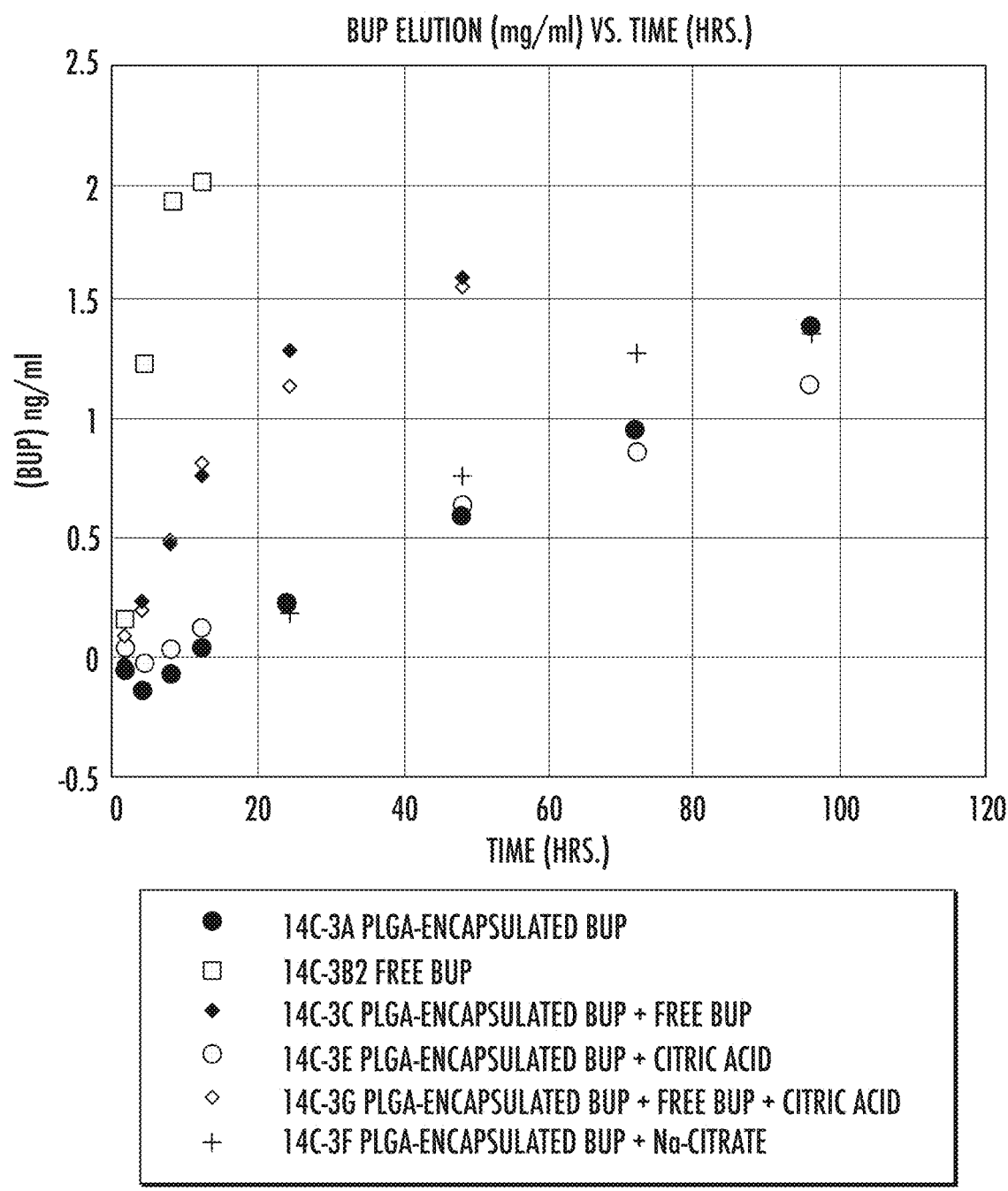

FIG. 15 illustrates the relative BUP concentration (mg/ml) vs. time (hrs.) as estimated from the UV absorption spectra of the supernatants that were sampled during the time evolution of the pH-2 water-soak experiments.

Figure 16:
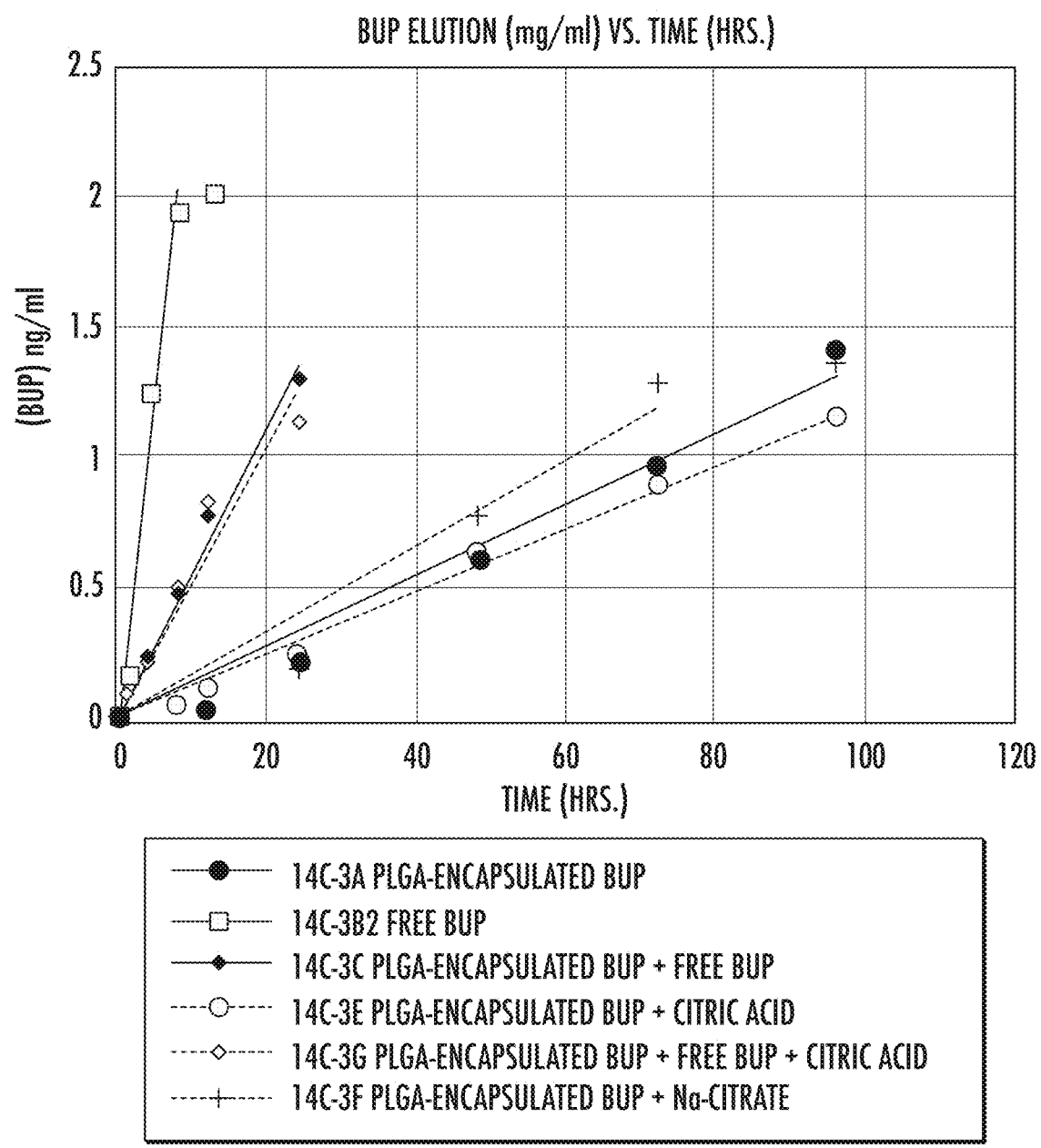

FIG. 16 illustrates the relative rates of BUP elution (mg/ml/hour) together with the data ranges used for establishing the best linear fitting parameters.

Figure 17:
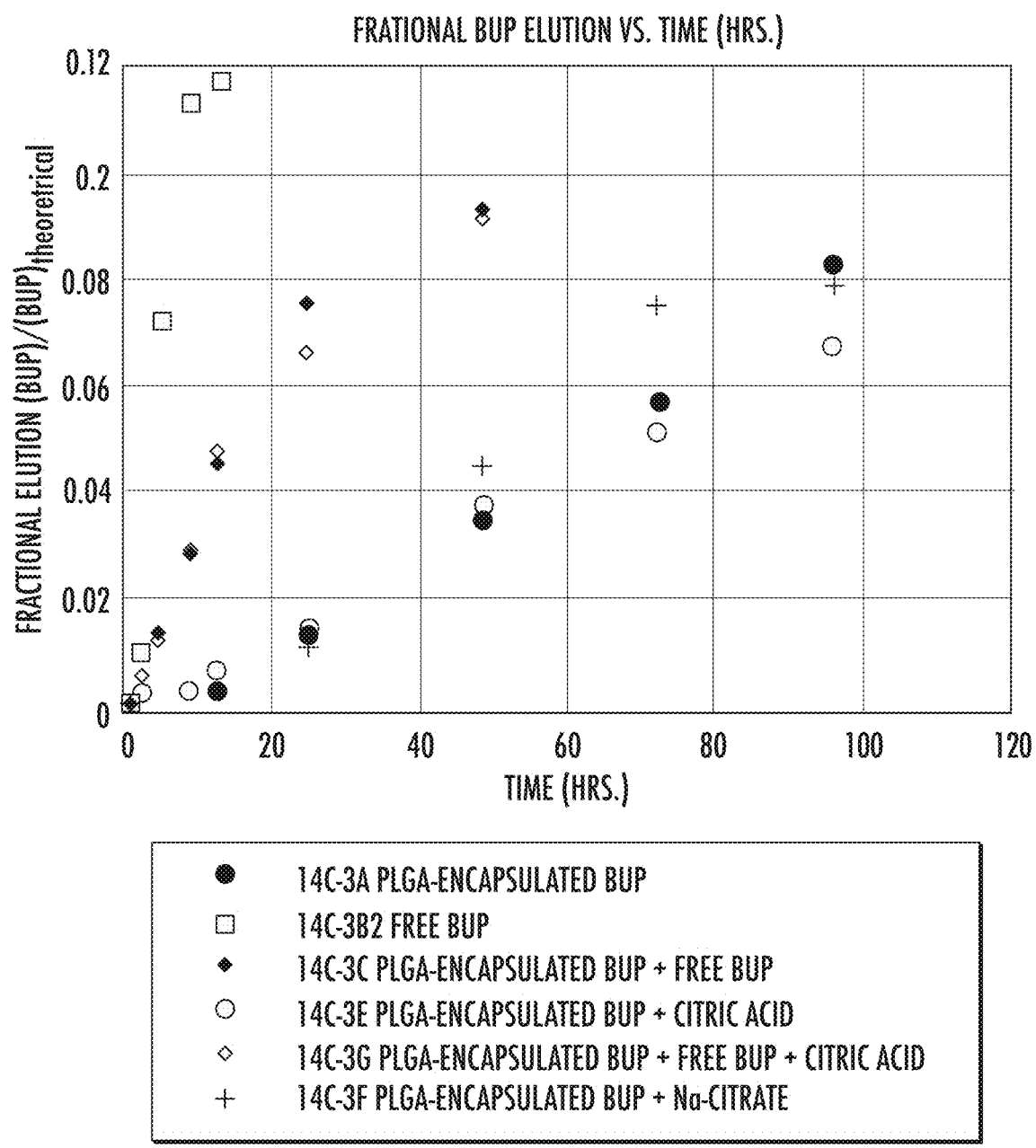

FIG. 17 illustrates the relative rates of BUP elution with the [BUP] expressed in terms of the fraction of eluted $BUP=[BUP]/[BUP]_{theoretical}=[BUP]/17.14$.

DESCRIPTION

A sustained release pharmaceutical formulation and system and method for delivery of the pharmaceutical formulation for, for example, pain management are described. The pharmaceutical formulation comprises an active ingredient optionally encapsulated in an encapsulant, a water-miscible and hygroscopic network-forming material, and, optionally, a reinforcing member. Embodiments of the pharmaceutical formulation and system and method include: 1) those comprising a dry powder mixture, including components that are first mixed as powders and then hydrated and masticated before end use; 2) those that are formulated with hydrophobic components and then hydrated before end use; 3) those that are formulated with hydrophobic components and then allowed to hydrate in vivo; 4) those that are formulated with hydrophobic components and then impregnated into the reinforcing member and hydrated and masticated before end use; 5) those that are formulated with hydrophobic components and then impregnated into the reinforcing member and allowed to hydrate in vivo; and 6) those that are formulated with either hydrophobic or hydrophobic components and then mixed with reinforcing members that are powders, fibers or granulated textiles, then hydrated and masticated before end use or allowed to hydrate in vivo. The reinforcing member may be reinforcing oxidized regenerated cellulose (ORC) or carboxymethyl cellulose sodium (CMC) powder or fibers, or impregnated knitted, woven or non-woven ORC and CMC textiles. The impregnated textile functions as a delivery system and provides a cost-effective, manufacturing-effective, and clinically advantageous set of options for retaining the formulation within the tooth extraction socket.

The network-forming material, like gelatin or others, is required in certain embodiments to act as a binder for the dispersed ingredients, particularly upon hydration of the pharmaceutical formulation to deter macroscopic phase separation and erosion during deployment and hydration. Upon hydration of the formulation, either in vivo or alternatively ex vivo via mastication with water prior to use, it is believed that phase-inversion occurs whereby the network-forming material or cellulose textile becomes a plasticized and entangled network that serves as a binder for the encapsulated active-ingredient particles as well as for other dispersed ingredients. Simultaneously, the hydrophobic components (e.g., oil, wax), remain dispersed within the hydrated matrix and resist undergoing macroscopic phase separation and exudation. The post-hydration binding capacity that is provided by the plasticized network is necessary to prevent premature erosion of the formulation from the dental extraction socket or wound. The state of the dispersion and the degree of gelatin aggregation throughout these phase-inversion transformation processes will have an impact on the time-dependent release profile of active ingredients.

In an alternative embodiment, the pharmaceutical formulation may be prepared without the use of the network-forming material, provided that the textile material is capable of becoming a binder for the dispersed encapsulated active ingredient when the formulation is hydrated. Upon hydration, either in vivo or alternatively ex vivo via mastication with water prior to use, it is hypothesized that phase-inversion occurs whereby the network-forming material, the reinforcing member, or both become plasticized and serve as a binder for the encapsulated active ingredient particles. The binding is necessary to prevent premature erosion of the pharmaceutical formulation from the dental extraction socket or wound. The state of the dispersion and the degree of aggregation throughout these transformation processes has an impact on the release profile of the active ingredient. Thus, the state of dispersion is an important factor that will impact the release profile. However, the key to consistent release performance will not necessarily be in achieving an aggregate-free state of dispersion. Instead, the key to release performance will be in achieving reproducibility and consistency for any given state of dispersion that simultaneously satisfies manufacturing constraints and end use performance targets.

The various embodiments of the pharmaceutical formulation have certain morphological and functional attributes in common. Namely, each embodiment is functionally capable of undergoing in vivo hydration. Each embodiment facilitates controlled time release delivery of active ingredient when deployed in fixed-volume applications, such as within dental extraction sockets. Each embodiment is capable of inter-mixing with oral fluids such as saliva and blood in vivo to yield homogeneous structures that remain cohesively intact for sustained periods of time, thus enabling each embodiment to perform simultaneously as hemostats and as sustained release devices. Each comprises a network-forming material as a binder phase that serves as a matrix for suspending particulates, including encapsulated microparticles, such as poly(lactic-co-glycolic acid) (PLGA) encapsulated bupivacaine (BUP). Moreover, each binder phase may further comprise a liquid carrier that modulates the rheo-mechanical characteristics of the pharmaceutical formulation.

Although the various embodiments of the formulation have many global similarities, there are also several important distinctions. One of the most important distinctions stems from the compositional and physico-chemical differences in the components that constitute each of their respective binder phases. For liquid components, the polarity of the compounding liquid and the propensity for the liquid carrier to cause gelation of gelatin are the delineating factors for the categorization. The recognition of the importance of this seemingly minor distinction is one that has facilitated the creation of several distinct embodiments, each having different structural and functional features.

An embodiment of the pharmaceutical formulation is compounded with a high polarity liquid, wherein the liquid is one that induces gelation of gelatin prior to the deployment of the formulation. A compliant dough-like material is formed that can be deployed for in vivo drug delivery. When the choice of polar liquid is water or a water solution, the formulation preferably takes the form of a pre-packaged dry-powder mixture that is hydrated prior to deployment. When the choice of the high-polarity liquid is one that is more conducive to shelf-stability, such as glycerin or a high polarity liquid solution such as glycerin and water, a compliant dough-like material is formed that can be deployed as a stand-alone device for in vivo drug delivery. The mixture can be compounded during manufacturing with the high polarity liquid to form a compliant dough-like material and packaged as a compliant, formable, shelf-stable device that can be directly deployed in end use environments without the need for mixing with water or saline solution. The preferred high polarity liquids for this application are biostable and resist microbial growth during storage. Although these types of formulations can be optionally mixed and hydrated with water if so desired, they are unique in that they can be directly deployed for in vivo hydration. These formulations can also be optionally reinforced with fibrous materials, such as knitted, woven, or non-woven cellulose textiles including hemostats, to form a composite like structure.

An embodiment of the pharmaceutical formulation is compounded with a low polarity liquid, wherein the liquid is one that does not induce premature gelation of gelatin prior to the deployment of the formulation. This embodiment of the pharmaceutical formulation is compliant, formable, shelf-stable and can be directly deployed in end use environments without the need for premixing with water or saline solution. Although these types of formulations can be optionally premixed and pre-hydrated with water if so desired, they are unique in that they can be directly deployed for in vivo hydration. These formulations can also be optionally reinforced with fibrous materials, such as knitted, woven and non-woven cellulose fiber textiles including hemostats.

Embodiments of the delivery system, wherein a pharmaceutical formulation is reinforced with a fibrous material to form a composite like structure, can also be packaged for deployment and then subsequently deployed for in vivo hydration. The fibrous component can be either knitted, woven or non-woven, but a particularly advantageous type of fibrous component for this purpose is a low knit density cellulose hemostat knitted textile, which when impregnated with the pharmaceutical formulation positively enhances the formulation by increasing its strength, its durability, and its functionality during deployment. These types of delivery systems can be optionally hydrated with water, but they are uniquely acceptable for direct deployment and for subsequent in vivo hydration. The delivery systems tend to resist erosion, and they can be used to achieve controlled time-release delivery profiles of active ingredients like bupivacaine over periods of multiple days.

In each of the embodiments, the pharmaceutical formulation is designed to co-disperse network-forming material together with a variety of other ingredients, including for example, either unimodal, bi-modal or tri-modal particle size distributions of active ingredients, particulates of active ingredients encapsulated by an encapsulating material, or mixtures thereof.

In one embodiment, the encapsulating material may comprise a polymer. Polyanhydrides and polyesters are two classes of polymers often used for controlled release purposes. Polyanhydrides are a class of polymers composed of hydrolytically labile anhydride linkages that can be easily modified by vinyl moieties or imides to create cross-linkable systems, permitting the tailoring of release rates to the degree of cross-linking density. Mass loss of polyanhydrides follows a surface degradation mechanism, and drug release is exclusively controlled by surface erosion processes. Polyesters such as poly($\varepsilon$-caprolactone) (PCL), poly(lactic acid) (PLA), and poly(lactide-co-glycolide) (PLGA) have been used in controlled-release formulations currently approved by the FDA. Among these polymers PLGA is one of the most studied diblock copolymers for microencapsulation. Unlike polyanhydrides, PLGA undergoes bulk erosion, with drug release occurring by both diffusion and erosion processes. The drug release kinetics are influenced by the several characteristics of the PLGA polymer, including copolymer composition, molecular weight, crystallinity, and drug-polymer interactions. In addition to polyanhydrides and polyesters, microparticles made from copolymers of polyanhydrides and polyesters have also been investigated for their ability to achieve better controlled release of drugs.

The polymer polylactic-co-glycolic acid (PLGA) is an encapsulant that is well known in the art. With PLGA, the higher the percentage of lactide units, the longer the polymer lasts before degrading in the presence of water. In addition, the higher the molecular weight of PLGA, the greater the mechanical strength. The degradation rates of PLGA can be influenced by different parameters including, for example, (i) the molecular weight, whereby degradation rates have been reported to range from several weeks to several months with increasing molecular weights ranging from 10-20 to 100 kDa; (ii) the ratio of glycolic acid (GA) to lactic acid (LA), whereby PLGA with a higher LA contents are less hydrophilic, absorb less water and subsequently degrade more slowly as a consequence of the presence of methyl side groups in poly-LA making it more hydrophobic than poly-GA (one exception to this rule being the 50:50 copolymer which exhibits faster degradation); (iii) stereochemistry, whereby mixtures of D and L lactic acid monomers are most commonly used for PLGA fabrication because the rate of water penetration is higher in amorphous D,L regions, leading to accelerated PLGA degradation; and (iv) end-group functionalization, whereby polymers that are end-capped with esters, as opposed to the free carboxylic acid, demonstrate longer degradation half-lives. In addition, the geometric shape of the reinforcing member will strongly affect PLGA degradation behavior by influencing the accessibility of water. It has also been reported that acidic surrounding media will accelerate PLGA degradation due to catalysis.

The glass transition temperature (Tg) of PLGA is reported to be above 37° C., thereby providing PLGA with polymer chain rigidity and macro rigidity under ambient conditions and at body temperature. Further, it has been noted that Tg of PLGA decreases with decreasing LA content, and with decreasing molecular weight.

PLGA copolymers are commercially available with various LA to GA ratios, including 50/50, 65/35, 75/25, and 85/15; with glass transition temperatures ranging from 45 to 55 degrees C.; with inherent viscosities ranging from 0.55 to 0.75 dL/g; with tensile strengths ranging from 6000 to 8000 psi; with elongations ranging from 3 to 10%; and with modulus values ranging from $2 \times 10^4$ to $4 \times 10^4$ psi. These products are also described as having degradation/resorption time windows that generally increase with increasing LA contents. PLGA having LA/GA ratios of 65/35 degrade in about 3-4 months, LA/GA ratios of 75/25 degrade in about 4-5 months, LA/GA ratios of 85/15 degrade in 5 to 6 months, and where ratios of 50/50 (the exception) degrade in about 1-2 months. Resomer RG504 available from Evonik (a poly(D,L-lactide-co-glycolic acid) copolymer with LA/GA=50/50, CAS #26161-42-2) is reported to have an inherent viscosity (IV) of 0.4 to 0.6 dL/g, a Tg of 46-50 degrees C., a molecular weight of 38,000-54,000 amu, and a degradation timeframe of less than 3 months. Other types of D,L-PLGA copolymers available from Evonik that are suitable for use in making devices of the types described herein include those with LA/GA ratios of 50/50 with IV ranging from 0.16 to 0.74; LA/GA ratios of 65/35 with IV ranging from 0.32 to 0.44; LA/GA ratios of 75/25 with IV ranging from 0.16 to 1.2; and LA/GA ratios of 85/15 with IV ranging from 1.3 to 1.7.

For the present sustained release formulation, suitable PLGA copolymer are amorphous types with LA/GA ratios ranging from 50/50 to 85/15, with IV values ranging from 0.16 to 1.7, and with Tg values ranging from 37 to 60 degrees C. More preferably, PLGA copolymers will include those with LA/GA ratios ranging from 50/50 to 75/25, with IV values ranging from 0.16 to 0.75, and with Tg values ranging from 40 to 55 degrees C.

In addition, materials other than PLGA polymers may also be used as encapsulants, such as naturally derived and synthetic polymers and oligomers. Preferred naturally derived encapsulants include carbohydrate polymers such as plant derived starch and starch derivatives, cellulose and cellulose derivatives; plant exudates such as gum arabic, gum karaya and mesquite gum; plant extracts such as galactomannans and soluble soybean; polysaccharides; marine derived carrageenan and alginate; microbial/animal derived xanthan, gellan, dextran, hyaluronic acid (natural and cross-linked), albumin, collagen, gelatin and chitosan; plant proteins such as gluten and isolates from pea and soy; microbial/animal derived proteins including caseins, whey proteins and gelatin; and plant and animal derived lipids including fatty acids, alcohols, glycerides, waxes such as carnauba wax and beeswax, and phospholipids. Preferred synthetic encapsulants include homopolymers of polyester-based synthetic polymers like poly (ε-caprolactone) (PCL), poly(glycolic acid) (PGA), poly (lactic acid) (PLA), and poly(phosphoesters) (PPE); poly(ethylene glycol) (PEG), also known as polyethylene oxide (PEO), Poly(2-oxazolines) (POX), polyvinyl alcohol (PVA), poly(N-vinylpyrrolidone) (PVP), blends of polyvinyl acetate (PVAc) and povidone (PVP), as well as diblock and triblock copolymers and graft polymers of the aforementioned. Other microencapsulant material examples can include hydrophobic materials coated via fluid bed technologies, such as paraffin wax, fractionated palm oil, hydrogenated palm oil, mono and diglycerides, hydrogenated cottonseed oil, hydrogenated soybean oil, hydrogenated castor oil, beeswax, carnauba wax, and distilled monoglycerides; aqueous-based coatings such as hydroxypropyl methylcellulose (HPMC), gums, poly(vinyl alcohol) polymers and copolymers, poly(vinyl pyrrolidone) polymers and copolymers, cellulose polymers, poly(maleic anhydride) polymers and copolymers, including acid forms, anhydride forms, acid salt forms, and mixtures thereof, collagens; and solvent-borne coatings such as ethyl cellulose dissolved in an alcohol. Other examples of natural and synthetic polymers known to those skilled in the art can include carbohydrates such as starch, modified starches, dextrins, sucrose, cellulose and chitosan; gums such as arabic gum, alginate and carrageenan; lipids such as wax, paraffin, monoglycerides and diglycerides, hydrogenated oils and fats; inorganic materials such as calcium sulfate and silicates; and proteins such as gluten, casein, gelatin and albumin; each employing encapsulation methods such as, spray drying, spray cooling, extrusion, coacervation, lyophilization, and emulsification (da Silva, P. T., et al, "Microencapsulation: concepts, mechanisms, methods and some applications in food technology," Ciencia Rural, Santa Maria, v. 44, n. 7, p. 1304-1311, July, 2014).

PLGA microspheres or microspheres made from the aforementioned materials can be manufactured by many methods of microencapsulation, incorporating active ingredients for the purpose of modulating drug delivery. There are preferred techniques that emphasize processes that have produced commercially significant products such as: coacervation; interfacial and in vivo polymerization; single and double emulsion techniques such as solvent evaporation, solvent extraction and cross-linking emulsion; supercritical fluid techniques such as rapid expansion of supercritical solution (RESS) and supercritical fluid anti-solvent crystallization (SAS) processes; spray drying; spray coating; centrifugal extrusion; and rotational suspension separation.

Active ingredients for pain management may include an anesthetic or mixture of anesthetics to reduce the sensation of pain in the area to which they are applied. These anesthetics can be formulated alone, as mixtures and can be combined with an anesthetic vehicle like water, a vasoconstrictor like epinephrin, a reducing agent like sodium metabisulfite, preservatives like methyl paraben, and buffers. Anesthetics can be amino esters such as amylocaine, ambucaine, benzocaine, butacaine, chloroprocaine, cocaine, cyclomethycaine, demethocaine (Larocaine), piperocaine, propoxycaine, procaine (novocaine), proparacaine and tetracaine (amethocaine). Anesthetics can also be amino amides such as articaine, bupivacaine, cinchocaine (dibucaine), etidocaine, levobupivacaine, lidocaine (lignocaine), mepivacaine, prilocaine, ropivacaine and trimecaine. Anesthetics can also come from naturally derived sources. Terpenoids, alkaloids and flavonoids are anesthetic agents of plant origin because they meet the mechanistic requirements to interact with receptors, channels and membranes. Naturally derived anesthetics include saxitoxin, neosaxitoxin, tetrodotoxin, thymol, menthol, eugenol, cocaine, spilanthol, capsaicin, eunal, propinal, propandid and propofol. Anesthetics as active ingredients can be racemic mixtures, or the R or S isomers of the anesthetic depending on absorption, distribution, potency, toxicity and therapeutic action requirements. Anesthetics as active ingredients can be the free base form or the ionized form as a hydrochloride salt.

Active ingredients for pain management may include analgesics like acetaminophen and ziconotide, that provide relief from pain without causing sleep or loss of consciousness.

Analgesics can be from the class of salicylates such as magnesium salicylate, aspirin, choline salicylate/magnesium salicylate, diflunisal, salsalate, aspirin/citric acid/sodium bicarbonate.

Analgesics can be from the class of nonsteroidal anti-inflammatory drugs (NSAIDS) such as ketoprofen, fenoprofen, tolmetin, diclofenac/misoprostol, piroxicam, sulindac, indomethacin, diclofenac, etodolac, ibuprofen, flurbiprofen, ketorolac, naproxen, meloxicam, diflunisal, esomeprazole/ naproxen, famotidine/ibuprofen, mefenamic acid, oxaprozin, nabumetone, bromfenac, and meclofenamate.

Analgesics can be from the class of Calcitonin gene-related peptide (CGRP) inhibitors such as fremanezumab, erenumab, galcanezumab and Eptinezumab.

Analgesics can be from the class of Cyclooxygenase-2 (Cox-2) inhibitors such as amlodipine, valdecoxib and celecoxib.

Analgesics can be from the class of antimigraine agents such as frovatriptan, acetaminophen/dichloralphenazone/isometheptene mucate, almotriptan, caffeine/ergotamine naproxen/sumatriptan, rizatriptan, naratriptan, eletriptan, sumatriptan, zolmitriptan, dihydroergotamine, and ergotamine.

Analgesics can be from the class of narcotics, such as meperidine, opium, methadone, hydromorphone, codeine, fentanyl, oxycodone, oxymorphone, nalbuphine, morphine, butorphanol, levorphanol, buprenorphine, propoxyphene, tramadol, tapentadol, pentazocine, hydrocodone, alfentanil, remifentanil, and sufentanil.

Although narcotic analgesics may be employed, non-narcotic types are preferred. If narcotic types are used, it is preferable that they be of the localized type, capable of agonizing localized neuroreceptors for localized pain relief, and incapable of crossing the blood brain barrier so as to minimize possible tendencies for addiction.

Analgesics can be combined to contain at least one analgesic in combination with another medicine or medicines, and when combined generally have different ways of working to relieve pain, such as acetaminophen/caffeine/magnesium salicylate, aspirin/meprobamate acetaminophen/butalbital, acetaminophen/caffeine, acetaminophen/caffeine/isometheptene mucate, acetaminophen/pamabrom/pyrilamine, aspirin/diphenhydramine, acetaminophen/pamabrom, acetaminophen/butalbital/caffeine, aspirin/butalbital/caffeine, acetaminophen/aspirin, acetaminophen/phenyltoloxamine, acetaminophen/aspirin/caffeine/salicylamide, aspirin/caffeine, acetaminophen/aspirin/caffeine, acetaminophen/caffeine/pyrilamine, acetaminophen/diphenhydramine, diphenhydramine/naproxen, diphenhydramine/ibuprofen, aspirin/caffeine/salicylamide, acetaminophen/magnesium salicylate/pamabrom, acetaminophen/phenyltoloxamine/salicylamide, acetaminophen/pyrilamine, and diphenhydramine/magnesium salicylate. Narcotic and non-narcotic analgesic combinations include belladonna/opium, aspirin/butalbital/caffeine/codeine, meperidine/promethazine, acetaminophen/butalbital/caffeine/codeine, ibuprofen/oxycodone, acetaminophen/pentazocine, hydrocodone/buprofen, buprenorphine/naloxone, acetaminophen/oxycodone, acetaminophen/caffeine/dihydrocodeine, acetaminophen/hydrocodone, naloxone/pentazocine, acetaminophen/tramadol, acetaminophen/propoxyphene, aspirin/oxycodone, naloxone/oxycodone, acetaminophen/codeine, morphine/naltrexone, acetaminophen/benzhydrocodone, aspirin/caffeine/dihydrocodeine, and naltrexone/oxycodone.

Active ingredients of these aforementioned types may also be optionally employed without the use of a polymer microencapsulant, blending them directly into the network forming matrix. Mixed types of microencapsulated and non-encapsulated types can also be employed.

Other types of active ingredients can also be included as encapsulated on non-encapsulated adjuncts to satisfy a number of medical purposes, including for example, anti-infectives, antiemetics, and chemotherapeutic agents.

Anti-infectives describe any medicine that is capable of inhibiting the spread of an infectious organism or by killing the infectious organism outright, encompassing antibiotics, antifungals, anthelmintics, antimicrobials, antimalarials, antiprotozoals, antituberculosis agents, and antivirals. In addition to the aforementioned active ingredients for pain management, antibiotic, antimicrobial and antifungal anti-infectives are preferred adjunct active ingredients. Antibiotics such as penicillin, amoxicillin, amoxicillin/clavulanic acid, clindamycin, azithromycin, and metronidazole are preferred adjunct active ingredients. Antifungals such as fluconazole, clotrimazole, nystatin, itraconazole, and amphotericin B are preferred adjunct active ingredients.

Antiemetics are drugs that are effective against vomiting and nausea. Antiemetics are typically used to treat the side effects of opioid analgesics, general anesthetics, and cancer chemotherapy. In addition to the aforementioned active ingredients for pain management, antiemetic drugs for post-surgical nausea such as dexamethasone, droperidol, granisetron, metoclopramide, and ondansetron are preferred adjunct active ingredients. Antiemetic drugs for chemotherapy nausea (e.g., chemotherapy for treating head and neck cancers) such as aprepitant, dexamethasone, dolasetron, granisetron, ondansetron, palonosetron, prochlorperazine, rolapitant, and cannabinoids are preferred adjunct active ingredients.

Chemotherapeutic agents, also referred to as antineoplastic agents, are used to directly or indirectly inhibit the proliferation of rapidly growing cells, typically in the context of malignancy. They are classified according to their mechanism of action and include alkylating agents, antimetabolites, topoisomerase inhibitors, and mitotic inhibitors. In addition to the aforementioned active ingredients for pain management, for cancer that arises in the head or neck region (in the nasal cavity, sinuses, lips, mouth, salivary glands, throat, or larynx), chemotherapeutic agents such as bleomycin sulfate, cetuximab, docetaxel, erbitux (Cetuximab), Hydrea (Hydroxyurea), Hydroxyurea, Keytruda (Pembrolizumab), Methotrexate, Nivolumab, Opdivo (Nivolumab), Pembrolizumab, Taxotere (Docetaxel), and Trexall (Methotrexate) are preferred adjunct active ingredients Pharmacokinetic modulating additives can be optionally encapsulated or used directly in the formulation mixture, for example, citric acid, ascorbic acid, palmitic acid, dodecanedioic acid, sebacic acid, fatty acids such as stearic acid, oil-soluble types or water-soluble types, to influence the conversion of anesthetic free base its respective acid form. Additives can be optionally encapsulated or used directly in the formulation mixture to prolong the duration of anesthetic analgesia, for example epinephrine, clonidine, dexmedetomidine, buprenorphine, dexamethasone, tramadol, sodium bicarbonate, and midazolam. Many materials are suitable for use as the water-miscible and hygroscopic network-forming component in the present pharmaceutical formulation. Hygroscopic network-forming polymer components can include soluble collagen and gelatin; tree exudates of which arabic, ghatti, karaya, and tragacanth are examples; seaweed colloids including agar, agarose, Irish moss, carrageenin, and alginates as examples; extracts from seeds of locust bean, locust kernel, and quince seed gums as examples; manufactured and modified dextrins; water-dispersible or water-soluble derivatives of cellulose; and the like. These types of hygroscopic network forming polymers can also be used as encapsulants for various active ingredients if so desired. In such cases, the encapsulant serves two purposes: it encapsulates the active ingredient to form a diffusion barrier; and it provides the capacity to form an entangled network when the device is hydrated either prior to end use, or in vivo.

Other types of synthetic water-miscible and hygroscopic network-forming components can also be employed. For example, poly(maleic anhydride) polymers and copolymers, including acid forms, anhydride forms, acid salt forms, and mixtures thereof are particularly useful for producing networks with varying degrees of water miscibility, varying degrees of erosion resistance, varying degrees of capacity for adhesion to membrane tissue, and varying levels of compliance in their hydrated state. One example of a class of such copolymers includes the free acid and anhydride forms of poly(maleic anhydride-co-vinyl methyl ether) (PMAVE). In its free acid form, the polymer has greater water miscibility, and exhibits higher tissue membrane adhesion characteristics. Water miscibility, solubility and adhesion can be controlled through a combination of factors, including for example, by controlling the mole ratio of free acid to anhydride within the copolymer, and by controlling the molecular weight and molecular weight distribution of the copolymer. In addition, by selective use of monovalent and divalent counterions, salts of the various types of free-acid copolymers can be formed, including for example, monovalent Na salts, di-valent Ca salts, di-valent Mg salts, and mixtures thereof. The rate of water ingress and the degree of water miscibility with these types of polymers increases with increasing mole % of free acid, and decreases with increasing acid salt complexation, and with increasing valency of the counterion, where Na salts are most soluble, and Ca and Mg salts are less soluble. The mechanical compliance characteristics of such polymers are also known to increase with increasing mole percentages of free acid, and to decrease with increasing mole percentages of cation complexation, and also with increasing valency of the counterion. With these types of controlling levers, including the mole ratio of free acid form to salt form to anhydride form, the mole ratio of Na to Ca to Mg counterions, the average molecular weights and molecular weight distributions of the polymer types or mixtures thereof, it is possible to create a broad range of mechanical properties, adhesive properties, water miscibility characteristics, and network forming properties.

Gelatin is classified as a mixture of water-soluble proteins of high average molecular weights, also present in collagen. The proteins are extracted by boiling skin, tendons, ligaments, bones, etc. in water. Type A gelatin is derived from acid-cured tissue and Type B gelatin is derived from lime-cured tissue. Below 35-40° C. gelatin swells in and absorbs 5-10 times its weight of water to form a gel. Gelatin is soluble in glycerol and acetic acid, and more soluble in hot than in cold water. It is practically insoluble in most organic solvents such as alcohol, chloroform, carbon disulfide, carbon tetrachloride, ether, benzene, acetone, and oils.

Bloom is a characteristic used to describe gelatin referring to gel strength. Bloom is related to molecular weight and is therefore a factor that affects the mechanical elasticity of gelatin in its plasticized, gelled state. Bloom tests can be conducted using a standardized measurement (e.g., the force required to depress a prescribed area of the surface of a 6.67% gelatin gel at 10° C. (50° F.) to a distance of 4 mm). The bloom values for one family of commercial gelatin brands from Rousselot® are reported to range from 75 to 300 grams. As such, the gelatins are classified as follows: 1) High bloom—gel strength above 200 grams; 2) Medium bloom—gel strength between 120 and 200 grams; and 3) Low bloom—gel strength less than 120 grams. There is a general relationship between bloom and average molecular weight, where Bloom number generally correlates with average molecular weights as follows: 50-125 (Low Bloom)= 20,000-25,000 amu; 175-225 (Medium Bloom)= 40,000-50,000 amu; and 225-325 (High Bloom)=50,000-100,000 amu.

A number of gelatin types can be employed in the sustained release pharmaceutical formulation, including porcine, bovine, piscine, vegetable, type-A, type-B, or mixtures thereof. Commercially available matrix proteins, for example Surgifoam and Gelfoam, may also be used. The bloom values may range from 50 grams up to 325 grams depending on the desired rate of fluid uptake and the desired mechanical compliance for the device. Gelatins with higher bloom values are generally slower to adsorb water and will lead to lower compliance when they are gelled. In addition, gelatin types having different bloom values can be mixed at different weight ratios to achieve intermediate water-uptake rates and intermediate compliance characteristics. Desirable properties of the sustained release pharmaceutical formulation can be achieved with bloom values ranging from about 50 to 325, but preferably from 100 to 300, and more preferably from about 150 to 250.

Viscosity is also an important factor that affects the rheological behavior of gelatin solutions. Once dissolved in water, gelatins with bloom values covering the aforementioned range will yield solutions having viscosities typically ranging from 1.5 to 7.5 mPa-s. Viscosity is measured by a standardized method whereby the flow time of 100 ml of a 6.67% gelatin solution at 60° C. (140° F.) is measured when the solution is passed through a standard pipette. Desirable properties of the pharmaceutical formulation can be achieved with viscosity values preferably ranging from about 1.5 to 7.5 mPa-s, and more preferably from about 3 to 6.5 mPa-s.

Particle size distribution is another important physical attribute for the sustained release pharmaceutical formulation. Generally, the larger the particle size (smaller mesh size), the lower the viscosity of the resulting dispersion at constant weight ratios of particle to carrier. This factor can be represented by the mesh size of standard screens that are used for testing particle size distributions of particulate materials. A single positive mesh value is interpreted to mean the mesh value at which 90% by weight of the particulates are retained by the mesh screen when a distribution of particulates is passed through the mesh. For example, a reported mesh value of 30 (corresponding to a particle size of about 0.6 mm) would indicate that 90% by weight of the particle size distribution is retained by a mesh 30 screen when a distribution is passed through the screen, further indicating that 90% by weight of the distribution contains particulates that are 0.6 mm or larger. For the case of Rousselot® brands of gelatin, products are reported to included 8 mesh (2.36 mm) and 18 mesh (1.00 mm) at the upper range, and 30 mesh (0.60 mm) and 60 mesh (0.25 mm) at the lower range. The sustained release pharmaceutical formulation can be adjusted with a variety of 90% mesh particle sizes ranging from about 400 mesh or higher (0.037 mm or lower) to about 8 mesh (2.36 mm). Particle size distributions and hence vehicle rheology and fluid uptake rates can be further adjusted by blending distributions with different mesh values (e.g., 350 mesh blended with 60 mesh) and at varying weight ratios to yield rheological characteristics and fluid uptake rates that are commensurate with the end use needs for the application. The sustained release pharmaceutical formulation preferably comprises gelatin having mesh values between about 8 and 400, but more preferably between about 18 and 230, and even more preferably between 35 and 140.

The reinforcing member may comprise a type of reinforcing scaffold for dry powdered mixtures or more preferably for powdered mixtures that have been dispersed into liquid so as to provide sufficient binding, mechanical support and cohesive integrity before hydration. When the reinforcing member is a knitted, woven or non-woven textile, the dry powder mixture or liquid dispersed mixtures may be dispersed into the interstitial spaces of the textile. The textile may comprise a fibrous cellulosic material such as, for example, SafeGauze® HemoStat™ Topical Hemostatic Dressing commercially available from AMD Medicom, Inc.; ActCel™ Hemostatic Gauze commercially available from Coreva Health Sciences; SURGICEL® Original Absorbable Hemostat, SURGICEL® FIBRILLAR™, SURGICEL® NU-KNIT® and SURGICEL SNoW™ commercially available from Ethicon, and others. The dry powder mixtures can also be reinforced with cellulosic powders like carboxymethyl cellulose sodium (CMC), SURGICEL® Powder Absorbable Hemostat, as well as chopped fibers of CMC or oxidized regenerated cellulose. The reinforcing members can also be a made from collagen, alginate, silk, hyaluronic acid, or chitosan, in the form of a sponge, electrospun felt, porous film or textile. The dry powder mixtures or liquid dispersed mixtures could be impregnated into the interstitial spaces of such scaffolds, and the resulting delivery device could be folded and placed into the tooth extraction socket, where the delivery device would then be allowed to hydrate in vivo. However, for reasons pertaining to erosion, the most desirable approach is to employ a liquid dispersed mixture.

When the reinforcing member is in the form of a flexible textile sheet or scaffold, its geometric shape as well as its weight percentage in the delivery system can have a significant effect on the mechanical properties and on the tactile handling characteristics of the delivery system. Suitable tactile characteristics have been observed when pharmaceutical formulations are impregnated into the interstitial spaces of flexible textile sheets or scaffolds having thicknesses of between 0.01 cm and 0.1 cm, and topical surface areas of between 0.5 $cm^2$ and 15 $cm^2$, and more preferably between 1 $cm^2$ and 9 $cm^2$, and even more preferably between 5 $cm^2$ and 7 $cm^2$. Suitable tactile characteristics have also been observed when the delivery system comprises a cellulose textile as a reinforcing member at a weight percentage of up to 15% by weight. Moreover, suitable tactile characteristics have also been observed when the mass of fiber per topical square centimeter is between 0.005 $g/cm^2$ to 0.05 $g/cm^2$, and more preferably between 0.008 $g/cm^2$ to 0.02 $g/cm^2$. The mass of fiber per topical square centimeter is a relative indicator of the bulk density of the reinforcing member, which can be calculated by dividing the average weight of the member by its topical surface area. It has also been found that one or more geometric configurations of the reinforcing member can be used alone or in combination to form the formulation-impregnated delivery system. In addition, depending on the geometric shape of the one or more members, the flexible textiles can be impregnated and folded in various ways to yield multilayered impregnated composite structures so that the final geometric shape of the delivery system is conducive to deployment by a clinician during end use. In a tooth extraction socket application, multiple geometric configurations of the delivery system are suitable so long as the tactile handling characteristics are acceptable, and as long as the delivery system can be folded, inserted, and conformed to the shape of a tooth extraction socket, and provided that the tooth extraction socket is adequately filled with the delivery system after deployment.

In order to maximize the amount of anesthetic or analgesic available for sustained delivery, there exists a need to simultaneously address the volume-restriction limitations presented by the size of the wound being treated and ensure that the device has enough mechanical integrity and cohesive strength to adhere to the wound mitigate erosion. The reinforcing scaffold for a dry powdered mixture provides sufficient binding and mechanical support (i.e., cohesive integrity) before hydration. One could disperse the dry powdered mixtures of the previous embodiments into the interstitial spaces of a soft knitted, woven or non-woven textile such as a fibrous cellulosic material (e.g., SafeGauze, SURGICEL® Original, FIBRILLAR, NU-KNIT and SNoW). Conceivably, dry powder mixtures could be impregnated into the interstitial spaces of such textiles, and the resulting device could be folded and placed into the tooth extraction socket, where the device would then be allowed to hydrate in vivo. However, even with this approach, the dry powders, although interstitially limited in their mobility, may still have the propensity to erode and to prematurely migrate before hydration. Thus, there exists a need to create a binder system that simultaneously binds the powdered mixtures together both before hydration, and after hydration, while simultaneously serving to minimize pre-hydration erosion potential. Ideally, such a binder system should be capable of being used to deliver active ingredients for pain management whether it is used alone, or whether it is used together with a reinforcing member such as a cellulosic textile. When used with a reinforcing member like a cellulose textile, the binder system should be compliant enough to allow for interstitial impregnation, through a process that minimizes potential damage to the PLGA microspheres (e.g., pressing at near ambient temperatures). Once impregnated, the resulting cellulosic composite should be compliant enough to be easily folded for placement into an oral tooth extraction socket or wound, and the tactile feel of the material (i.e., stiffness and compliance) should be sufficient so as to minimize the potential for discomfort by the patient.

It would also be desirable for the non-hydrated binder system to be optionally useful alone without the use of a reinforcing textile. In such cases, the binder system could be allowed to hydrate in vivo, or it could be pre-hydrated and masticated before insertion into the tooth extraction socket. If the binder is allowed to hydrate in vivo, it must retain enough mechanical integrity to resist erosion until it hydrates with fluids in the tooth extraction socket. On the other hand, the non-hydrated binder, when impregnated into a reinforcing member (i.e., a cellulosic textile), would resist erosion to a greater degree than a non-reinforced binder system, and thus may be a preferable alternative for in vivo hydration.

Thus, the sustained release pharmaceutical formulation comprising a network-forming material optionally impregnates interstitial spaces of the reinforcing agent, such as a knitted, woven or non-woven fibrous material, for example, a cellulosic material like SafeGauze or Surgicel Original. A fibrous textile can be fit into a tooth extraction socket, wherein the textile is impregnated with a highly compliant formulation to the degree permitted by the volume restriction associated with the end use application. This device takes advantage of the macroscopic free volume that exists within the interstitial spaces of the textile and the mechanical reinforcing capability of the textile. Importantly, mechanical reinforcement enables the use of mechanically weaker binder formulations that would otherwise be difficult if not impossible to handle with a pre-hydrated powdered mixture approach. Highly compliant and mechanically weaker formulas can equate to the use of lower binder levels and higher microsphere concentrations to achieve higher bupivacaine dosages. Highly compliant network forming materials would also be conducive to simple industrial manufacturing methods for filling the interstitial spaces of the textile without damaging the PLGA microspheres, such as continuous pressing under near-ambient conditions while using the textile as a moving web.

In addition, if the fibrous material is chosen from a group of materials with known hemostatic properties, then improved hemostatic properties can be simultaneously and synergistically imparted to the delivery device, making it thereby possible for the delivery device to simultaneously satisfy two additional needs, in addition to minimizing prep time and to expanding the upper limit of drug deployment dosages for controlled time-release. First, a hemostatic fibrous member can impart characteristics that allow the pharmaceutical formulation to perform the function of a hemostat during deployment, which can help to facilitate and thereby satisfy the clinical need for clot-formation and protective scab formation. Secondly, the fibrous reinforcement can continue to facilitate the formation of a mechanically stable, compliant, persistent, and erosion-resistant scaffold-like composite that resists dislodging during use by simultaneously interacting with cavity fluids such as saliva and blood and with formula ingredients as they inter-diffuse and mix together under static conditions over time. This function would help protect the resulting scab from dislodging and would thereby help to prevent the painful occurrence of dry socket, a very important clinical need.

Thus, the use of hemostatic fibrous reinforcement material in the delivery device simultaneously provides many desirable features. The fibrous reinforcement facilitates initial composite reinforcement of the pharmaceutical formulation during manufacturing, during storage, and during initial deployment. The fibrous reinforcement allows for the optional use of lower network-forming material levels in the formula thereby expanding the upper limit for dispersed active ingredient and drug dosage, and for the optional use of lower levels of higher molecular weight network-forming materials in the binder phase of the formulation thereby providing reduced viscosity for ease of manufacturing and for higher initial compliance for handling efficacy. The fibrous reinforcement provides the advantage of hemostatic properties and simultaneous composite reinforcement during initial deployment into the socket and, if the fiber reinforcing member is properly chosen, the fiber reinforcing member can also continue to reinforce the composite during extended periods under static conditions after deployment, thereby facilitating in vivo composite formation with fluids in the socket while minimizing the propensity for erosion. This can facilitate formation of an in vivo composite that not only protects the forming scab from premature dislodging, but provides a vessel for the formulation to persist and to continue to perform its drug delivery function over prolonged periods without being prematurely ejected or eroded from the tooth extraction socket.

It can be appreciated by those skilled in the art of composite materials that the physical properties and handling-related characteristics of composites like those described herein can be influenced by many fiber-related factors including, for example, the density of individual fibers and fiber bundles; the density of knitted, woven or non-woven textiles comprising fibers and fiber bundles; the bulk density of the fibrous members whether they are knitted, woven or non-woven; the geometric length of fibers and fiber bundles; the total surface area per unit weight of the fibrous members; the surface wetting characteristics of the fibrous members towards both hydrophobic and hydrophilic materials; the volume and weight ratios of the fibrous members to the formula members; and among other factors, the rate of dissolution of the fibers in vivo, as influenced by their solubility, their degree of oxidation, their molecular weight, and their surface wetting characteristics. Each of these fiber-related factors, either alone or in any combination, can have a profound impact on the composite device's manufacturability, on its mechanical properties during initial deployment, and on its dynamically evolving properties as the device experiences static diffusion and intermixing with tooth extraction socket fluids during the entire timeframe associated with the near static condition of the in vivo environment, particularly during the entire end use period associated with the wound healing cycle and with the drug delivery.

As one aspect of this invention, it can be appreciated that the choice of the fibrous member for the composite device is an important one, and that the material can be tuned to the application by controlling the degree of oxidation which affects solubility, the molecular weight of the cellulose, the fiber surface area per unit volume, the fiber bundle density, the bulk knit density, and the like. Aside from these tunable factors, it is also possible to use a mixture of fibrous member types. For example, the fibrous composite could be comprised of both a relatively fast-dissolving type of fiber member (e.g., SafeGauze), and a relatively slow-dissolving member (e.g., Surgicel Original). Use of multiple fiber types can impart combinations of desirable characteristics, including faster initial wetting and better initial adhesion during deployment from the more soluble fiber member, and longer-term composite integrity during the in vivo use period associated with dynamic changes in properties owing to inter-diffusion of tooth extraction socket fluids with the device from the less soluble fiber member.

In one aspect, pH modulators may be used as a component to adjust the pH of the formulation. Bases or buffering additives, such as di-sodium citrate, and acidic additives, such as ascorbic acid or citric acid, can be provided at selected levels. Initial gelation rates and viscosities of gelatin can be modulated by protonation, for example, with citric acid. Protein-moiety protonation induces faster gelation and higher relative viscosities. Thus, slower or faster gelation rates can be achieved by modulating pH as desired. As such, gelatins can be used for formulating PLGA microsphere-containing formulations with mechanical and gelation characteristics that vary depending upon gelatin-type and pH.

It is important to recognize that the efficacy of the device will be impacted by the diffusion rate of active ingredients, such as bupivacaine. This diffusion rate will not only be affected by microencapsulation of bupivacaine with PLGA, it will also be affected by the water-solubility of bupivacaine, which is affected by the equilibrium concentration of bupivacaine's protonated acidic-form in competition with its non-protonated free-base form. In the presence of Bronsted acids (e.g., protons from citric acid, protons from protonated amine moieties from the gelatin protein, etc.), the free-base form of bupivacaine and drugs with similar chemical structures will protonate to some degree, and the more water-soluble protonated form will exist in equilibrium with the less water-soluble free-base form. To this end, there can be an advantage associated with using pH-modulators like citric acid to assist in controlling the effective solubility of bupivacaine.

The relative concentrations of protonated and non-protonated bupivacaine structures will be affected by all competitive acid-base reactions, including those involving protein amine moieties. For example, given that different proteins will exhibit differing degrees of acid neutralization capacity, and given that the relative viscosities can increase in the presence of a proton source (this is demonstrated in Example 1), it follows that free base drug diffusion rates will differ in the presence of different protein-types (i.e., for reasons pertaining to drug solubility, and for reasons pertaining to diffusion rates being attenuated by increased viscosity). PLGA hydrolysis rates will also be affected by pH, and by competitive equilibrium reactions with other Bronsted bases (e.g., di-sodium citrate, protein amines, and the free-base form of bupivacaine).

Thus, if one were to add an acid such as citric acid to a pharmaceutical formulation with the intent of skewing the bupivacaine acid-base equilibrium towards the more water-soluble protonated form, the relative equilibrium concentration of the more soluble protonated form would vary depending on the composition of the chemical environment. For example, a chemical environment comprised of different types of Bronsted bases (e.g., protein amines from various types of gelatins), and different types of Bronsted acids (e.g., citric acid, ascorbic acid, sebacic acid, etc.) would lead to different equilibrium concentrations of the more water-soluble, protonated form of bupivacaine. Accordingly, apparent drug activity and release rates would be affected for this reason. Similarly, if the hydrochloride salt of bupivacaine (i.e., the more water-soluble protonated form) were added to a formulation with these types of gelatins under pH neutral conditions (i.e., with no additional acid or base), the protonated bupivacaine would enter into equilibrium with competitive Bronsted bases from the protein gelatins whereby the acid neutralization capacity of the protein would govern the ultimate equilibrium concentration of the more water-soluble protonated form of the drug.

Importantly, the pH of the chemical environment will also have an impact on the rheological characteristics of the formulation. This in turn will not only have an impact on the diffusion rate of active molecules like bupivacaine, but it will also have an impact on the compliance characteristics of the formulation, which in turn will affect its formability within a fixed volume cavity, such as a tooth extraction socket.

The effects of pH on properties of the network-forming material can be appreciated by one of ordinary skill in the art. The ratio of citric acid or other alternative acids to protein can be used to achieve a gel network with suitable mechanical integrity. Higher citric acid to gelatin ratios would lead to even faster gelation rates as would lower levels of water.

For rheological purposes, a pharmaceutical formulation comprising powdered mixtures may be developed with commercial gelatins, whereby a formulation will optionally incorporate a level of citric acid or other types of acids, which when mixed together with an appropriate ratio of water to solids will allow for a rate of gelation that is desirable for clinical use. Further, the formula composition can be controlled so as to exhibit appropriate elastic modulus and compliance characteristics by modulating factors such as the water level, the molecular weight distribution of the gelatin (Mw/Mn), the concentration of acid, and the type of acid additive, etc. Simultaneously, it is understood that a balance would be achieved with other factors that impact the efficacy of the pharmaceutical formulation, including the aforementioned chemical environment factors that affect the solubility and diffusion of bupivacaine, including the initial concentration of bupivacaine in its free-base and in its acidic form and the ultimate equilibrium concentration of both species within the end use chemical environment.

In one aspect, the pharmaceutical formulation delivers a maximum level dosage of bupivacaine (BUP) into a fixed volume cavity, assuming an occupied formula volume of 1 cc for the oral post tooth-extraction cavity. The target dosage range for bupivacaine is between a level approaching possible toxicity on the high-delivery side and a level representing clinical usefulness on the low-delivery side. The formulation composition is dependent on the bupivacaine target dosage level due to the unique occupied volume limitation for this type of end use application, with a maximum bupivacaine dose estimate targeted to be up to 360 mg over a 4-day period (90 mg/day×4). Three different pathways were identified to address the problem of maximizing dosage: (1) increasing bupivacaine-loading to its maximum theoretical level of about 50% w/w within the PLGA microspheres; (2) minimizing the network-forming material levels to the extent permitted without simultaneously deteriorating mechanical properties; and (3) minimizing the level of water required for hydration/mastication to the extent tolerable without experiencing unmanageable decreases in compliance.

In an embodiment, dry powders of bupivacaine-loaded PLGA microspheres and gelatin would be masticated with water to be delivered as a compliant dough-like material in end use for a desirable bupivacaine release profile. Volume restriction for the application estimated to be ca. 0.55 cc causes the dosage of bupivacaine to be severely limited by the occupied volume fraction of binder and water. Higher levels of bupivacaine loading in the PLGA microspheres are desirable for achieving useful bupivacaine delivery dosages, higher than the 20% w/w level that was used in the prior art since this level would only lead to maximum dose deliveries of less than 60 mg. Lower binder levels are required to maximize the microsphere content and hence the bupivacaine delivery dosage, which is a constraint that weakens the composite and necessitates not only better network-forming binders, but higher levels of volume-occupying water for plasticization. Lower binder levels necessitate higher molecular weight network-forming gels that are susceptible to time-dependent reductions in compliance owing to diffusion-rate limitations which impact the time required for the network to reach its equilibrium state. Diffusion rates and time-dependent compliance behavior are further confounded by both the particle size distribution of the microspheres, which affects the bupivacaine time-release profile, and by the size of gelatin particulates. From a mechanical property perspective, it is desirable to maximize the smaller particle size fraction while simultaneously balancing the overall distribution to achieve the desired bupivacaine release profile since smaller particles will release faster than larger ones.

One embodiment of the sustained release pharmaceutical formulation using powder mixtures appears to deliver a dosage of about 140 mg bupivacaine to a 0.55 cc cavity, and only then by assuming that the % bupivacaine loading in the microspheres is increased from 20% to 50% by weight. Low gelatin binder levels are also required to maximize the volume fraction of microspheres and bupivacaine. It appears that the lower limit threshold for the network-forming material is approximately 18% of the dry weight. At these levels, a network-forming gel like bovine gelatin is preferred as having sufficient strength to bind the spheres together. If the product is intended to be masticated with water, and if higher bupivacaine dosages are desired, then the occupied volume of water must also be accounted for, and the water-level should be minimized since it will effectively dilute the microsphere concentration and will further reduce the maximum bupivacaine delivery dosage. For reasons pertaining to mechanical properties, it is also preferable to skew the PLGA particle size distribution towards small particles to the degree that this can be tolerated depending on bupivacaine release profile targets. Larger microspheres made via an emulsion process provide qualitatively lower formula viscosities than their spinning-disc/spray-dried counterparts. In essence, this equates to a higher PLGA loading potential during mixing, which is also directionally preferred for achieving higher bupivacaine dosages; but only to the degree that adequate compliance and cohesive strength can be maintained. The D50=42.1 micron emulsion particles were also observed to mix more uniformly with faster wetting than their similarly-sized spinning-disc spray-dried counterparts, the D50=42.7 micron placebo PLGA microspheres. Again, smaller particles, D50=3.4 microns as made by spinning-disc methods, by spray-drying, or by emulsion-solvent extraction processes, are desirable for reasons pertaining to mechanical properties, but only to the degree that their higher surface-to-volume ratios and release characteristics can be conducive to achieving specific time-dependent bupivacaine release profile targets.

Although release profile targets will be end use specific, it should be understood that there will be several adjustable factors besides PLGA surface-to-volume ratios that can also conceivably be used to modulate and control the time-release profiles of bupivacaine and the like. For example, citric acid (a Bronsted acid) or di-sodium citrate (a Bronsted base) was observed to be viable with no obvious deleterious effects on rheology or properties of the delivery system. Citric acid was observed to enhance binder system network formation of the network-forming material. From this perspective, these types of compounds can serve dual functions: not only can they be used to modulate the physical properties of the binder system, their activity can also be exploited for the dual purpose of modulating the solubility of the bupivacaine free base. For example, a Bronsted acid will enhance the solubility of bupivacaine free base as it is released from a PLGA particle, thereby enhancing its bioavailability. Conversely, a Bronsted base would skew the acid-base equilibrium towards more bupivacaine free base, thereby reducing its bioavailability. Further, these types of compounds can be employed directly as powdered ingredients, which would make them immediately available upon device hydration. In addition, these types of compounds can be optionally and separately microencapsulated, which would attenuate their availability for acid-base interactions with bupivacaine in its acidic form or its free-base form. By balancing these types of formulation levers, it can be appreciated that one could achieve targeted bupivacaine release profiles while simultaneously employing higher fractions of high surface-to-volume particles if so desired. For example, with the combined use of these levers, one could potentially use a higher fraction of 3.4 um particles than would otherwise be viable. Again, this direction might be desirable for reasons pertaining to achieving improved mechanical properties, which in turn could be leveraged to achieve lower net binder levels, including the network-forming material, and higher net PLGA levels and accompanying higher net bupivacaine dosages if so desired.

As described above, hydrophobic components in the pharmaceutical formulation and related delivery devices can be desirable from the standpoint that they can be formulated to yield dough-like materials with compliance characteristics that are conducive to end use deployment, without having to rely upon pre-deployment swelling and gelation of the gelatin particulates. Thus, the pharmaceutical formulation comprising hydrophobic components and related delivery devices are ones whereby the gelatin particulates remain intact during manufacture and storage, and do not yield macroscopic chain-entangled gelled networks until they become exposed to a tooth extraction socket and its fluids after deployment unless the option of pre-deployment hydration is exercised.

It is important to note that each of the embodiments of the present formulation will eventually become hydrated with fluids from the tooth extraction socket after deployment. This is predominantly due to the presence of the hygroscopic, water-absorbing network-forming polymer, like gelatin, or to the presence of other water-absorbing materials such as cellulose fibers. However, in order to render the devices as compliant and conformable prior to their deployment, it is desirable that they be properly formulated in advance of deployment, so that the clinician does not have to spend time meticulously measuring and premixing materials before they can be used. In other words, it is desirable to have a device that is already a compliant solid without having to be premixed with fluids like saline solutions or water.

In an embodiment of the present formulation comprising at least one hydrophilic component, water may be used as a plasticizer to hydrate and to masticate blends of the powder ingredients to yield a compliant dough-like mixture (e.g., water+bovine gelatin with PLGA-encapsulated BUP as described in Example 12). In these cases, water is the primary liquid ingredient in the pharmaceutical formulation, and the mechanical integrity of the formulation is achieved by virtue of gelation and network formation prior to the deployment. The compliance and conformability of this formulation is controlled by the ratio of water to gelatin (w/w) with consideration also given to the total % solids in the plasticized mixture. Importantly, water is used as a liquid plasticizer for the gelatin polymer in this embodiment. A plasticizer is generally a liquid (sometimes a solid) that when blended with a polymer, increases the fraction of free volume, which in turn lowers the polymer glass transition temperature, and consequently lowers the elastic modulus, and increases the compliance. Plasticizers are known to be at least partially miscible with the polymers that they plasticize.

In an embodiment of the present formulation comprising at least one hydrophobic component, oils with optional waxes are used as liquid carriers to suspend hygroscopic, water-absorbing network-forming materials, such as gelatin powders together with other dispersed ingredients, including PLGA-encapsulated BUP, free (non-encapsulated) BUP, and citric acid, to name a few. This embodiment achieves pre-deployment conformability and compliance characteristics not by plasticization of a polymeric continuous phase, but instead by virtue of other interactive factors that impact the rheological properties of suspensions, including the ratio of hydrophobic liquid to wax, which controls the viscosity of the liquid carrier and affects the viscosity of the resulting vehicle, the particle size distributions of dispersed ingredients, and the total percentage of dispersed solids, to name a few. In these cases, the mechanical integrity of the pre-deployed formulation is not achieved by virtue of gelling a polymer with a plasticizer to yield a reinforcing polymer network, but instead by virtue of fiber reinforcement by impregnating knitted or woven cellulose textiles or non-woven fibers with non-gelled suspensions to yield fiber-reinforced composite-like structures.

Thus, one of the primary distinctions between the hydrophilic and hydrophobic formulations and delivery systems relates to pre-deployment morphology. By design, a hydrophilic formulation or delivery system is comprised of a water-miscible hygroscopic polymer network that is homogenously gelled and pre-plasticized with a liquid such as water, glycerin, honey, polyethylene glycols, polypropylene glycols, etc. By contrast, the hydrophobic formulation or delivery system contains inter-dispersed suspended particulates of water-miscible and hygroscopic network-forming polymers like gelatin that have the latent potential to form gelled networks once exposed to water after deployment, but in their pre-deployment state, they are made to persist as morphologically discrete entities suspended within and wetted by a hydrophobic liquid. These hydrophobic formulations and delivery systems (sometimes interchangeably referred to as devices herein) do not rely on gelatin plasticization and network formation to achieve their pre-deployment properties. However, after deployment, they are morphologically designed to accept water through diffusion of oral fluids like saliva and blood, which allows for post-deployment polymer network formation, analogous to what occurs in the pre-deployment stage with a hydrophilic formulation or device. At that point after the deployment, the development of a gelled polymer network from water-ingress can have the added benefit of providing an additional mechanism of mechanical reinforcement, augmenting that which may already be provided by inter-dispersed cellulose fibers.

With these morphological considerations in mind, the differences between a hydrophilic and hydrophobic embodiment of the pharmaceutical formulation can be further reduced to another important design-controlling distinction, namely, the nature of the liquid component that is used in formulation. Generally, a liquid that leads to pre-deployment gelation of the network forming component is best suited and preferred for use in preparing the hydrophilic embodiment of the formulation. A liquid that does not lead to pre-deployment gelation of the network forming component, or at least little to no gelation for a period of time after manufacture that coincides with the desired shelf-life prior to deployment, is best suited and preferred for use in preparing the hydrophobic embodiment of the formulation. The delineation between a liquid that leads to gelation of the network forming component and one that does not lead to gelation can be defined by a suspension test as demonstrated Example 14. In general, if there are no signs of gelation within a predetermined monitoring time window, then the liquids are considered to be candidates for use as a "hydrophobic" component of the formulation. Mineral oil, caprylic triglyceride, isopropyl palmitate, and coconut oil are such liquids. Liquids that are observed to lead to gelation of gelatin within the time monitoring window are considered to be good candidates for use as a "hydrophilic" component of the formulation. Glycerin and water are such liquids. Note that similar tests can be employed to test the miscibility of carrier liquids with other dispersed ingredients.

In some circumstances, the degree of hydrophilicity and hydrophobicity of a liquid can also be gauged by parameters that pertain to molecular-level properties such as polarity (e.g., dipole moment forces from permanent dipoles), dispersion forces (e.g., non-permanent dipoles or van der Walls forces), and hydrogen bonding forces. Indices such as the Hildebrand Solubility Parameter (HSP) or Hansen Solubility Parameter (HAN) of liquids and polymers (J. Brandrup and E. H. Immergut, *Polymer Handbook*, Third Edition, John Wiley & Sons, New York, 1989, pp. 519-559), as well as Hoy solubility parameters (HOY), have been developed in attempts to better quantify what is meant by "hydrophilicity" and "hydrophobicity." Hoy solubility parameters (HOY), like Hansen Solubility parameters (HAN) are based on chemical group methods of calculating energetic contributions from dispersion forces, polar forces, and hydrogen bonding forces. These contributions are summed to yield the total solubility parameter by taking the square root of the sum of the squares. Generally, although the estimation methods differ for the HAN and HOY terms, the sums of the contributions from HAN and HOY parameters produce similar total solubility parameter estimates, which are also considered to be equivalent to HSP values (i.e., HSP~ $HAN_{total}$~$HOY_{total}$).

It is generally understood by those skilled in the art that polymers and liquids tend to be more miscible when their solubility parameters are similar in magnitude to one another, as the differences between them approach zero. Conversely, polymer/solvent pairs become less miscible as their solubility parameters diverge from one another, as the differences between them become greater.

For the purposes of the present invention, the most hydrophobic liquids can be defined as those with either a small or no permanent dipole moment, and with a low capacity to participate in hydrogen bonding. These types of liquids have been observed to be the least compatible with highly polar and water-soluble protein-based polymers like gelatin, which explains why the gelatin particulates remain dispersed and stable over time when suspended (i.e., not gelled) in formulations comprised of such liquid carriers. These types of liquids would also be expected to have limited compatibility with other polar molecules, such as water and BUP-HCl, thus rendering them as relative deterrents against both molecular-level and macro-level diffusion during the end use application. This behavior renders such liquids as useful levers in achieving specific control over time-release profiles. In the present formulation, an example of this type of liquid is represented by a paraffinic hydrocarbon like mineral oil.

On the other side of the spectrum, liquids with permanent dipoles and with higher capacities for hydrogen bonding can be classified as being less hydrophobic and more hydrophilic. In the present pharmaceutical formulation, this type of liquid is represented by water in one extreme (HSP=approximately 48 MPa$^{1/2}$). These types of liquids are highly compatible with hygroscopic polymers like gelatin, which explains why the dispersed gelatin particulates do not persist in formulations containing water, but instead become swollen through diffusion and plasticization, leading to the coalescence of the particulates through polymer chain entanglement, and leading ultimately to gelation and to solid network formation prior to deployment of the pharmaceutical formulation.

Note that for the case of a pharmaceutical formulation that is prepared with hydrophobic components like oils or waxes, the more hygroscopic components, like gelatin particles and cellulose fibers, remain discrete and intact prior to hydration, either as dispersed, non-gelled particulates, or as inter-meshed fibrous entities. In these cases, the oils and waxes that constitute a continuous phase of the pharmaceutical formulation serve to facilitate the dispersion of other ingredients like gelatin, PLGA microparticles, BUP, and citric acid. Note that optional surfactants can also be added to assist in stabilizing such dispersions.

In its pre-deployment morphological state, the mechanical integrity of the pharmaceutical formulation comprising a hydrophobic component may be derived from its reinforcement with cellulose fibers. Importantly, the morphology of the hydrophobic formulation has been designed to adsorb polar liquids like water. Thus, when a polar liquid (e.g., water, glycerin, polyethylene glycol, mixtures thereof, or fluids from the tooth extraction socket, etc.) is intermixed with a formulation having the hydrophobic component, the morphology of the formulation accommodates the adsorption of the polar liquid without producing the side-effect of macroscopic phase separation of other components. This behavior is consistent with a morphological change that occurs when polar liquids are mixed with the formulation, whereby the more hygroscopic components like gelatin or cellulose begin to absorb the polar liquid, becoming plasticized, and then begin to coalesce into a gelled network matrix such that the new continuous phase contains the gelled network matrix, including polar liquid+gelatin+cellulose, inter-dispersed together with the hydrophobic components, the oils and waxes that previously constituted the continuous phase prior to hydration. At this stage, other dispersed ingredients like PLGA, BUP, BUP-HCl, citric acid, etc., that were previously dispersed in the oil-based continuous phase, either remain dispersed within the oil-phase components that themselves become inter-dispersed within the gelled matrix, or they become directly dissolved in the water that diffuses into the newly-formed continuous phase of the gelled matrix. Importantly, the plasticization, the chain-entanglement, the ensuing gelation, and the ultimate network formation that accompanies this adsorption process are desirable attributes for the hydrophobic pharmaceutical formulation. Most importantly, and by design, this morphological change is made to occur in vivo and does not have to occur during the pre-deployment stage or during the storage period.

The latent capacity for a pharmaceutical formulation comprising a hydrophobic component to adsorb a polar H-bonding liquid like water is not only a desirable and surprising attribute that arises from the synergistic interactions among the component ingredients of the formulation, it is a measurable attribute that can be used to specify a distinguishing characteristic of a hydrophobic pharmaceutical formulation. Namely, a hydrophobic pharmaceutical formulation, as used herein, is one that after being mixed via physical mastication with water at a minimum ratio of water to device=0.2/1 w/w, or more preferably 0.33/1 w/w, or even more preferably 0.44/1 w/w or higher, does not exhibit macroscopic phase separation under static conditions for a period of at least 1 hour, and preferably for 2 or more hours, and more preferably for 24 hours. The formulation further retains the added water for said period of time under static conditions without exhibiting visual indications of macro phase separation of water or other components.

As stated previously, if the end-product objective is to minimize active-ingredient dilution in the pharmaceutical formulation while simultaneously achieving mechanical compliance characteristics that are desirable for deployment, then gelation of gelatin or other macromolecular hygroscopic network-forming components would be most desirable if it were made to occur after deployment and not before. Thus, the pharmaceutical formulation comprising a hydrophobic liquid like mineral oil or others as shown in Table 14-3 represents a preferred approach towards achieving this objective.

On the other hand, when compared to hydrophobic liquids like mineral oil, hydrophilic liquids like water and glycerin are more compatible and more miscible with polar molecules like BUP-HCl, a fact which is consistent with the observation of faster active ingredient diffusion rates exhibited by the pharmaceutical formulation pre-plasticized with water as opposed to those prepared with mineral oil as the liquid vehicle carrier. Hence, if the end-product objective is to maximize the release rates of water-soluble active-ingredients while simultaneously achieving mechanical compliance characteristics that are desirable for deployment, then gelation of gelatin or other hygroscopic network-forming components with hydrophilic liquids like water and glycerin could be a desirable approach before deployment. Thus, the pharmaceutical formulation comprising a hydrophilic component represents a method of approach towards achieving this objective, but only if the resulting dilution of active ingredients can be tolerated in the end use application.

Again, in the absence of gelation, the hydrophobic pharmaceutical formulation achieve their initial mechanical cohesive integrity through a mechanism that is independent of gelled network formation. Specifically, if the formulation is to have the compliance characteristics of a cream, it can then be used to disperse active ingredients, and it can then be impregnated into a fibrous textile which serves as a reinforcing scaffold forming a delivery device before its deployment. The reinforced device is therefore made to have cohesive integrity and compliance which renders it as sufficiently acceptable for use by the clinician during its deployment. It is only later, after deployment, that the dispersed gelatin particulates and wetted and impregnated cellulose fibers begin to swell with liquids from the tooth extraction socket, leading to their chain entanglement, and ultimately to their network formation and to an accompanying change in morphology. The gelled network then becomes a type of reinforcing scaffold for the device in vivo, serving to enhance the cohesive strength of the pharmaceutical formulation, which enhances its mechanical integrity after deployment, and not before.

Other liquids besides mineral oil, such as caprylic triglyceride and isopropyl palmitate, are more polar than mineral oil, and they have at least some capacity for hydrogen bonding. However, their polarity and H-bonding characteristics are insufficient to cause gelation of the gelatin particulates that are suspended within them. Thus, although these types of liquids have permanent dipoles and therefore have some capacity for hydrogen bonding, they are poor plasticizers for gelatin. For the purposes of description, a pharmaceutical formulation or delivery device comprised of such liquids may be referred to as "hydrophobic". The "hydrophobic" formulation containing them have a distinguishing attribute in common: the liquid carriers that serve to suspend and bind the ingredients do not promote the gelation of the gelatin particulates, and they are either immiscible with gelatin or have limited miscibility under ambient conditions. Consequently, macromolecular chain entanglement and gelation do not occur when the particulates are suspended in such liquids.

However, liquids that are deemed as being suitable for use as a hydrophobic ingredient can also perform other functions when formulated into the pharmaceutical formulation. For example, the HAN of isopropyl palmitate is reported as 15.3 $MPa^{1/2}$. Although these types of liquids are recognized as being more polar than mineral oil, for the purposes of the formulation, they are still classified as being relatively hydrophobic in that they do not diffuse and swell gelatin particulates in the way that water does. Instead, the gelatin protein particulates persist in such formulations until they are subjected to hydration during end use. Nevertheless, the permanent dipole moments of these liquids would be anticipated to render them as more amenable to facilitating molecular-scale diffusion of small polar molecules than would mineral oil. Thus, liquids of these types can be useful to modulate diffusion rates of active ingredients, thereby providing an additional lever to achieve intermediate controlled-release time profiles. In addition, hydrophobic liquids with higher polarity than mineral oil can also serve the secondary purpose of lowering the Tg of PLGA via plasticization. This would result in a faster rate of diffusion of encapsulated ingredients because a lower Tg will equate to a higher fraction of free volume, which in turn would translate to lower potential energy barriers for diffusion of small molecules across the PLGA polymer gradient from within the PLGA particle and into the matrix.

There are occasions when the use of a pharmaceutical formulation comprising a hydrophilic component gelled with a hydrophilic liquid before deployment would be desirable for end use. For example, a hydrophilic formulation that is mixed with water can be useful in achieving relatively fast time-release profiles of water-soluble ingredients. This embodiment of the pharmaceutical formulation is first premixed and pre-plasticized with water, glycerin, polyethylene glycols, other polyhydric alcohols, or mixtures thereof. This embodiment is analogous to the hydrophobic embodiment, but they are made with a polar H-bonding liquid as the primary liquid ingredient instead of oils and waxes, and they are designed to gel prior to deployment instead of afterwards. Thus, as long as they are shelf-stable against microbial growth, these types of pre-gelled formulations can be used as control-release delivery devices on their own—without fiber reinforcement. However, they can also be optionally reinforced with a fibrous cellulose hemostat to form a composite structure.

As noted by Jaymin C. Shah and Manoj Maniar in *Journal of Controlled Release,* 23 (1993) 261-270, controlled release of active ingredients like BUP from polymeric matrices can occur via diffusion, dissolution or erosion of the polymer. The authors note that erosion or diffusion processes are generally assumed to control the rate of drug release. Hence, if the drug and its conjugate salt have low water solubility, then it is anticipated that the dissolution rate of the drug could have a significant effect on the release-kinetics of the drug.

It should also be realized that diffusion and erosion are interactive processes, and that diffusion involves not just the egress of active ingredients from the formulation, but ingress of water and fluids from the chemical environment where the formulation is deployed. As fluids diffuse into the formulation via both macro and molecular-level pathways, the matrix polymer can become more susceptible to erosion, either through dissolution of volume elements from the exposed surfaces, from the macro separation of particulates near the surfaces, or through a combination of the two.

As noted earlier, one advantage of using fibrous reinforcement for a delivery device is that it can improve the cohesive integrity of the pharmaceutical formulation, and thereby render it to be more erosion resistant. When a formulation erodes during end use, internal cohesive failures of the matrix can cause particulates of the device to become macroscopically separated from the original structure. During end use, fluids can permeate into the matrix phase through a combination of macroscopic and microscopic diffusion mechanisms. Macroscopic diffusion can occur through permeable boundaries that are present from defects like void elements arising from entrapped air between partially bonded matrix polymer particulates (e.g., gelatin particulates), or from matrix polymer that is partially delaminated from the surfaces of weakly bonded elements or components that are dispersed within the matrix.

If the pharmaceutical formulation comprises a polymer that is hygroscopic, molecular level diffusion of hydrous liquids can occur along every frontal boundary that becomes available to the fluid. When the fluid macroscopically diffuses into the matrix along a frontal boundary, it also can begin to permeate into the matrix polymer through a process of molecular-level diffusion. As a volume element of a matrix polymer begins to expand from the ingress of lower molecular weight fluids, it can become plasticized by the fluid, leading to an increase in the fraction of free volume within the matrix polymer phase, and to a subsequent further increase in the rate of molecular level diffusion, both into and out of the matrix polymer network.

An increase in free volume at the molecular level also leads to a number of additional physical changes in the matrix polymer phase, including a decrease in the glass transition temperature, an accompanying decrease in modulus, a decrease in ultimate stress to failure (i.e., lower strength), and to an accompanying acceleration in the rate of molecular level diffusion of molecules both into and out of the matrix polymer phase. The macro volume expansion of the liquid-occupied volume element, which is the polymer volume element that has become diffusion-permeated and plasticized by fluids, leads to the development of localized stresses that tend to accumulate at weak boundaries, which are at frontal boundaries that separate swollen volume elements from other volume elements that have not yet been permeated and are not yet swollen. Defects sites near these boundary regions become particularly susceptible to localized stress-induced tensile and shear types of failures. The ensuing number of internal cohesive failure events can begin to increase and even to accelerate from excessive strains at weak junctures, for example at cell walls of macroscopic voids, at the interfaces of weakly bonded particulates, etc. The cycle continues as more macroscopic pathways develop for the macroscopic ingress of even more fluids, leading to a further increase in the number of pathways for molecular level diffusion, which then leads to an increase in the number of swollen volume elements, which then leads to the further development of more localized stresses. Hence, the cascade continues, culminating in an acceleration in the rate of occurrence of ultimate failure events.

The interconnected processes of erosion and diffusion can also affect the efficacy of the pharmaceutical formulation. Clearly, as erosion occurs, the total amount of surface area simultaneously increases. This will affect one of the primary functions of the formulation- to achieve and maintain a specific time-controlled release profile of one or more active ingredients during end use. An increase in the total surface area from erosion leads to an acceleration of molecular-scale diffusion of active ingredients across the growing number of concentration gradients that are provided by the growing number of interfacial boundaries. This process will not only impact the molecular level diffusion rates through the matrix polymer, it can impact the molecular level diffusion rates through other types of secondary diffusion barriers that have been purposely put into place, such as the diffusion barrier created by an encapsulating PLGA polymer which serves to impede the molecular-level diffusion rate of its encapsulated active ingredients like BUP or BUP-HCl.

Any process that leads to an increase in free volume of a polymer will subsequently lead to an increase in the number of molecular pathways that are available for molecular level diffusion. Importantly, diffusion of small molecules will occur across passive boundaries where a concentration gradient is in existence (i.e., Fickian diffusion). Aside from relative polarity considerations, the rate of diffusion depends on the fraction of free volume within the materials on both sides of the frontal boundary, as well as the relative concentration of the diffusing species on both sides. Thus, as fluids begin to have access to the surfaces of PLGA particles within the formulation, they can permeate the surfaces of the particles and thereby increase free volume, and then increase the rate of diffusion of small molecules that are encapsulated and contained within them. To add even more complexity to this scenario, if the fluid contains water, PLGA can hydrolyze. The hydrolysis process leads to a decrease in molecular weight, to the production of more chain ends, and thus to a further increase in free volume which further enhances the rate of diffusion. A gelatin matrix polymer with polypeptide sequences will also be susceptible to the same type of hydrolysis-initiated acceleration of free volume. Thus, each molecular level diffusion barrier that is purposely set in place to control the release of drugs and the like can become altered and affected by a cascade of macroscopic and molecular-level events. These events will collectively affect the global time release profile of the formulation. Of course, when harnessed for the purpose of achieving specific control-release profiles over sustained periods of time, these mechanisms can be useful. On the other hand, if these processes occur too quickly, it may become difficult if not impossible to achieve longer-term sustained release.

Importantly, composite structures can be used to reduce the rate of occurrence of internal cohesive failure events of the types described above. In a composite-like structure, the matrix can be reinforced with fibers or with particulates, which serve as scaffolds that can help to hold a mechanically weaker matrix phase in place by reducing the probability of crack growth and propagation along any one single boundary via distributing stresses from swelling over larger volume elements and hence over multiple boundaries within the structure, thereby reducing the magnitudes of localized stresses and strains, and hence reducing the number and frequency of catastrophic failure events. Lower levels of localized stresses will translate to lower localized strains, which in turn, depending on the geometric structure of the defect site, can lead to sustained mechanical and cohesive integrity of the delivery device over longer periods of time.

The pharmaceutical formulation compromising a hydrophobic component lends itself well to the creation of fiber-reinforced composites, primarily because by design, the formulation that is used to impregnate the fibers are not pre-gelled into macro polymeric networks. Instead, the formulation is, with their hydrophobic liquid carriers, remaining compliant and moldable for long periods of time. The gelatin particulates suspended therein do not begin to gel and swell until they are exposed to fluids within the tooth extraction socket. Even then, the rate of water ingress is diminished owing to the hydrophobic nature of the formulation. All of this translates to an extended working time for accomplishing the manufacturing steps that are required to make a composite delivery device, including the time needed to complete multiple process steps, such as mixing, metering, impregnating, conveying, cutting, and packaging.

On the other hand, the creation of a composite reinforced delivery device including a pharmaceutical formulation comprising a hydrophilic component poses a different set of challenges. Importantly, from a process manufacture perspective, if fiber reinforcement is to be employed, then it is preferable to intermix and to pre-wet the cellulose fibrous components with the pharmaceutical formulation prior to the onset of appreciable gelation. This is because the fibers can be more easily wetted and intermeshed with the formulation when the formulation exhibits low viscosity and minimal elastic recovery as it would prior to gelation. In order to accomplish this process step, there needs to be ample working time prior to gelation to facilitate the total time requirements for vehicle mixing, metering, wetting, and infiltration or impregnation of the fibrous material. For example, when water is mixed with GLBG at a 2/1 (w/w) ratio, gelation and elastic network formation is observed to begin almost immediately. However, for the case of glycerin, the work time window prior to the onset of gelation was observed to be significantly longer, thereby making glycerin a more practical choice as a liquid for creating hemostatic fiber-reinforced hydrophilic devices.

It is understood by those skilled in the art that within some time-period after mixing liquids like water or glycerin with gelatin, gelation will begin to occur, and the initial suspension of discrete gelatin particulates will become transformed into an elastic gelled network of surface-bonded, aggregated gelatin particulates. The time-period preceding gelation is herein referred to as "the work-time" and defines the window of time that enables the delivery device to be made through the process of impregnating a fibrous substrate. As long as the process is initiated during the work-time, prior to gelation, the viscosity and elasticity of the formulation will be low enough to enable facile impregnation of fibrous substrates with high expediency. Thus, it is desirable that the gelation process be made to occur after the fibrous textile is impregnated with the formulation, and not before.

For the purposes of creating a fiber-reinforced delivery device with a pharmaceutical formulation comprising a hydrophilic component, it is desirable that the liquid component be miscible enough with the hygroscopic network-forming component to lead to gelation and to the formation of a plasticized polymer network, including gums like gelatin, gum arabic, ghatti, karaya, tragacanth, agar, Irish moss, carrageenin, alginates, seed extracts of which include locust bean, locust kernel, and quince seed gums as examples, manufactured and modified dextrins and British gums, water-dispersible or soluble derivatives of cellulose, etc. It is further desirable that the work-time prior to gelation be long enough to facilitate all of the process steps that are required for product formation, such as vehicle mixing, metering, conveying, wetting, or pressing. If a continuous or semi-continuous process is used to meter and convey the formulation onto a web of fibrous material, such as the cellulose hemostat, then the web could be optionally conveyed through a forced air or infrared heated oven to facilitate faster gelation. Regardless of the use of ovens, once the gelation process is complete, the resulting vehicle-impregnated composite can be cut to achieve the desired geometric size for the application, and then the resulting delivery device can be packaged for storage prior to deployment. If an additive manufacturing process is used to meter and convey the formulation onto a web or discrete sheets of fibrous material, such as the cellulose hemostat, then the formulation could be propelled from a three dimensional printer nozzle or printer jet onto the web or discrete sheets, resulting in vehicle impregnated composites of the desired geometric size for the application, and then the resulting delivery device can be packaged for storage prior to deployment. Three-dimensional printing would also result in the creation of customized dose and dosage forms impregnated into the reinforcing member if so desired.

Regarding storage, it is further desirable that the liquid component be biostable, either on its own, or through the incorporation of preservatives that guard against bacterial growth during periods of product manufacturing, packaging and storage. It is also desirable that the liquid lead to formation of a gelled polymer network after textile impregnation and not before. One example of a liquid that meets both criteria is glycerin. Other liquids can be used, including for example, propylene glycol, polyethylene glycols and polypropylene glycols of various molecular weights, water-based natural products like honey, polyhydric alcohols and derivatives of the same, as well as mixtures of any of these types.

It is also important that the fibrous components of the composite delivery device be resistant to deterioration, swelling, or dissolution by the hydrophilic liquid. SURGICEL® Original Absorbable Hemostat (SO) textiles were determined to be resistant to glycerin. In a separate experiment, pre-cut SO textiles ((1.8×3.8 cm) were separately drop-coated with glycerin and water. After 24 hours, the glycerin-coated textile was observed to retain its meshed structure with no noticeable evidence of dissolution or physical changes (e.g., no shrinkage or swelling). In a similar test, the SO textile was also observed to be more resistant to water than its SafeGauze counterpart. SafeGauze dissolved upon exposure to water as shown in Example 5, whereas SO showed no apparent signs of dissolution within a 24-hour window of testing (only shrinkage).

Regardless of whether the pharmaceutical formulation comprises hydrophobic or hydrophilic components, the resistance of the fibrous material to water dissolution or to degradation can be an important and desirable attribute, particularly after deployment. Although it is desirable that the fibrous material eventually degrade and become bioabsorbed, it is still desirable that the fibrous material maintain integrity for a period of time during the post-deployment lifetime, mainly because the retention of a composite structure with fibrous reinforcement is conducive to maximizing macroscopic erosion resistance, which is another desirable attribute for longer-term durability if deployed in a tooth extraction socket application.

In one embodiment of the sustained release pharmaceutical formulation, a solid, flexible pain management delivery device comprises a mixture of 10-20% of a network-forming binder material and 80-90% bupivacaine-loaded PLGA microspheres, wherein the mixture is impregnated within a fibrous matrix material, such as a flexible water-soluble cellulose fiber textile. The network-forming binder material may comprise one or more components alone or in combination, including a wax component (e.g., carnauba, palm, beeswax), a gelatin component (e.g., GLBG, GLPG, SF), and an oil (e.g., mineral oil or soy or palm oil). The mixture may further comprise an optional pH modulator (e.g., citric acid, di-Na-citrate). If a wax is employed, it is preferred that it be ingestible. Oils and extenders should be USP-grade and also ingestible. PLGA average particle sizes can range between 1 and 80 microns, with active ingredients comprising 1 to 50% by weight of the PLGA encapsulated particulates, and where one preferred PLGA particle size distribution comprises maximizing the % of small particles (e.g., 3.4 micron) while simultaneously balancing all of the aforementioned considerations for controlling drug-release profiles as in the sustained release formulation comprising the powdered mixture embodiments.

Thus, in order to maximize solids while simultaneously providing a network-forming material binder component (e.g., GLBG) capable of binding PLGA spheres upon hydration, it is desirable to maximize the particle size of the ground gelatin component. This mixture comprises 83.72% total solids in mineral oil, capable of delivering 206 mg bupivacaine to a 0.55 cc cavity.

Determining the optimum level of wax/oil required to facilitate textile-impregnation requires consideration of 1) compliance of the mixture, 2) cohesive strength of the mixture, 3) in vivo hydration rate of the mixture, 3) mechanical properties of the mixture as a function of time during the in vivo hydration process, 4) conduciveness of the mixture to textile impregnation processes (e.g., solvent-free, minimal pressure, minimal temperature, textile wettability, etc.), and 5) capacity to pre-hydrate with water before insertion into the tooth extraction socket.

A pharmaceutical formulation is possible with a low melting wax, or with an oil/wax blend, or with a low Tg polymer (lower than the Tg of the PLGA). A simple pressing process may be used to consolidate the textile with the PLGA spheres under ambient conditions. Optionally, gelatin may be omitted from the formulation to thereby allow the cellulose to become the binder when it hydrates. Omission of the gelatin would make more "room" for bupivacaine loaded PLGA microspheres.

Selective surface-active molecules or surfactants can be optionally incorporated into the mixture for the purpose of further controlling the batch-to-batch consistency and rheological characteristics of the pharmaceutical formulation to the degree necessary for achieving desired reproducibility, tactile feel, and efficacy. Such additives can be used for stabilizing oil-in-water dispersions or emulsions, water-in-oil dispersions or emulsions, and solid-in-oil dispersions. Surface active agents with surfactant properties can include additives such as lecithin, fatty acid esters, non-ionic polymers (e.g., polyvinyl alcohol), and the like. Optional surfactants can include those known to the art, including those where the overall effective HLB value is conducive to the formation of water-in-oil emulsions (HLB<6), and those conducive to the formation of oil-in-water emulsions. The amount should be about 0.15 to 5.0 weight percent of the composition, and preferably 0.5 to 2.0 percent by weight. As is well known to those of ordinary skill in this art, the HLB value is determined by a standardized technique for measuring the solubility of a surfactant. Said surfactant may be anionic, cationic or non-ionic with respect to its hydrophilic portion. However, it is preferable that the surfactant be biocompatible and ingestible. Examples of surfactants can include polysorbates, mono-fatty acid esters of polyoxyethylene sorbitan such as Tween-20 and Tween-80, polyglycerol polyricinoleate, monoglycerides, lecithins, citric acid esters, glycolipids, fatty alcohols and fatty acids, ethoxylated polyhydroxystearate esters, glyceryl monooleate, polyglyceryl esters, sorbitan esters, and propylene glycol esters. Other examples of ingestible surfactants known in the art can be found in RK Sharma, Surfactants: Basics and Versatility in Food Industries, PharmaTutor, 2014, 2(3), 17-29.

These types of additives can be optionally incorporated within one or two stages: (1) during the PLGA particle manufacturing process, or (2) separately, during the compounding process within the formulated vehicle to the degree required to facilitate efficient rheological control for compounding, for subsequent optional textile-impregnation, or for rheological properties after hydration. The decisions regarding these additives will be primarily based on or weighted by rheological responses associated with manufacturing, for example shear-dependent viscosity, and on the tactile-feel of the product in its end use, in particular viscosity prior to hydration and compliance after hydration.

Statistical formulation design of experiments (DOE's) can be used to make weighted use of the aforementioned factors to modulate release profiles. The release profile responses can then be modeled along with rheological responses to achieve a navigable design space as a function of all formulation factors for the ultimate co-optimization of the response sets, co-optimization of release responses and rheological responses that impact manufacturability and end use tactile characteristics. Standard operating procedures for the compounding and manufacturing process will insure achievement of a consistent state of dispersion within the optimized formulated product. This consistency in raw materials and manufacturing processes will be paramount to product consistency, reliability, and efficacy.

For the case of pharmaceutical formulations employing hydrophobic components, oils are can be premixed with a wax at elevated temperatures above the melt temperature of the wax to form solutions. The solutions are then allowed to cool, causing a portion of the wax to recrystallize into micro-crystallites, which then remain suspended within the oil carrier. The resulting mixtures of oil and wax have higher viscosity than neat oil and are therefore desirable for use in formulating stable dispersions of particulates that can resist settling over time. It can be appreciated that the rate of cooling can be used to modulate the size of the resulting micro-crystallites, with fast cooling generally leading to smaller crystallites, and with slow cooling or annealing leading to larger crystallites. Either way, the purpose is to yield gelatinous mixtures, which serve as vehicles for suspending particulates of network-forming polymers and active ingredients within the pharmaceutical formulation. The viscosities of gelatinous mixtures of oil and wax may be modulated by changing the ratio of oil to wax, the wax type, and the oil type. It is also possible to mix combinations of different types of waxes with different types of oils at different ratios. One of the advantages of the latter approach can be to minimize the level of oil in the gelatinous mixture and hence in the final formulation. Mixtures of hydrophobic waxes and oils can be used as components of the binder material in a formulation for impregnation into a cellulose textile.

Several types of oils or mixtures of oils could also be used in combination with a wax at ratios of total oil to wax that are sufficient for enabling certain desirable physical attributes, including melting point depression of the wax, increase in compliance of the resulting mixture, compressibility of the resulting mixture for textile impregnation, temperature-dependent viscosity of the resulting mixture, % PLGA and % gelatin loading in the mixture, and the like. The typical oil to wax w/w ratio can be in the range of 0.01/1 (still solid and wax-like) to 10/1 (weak gelatinous amalgam) or higher.

The choice of oil type and oil amount will also depend on other types of physical-chemical factors. Examples of such factors include: 1) the degree that it is desirable to minimize the total oil level in the final formulation mixture; 2) the threshold level of oil needed to impart a sense of flavor if desired; 3) the threshold level of an oil needed to impart analgesic effects; and 3) the solubility characteristics of other desirable solid active ingredients within the oil phase.

Examples of oil types that can be used alone or in combination include mineral oil, isopropyl palmitate, caprylic triglyceride, coconut oils, vegetable oils like soy oil, corn oil, sunflower oil, castor oil, and canola oil, aloe, apricot, argan, avocado, camelina, D-limonene, olive oils, grapeseed oil, hempseed oil, palm oil, rice bran oil, rosehip oil, safflower oil, sesame oil, soy lecithin, almond oil, tamanu oil, vitamin E, walnut oil, wheat germ oil, fish oils, and others.

Examples of oils or infused oils that can be used alone or in combination with oils mentioned above to impart flavor or analgesic effects include, for example, oils of spearmint, peppermint, wintergreen, clove, cinnamon, palo santo, lavender, juniper, oregano, thyme, geranium, ginger, nutmeg, pine, rose, nutmeg, clove, coriander, citronella, lemon, anise, tea tree, orange, turmeric, allspice, ho wood, cypress, and *eucalyptus* as reported by Silva, J. et al., in the *Journal of Ethnopharmacology*, Volume 89, Issues 2-3, December 2003, Pages 277-283.

A simplified manufacturing process for the hydrophobic embodiment would involve a continuous process method comprising the steps of 1) a carrier (e.g., a release-lined paper) is coated with any of the wax-based embodiments described herein (with or without the addition of dispersed gelatin particles) to yield a coated continuous web; 2) the tackiness of the wax-based coating is made sufficient so as to facilitate contact adhesion with PLGA particles (either by means of formula ratios, temperature, or both); 3) microencapsulated particles containing active ingredients such as BUPIVACAINE are metered and distributed uniformly along the moving web, or the web is moved through a fluidized bed of microencapsulated particles to achieve contact adhesion of the particles to the web with optional self-minimization of deposition; 4) the knitted, woven or non-woven cellulose material is contact-pressed over the moving web with press rollers; 5) the resulting composite is optionally die-cut into prescribed shapes and weights; 6) the release material is peeled away from the device, or is allowed to remain intact before the device is packaged. The release liner material could even be synonymous with the lower member of the package for the device, where the upper component member of the package could be another type of release layer that is used to sandwich and form a seal around the device during packaging under sterile conditions.

Another manufacturing process for the hydrophobic embodiment would involve an additive manufacturing process method comprising the steps of 1) a knitted, woven or non-woven cellulose textile is sized, cut and secured to fit the printing bed of a three-dimensional printer; 2) the formulation comprised of the gelatin, the microencapsulated particles containing active ingredients such as BUPIVACAINE, and a wax or oil vehicle are propelled through a moving three-dimensional printer nozzle or jet to distribute uniformly along the stationary textile; 3) different ratios of active ingredients, gelatin and hydrophobic additives could be altered in a programmed fashion to produce a variety and customized range of active ingredient doses and dosage forms across a single sheet; 4) the resulting composite is optionally die-cut into prescribed shapes and weights. Additionally, the reinforcing member could be in the form of a particle or chopped fiber, added directly to the formulation mixture and three-dimensionally printed in a similar fashion into discrete sheets to be packaged and sterilized for use.

Certain hydrophobic formulations have been observed to have rheological characteristics that are conducive to the use of a sigma-blade blending process for preparing mixtures under ambient conditions, whereby the PLGA powders and gelatin particulates could be added to form dough-like mixtures in a batch or semi-continuous batch process. For formulations comprising mixtures of wax and oil, melt-recrystallization steps could also be optionally employed to produce stiffer or less stiff mixtures upon cooling. In addition, shear mixing of hydrophobic formulas could be performed with the intent of generating shear-induced heat. The resulting process temperature could be controlled and maintained at temperatures of less than the Tg of PLGA, and the mixture could then be directly dispensed onto a textile for impregnation while cooling. Dispensing could be done directly into a kit comprising a blister package containing pre-inserted and precut textiles, or onto a larger textile, which would then be subsequently cut into desired dimensions for end use. A compression step could be employed to help insure impregnation of the interstitial spaces if necessary.

In one embodiment of the above device, a solid, flexible formulated pain management device comprises a mixture of 10-20% of a binder material and 80-90% bupivacaine-loaded PLGA microspheres, wherein the mixture is impregnated within a fibrous matrix material, such as a flexible water-soluble cellulose fiber textile, wherein the binder material is comprised of one or more components alone or in combination. The binder material may comprise a wax component (e.g., carnauba, palm, beeswax), a gelatin component (e.g., GLBG, GLPG, SF), and an oil (e.g., mineral oil, soy oil, or palm oil as optional hydrophobic component). The mixture may further comprise an optional pH modulator (e.g., citric acid, di-Na-citrate). If a wax is employed, it is preferred that it be edible/ingestible. Oils/extenders should be USP-grade and also ingestible. A preferred PLGA particle size distribution comprises maximizing the % of small particles (e.g., D50=3.4 micron) while simultaneously balancing all of the aforementioned considerations for controlling drug-release profiles as mentioned previously in discussions pertaining to the powdered mixture embodiments of hydrophilic devices. In Examples 3 through 8, a 30/70 w/w blend of 3.4 um and 42.7 um PLGA microspheres were used to demonstrate the concepts leading to the formulation of a unique hydrophobic controlled-release delivery device.

An embodiment of a manufacturing process for a pharmaceutical formulation comprising a hydrophobic component involves the use of a continuous web coating process method whereby a moving carrier, such as a wax or silicone release-lined paper, a knitted, woven or non-woven hemostatic textile, etc., is first coated with any of the wax-based mixtures as described herein, optionally with or without the addition of dispersed gelatin particles, to yield a coated continuous web. The tackiness of the wax-based coating on the moving web is intended to facilitate contact-adhesion with PLGA particles containing bupivacaine (BUP). The PLGA particles are metered and distributed uniformly along the moving web using mechanisms such as passing the web through a fluidized air chamber, drop-metering PLGA powder directly onto a moving web, spinning-disc dry-metering PLGA particles as they are being formed during the microencapsulation manufacturing process, or passing the web through a fluidized bed of PLGA particles to achieve contact adhesion between the particles and the web with optional self-minimization of deposition. A knitted, woven or non-woven cellulose hemostat material is then optionally contact-pressed over the moving web with press rollers. The resulting composite is optionally die-cut into prescribed shapes and weights. If the moving carrier is a wax or silicone coated release paper, then the paper is optionally peeled away from the device, or it is allowed to remain intact before the device is packaged, or if the moving carrier is a fibrous hemostat, then the entire impregnated assembly is packaged.

In another embodiment of the manufacturing process, the moving carrier could be an integral component of the product package itself. In this case, a heat-sealable material like polyethylene terephthalate (PET), high density polyethylene (HDPE), or a foil laminate could be used as the first moving carrier, which is then coated with the wax-based amalgams as described herein, and then passed through any one of the PLGA coating processes as described above. The carrier is then contact pressed with a knitted, woven or non-woven hemostat textile, followed by contact pressing with an upper component package layer such as PET, a foil laminate, or an HDPE film. The composite is then finally die-cut and pressure-sealed with optional heat to yield the final packaged device.

Hydrophobic formulations containing amalgamized dispersions of particulates in mixtures of oil and wax, such as gelatin particulates, particulates of active ingredients, and particulates of active ingredients encapsulated with encapsulating materials, exhibit rheological characteristics that are conducive to the use of batch mixing processes under ambient conditions (e.g., a sigma-blade blending process). In one process, mixtures of oil and wax are first prepared, and then amalgams are prepared by blending the pre-mixed oil/wax mixtures with gelatin particulates, and then the PLGA powders are metered into the amalgams to form dough-like mixtures. Similarly, continuous mixing processes could also be employed, such as single screw or twin-screw extruders with appropriate mixing zones and metering zones for continuous shear mixing under near-ambient conditions, followed by an exit die for cutting and metering aliquots of the mixtures onto a continuous moving web for packaging. A melt-recrystallization step could also be optionally employed, which would likely lead to stiffer mixtures upon cooling. In addition, shear mixing of higher viscosity formulations could be performed with the intent of generating shear-induced heat if so desired. The processing temperature could then be controlled and maintained with air or liquid cooling, so that the temperature of the mixture remains lower than the glass transition of PLGA (e.g., the Tg of RG504 PLGA is 46-50 degrees C.) in order to minimize premature process-induced BUP diffusion. The mixture could then be directly dispensed onto a textile while molten and hot for easier impregnation while cooling. The delivery device could then be directly dispensed into a kit comprising a blister package with pre-inserted individual textiles, or directly onto a larger continuous moving web of textile, which could then be subsequently cut into desired dimensions for end use. A compression step could be employed to help insure impregnation of the interstitial spaces if necessary. For formulations that are deployed without fibrous reinforcement, metering and dispensing of the formulations could be performed directly into blister packages for subsequent sealing, shipping, and storage.

The manufacturing processes as described above for pharmaceutical formulations comprising hydrophobic ingredients would not be applicable to pharmaceutical formulations comprising hydrophilic ingredients of the types described in Examples 1 and 2. However, for pharmaceutical formulations comprising hydrophilic ingredients of the types described in Example 15, any of the aforementioned batch or continuous processes could be similarly adapted and employed for the manufacture of hydrophilic delivery devices.

As demonstrated in Example 1, certain additives like citric acid can have a positive impact on the gelation characteristics and on the mechanical property characteristics of binder components. These same additives can also be used to modulate the chemical environments within hydrophobic and hydrophilic devices; particularly during in vivo hydration, where fluids such as saliva and blood can diffuse from the tooth extraction socket into the device, and active ingredients can diffuse out of the device.

The overall impact of pH modulators can be to alter diffusion characteristics via at least two different mechanisms: 1) by impacting the solubility of active ingredients within the device; and 2) by altering the mechanical properties of the diffusing medium which in turn impacts free volume and the resulting rate of molecular-scale diffusion through the medium.

The effects of pH on gelatin binder properties can be appreciated with the results presented in Example 1, where unlike formulas made under pH-neutral conditions, the relative viscosities of formulas made with citric acid were observed to undergo significant changes within five hours of mixing, and even more so within one day after mixing.

Certain gelatins were observed to form low-modulus elastic networks (plasticized with water) at faster rates in the presence of citric acid than in the absence of citric acid. It follows that by controlling the ratio of citric acid (or other alternative acids) to protein, the rate of network gelation can be modulated, implying that the mechanical resistance to diffusion can be similarly modulated and controlled. Higher citric to gelatin ratios would likely lead to even faster gelation rates (as would lower levels of water).

Similarly, a hydrophobic device can also be formulated with a pH modulator such as citric acid or di-sodium citrate. As demonstrated in Example 13, this can be accomplished by dispersing the ingredients as powders within the formulation vehicle. Given that hydrophilic additives will have limited solubility in the oil carriers that are used in hydrophobic devices, the additives will remain dispersed and undissolved until the device becomes hydrated, either in vivo, or prior to deployment. However, it is also possible to incorporate oil-soluble or partially oil-soluble protic acids into hydrophobic devices if so desired (e.g., long-chain fatty acids such as stearic acid, lauric acid, sebacic acid, etc.).

Importantly, any of these types of pH-modulator additives can be optionally microencapsulated with polymers like PLGA, or with other types of polymers, to control solubility and rate of release within the end use chemical environment.

Simultaneously, it can be appreciated that a balance would have to be achieved with other factors that impact the efficacy of the device, including the aforementioned chemical environment factors that affect the solubility and diffusion of bupivacaine (e.g., the initial concentration of bupivacaine in its free-base and in its acidic form; and the ultimate equilibrium concentration of both species within the end use chemical environment).

Hydrophobic oils and mixtures of oils with waxes can be considered as carriers for various dispersed ingredients that constitute the binder phase of a delivery vehicle for a hydrophobic formulation or delivery system. Again, examples of dispersed ingredients can include one or more of gelatin particulates, other network forming polymers, PLGA microspheres containing active ingredients like BUP free base or BUP-HCl, other types of active ingredients, including those encapsulated with PLGA, those encapsulated with alternative encapsulating materials, or those with no encapsulant, citric acid powder, di-sodium citrate powder, BUP free-base, BUP-HCl, and others. Many types of oils, oil mixtures, or oil/wax mixtures can be employed, provided that they meet the criteria for use in a hydrophobic device as described by tests presented in Example 14. Examples of oils that satisfy these criteria include mineral oil as described in Example 8, isopropyl palmitate or caprylic triglyceride as described in Example 10, or coconut oil as described in Example 16.

Again, these types of oils or others can also be used in combination with waxes to modify the rheological characteristics of the liquid carrier, and to modify the rheological and mechanical compliance characteristics of the resulting device. Examples of waxes include carnauba wax, beeswax, paraffin wax, palm wax and mixtures thereof as described in Example 8, as well as others. A wax or wax-mixture is typically employed at levels such that the total oil to wax ratio facilitates the achievement and control of certain desirable physical attributes or property characteristics, including, for example: 1) melting point depression of the wax; 2) an increase or decrease in the compliance of the resulting vehicle; 3) an increase in the cohesive integrity of the vehicle; 4) an increase or decrease in the viscosity of the resulting vehicle, such that dispersed ingredients within the vehicle remain dispersed without settling; 5) achievement of vehicle compliance with minimal elastic recovery to facilitate textile-impregnation processes; 6) achievement of a temperature-dependent viscosity characteristics that are conducive to shear mixing processes for vehicle manufacturing; 7) achievement of the ability to control or maximize the % PLGA and hence the % BUP in the vehicle, which can increase the dosage potential of the vehicle if so desired; and 8) achievement of the ability to control or maximize the % gelatin loading in the vehicle if so desired. The typical oil to wax w/w ratio for satisfying these purposes can be in the range of 0.01/1 (still solid wax-like) to 10/1 (weak gelatinous amalgam) or even higher if so desired.

Example 1. Limitations Pertaining to the Preparation of Hydrophilic Devices

Part-A: Evaluation of Protein Binders

A series of commercially available materials were evaluated for their relative water solubility, gelation, and network-forming characteristics, including: 1) bovine collagen powder available from Great Lakes Gelatin Company, Grayslake, IL, Kosher, 100% hydrolyzed collagen hydrolysate from bovine hide, >90% protein, bloom 0 g, viscosity 5.5-7.5 mPa-s, pH 5.0-6.5, US Pharmacopeia consumer grade; 2) piscine collagen powder available from Zint LLC, (referred to as Marine Collagen, type-1 hydrolyzed fish collagen); 3) bovine gelatin (GLBG) powder (Great Lakes Gelatin Company, Grayslake, IL, type B, unflavored Kosher beef hide, bloom 225 g, viscosity 34-40 mp, pH 4.1-5.5, 88-92% protein, US Pharmacopeia consumer grade; 90% mesh estimated to be between about 35 and 70 (i.e., 0.5 mm to 0.2 mm)); 3) porcine gelatin (GLPG) powder available from Great Lakes Gelatin Company, Grayslake, IL, type A, unflavored, 88-92% protein, bloom 225 g, viscosity 34-40 mp, pH 4.3-5.7, US Pharmacopeia consumer grade; and 4) Surgifoam (SF) absorbable gelatin powder made from absorbable porcine gelatin sponge, U.S.P., available from Ferrosan Medical Devices, distributed by Ethicon, Inc.

Using either a spatula, a vortex mixer, or both, each of the gelatin powders was hand-mixed with distilled water under ambient conditions in separate glass containers at selected weight ratios (w/w water to powder): 1/1, 2/1, 3/1, 10/1, 15/1, and 25/1. The samples were qualitatively compared at selected time periods (t) after mixing: 5 minutes, 15 minutes, 1 hour, 5-6 hours, 24 hours, 4 days, and 2 weeks for their relative viscosity characteristics as gauged by their pourability and by their resistance to stirring with a spatula. Collagen samples were similarly mixed and evaluated, but the weight ratios of water to powder were limited to 1/1, 2/1, and 3/1 (w/w) owing to their poor network-forming characteristics and lack of gelation. SF samples were evaluated at the 3/1 and 25/1 w/w water to powder ratios for comparison to the two other gelatin types from Great Lakes (i.e., GLPG and GLBG). pH values were measured for each of the 25/1 (w/w) water/gelatin samples at t=24 hours after mixing.

In general, the relative viscosity characteristics of all samples were observed to increase with decreasing levels of water. Several days after mixing the samples, the commercial collagen samples were observed to exist as either low viscosity liquid solutions or as liquid dispersions and remained pourable. Each of the collagen samples remained pourable even at t=2 weeks after mixing. Qualitative observations pertaining to the collagen samples are provided in Table 1-1.

cosity gelled networks, where the time to gelation was generally observed to increase with increasing levels of water.

Importantly, gelatin protein polymers with these types of network-forming characteristics are preferred over their collagen counterparts for use in the pharmaceutical formulations as described herein. These types of network-forming polymers exhibit mechanical property and cohesive strength characteristics that render them as acceptable for use as binder-phase components for other dispersed ingredients to be discussed in subsequent examples. In this example, the gelatin proteins with Bloom values like those reported for

TABLE 1-1

Relative viscosity characteristics of collagen samples after mixing with distilled water under ambient conditions at weight ratios of water to collagen (w/w) of 1/1, 2/1, 3/1, 10/1, 15/1, and 25/1. The samples were qualitatively compared at various time periods after mixing, including 5 minutes, 6 hours, 24 hours, 4 days, and 2 weeks.

| Sample Type and w/w water to collagen ratio | 5 minutes after mixing | 6 hours after mixing | 24 hours after mixing | 4 days after mixing | 2 weeks after mixing |
|---|---|---|---|---|---|
| Great Lakes Bovine Collagen 1/1 | Pourable liquid, clear solution | Pourable liquid, clear solution | Pourable liquid, clear solution | Pourable liquid, clear solution | Pourable liquid, clear solution |
| Great Lakes Bovine Collagen 2/1 | PPourable liquid, clear solution | Pourable liquid, clear solution | Pourable liquid, clear solution | Pourable liquid, clear solution | Pourable liquid, clear solution |
| Great Lakes Bovine Collagen 3/1 | Pourable liquid, clear solution | Pourable liquid, clear solution | Pourable liquid, clear solution | Pourable liquid, clear solution | Pourable liquid, clear solution |
| Zint Collagen 1/1 | Pourable liquid, hazy dispersion, partial solution | Pourable liquid, hazy dispersion, partial solution | Pourable liquid, hazy dispersion, partial solution | Pourable liquid, hazy dispersion, partial solution | Pourable liquid, hazy dispersion, partial solution |
| Zint Collagen 2/1 | Pourable liquid, hazy dispersion, partial solution | Pourable liquid, hazy dispersion, partial solution | Pourable liquid, hazy dispersion, partial solution | Pourable liquid, hazy dispersion, partial solution | Pourable liquid, hazy dispersion, partial solution |
| Zint Collagen 3/1 | Pourable liquid, hazy dispersion, partial solution | Pourable liquid, hazy dispersion, partial solution | Pourable liquid, hazy dispersion, partial solution | Pourable liquid, hazy dispersion, partial solution | Pourable liquid, hazy dispersion, partial solution |

By contrast, the gelatin samples exhibited significantly higher relative viscosities than their collagen counterparts at equivalent water to solid ratios. Unlike the collagen samples, the gelatin samples were also observed to form high viscosity gelled networks, where the time to gelation was generally observed to increase with increasing levels of water.

GLBG and GLPG (e.g., 225 g) are preferred over their counterparts with lower Bloom values, such as the collagen proteins. Qualitative observations pertaining to the gelatin samples are provided in Table 1-2.

TABLE 1-2

Relative viscosity characteristics of bovine and porcine gelatin samples after mixing with distilled water under ambient conditions at weight ratios of distilled water to gelatin (w/w) of 1/1, 2/1, 3/1, 10/1, 15/1, and 25/1. The samples were qualitatively compared at select time periods after mixing (t), including 5 minutes, 15 minutes, 1 hour, 6 hours, 24 hours, 4 days, and 2 weeks. Note that pH measurements were taken for the 25/1 samples at t = 24 hours after mixing.

| Sample Type and w/w water to gelatin ratio | 5 minutes after mixing | 15 minutes after mixing | 1 hour after mixing | 6 hours after mixing | 24 hours after mixing | 4 days after mixing | 2 weeks after mixing |
|---|---|---|---|---|---|---|---|
| Great Lakes Bovine Gelatin 1/1 | Gelation, not pourable | | Increasing gel stiffness | Increasing gel stiffness | Elastic gel network | No change | No change |
| Great Lakes Bovine Gelatin 2/1 | Gelation, not pourable | | Increasing gel stiffness | Increasing gel stiffness | Elastic gel network | No change | No change |
| Great Lakes Bovine Gelatin 3/1 | Gelation, not pourable | | Increasing gel stiffness | Increasing gel stiffness | Elastic gel network | No change | No change |
| Great Lakes Bovine Gelatin 10/1 | | Gelation, not pourable | Increasing gel stiffness | Increasing gel stiffness | Increasing gel stiffness | Elastic gel network | No change |
| Great Lakes Bovine Gelatin 15/1 | | Gelation, not pourable | Increasing gel stiffness | Increasing gel stiffness | Increasing gel stiffness | No change | No change |
| Great Lakes Bovine Gelatin 25/1 | | Hazy dispersion, pourable liquid | Hazy dispersion, pourable liquid | Hazy dispersion, pourable liquid | Hazy dispersion, pourable liquid, pH = 5.8 | Hazy dispersion, pourable liquid | Weak gel, Pourable after shaking |
| Great Lakes Porcine Gelatin 1/1 | Gelation, not pourable | | Increasing gel stiffness | Increasing gel stiffness | Elastic gel network | No change | No change |
| Great Lakes Porcine Gelatin 2/1 | Gelation, not pourable | | Increasing gel stiffness | Increasing gel stiffness | Elastic gel network | No change | No change |
| Great Lakes Porcine Gelatin 3/1 | Gelation, not pourable | | Increasing gel stiffness | Increasing gel stiffness | Elastic gel network | No Change | No change |

TABLE 1-2-continued

Relative viscosity characteristics of bovine and porcine gelatin samples after mixing with distilled water under ambient conditions at weight ratios of distilled water to gelatin (w/w) of 1/1, 2/1, 3/1, 10/1, 15/1, and 25/1. The samples were qualitatively compared at select time periods after mixing (t), including 5 minutes, 15 minutes, 1 hour, 6 hours, 24 hours, 4 days, and 2 weeks. Note that pH measurements were taken for the 25/1 samples at t = 24 hours after mixing.

| Sample Type and w/w water to gelatin ratio | 5 minutes after mixing | 15 minutes after mixing | 1 hour after mixing | 6 hours after mixing | 24 hours after mixing | 4 days after mixing | 2 weeks after mixing |
|---|---|---|---|---|---|---|---|
| Great Lakes Porcine Gelatin 10/1 | | Gelation, not pourable | Increasing gel stiffness | Increasing gel stiffness | Increasing gel stiffness | No change | No change |
| Great Lakes Porcine Gelatin 15/1 | | Hazy dispersion, pourable liquid | Hazy dispersion, pourable liquid | Hazy dispersion, pourable liquid | Gelation, not pourable | No change | No change |
| Great Lakes Porcine Gelatin 25/1 | | Hazy dispersion, pourable liquid | Hazy dispersion, pourable liquid | Hazy dispersion, pourable liquid | Hazy dispersion, pourable liquid, pH = 5.19 | Hazy dispersion, pourable liquid | Weak gel, Pourable after shaking |
| Surgifoam 3/1 | Gelation, not pourable | | No change | | Non-elastic compliant gel | Highly compliant gel | |
| Surgifoam 25/1 | | | High compliance, high viscosity gel, moves with shaking but does not pour | No change | No change, pH = 5.25 | No change | No change |

The Great Lakes porcine gelatin (GLPG) was observed to produce lower relative viscosity mixtures than the Great Lakes bovine gelatin (GLBG) at the same water/powder weight ratios. The gelatin viscosity trends were similarly manifest at all water/powder weight ratios up to a 25/1. After initial mixing, each of the 25 to 1 water/gelatin samples were low-viscosity pourable liquids. After several days, the 25/1 GLBG sample had become a more homogeneous gel, but it was still pourable after shaking. The 25/1 GLPG sample was also still pourable, and it was lower in viscosity than the 25/1 GLBG sample. The GLPG sample had also phase separated into a partial gel with a clear supernatant. The two gelatin protein types exhibited slightly different pH values from one another at the 25 to 1 water/powder weight ratio.

In the next step, comparisons were made between Surgifoam (SF) gelatin and the porcine and bovine gelatins using a 25/1 weight ratio of distilled pH-neutral water to powder and a 3/1 weight ratio of distilled pH-neutral water to powder. Unlike the 25/1 w/w GLBG and GLPG samples, the comparative 25/1 w/w SF sample was observed to form a high viscosity non-pourable gel within 1 hour after mixing. By contrast, the GREAT LAKES bovine and porcine gelatins formed hazy, lower viscosity dispersions, and they remained pourable throughout a 4-day observation period. The 25/1 w/w SF sample was observed to have a slightly lower pH than the comparative GLBG and GLPG samples.

When comparing the 3/1 w/w samples, the SF gelatin formed an immediate gel which was highly compliant, pliable, and moldable. By contrast, the GLBG and GLPC gelatins were much slower to gel than SF. These trends were parallel to those observed when comparing the 25/1 w/w samples. After 1 day, the SF sample had become akin to a dry-blend with some cohesive strength, and with the capacity for much higher liquid adsorption. The 3/1 w/w SF sample was easily broken with a spatula, and it was still high in compliance. By contrast, the 3/1 w/w GLBG sample had become a fully cohesive rubbery network with better cohesive strength and better cohesive integrity than the 3/1 w/w SF sample. The GLPG sample behaved similarly to the GLBG sample. In mechanical terms, the 3/1 w/w SF sample retained a high degree of malleability and re-formability with high compliance and low elasticity, whereas the GLBG and GLPG samples exhibited higher elastic storage modulus characteristics. After 4 days, these trends remained the same, SF was high in compliance, and the GLBG and GLPG samples exhibited elastic recovery. Thus, although the GLBG and GLPG samples were slower to gel than SF, once they did gel, the GLPC and GLBG samples were more elastic and less compliant than the comparative SF sample.

Part-B: Evaluation of Protein Binders with a pH Modulator (Citric Acid)

The differences in pH among the three gelatin samples, SF, GLBG, and GLPG, justified a separate test with citric acid to see if the protein types would exhibit different degrees of acid neutralization capacity, different relative rates of gelation, or both. Using the same procedures as outlined above, a comparison was made between the three gelatin samples at a 25/1 weight ratio of distilled water to solids using a 1% citric acid solution having a pH of 2.2. Unlike pH-neutral water, the slightly acidic citric acid solution caused immediate partial-gelation of the proteins, resulting in higher immediate relative viscosities for all three samples, including Surgifoam.

The relative viscosity trends at t=1 hour after mixing were the same as those observed under pH neutral conditions, but all samples were higher in viscosity than those made without citric acid. Qualitative observations at t=1 hour were recorded as follows: SF was a cohesively weak gel that was moveable with shaking but was not pourable; GLBG was a hazy gelled dispersion, but it was still pourable; and GLPG was a hazy gelled dispersion but it was still pourable. Qualitative relative viscosity trends were recorded as follows: SF was much more viscous than GLBG which was more viscous than GLPG.

The pH of the samples at t=1 hour after mixing were lower than those of their counterparts that were mixed under pH-neutral conditions, but slightly higher than 1% citric acid solution itself, thereby providing evidence for some degree of acid buffering and neutralization capacity. Thus, acid neutralization via protein-amine protonation was observed to accompany the faster rate of viscosity rise. The pH values for samples mixed with the 1% citric acid solution were observed to trend similarly to those that were measured under pH neutral conditions at t=1 hour. The resultant pH values in the presence of 1% citric acid solution were 2.84 for the 25/1 w/w SF sample, 3.12 for the 25/1 w/w GLBG sample, and 2.94 for the 25/1 w/w GLPG sample. The respective pH values for the samples measured under pH neutral conditions were 5.25 for the 25/1 w/w SF sample, 5.80 for the 25/1 w/w GLBG sample, and 5.19 for the 25/1 w/w GLPG sample.

At a time of t=5 hours after mixing, the relative viscosity characteristics of the samples were observed to increase. The GLBG sample was shakable and still pourable. The GLPG sample had turned into a transparent gel and was shakable and still pourable. Thus, protein-moiety protonation induced faster gelation and higher relative viscosities in all three cases. Importantly, after t=24 hours, the trends were observed to become magnified. Although the SF sample had remained unchanged as a high viscosity compliant gel that was not pourable, the 25/1 w/w GLBG and GLPG samples had become completely gelled. They were no longer shakable, nor were they pourable. When a spatula was placed into the gels, the relative viscosity trends were as follows: the GLBG sample was more viscous than the GLPG sample which was only slightly more viscous than the SF sample. By contrast, the comparative samples that were mixed under pH-neutral conditions were observed to remain as pourable liquids at t=24 hours, t=4 days, and t=2 weeks. Thus, citric acid had not only successfully induced a faster rate of gelation, it had facilitated a change in the relative viscosity characteristics of the resulting gelled networks.

These results show that the acidity of the chemical environment can be used to modulate the mechanical behavior of the binder phase in formulations with gelatin proteins. As such, this example demonstrates that acids, such as citric acid and others, can be used as optional components into formulations for the purpose of modulating gelation rates and mechanical property characteristics of the resulting formulations. Importantly, this result demonstrates that the pH of the chemical environment will have an impact on the rheological characteristics of the formulation. This in turn will not only have an impact on the diffusion rate of active molecules like bupivacaine, but it will also have an impact on the compliance characteristics of the formulation, which in turn will affect its formability, or compliance, when affixed within a static volume cavity such as a tooth extraction socket.

Part-C: Statistically Designed Experiments (DOE) for Formulations to Deliver Targeted Dosages of Bupivacaine (BUP)

A statistical DOE was performed for the purpose of investigating the viability of providing a system to deliver a targeted theoretical-maximum level of bupivacaine (BUP) into a fixed volume cavity. A Taguchi 4-factor 3-level statistical design template was chosen for this work owing to its ability to provide maximum learning potential via trend analyses while simultaneously preserving economy of scale, materials, and time. Multiple DOE drafts were conceptualized with one of the overall objectives being to use the data to develop a qualitative and cursory understanding of the impact of poly(lactic-co-glycolic acid) (PLGA) particle size distribution and gelatin binder content on the relative hydration behavior, rheology characteristics, and compliance characteristics of resulting devices. Observations were made in three stages: (i) immediately after mixing, (ii) as a function of time after mixing, and (iii) with additional hydration after mixing. Initial work was done with placebo microspheres only. Note that 20% w/w bupivacaine loaded PLGA microspheres were used in subsequent experiments for analytical studies.

Initially, the target dosage range for bupivacaine was estimated to be between a level approaching possible toxicity on a high-delivery side and a level representing clinical usefulness on a low-delivery side. The upper limit of BUP was estimated to be 360 mg over a 4-day period (90 mg/day×4). Importantly, because of the unique fixed volume constraint in the end use application, the theoretical formulation composition for the upper limit and the lower limit for the % gelatin binder and the % of dispersed PLGA microspheres were observed to be dictated by the bupivacaine target dosage level. Due to the unique occupied volume limitation for this type of end use application, estimated as 1 cc in this example, any change in the weight % of the gelatin binder necessitates an opposite change in the weight % of the PLGA microspheres. Given that the PLGA microspheres function as the carriers for the active BUP molecules, it follows that higher BUP dosages necessitate higher percentages of PLGA microspheres and lower percentages of binder.

Initially, attempts were made to achieve the theoretical upper limit dosage of BUP by using 20% w/w loading of the PLGA microspheres. However, with a maximum bupivacaine target of 360 mg over a 4-day period (90 mg/day×4), the target was determined to be not viable. In order to achieve the targeted upper dosage limit with 20% w/w BUP-loaded PLGA microspheres in a fixed volume cavity, the formulation would have to be prepared with little to no binder. In the absence of binder, the device would have no cohesive integrity, and the PLGA microspheres would easily erode away and evacuate the tooth extraction socket. For this reason, calculations were performed in an attempt to satisfy a condition whereby the upper limit for BUP dosage would be delivered into a single tooth extraction socket cavity estimated to be 1 cc in volume via a formulation comprising PLGA microspheres dispersed within a hydrated gelatin binder. The target was deemed to be achievable only by increasing the theoretical % w/w BUP loading of the PLGA microspheres to a level that enabled the use of a binder together with additional of fluids for hydration of the device.

Three different pathways were identified to approach the problem of maximizing dosage: (1) increasing bupivacaine-loading to its maximum theoretical level of about 50% w/w within the PLGA microspheres; (2) minimizing the gelatin binder levels to the extent permitted without simultaneously deteriorating mechanical properties; and (3) minimizing the level of water required for hydration/mastication to the extent tolerable without experiencing unmanageable decreases in compliance. With these limitations in mind, "DRAFT-1 DOE" was created to study the effects of four factors:

FACTOR-1=weight percent solids in the hydrated formula (PLGA microspheres+SF=50%, 53%, and 56%);

FACTOR-2=interchangeable choice between binder-type (SF, GLBG, GLPG) or pH-modulator (standard pH water, 1% citric acid solution, 1% di-sodium citrate solution);

FACTOR-3=the weight fraction of small (D50=3.4 micron) PLGA particles as a percentage of all PLGA particles (0, 0.05, 0.1);

FACTOR-4=the weight fraction of D50=42.7 micron spinning-disc-dried PLGA particles (0, 0.15, 0.3), wherein D50=42.1 micron emulsion PLGA particles constituted the balance (e.g., 1, 0.8, 0.6).

Based on the DRAFT-1 DOE constraints, the maximum viable dosage target for bupivacaine was theoretically determined to be 300 mg in a 1 cc fixed volume cavity, which was a level that was closer to the original 360 mg dosage target. Although higher bupivacaine dosages would theoretically still be possible, it was recognized that an appropriate level of gelatin binder would still be needed to hold the formula together during hydration. Again, although PLGA microspheres were used for this experiment, it was assumed that 50% bupivacaine-loading of the PLGA microspheres would also be possible. Surgifoam (SF) powder was initially used as the binder. Table 1-3 provides information on the PLGA microspheres provided by Southwest Research Institute (SWRI). Tables 1-4 and 1-5 reveal pertinent DRAFT-1 DOE calculations based on the initial constraints as described above. The gelatin binder and PLGA microsphere powders were dry-mixed at the specified weight ratios, and selected dry mixtures were then mixed with water at specified weight ratios using a hand-held spatula.

TABLE 1-3

PLGA microsphere information from Southwest Research Institute (SWRI).

Figure 7A:
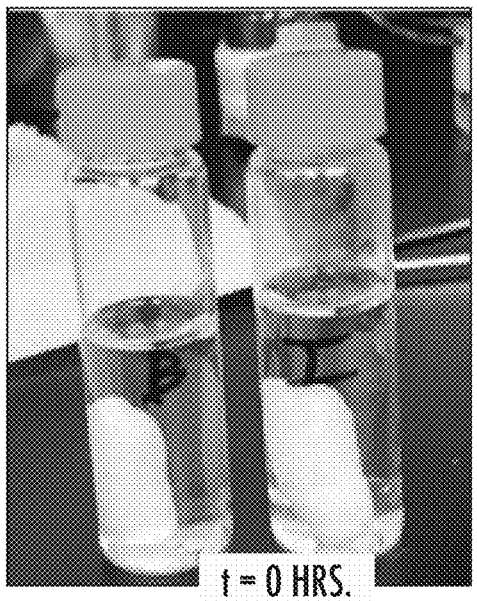
FIG. 7a is a photograph showing hydrophilic system samples 918-1B (left) and 918-1i (right) at t=0 hours after incubation at 37 degrees C. during the pH-2 soak experiment.
Figure 7B:
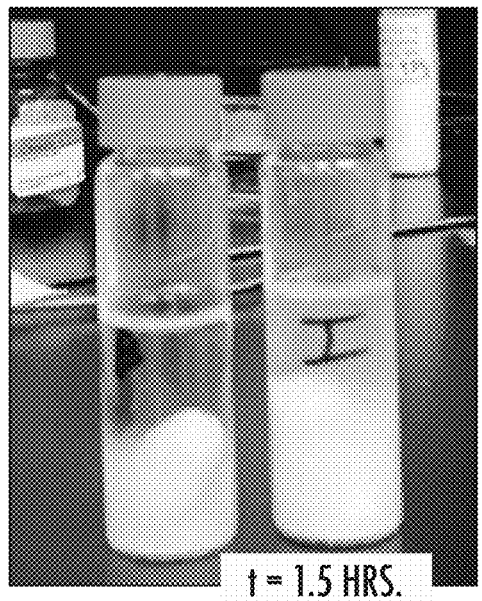
FIG. 7b is a photograph showing hydrophilic system samples 918-1B (left) and 918-1i (right) at t=1.5 hours after incubation at 37 degrees C. during the pH-2 soak experiment.
Figure 7C:
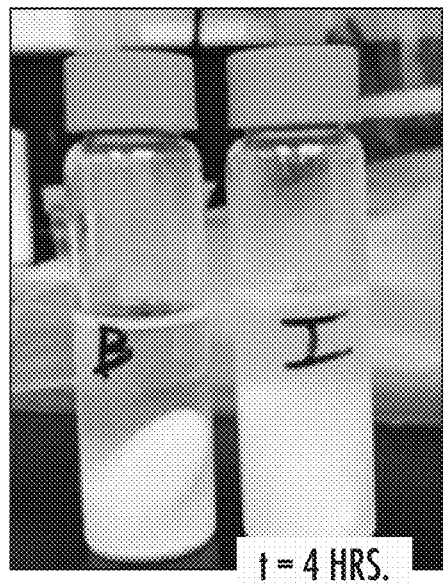
FIG. 7c is a photograph showing hydrophilic system samples 918-1B (left) and 918-1i (right) at t=4 hours after incubation at 37 degrees C. during the pH-2 soak experiment.
Figure 7D:
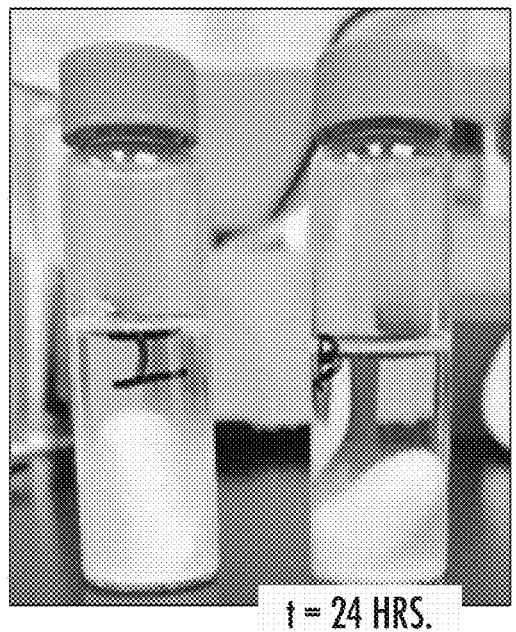
FIG. 7d is a photograph showing hydrophilic system samples 918-1B (right) and 918-1i (left) at t=24 hours after incubation at 37 degrees C. during the pH-2 soak experiment.
Figure 7E:
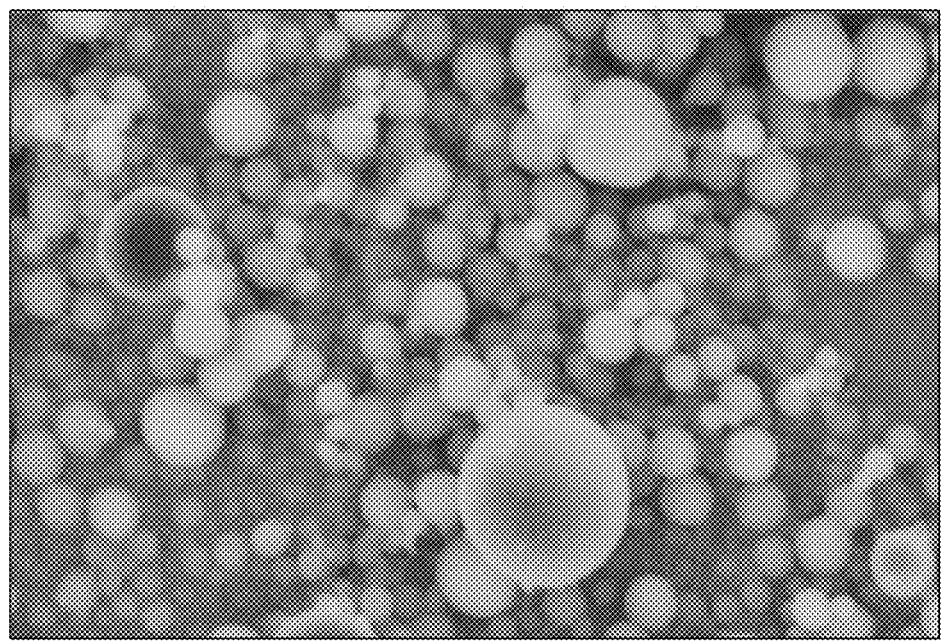
FIG. 7e is a scanning electron micrograph of BUP containing PLGA microspheres produced using the spray drying atomization method.
Figure 7F:
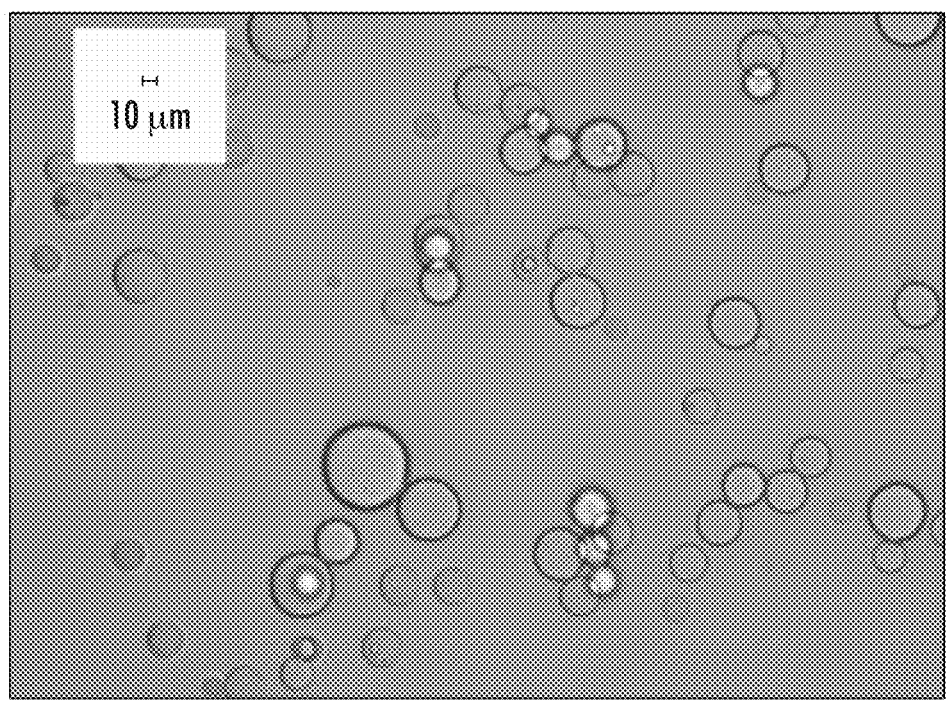
FIG. 7f is an optical microscope image (200× magnification) of BUP containing PLGA microspheres produced using the emulsion, solvent extraction method.

| Sample ID (NB: 18-0202-015-) | Bupivacaine Free Base Loading (Theoretical Wt %) | Polymer Matrix | Process/Comments | Amount of Sample (grams) | D (0.1) microns | D (0.5) microns | D (0.9) microns |
|---|---|---|---|---|---|---|---|
| 5 | 0% Placebo | Resomer RG 504 | Spray drying using spinning disk Low recovery due to agglomeration and sticking inside of atomization chamber | 3.7 g | 19.2 | 42.7 | 88.5 |
| 6 | 20% | Resomer RG 504 | Spray drying using spinning disk Low recovery due to agglomeration and sticking inside of atomization chamber | 0.6 g | 24.5 | 52.1 | 101.4 |
| 7 | 0% Placebo | Resomer RG 504 | Spray drying using two-fluid nozzle | 4.0 g | 1.4 | 3.4 | 9.2 |
| 10 | 20% | Resomer RG 504 | Spray drying using two-fluid nozzle | 5.0 g | 1.0 | 3.5 | 7.0 |
| 9 | 0% Placebo | Resomer RG504 | Emulsion, Solvent-extraction; photo provided in FIG. 7f | 4.4 g | 27.8 | 42.1 | 63.4 |

TABLE 1-4

DOE DRAFT-1 specifications calculations for creation of dry compositions and for calculations presented in Table 1-5.

| Expt. | FACTOR-1 Wt. % Solids in hydrated formula | FACTOR-2 Gelatin Type | Optional Factor-2 Hydration Solution Type | FACTOR-3 weight fraction of D50 3.4 um PLGA microspheres | FACTOR-4 weight fraction of D50 42.7 um PLGA microspheres | weight fraction of D50 42.7 um PLGA microspheres |
|---|---|---|---|---|---|---|
| 1 | 50.47% | SF | pH-neutral | 0 | 0 | 1 |
| 2 | 50.47% | GLBG | 1% citric in water | 0.05 | 0.15 | 0.8 |
| 3 | 50.47% | GLPG | 1% Na-citrate in water | 0.1 | 0.3 | 0.6 |
| 4 | 53.47% | SF | standard | 0.05 | 0.3 | 0.65 |
| 5 | 53.47% | GLBG | 1% citric in water | 0.1 | 0 | 0.9 |
| 6 | 53.47% | GLPG | 1% Na-citrate in water | 0 | 0.15 | 0.85 |
| 7 | 56.47% | SF | pH-neutral | 0.1 | 0.15 | 0.75 |
| 8 | 56.47% | GLBG | 1% citric in water | 0 | 0.3 | 0.7 |
| 9 | 56.47% | GLPG | 1% Na-citrate in water | 0.05 | 0 | 0.95 |
| 10 | 53.47% | SF | pH-neutral | 1 | 0 | 0 |
| 11 | 53.47% | SF | pH-neutral | 0 | 1 | 0 |
| 12 | 53.47% | SF | pH-neutral | 0 | 0 | 1 |
| 13 | 25.00% | SF | pH-neutral | 0 | 0 | 1 |

TABLE 1-5

DOE DRAFT-1 calculations of pertinent composition information based on the constraints presented in Table 1-4. Although placebo PLGA microspheres were used in preparing samples, calculations were performed to estimate a theoretical dosage of BUP delivery to a tooth extraction socket of 1 cc volume, assuming that the PLGA microspheres were loaded with 50% BUP by weight.

| Formulation | 1 | 2 | 3 | 4 | 5 | 6 |
|---|---|---|---|---|---|---|
| Target Bupivacaine Dose over 4-Day Period (grams) | 0.300 | 0.300 | 0.300 | 0.300 | 0.300 | 0.300 |

TABLE 1-5-continued

DOE DRAFT-1 calculations of pertinent composition information based on the constraints presented in Table 1-4. Although placebo PLGA microspheres were used in preparing samples, calculations were performed to estimate a theoretical dosage of BUP delivery to a tooth extraction socket of 1 cc volume, assuming that the PLGA microspheres were loaded with 50% BUP by weight.

| | | | | | | |
|---|---|---|---|---|---|---|
| Estimated Tooth extraction socket Volume (cm$^3$) | 1.3 | 1.3 | 1.3 | 1.3 | 1.3 | 1.3 |
| Estimated density of hydrated formula (g/cc) | 1.1 | 1.1 | 1.1 | 1.1 | 1.1 | 1.1 |
| Estimated grams of hydrated formula delivered to tooth extraction socket (g) | 1.43 | 1.43 | 1.43 | 1.43 | 1.43 | 1.43 |
| Theoretical wt. % Bupivacaine in microspheres | 50% | 50% | 50% | 50% | 50% | 50% |
| Estimated weight of drug-dosed microspheres in hydrated formula (g) | 0.60 | 0.60 | 0.60 | 0.60 | 0.60 | 0.60 |
| Estimated % Total Solids in Hydrated Formula | 50.47% | 50.47% | 50.47% | 53.47% | 53.47% | 53.47% |
| Wt. % Microspheres dispersed in hydrated formula | 41.96% | 41.96% | 41.96% | 41.96% | 41.96% | 41.96% |
| Wt. % Gelatin in hydrated formula | 8.51% | 8.51% | 8.51% | 11.51% | 11.51% | 11.51% |
| Wt. % Water in hydrated formula | 49.53% | 49.53% | 49.53% | 46.53% | 46.53% | 46.53% |
| Estimated Total Solids in Hydrated Formula Delivered to Cavity (g) | 0.721721 | 0.721721 | 0.721721 | 0.764621 | 0.764621 | 0.764621 |
| Estimated wt. gelatin delivered to cavity (g) | 0.12 | 0.12 | 0.12 | 0.16 | 0.16 | 0.16 |
| Estimated Water weight delivered to tooth extraction socket (g) | 0.71 | 0.71 | 0.71 | 0.67 | 0.67 | 0.67 |
| Estimated wt. % drug-dosed microspheres in dry formula | 83.13% | 83.13% | 83.13% | 78.47% | 78.47% | 78.47% |
| Estimated wt. % gelatin in dry formula | 16.87% | 16.87% | 16.87% | 21.53% | 21.53% | 21.53% |
| Ratio of water to gelatin | 5.82 | 5.82 | 5.82 | 4.04 | 4.04 | 4.04 |

| Formulation | 7 | 8 | 9 | 10 |
|---|---|---|---|---|
| Target Bupivacaine Dose over 4-Day Period (grams) | 0.300 | 0.300 | 0.300 | 0.300 |
| Estimated Tooth extraction socket Volume (cm$^3$) | 1.3 | 1.3 | 1.3 | 1.3 |
| Estimated density of hyrdated formula (g/cc) | 1.1 | 1.1 | 1.1 | 1.1 |
| Estimated grams of hydrated formula delivered to tooth extraction socket (g) | 1.43 | 1.43 | 1.43 | 1.43 |
| Theoretical wt. % Bupivacaine in microspheres | 50% | 50% | 50% | 50% |
| Estimated weight of drug-dosed microspheres in hydrated formula (g) | 0.60 | 0.60 | 0.60 | 0.60 |
| Estimated % Total Solids in Hydrated Formula | 56.47% | 56.47% | 56.47% | 53.47% |
| Wt. % Microspheres dispersed in hydrated formula | 41.96% | 41.96% | 41.96% | 41.96% |
| Wt. % Gelatin in hydrated formula | 14.51% | 14.51% | 14.51% | 11.51% |
| Wt. % Water in hydrated formula | 43.53% | 43.53% | 43.53% | 46.53% |
| Estimated Total Solids in Hydrated Formula Delivered to Cavity (g) | 0.807521 | 0.807521 | 0.807521 | 0.764621 |
| Estimated wt. gelatin delivered to cavity (g) | 0.21 | 0.21 | 0.21 | 0.16 |
| Estimated Water weight delivered to tooth extraction socket (g) | 0.62 | 0.62 | 0.62 | 0.67 |
| Estimated wt. % drug-dosed microspheres in dry formula | 74.30% | 74.30% | 74.30% | 78.47% |
| Estimated wt. % gelatin in dry formula | 25.70% | 25.70% | 25.70% | 21.53% |
| Ratio of water to gelatin | 3.00 | 3.00 | 3.00 | 4.04 |

| Formulation | 11 | 12 | 13 |
|---|---|---|---|
| Target Bupivacaine Dose over 4-Day Period (grams) | 0.300 | 0.300 | 0.000 |
| Estimated Tooth extraction socket Volume (cm$^3$) | 1.3 | 1.3 | 1.3 |
| Estimated density of hyrdated formula (g/cc) | 1.1 | 1.1 | 1.1 |
| Estimated grams of hydrated formula delivered to tooth extraction socket (g) | 1.43 | 1.43 | 1.43 |
| Theoretical wt. % Bupivacaine in microspheres | 50% | 50% | 50% |

TABLE 1-5-continued

DOE DRAFT-1 calculations of pertinent composition information based on the constraints presented in Table 1-4. Although placebo PLGA microspheres were used in preparing samples, calculations were performed to estimate a theoretical dosage of BUP delivery to a tooth extraction socket of 1 cc volume, assuming that the PLGA microspheres were loaded with 50% BUP by weight.

| | | | |
|---|---|---|---|
| Estimated weight of drug-dosed microspheres in hydrated formula (g) | 0.60 | 0.60 | 0.00 |
| Estimated % Total Solids in Hydrated Formula | 53.47% | 53.47% | 25.00% |
| Wt. % Microspheres dispersed in hydrated formula | 41.96% | 41.96% | 0.00% |
| Wt. % Gelatin in hydrated formula | 11.51% | 11.51% | 25.00% |
| Wt. % Water in hydrated formula | 46.53% | 46.53% | 75.00% |
| Estimated Total Solids in Hydrated Formula Delivered to Cavity (g) | 0.764621 | 0.764621 | 0.357468345 |
| Estimated wt. gelatin delivered to cavity (g) | 0.16 | 0.16 | 0.36 |
| Estimated Water weight delivered to tooth extraction socket (g) | 0.67 | 0.67 | 1.07 |
| Estimated wt. % drug-dosed microspheres in dry formula | 78.47% | 78.47% | 0.00% |
| Estimated wt. % gelatin in dry formula | 21.53% | 21.53% | 100.00% |
| Ratio of water to gelatin | 4.04 | 4.04 | 3.00 |

Formula #12 represented an intermediate region in the statistical design of experiments (DOE) matrix with an intermediate dry weight % of gelatin binder. A statistically designed experiment like a Taguchi design can be thought of as a multi-dimensional exploration space, where the dimensional boundaries of the space are dictated by the upper and lower factor limits. This space that is encompassed by the DOE is often referred to as the "design space." When the statistically designed experiment is executed, some of the experiments will be executed with a set of factor values that cause the resulting sample to reside closer to the middle of the design space than others. Formula #12 is such a sample. Formula #12 also called for a 4/1 w/w ratio of water to gelatin binder. After mixing the #12 powdered formula with water, the hydrated formula #12 was observed to be relatively dry with significantly lower compliance than a comparable 4/1 w/w water to neat SF mixture, and lower in compliance than a 3/1 w/w water to neat SF mixture. Within 12 hours of aging inside of a sealed vial, formula #12 had become exceedingly stiff and non-compliant. The formulation was deemed to be too stiff and non-compliant for use in the end-application. Based on observations taken from the prior gelatin/water mixing experiments, as described in Parts A and B of Example 1 above, this time-dependent change in compliance was likely due to incomplete gelation during the initial mixing process coupled with a time-dependence that was needed to achieve equilibrium network formation after mixing.

In the next step, additional water was added to the hydrated #12 formula, adjusting the sample to 5.8/1 w/w water to SF in an attempt to achieve better formability. The initial result was improved plasticization and higher compliance. This result showed that with higher levels of water, higher compliance characteristics were possible, and mechanical efficacy for end use deployment was indeed possible. However, the addition of more water only served to dilute the weight percentages of all solids, including active ingredients like BUP. In a volume restricted application, this works against the goal of achieving higher bupivacaine dosage levels.

In the present example, 1 cc was used as an estimate for the volume of a tooth extraction socket cavity. Given that the volume of a tooth extraction socket can vary from individual-to-individual, even lower socket volumes will be encountered during end use and deployment. Given that there are volume-restricted limitations for the hydrated formulation in this application, it would be even more difficult to achieve higher bupivacaine dosages with smaller cavity volumes. In order to illustrate this problem, the estimated cavity volume was reduced to 0.55 cc for a test-set of calculations using the DOE DRAFT-1 factor constraints.

Based on a tooth extraction socket volume estimate of about 0.55 cc, Formula #12, comprising about 21% Surgifoam binder on a dry weight % basis, and the entire DRAFT-1 DOE space was deemed to be incapable of delivering a targeted bupivacaine dosage of 360 mg. In fact, based on a 0.55 cc volume, Formula #12 would deliver only about 150 mg of BUP at best. Substantially higher PLGA microsphere levels and lower binder levels would be required to increase the bupivacaine dosage. Given that Surgifoam was found to be a relatively weak network-forming gel at low concentrations (see Part A above); and given that even more water would be needed to plasticize a formula with progressively lower concentrations of binder, it was hypothesized that SF would not be a suitable binder. This hypothesis was put to the test as described below.

Part-D. Limitations of High BUP Dosage Delivery Devices with SF as a Binder

Using Surgifoam as the binder, the dosage of bupivacaine was pushed to higher levels. Table 1-6 provides specifications for a DOE entitled "DRAFT-4," having the same factors as DRAFT-1 described in Part-C above, but with new upper and lower limits. Table 1-7 provides the wet, hydrated weight percent compositions of the DOE DRAFT-4 formulas. In conceptualizing DRAFT-4, formula #12 of DRAFT-1 became an upper boundary point in the DOE space with approximately 21% gelatin binder on a dry weight % basis, referred to as formula #1 with SF in DOE DRAFT-4. The lowest binder level of the DRAFT-4 DOE was about 16% gelatin, formula #7 with SF and formula #7B with GLBG. Table 1-8 provides additional information on three specific DOE DRAFT-4 formulas that were mixed and evaluated.

TABLE 1-6

DOE DRAFT-4 specifications calculations for creation of dry compositions, and for calculations presented in Table 1-7. The Factor-3 distribution types were defined as follows, where PLGA particle sizes were combined according to the following equation: X = weight fraction of 3.4 micron PLGA particles; Y = weight fraction of 42.7 micron PLGA particles; 1 − X − Y = weight fraction of 42.1 micron PLGA particles; type-1 = 0*X with 0*Y; type-2 = 0.05*X with 0.15*Y; type-3 = 0.1*X with 0.3*Y.

| Expt. | FACTOR-1 Bupivacaine dosage (g) | FACTOR-2 Gelatin Type | FACTOR-3 PLGA micro-sphere distribution-type | FACTOR-4 Hydration Solution Type |
|---|---|---|---|---|
| 1 | 0.300 | SF | 1 | pH-neutral |
| 2 | 0.300 | GLBG | 2 | 1% citric |
| 3 | 0.300 | GLPG | 3 | 1% di-Na citrate |
| 4 | 0.330 | SF | 2 | 1% di-Na citrate |
| 5 | 0.330 | GLBG | 3 | pH-neutral |
| 6 | 0.330 | GLPG | 1 | 1% citric |
| 7 | 0.360 | SF | 3 | 1% citric |
| 8 | 0.360 | GLBG | 1 | 1% di-Na citrate |
| 9 | 0.360 | GLPG | 2 | pH-neutral |
| 10 | 0.300 | SF | 100% 3.4 um | pH-neutral |
| 11 | 0.300 | SF | 100% 42.7 um | pH-neutral |
| 12 | 0.300 | SF | 1 | pH-neutral |
| 13 | 0.000 | SF | No PLGA | pH-neutral |
| 7B | 0.360 | GLBG | 3 | 1% citric |

TABLE 1-7

Hydrated) weight % compositions for DOE DRAFT-4.

| Expt. | Wt. % gelatin | Wt. % PLGA Microspheres | Wt. % water solution |
|---|---|---|---|
| 1 | 11.51% | 41.96% | 46.53% |
| 2 | 11.51% | 41.96% | 46.53% |
| 3 | 11.51% | 41.96% | 46.53% |
| 4 | 10.68% | 46.15% | 43.16% |
| 5 | 10.68% | 46.15% | 43.16% |
| 6 | 10.68% | 46.15% | 43.16% |
| 7 | 8.70% | 44.46% | 46.84% |
| 8 | 9.85% | 50.35% | 39.80% |
| 9 | 9.85% | 50.35% | 39.80% |
| 10 | 11.51% | 41.96% | 46.53% |
| 11 | 11.51% | 41.96% | 46.53% |
| 12 | 9.05% | 32.99% | 57.95% |
| 13 | 19.84% | 0.00% | 80.16% |
| 7B | 8.70% | 44.46% | 46.84% |

TABLE 1-8

DOE DRAFT-4 calculations of pertinent composition information based on the constraints presented in Table 1-6. Although placebo PLGA microspheres were used in preparing samples, calculations were performed to estimate a theoretical dosage of BUP delivery to a tooth extraction socket of 1.3 cc volume, assuming that the PLGA microspheres were loaded with 50% BUP by weight.

| Formulation | 1 | 7 | 7B |
|---|---|---|---|
| Target Bupivacaine Dose over 4-Day Period (grams) | 0.300 | 0.360 | 0.360 |
| Estimated Tooth extraction socket Volume (cm³) | 1.3 | 1.3 | 1.3 |
| Estimated density of hydrated formula (g/cc) | 1.1 | 1.1 | 1.1 |
| Estimated grams of hydrated formula delivered to tooth extraction socket (g) | 1.43 | 1.43 | 1.43 |
| Theoretical wt. % Bupivacaine in microspheres | 50% | 50% | 50% |
| Estimated weight of drug-dosed microspheres in hydrated formula (g) | 0.60 | 0.72 | 0.72 |
| Estimated % Total Solids in Hydrated Formula | 53.47% | 60.20% | 60.20% |
| Wt. % Microspheres dispersed in hydrated formula | 41.96% | 50.35% | 50.35% |
| Wt. % Gelatin in hydrated formula | 11.51% | 9.85% | 9.85% |
| Wt. % Water in hydrated formula | 46.53% | 39.80% | 39.80% |
| Estimated Total Solids in Hydrated Formula Delivered to Cavity (g) | 0.764621 | 0.86087619 | 0.860876 |
| Estimated wt. gelatin delivered to cavity (g) | 0.16 | 0.14 | 0.14 |
| Estimated Water weight delivered to tooth extraction socket (g) | 0.67 | 0.57 | 0.57 |
| Estimated wt. % drug-dosed microspheres in dry formula | 78.47% | 83.64% | 83.64% |
| Estimated wt. % gelatin in dry formula | 21.53% | 16.36% | 16.36% |
| Ratio of water to gelatin | 4.04 | 4.04 | 4.04 |
| Binder Type | SF | SF | GLBG |
| Water Type | pH-neutral | 1% citric | 1% citric |
| Sphere distribution type | 1 | 3 | 3 |

Upon mixing formula #7 with Surgifoam as the binder, the resulting device was observed to be a non-compliant dry-blend at a 4 to 1 water/binder w/w ratio. Addition of more water for plasticization was fruitless owing to weakening of the binder network. Upon mixing formula #1 with an even higher SF binder level, the resulting device was also observed to be a non-compliant dry-blend at a 4 to 1 water/binder w/w ratio. Thus, with Surgifoam gelatin appearing to be an unacceptable binder at low binder levels and at higher water/binder w/w ratios, a new analogous formula was made with the Great Lakes bovine gelatin (formula 7B). Although neat GLBG was previously observed to be slower to gel and slower to reach equilibrium compliance than neat SF (see Part-A above), it was also noted to become a stronger and more elastic gel than SF when plasticized with water at equivalent water to gelatin weight ratios. The ability of GLBG to form a stronger gelled network than SF was hypothesized to be a possible solution to the problem of trying to balance the need for achieving acceptable composite properties at the low binder levels and at the higher volume fractions of microspheres that are needed for delivery of higher bupivacaine dosages to small fixed-volume cavities. Indeed, upon mixing with water, Formula #7B was observed to congeal to form a dough-like material at a 4 to 1 water/binder weight ratio. The compliance of Formula #7B was still relatively low, but unlike Surgifoam, Formula #7B had nevertheless congealed to form a compliant solid, which was not a flaky dry-blend.

Thus, at the low binder levels necessitated by volume restrictions and by elevated BUP target delivery dosages, the preferred binder is one that is strong enough to provide acceptable cohesive integrity, and it is also one that has the ability to provide acceptable gel-network formation at relatively low concentrations. In this regard, even though neat GLBG is less compliant than neat SF when plasticized with equivalent levels of water, a more elastic, lower-compliance gelatin such as GLBG is preferred as a binder over Surgifoam when it is used in a composite mixture containing PLGA microspheres dispersed in a hydrated gelatin matrix.

Hydrated formula #7B became increasingly stiff and lower in compliance as it was aged in a closed container, consistent with the time-dependent changes in rheological characteristics that were observed in the prior experiments with gelatin and water alone. Thus, GLBG, like Surgifoam, was observed to still require higher levels of water for plasticization. Again, although GLBG was deemed to be a better binder than SF, this is not a desirable direction for achieving higher bupivacaine dosages in a fixed volume end use application. These results also showed that network formation would be time-dependent, and that equilibrium conditions might require several hours or more at any given water-level.

Example 2. Design of a Controlled Release Device for Delivering BUP within a Volume-Restricted End Use Application A statistically designed experiment entitled "DOE DRAFT-6" was constructed to demonstrate the limitations of an embodiment whereby dry powders of bupivacaine-loaded PLGA microspheres and gelatin would be pre-masticated with water and then delivered as a compliant dough-like material during end use. Given the limitations of SF as demonstrated in Example 1, the gelatins of choice for this example were GLBG and GLPG.] Note that neat SF gels are routinely used by clinicians as hemostats to fill the tooth extraction socket in post tooth extraction applications. As such, neat SF gels are recognized by clinicians as having reasonably acceptable mechanical compliance and formability characteristics. For this reason, neat SF gels were used as qualitative benchmarks for targeting acceptable compliance characteristics, while simultaneously attempting to maximize the theoretical BUP dosage delivery limits.

The goal of the DOE DRAFT-6 experiment was to create a viable mixture that could be used for the following purposes: 1) for use in analytical testing to investigate and develop desirable bupivacaine time-release profiles; 2) to simultaneously provide mechanical compliance characteristics similar to what many clinicians would recognize as an acceptable benchmark similar to neat SF gelled with water; 3) to simultaneously maximize the theoretical dosage limit of BUP while working with restrictions presented by a fixed volume constraint; and 4) to produce a viable end use formulation that can be pre-hydrated with water before deployment to deliver relatively high dosages of BUP in a volume-restricted end use application.

Considerations for the conceptualization and creation of DOE DRAFT-6 can be summarized as follows:

(1) the volume restriction for the end-application, estimated to be ca. 0.55 cc in this example, causes the upper limit dosage of bupivacaine to be severely constrained. In order to retain mechanical efficacy, compliance and formability, there is a need for some minimum level of binder and water, which places a limitation on the maximum weight % concentration of PLGA microspheres that can be incorporated into the device for use and deployment in a volume-restricted environment;

(2) higher levels of bupivacaine loading in the PLGA microspheres would be required to reach bupivacaine delivery dosages of >60 mg. A level of 20% w/w BUP in the PLGA microspheres would lead to maximum dose deliveries of less than 60 mg;

(3) lower binder levels would be required to maximize the microsphere content and hence to maximize the bupivacaine delivery dosage. This is a constraint that weakens the composite and necessitates not only the use of better network-forming binders, but also higher levels of volume-occupying water for plasticization;

(4) lower binder levels necessitate higher molecular weight network-forming gels that are susceptible to time-dependent reductions in compliance owing to diffusion-rate limitations which impact the time required for the gelling network to reach its equilibrium state; and (5) diffusion rates and time-dependent compliance characteristics are further confounded by both the particle size distribution of the microspheres, which also affects the bupivacaine time-release profile, and by the particle sizes of the gelatin particulates.

Other considerations included identifying the controlled factors for DOE DRAFT-6 and determining the boundary limits for factors. A general description of the factors and considerations pertaining to boundary limits are described here:

Factor-1: the weight % binder range was chosen to help produce a potentially viable device while maximizing the bupivacaine dosage within the limitations of the embodiment;

Factor-2: the gelatin type, where GLBG and GLPG and mixtures thereof were chosen to help achieve acceptable mechanical properties at the low binder levels necessitated by the desire to achieve higher bupivacaine dosages with the 0.55 cc volume constraint;

Factor-3: the microsphere distribution type, where different particle size distributions would lead to different surface-to-volume ratios for the purposes of impacting mechanical properties, and for the purpose of modulating bupivacaine release and diffusion rates; and Factor-4: the use of pH modulators, which affect gel-rate and gel strength. The pH modulators are also anticipated to affect bupivacaine free-base solubility, bupivacaine release rate, lactic acid formation rate, and lactate neutralization.

The DOE factors and levels for DRAFT-6 are provided in Table 2-1. A Taguchi 4-factor, 3-level design template was employed, represented by experiments 1 through 9 in Table 2-1, along with four additional one-off experiments, 10 through 13, where #13 represented a 4.04/1 w/w water to SF benchmark.

The statistical DOE factors included: 1) the weight % of gelatin binder on a dry-basis, wherein the range was chosen so as to produce a potentially viable device while maximizing BUP dosage (21.53%, 18.80%, 16.36%); 2) the gelatin type (GLBG, GLPG, and a 50/50 w/w mixture of the two); 3) microsphere particle size distribution-type using mixtures of the PLGA microspheres from SWRI that were described in Example 1 (distribution type-1i=100% D50 42.1 micron emulsion particles; distribution type-2=80% D50 42.1 micron emulsion particles+15% D50 42.7 micron spinning-disc particles+5% D50 3.4 micron spinning-disc particles; distribution type-3=60% D50 42.1 micron emulsion particles+30% D50 42.7 micron spinning-disc particles+10% D50 3.4 micron spinning-disc particles); and 4) pH modulators incorporated into solutions with distilled water for hydrating the dry powder mixtures (pH-neutral water, 1% citric acid solution, and 1% di-sodium citrate solution) which have been shown to affect gel-rate and gel strength and are anticipated to affect BUP free-base solubility, BUP release rate, lactic acid formation rate, and lactate neutralization.

For the purposes of this example, the hydrated formula mixture weights were targeted to be between 0.7 g and 0.9 g. The initial water to gelatin binder ratio was specified to be 4.04/1 w/w. Calculations depicting various attributes of DOE DRAFT-6 are provided in Tables 2-2, 2-3, and 2-4, respectively. With the restraint that the cavity volume was estimated to be 0.55 cc in this example, the bupivacaine delivery dosages were limited to those as described in Table 2-5.

Samples 10, 11, and 12 comprising segregated particle distributions were mixed first, followed by the statistical DOE-space samples 1 through 9. Whenever possible, qualitative trends and observations were noted immediately after mixing. Given that it takes time for the networks to reach equilibrium, the hydrated samples made with a weight ratio of water to gelatin of 4.04/1 w/w were placed into closed containers for 24 hours. The hydrated samples were then removed and were qualitatively ranked for their relative compliance, for their relative degree of re-formability, and for their relative tackiness during handling. In the next step, a small amount of additional water was added to rehydrate the samples. The added level of water resulted in an increase in the total weight ratio of water to gelatin binder from an initial value of 4.04/1 w/w to a value of 5.54/1 w/w. This had the effect of diluting the fixed-volume compositions and allowed for qualitative ranking of relative cohesive strength after aging. The rehydrated compositions are provided in Table 2-5.

Whenever possible, the qualitative rankings were used as responses for trend analyses, and for determining the significance of the controlled factors. Design-Ease 9 DOE software (Stat-Ease, Inc.) was used to test for significance of differences at the 95% confidence level (CL).

TABLE 2-1

DOE DRAFT-6 specifications calculations for creation of dry compositions, and for calculations presented in Tables 2-2, 2-3, 2-4, and 2-5. The Factor-3 distribution types were defined as follows, where PLGA particle sizes were combined according to the following equation: X = weight fraction of 3.4 micron PLGA particles; Y = weight fraction of 42.7 micron PLGA particles; 1 − X − Y = weight fraction of 42.1 micron PLGA particles; type-1 = 0*X with 0*Y; type-2 = 0.05*X with 0.15*Y; type-3 = 0.1*X with 0.3*Y.

| Expt. | FACTOR-1 wt. % gelatin in dry formula | FACTOR-2 Gelatin Type | FACTOR-3 PLGA microsphere distribution-type | FACTOR-4 Hydration Solution Type |
|---|---|---|---|---|
| 1 | 21.53% | GLBG | 1 | pH-neutral |
| 2 | 21.53% | GLPG | 2 | 1% citric |
| 3 | 21.53% | 50/50 GLBG/GLPG | 3 | 1% di-Na citrate |
| 4 | 18.80% | GLBG | 2 | 1% di-Na citrate |
| 5 | 18.80% | GLPG | 3 | pH-neutral |
| 6 | 18.80% | 50/50 GLBG/GLPG | 1 | 1% citric |
| 7 | 16.36% | GLBG | 3 | 1% citric |
| 8 | 16.36% | GLPG | 1 | 1% di-Na citrate |
| 9 | 16.36% | 50/50 GLBG/GLPG | 2 | pH-neutral |
| 10 | 18.80% | GLBG | 100% 3.4 μm | pH-neutral |
| 11 | 18.80% | GLBG | 100% 42.7 μm | pH-neutral |
| 12 | 18.80% | GLBG | 1 | pH-neutral |
| 13 | 100.00% | SF | No PLGA | pH-neutral |

TABLE 2-2

Dry weight % compositions for DOE DRAFT-6.

| Expt. | Wt. % gelatin | Wt. % PLGA Microspheres |
|---|---|---|
| 1 | 21.5% | 78.5% |
| 2 | 21.5% | 78.5% |
| 3 | 21.5% | 78.5% |
| 4 | 18.8% | 81.2% |
| 5 | 18.8% | 81.2% |
| 6 | 18.8% | 81.2% |
| 7 | 16.4% | 83.6% |
| 8 | 16.4% | 83.6% |
| 9 | 16.4% | 83.6% |
| 10 | 18.8% | 81.2% |
| 11 | 18.8% | 81.2% |
| 12 | 18.8% | 81.2% |
| 13 | 100.0% | 0.0% |

TABLE 2-3

Wet (hydrated) weight % compositions for DOE DRAFT-6; water to gelatin w/w ratio was specified to be 4.04/1.

| Expt. | Wt. % gelatin | Wt. % PLGA Microspheres | Wt. % water solution |
|---|---|---|---|
| 1 | 11.51% | 41.96% | 46.53% |
| 2 | 11.51% | 41.96% | 46.53% |
| 3 | 11.51% | 41.96% | 46.53% |
| 4 | 10.69% | 46.15% | 43.16% |
| 5 | 10.69% | 46.15% | 43.16% |

TABLE 2-3-continued

Wet (hydrated) weight % compositions for DOE DRAFT-6; water to gelatin w/w ratio was specified to be 4.04/1.

| Expt. | Wt. % gelatin | Wt. % PLGA Microspheres | Wt. % water solution |
|---|---|---|---|
| 6 | 10.69% | 46.15% | 43.16% |
| 7 | 9.85% | 50.35% | 39.80% |
| 8 | 9.85% | 50.35% | 39.80% |
| 9 | 9.85% | 50.35% | 39.80% |
| 10 | 10.69% | 46.15% | 43.16% |
| 11 | 10.69% | 46.15% | 43.16% |
| 12 | 10.69% | 46.15% | 43.16% |
| 13 | 19.84% | 0.00% | 80.16% |

TABLE 2-4

Wet (re-hydrated) weight % compositions for DOE DRAFT-6; water to gelatin w/w ratio was 5.54/1.

| Expt. | Wt. % gelatin | Wt. % PLGA Microspheres | Wt. % water solution |
|---|---|---|---|
| 1 | 9.82% | 35.78% | 54.40% |
| 2 | 9.82% | 35.78% | 54.40% |
| 3 | 9.82% | 35.78% | 54.40% |
| 4 | 9.21% | 39.78% | 51.01% |
| 5 | 9.21% | 39.78% | 51.01% |
| 6 | 9.21% | 39.79% | 51.00% |
| 7 | 8.58% | 43.87% | 47.55% |
| 8 | 8.58% | 43.87% | 47.55% |
| 9 | 8.58% | 43.87% | 47.55% |
| 10 | 9.21% | 39.78% | 51.01% |
| 11 | 9.21% | 39.78% | 51.01% |
| 12 | 9.21% | 39.78% | 51.01% |

TABLE 2-5

DOE DRAFT-6 calculations of pertinent composition information based on the constraints presented in Table 2-1. Although placebo PLGA microspheres were used in preparing samples, calculations were performed to estimate a theoretical dosage of BUP delivery to a tooth extraction socket of 0.55 cc volume, assuming that the PLGA microspheres were loaded with 50% BUP by weight.

| Formulation | 1 | 2 | 3 |
|---|---|---|---|
| Target Bupivacaine Dose over 4-Day Period (grams) | 0.127 | 0.127 | 0.127 |
| Estimated Tooth extraction socket Volume (cm$^3$) | 0.55 | 0.55 | 0.55 |
| Estimated density of hydrated formula (g/cc) | 1.1 | 1.1 | 1.1 |
| Estimated grams of hydrated formula delivered to tooth extraction socket (g) | 0.605 | 0.605 | 0.605 |
| Theoretical wt. % Bupivacaine in microspheres | 50% | 50% | 50% |
| Estimated weight of drug-dosed microspheres in hydrated formula (g) | 0.25 | 0.25 | 0.25 |
| Estimated % Total Solids in Hydrated Formula | 53.47% | 53.47% | 53.47% |
| Wt. % Microspheres dispersed in hydrated formula | 41.96% | 41.96% | 41.96% |
| Wt. % Gelatin in hydrated formula | 11.51% | 11.51% | 11.51% |
| Wt. % Water in hydrated formula | 46.53% | 46.53% | 46.53% |
| Estimated Total Solids in Hydrated Formula Delivered to Cavity (g) | 0.323499306 | 0.323499306 | 0.323499306 |
| Estimated wt. gelatin delivered to cavity (g) | 0.07 | 0.07 | 0.07 |
| Estimated Water weight delivered to tooth extraction socket (g) | 0.28 | 0.28 | 0.28 |
| Estimated wt. % drug-dosed microspheres in dry formula | 78.47% | 78.47% | 78.47% |
| Estimated wt. % gelatin in dry formula | 21.53% | 21.53% | 21.53% |
| Ratio of water to gelatin | 4.04 | 4.04 | 4.04 |
| Binder Type | GLBG | GLPG | 50/50 GLBG/GLPG |
| Water Type | pH-neutral | 1% citric | 1% diNaCitrate |
| Sphere distribution type | 1 | 2 | 3 |

| Formulation | 4 | 5 | 6 |
|---|---|---|---|
| Target Bupivacaine Dose over 4-Day Period (grams) | 0.140 | 0.140 | 0.140 |
| Estimated Tooth extraction socket Volume (cm$^3$) | 0.55 | 0.55 | 0.55 |
| Estimated density of hydrated formula (g/cc) | 1.1 | 1.1 | 1.1 |
| Estimated grams of hydrated formula delivered to tooth extraction socket (g) | 0.605 | 0.605 | 0.605 |
| Theoretical wt. % Bupivacaine in microspheres | 50% | 50% | 50% |

TABLE 2-5-continued

DOE DRAFT-6 calculations of pertinent composition information based on the constraints presented in Table 2-1. Although placebo PLGA microspheres were used in preparing samples, calculations were performed to estimate a theoretical dosage of BUP delivery to a tooth extraction socket of 0.55 cc volume, assuming that the PLGA microspheres were loaded with 50% BUP by weight.

| | | | |
|---|---|---|---|
| Estimated weight of drug-dosed microspheres in hydrated formula (g) | 0.28 | 0.28 | 0.28 |
| Estimated % Total Solids in Hydrated Formula | 56.84% | 56.84% | 56.84% |
| Wt. % Microspheres dispersed in hydrated formula | 46.15% | 46.15% | 46.15% |
| Wt. % Gelatin in hydrated formula | 10.69% | 10.69% | 10.69% |
| Wt. % Water in hydrated formula | 43.16% | 43.16% | 43.16% |
| Estimated Total Solids in Hydrated Formula Delivered to Cavity (g) | 0.34386857 | 0.34386857 | 0.34386857 |
| Estimated wt. gelatin delivered to cavity (g) | 0.06 | 0.06 | 0.06 |
| Estimated Water weight delivered to tooth extraction socket (g) | 0.26 | 0.26 | 0.26 |
| Estimated wt. % drug-dosed microspheres in dry formula | 81.20% | 81.20% | 81.20% |
| Estimated wt. % gelatin in dry formula | 18.80% | 18.80% | 18.80% |
| Ratio of water to gelatin | 4.04 | 4.04 | 4.04 |
| Binder Type | GLBG | GLPG | 50/50 GLBG/GLPG |
| Water Type | 1% diNaCitrate | pH-neutral | 1% citric |
| Sphere distribution type | 2 | 3 | 1 |

| Formulation | 7 | 8 | 9 |
|---|---|---|---|
| Target Bupivacaine Dose over 4-Day Period (grams) | 0.152 | 0.152 | 0.152 |
| Estimated Tooth extraction socket Volume (cm³) | 0.55 | 0.55 | 0.55 |
| Estimated density of hydrated formula (g/cc) | 1.1 | 1.1 | 1.1 |
| Estimated grams of hydrated formula delivered to tooth extraction socket (g) | 0.605 | 0.605 | 0.605 |
| Theoretical wt. % Bupivacaine in microspheres | 50% | 50% | 50% |
| Estimated weight of drug-dosed microspheres in hydrated formula (g) | 0.30 | 0.30 | 0.30 |
| Estimated % Total Solids in Hydrated Formula | 60.20% | 60.20% | 60.20% |
| Wt. % Microspheres dispersed in hydrated formula | 50.35% | 50.35% | 50.35% |
| Wt. % Gelatin in hydrated formula | 9.85% | 9.85% | 9.85% |
| Wt. % Water in hydrated formula | 39.80% | 39.80% | 39.80% |
| Estimated Total Solids in Hydrated Formula Delivered to Cavity (g) | 0.364216852 | 0.364216852 | 0.364216852 |
| Estimated wt. gelatin delivered to cavity (g) | 0.06 | 0.06 | 0.06 |
| Estimated Water weight delivered to tooth extraction socket (g) | 0.24 | 0.24 | 0.24 |
| Estimated wt. % drug-dosed microspheres in dry formula | 83.64% | 83.64% | 83.64% |
| Estimated wt. % gelatin in dry formula | 16.36% | 16.36% | 16.36% |
| Ratio of water to gelatin | 4.04 | 4.04 | 4.04 |
| Binder Type | GLBG | GLPG | 50/50 GLBG/GLPG |
| Water Type | 1% citric | 1% diNaCitrate | pH-neutral |
| Sphere distribution type | 3 | 1 | 2 |

| Formulation | 10 | 11 | 12 |
|---|---|---|---|
| Target Bupivacaine Dose over 4-Day Period (grams) | 0.140 | 0.140 | 0.140 |
| Estimated Tooth extraction socket Volume (cm³) | 0.55 | 0.55 | 0.55 |
| Estimated density of hydrated formula (g/cc) | 1.1 | 1.1 | 1.1 |
| Estimated grams of hydrated formula delivered to tooth extraction socket (g) | 0.605 | 0.605 | 0.605 |

TABLE 2-5-continued

DOE DRAFT-6 calculations of pertinent composition information based on the constraints presented in Table 2-1. Although placebo PLGA microspheres were used in preparing samples, calculations were performed to estimate a theoretical dosage of BUP delivery to a tooth extraction socket of 0.55 cc volume, assuming that the PLGA microspheres were loaded with 50% BUP by weight.

| | | | |
|---|---|---|---|
| Theoretical wt. % Bupivacaine in microspheres | 50% | 50% | 50% |
| Estimated weight of drug-dosed microspheres in hydrated formula (g) | 0.28 | 0.28 | 0.28 |
| Estimated % Total Solids in Hydrated Formula | 56.84% | 56.84% | 56.84% |
| Wt. % Microspheres dispersed in hydrated formula | 46.15% | 46.15% | 46.15% |
| Wt. % Gelatin in hydrated formula | 10.69% | 10.69% | 10.69% |
| Wt. % Water in hydrated formula | 43.16% | 43.16% | 43.16% |
| Estimated Total Solids in Hydrated Formula Delivered to Cavity (g) | 0.34386857 | 0.34386857 | 0.34386857 |
| Estimated wt. gelatin delivered to cavity (g) | 0.06 | 0.06 | 0.06 |
| Estimated Water weight delivered to tooth extraction socket (g) | 0.26 | 0.26 | 0.26 |
| Estimated wt. % drug-dosed microspheres in dry formula | 81.20% | 81.20% | 81.20% |
| Estimated wt. % gelatin in dry formula | 18.80% | 18.80% | 18.80% |
| Ratio of water to gelatin | 4.04 | 4.04 | 4.04 |
| Binder Type | GLBG | GLBG | GLBG |
| Water Type | pH-neutral | pH-neutral | pH-neutral |
| Sphere distribution type | 3.4 micron | 42.7 micron | 42.1 micron |

Qualitative trend analysis after initial mixing of samples 10, 11, and 12 revealed that the highest cohesive strength was achieved in the sample made with the D50=3.4 micron microspheres, followed by the sample made with the D50=42.1 micron microspheres. This trend also seemed to manifest itself among the DOE-space samples 1-9. Samples with the highest fraction of 3.4 micron particles trended towards displaying the best cohesive strength after mixing. This result indicates that from a mechanical property perspective, it is desirable to maximize the smaller particle size particle fraction while simultaneously balancing the overall distribution to achieve the desired bupivacaine release profile, particularly since smaller particles will release BUP faster than larger ones owing to their higher surface to volume ratio.

The 42.1 microsphere particles led to expedient mixing with minimal clumping when compared to their 42.7 micron spinning-disc-dried counterparts. It is noted that the 42.7 micron spinning-disc-dried particles were also agglomerated, whereas the 42.1 micron emulsion particles were more free-flowing.

Qualitative compliance was observed to increase with increasing gelatin binder level, as expected, and with fewer microspheres.

Because the samples were initially evaluated while they were in a dynamic state before they had reached their time-dependent equilibrium properties, the samples were placed in closed containers and were then allowed to equilibrate for 24 hours. Qualitative trend analyses at t=24 hours after mixing showed that each of the samples had increased in stiffness, a result which was consistent with the earlier DRAFT-1 DOE results of Example 1. Sample #10, which was made exclusively with 3.4 micron particles, continued to exhibit higher cohesive strength characteristics than any of the other samples.

Statistical trend analyses of the categoric factors from the DOE space indicated that the qualitative relative compliance response at t=24 hours after mixing with water was significantly affected by the weight % binder and by the binder-type at the 95% confidence level (CL), with p values <0.05, and with higher binder leading to higher compliance. These results showed that the minimum tolerable threshold for the binder level is between 21.5% and 18.8% by weight of the dry formula, with GLBG bovine gelatin being the preferred binder. Of course, higher levels of binder and water would always be helpful from a mechanical property perspective, but this would be counter to the objective of developing a formula with maximal BUP dosage potential.

Statistical trend analyses also revealed that the relative tack response characteristics scaled significantly with the weight % binder at the 95% CL. Within the DOE space, the minimum binder threshold for achieving the best tack appeared to be at or near about 19% by weight of the dry formula (p<0.05). This result reaffirms that for the purpose of creating a powder-based formula, the dry binder level should be maximized to a level of greater than about 18%. Even higher levels would be desirable, but only to the degree that lower bupivacaine delivery dosages can be tolerated in the application.

After rehydration with additional water, each of the samples was observed to exhibit an increase in relative compliance. Again, sample #10, which was made exclusively with 3.4-micron particles, was unique in that it exhibited the best physical properties. Specifically, sample #10 exhibited the highest relative cohesive strength and homogeneity of all the samples. This observation was consistent with the DOE-space trend analyses. Namely, the relative cohesive strength characteristics for the rehydrated formulas were qualitatively observed to increase as the percentage of 3.4 micron particles was increased within the formulation by employing sphere distribution type-2 or type-3 as depicted in Table 2-1, wherein type-2 equates to the particle distribution being comprised of 5% D50=3.4 micron particles and type-3 equates to the particle size distribution being comprised of 10% D50=3.4 micron particles vs. type-1 which contains no added D50=3.4 micron particles.

The results suggest that the dispersed PLGA particles augment the mechanical properties of the hydrated gelatin network. In other words, the PLGA particles do not simply behave as dispersed filler particles which deteriorate mechanical properties or provide no improvement. Instead, they behave as reinforcing fillers which improve mechanical properties. This means that they not only perform a primary function of encapsulating active ingredients for controlled-release, they also perform a beneficial secondary function of reinforcing the hydrated binder matrix, with smaller PLGA particle sizes having a more pronounced positive effect. This further implies that the PLGA microspheres will not only provide a first diffusion barrier for the release of BUP or other active ingredients, but its reinforcing presence in the matrix will also affect the compliance of the hydrated gelatin polymer itself, which in turn will further augment diffusion rates of BUP through the gelled matrix phase once the BUP has already diffused from the dispersed PLGA microspheres and into the gelled matrix. Also, from a macroscopic perspective, the mechanical reinforcement of the gelled gelatin binder by PLGA particles will also increase the resistance to erosion of the formulation within the end use application.

Trend analyses of the rehydrated samples also revealed a moderately detectable effect of pH-modulator on cohesive strength after re-hydration (p-value~0.10), with citric acid having a positive effect on cohesive strength and with di-sodium citrate having no detectable effect. Although these trends were not as significant at the 95% CL as other trends, they were nevertheless reasonable, particularly in light of the other qualitative findings that were presented in Example 1. Namely, the presence of citric acid was shown in Example 1 to lead to an increase in gelation rates for the neat proteins. Indeed, this trend seemed to manifest itself even when the gelatin proteins were used as binders in samples containing dispersed PLGA microspheres.

Based on the collective set of DOE responses, an embodiment of a delivery system using a formulation comprising a powdered mixture appears restricted to deliver a dosage of no more than about 140 mg bupivacaine to a 0.55 cc cavity, and only then by assuming that the % bupivacaine loading in the PLGA microspheres is increased from 20% to 50% by weight. Low gelatin binder levels are also required to maximize the volume fraction of microspheres and bupivacaine. It appears that the lower limit threshold for the binder is approximately 18% of the dry weight. At these relatively low levels, a network-forming gelatin like GLBG (Bloom=225 g) is preferred for its ability to impart the type of cohesive strength that is needed to bind the spheres together when the device is hydrated.

If the product is intended to be premixed with water, and if higher bupivacaine dosages are desired, then the occupied volume of water must also be accounted for, and the water-level should be minimized since it will effectively dilute the microsphere concentration and will further reduce the maximum bupivacaine delivery dosage to levels less than 140 mg if too much water is employed.

For reasons pertaining to mechanical properties, it is also preferable to skew the PLGA particle size distribution towards smaller particles, but only to the degree that this can be tolerated depending on bupivacaine time-release profile targets.

Larger PLGA microspheres made via an emulsion process provide qualitatively lower formula viscosities than their spinning-disc/spray-dried counterparts. In essence, this equates to a higher PLGA loading potential during mixing, which is also directionally preferred for achieving higher bupivacaine dosages, but only to the degree that adequate compliance and cohesive strength can be maintained. The D50=42.1 micron emulsion particles were also observed to mix more uniformly with faster wetting than their similarly-sized spinning-disc spray-dried counterparts, the D50=42.7 micron placebo PLGA microspheres. The emulsion particles (42.1 um) are thus preferred for the present application to the degree that larger particles are needed to achieve targeted release profiles.

Again, smaller particles (D50=3.4 microns) made by spinning-disc methods, by spray-drying with spinning disc, or by emulsion processes are desirable for reasons pertaining to mechanical properties, but only to the degree that their higher surface-to-volume ratios and release characteristics can be conducive to achieving specific time-dependent bupivacaine release profile targets.

Although release profile targets will be end use specific, it should be appreciated from these teachings that there will be several adjustable factors besides PLGA surface-to-volume ratios that can also conceivably be used to modulate and control the time-release profiles of bupivacaine and the like. For example, citric acid (a Bronsted acid) or di-sodium citrate (a Bronsted base) was observed to be viable with no obvious deleterious effects on rheology or properties of the delivery system. Citric acid was observed to enhance binder network formation. From this perspective, these types of compounds can serve dual functions. They can be used to modulate the physical properties of the binder system, and their activity can also be exploited for the dual purpose of modulating the solubility of the bupivacaine free base.

For example, a Bronsted acid will enhance the solubility of bupivacaine free base as it is released from a PLGA particle, thereby enhancing its bioavailability. Conversely, a Bronsted base would skew the acid-base equilibrium towards more bupivacaine free base, thereby reducing its bioavailability. Further, these types of compounds can be employed directly as powdered ingredients, which would make them immediately available upon hydration of the device. In addition, these types of compounds can be optionally and separately microencapsulated, which would attenuate their availability for acid-base interactions with bupivacaine, either with bupivacaine's acidic form or its free-base form.

By balancing these various types of formulation levers in combination, use of citric acid and use of a gelatin with a higher Bloom value like GLBG, it can be appreciated that one could achieve targeted bupivacaine release profiles while simultaneously employing higher fractions of high surface-to-volume particles if so desired. For example, with the combined use of these levers, one could potentially use a higher fraction of 3.4 micron PLGA particles than would otherwise be viable. Again, this direction might be desirable for reasons pertaining to achieving improved mechanical properties, which in turn could be leveraged to achieve lower net binder levels and higher net PLGA levels with higher net bupivacaine dosages.

Based on the above results, a mixed-particle size distribution delivery system to evaluate bupivacaine release profiles would use the particle size distribution of Formula #7, and would employ the GLBG binder at the levels used in Formulas #4, #5, and #6. The water-level required for pre-hydration should be minimized since adding more water equates to bupivacaine dilution. Furthermore, if the bupivacaine's release character can be adequately controlled, it would also be desirable to employ citric acid in the water phase at a concentration of 1% by weight or higher. The fraction of small particles should then be increased to the degree permitted based on the targeted bupivacaine release profiles. It is also preferable to increase the binder level to the degree permitted based on the target bupivacaine dosage and based on the required level of liquid water volume that is needed to achieve the desired compliance for any particular end use.

Example 3. Testing Surgifoam Gelatin as a Binder Component for Use in a Formulation with Mineral Oil In a first step, 0.1 g of Surgifoam was weighed into a small beaker. In order to batch a formula analogous to #7, #8, or #9 from DOE DRAFT-6 in Example 2, one would have to add 0.4039 g of water to the SF to achieve a liquid to gelatin weight ratio=4.04/1 w/w. However, since the goal of this example is to reduce the volume fraction of non-PLGA components to facilitate higher PLGA microsphere and BUP concentrations in the final formulation, the dry SF would have to be mixed with less than this amount of liquid. From a compliance perspective, this would be directionally incorrect if water were to be chosen as the liquid. However, if a different type of liquid were to be chosen, such as one that had the ability to simply disperse the gelatin particles without diffusing into the particles and without prematurely gelling the particles, then the concept of using less liquid might become more plausible. In this example, mineral oil (MO) was chosen as the liquid in place of water (Aldrich Heavy wt. CAS 8020-83-5, product 33,076-0).

In step 2, 0.1055 g mineral oil was added to 0.1 g SF, but it formed a dry blend.

In a third step, more mineral oil was added to bring the net addition to 0.1524 g. The SF powder began to consolidate into an array of surface-wetted particles, but the blend was still too dry and had very little cohesive integrity and could not be pressed or formed into a shape.

In step 4, more mineral oil was added, bringing the total to 0.2074 g. Again, it was noted that more oil would still be needed to form a compliant dispersion/mixture.

In step 5, the total oil level was increased to 0.3044 g. The blend was continuing to consolidate and pack into a weak amalgam, but it was still too dry and too cohesively weak to form a compliant mixture/dispersion. Based on this result, the approach of using MO with Surgifoam was abandoned because the objective was to minimize non-PLGA components while still maintaining sufficient compliance and cohesive strength to facilitate fibrous textile-impregnation. It was reasoned that a gelatin binder with a larger average particle size might produce a liquid dispersion with less oil, while still providing enough cohesive strength and compliance for subsequent textile impregnation.

Example 4. Testing GLBG as a Binder Component for Use in a Formulation with Mineral Oil (Formula #14A)

In a first step, 0.1054 g MO was added to 0.1022 g GLBG. Owing to the larger particle size of the GLBG, a completely wet and flowable/compliant amalgam was formed with only a 1/1 w/w ratio of liquid oil to gelatin. Thus, in order to maximize the % solids while simultaneously minimizing the % liquid in the device formula, and in order to simultaneously provide a hydrophilic binder component (e.g., GLBG) capable of binding PLGA spheres upon hydration, this result shows that it is desirable to increase the particle size of the ground gelatin component, and even to maximize the gelatin particle size to the degree permissible by the end use application.

In the next step, 0.1328 g of the 3.4-micron PLGA microspheres, and 0.2991 g of the 42.7-micron PLGA microspheres were weighed into a separate small beaker, approximately 70/30 w/w large to small PLGA particles, consistent with Example 2. At this point, the mix was consolidated with a small spatula into a dry cake. This mixture contained approximately 83.5 weight % total solids dispersed in mineral oil, capable of delivering approximately 206 mg bupivacaine to a 0.55 cc cavity. This is listed as Formula #14A in Table 5-1. It is noted that if Formula #14A were able to hydrate in vivo, then 14A could also be useful without fiber reinforcement.

Example 5. Preparation of a Controlled-Release Delivery Formulation Comprising a Mixture for Stand-Alone Use or for Optional Impregnation into a Cellulose Fiber Textile (Formula #14B)

A sample mixture, Formula #14B, analogous to Formula #14A was prepared with the use of additional mineral oil (MO) for the purpose of insuring that the mixture could be easily pressed and impregnated into a cellulose fiber textile to form a reinforced composite-like structure. The ratio of large to small PLGA particles in this example was chosen to be 70/30 (w/w). This ratio was chosen based on results presented in Example 2 above, wherein the use of higher fractions of small PLGA particles was determined to be preferred for achieving suitable cohesive strength characteristics for hydrated devices. Spin-disc spray-dried 42.7-micron microparticles were used in this example to demonstrate the concept.

Initially, 0.0985 g of additional mineral oil (MO) was added to Formula #14A from Example 4, bringing the total level to 0.2039 g mineral oil. At this point the amalgam became a tacky paste. In spite of having a lower weight percentage of liquid carrier, Formula #14B had a lower relative viscosity than analogous formulas from Example 2 that were made with water as the liquid carrier. Specifically, formulas #1, #2, and #3 in DOE DRAFT-6 each contained approximately 53% solids by weight with water as the liquid carrier. By contrast, formula #14B was comprised of 72.36% solids by weight with oil as the carrier. Thus, by substituting oil for water as the liquid carrier, it was discovered that a compliant vehicle could be formed with a higher weight percentage solids. Consequently, Formula #14B was estimated to be capable of delivering 177 mg bupivacaine to a 0.55 cc tooth extraction socket assuming a 50% w/w loading of BUP in the PLGA microspheres as shown in Table 5-1. By contrast, as previously noted in Table 2-5, comparable formulas with water as the carrier were only capable of delivering BUP dosages of 127 to 150 mg at best.

Thus, the use of a mineral oil carrier resulted in a lower viscosity paste with higher weight % solids than analogous samples made with a water carrier alone. This type of formulation could be used as-is by adding it directly to a tooth extraction socket and by allowing it to hydrate in vivo without textile impregnation and without pre-masticating with water. This would result in the highest BUP dosage delivery potential for the formulation. Alternatively, a formulation like Formula #14B could be optionally pre-masticated with water, and then deployed in its hydrated state if so desired. Finally, the lower relative viscosity of Formula #14B compared to Formula #14A can also render it as useful for subsequent hemostat textile-impregnation and reinforcement as demonstrated in Example 6 below.

TABLE 5-1

Calculations of pertinent composition information for Formula #14B from the present example and Formula #14A from Example 4. Although placebo PLGA microspheres were used in preparing these samples, calculations were performed to estimate a theoretical dosage of BUP delivery to a tooth extraction socket having 0.55 cc volume and assuming that the PLGA microspheres were loaded with 50% BUP by weight. These dosage delivery estimates are for an embodiment wherein the formulation comprises an oil carrier that does not cause gelation, and wherein BUP-loaded PLGA microspheres are suspended in the formulation to yield a compliant device that can be used for placement into a tooth extraction socket for subsequent in vivo hydration.

| Formulation | 14A | 14B |
|---|---|---|
| Target Bupivacaine Dose over 4-Day Period (grams) | 0.206 | 0.177 |
| Estimated Tooth extraction socket Volume (cm$^3$) | 0.55 | 0.55 |
| Estimated density of mixture (g/cc) | 1.1 | 1.1 |
| Estimated grams of "mixture" delivered to tooth extraction socket (g) | 0.605 | 0.605 |
| Wt. % Bupivacaine in microspheres | 50% | 50% |
| Estimated weight of drug-dosed microspheres in "mixture" (g) | 0.41 | 0.35 |
| Estimated % Total Solids in "mixture" | 83.72% | 72.36% |
| Wt. % Microspheres dispersed in "mixture" | 67.98% | 58.51% |
| Wt. % gelatin in "mixture" | 15.74% | 13.85% |
| Wt. % wax/oil in "mixture" portion of formula | 16.28% | 27.64% |
| Estimated Total Gelatin + PLGA/BUP Solids in "mixture" Delivered to Cavity (g) | 0.506535787 | 0.437807676 |
| Estimated wt. gelatin delivered to cavity (g) | 0.10 | 0.08 |
| Estimated wax/oil weight delivered to tooth extraction socket (g) | 0.10 | 0.17 |
| Estimated wt. % drug-dosed microspheres in dry formula (excluding wax/oil) | 81.20% | 80.86% |
| Estimated wt. % gelatin in dry mixture (excluding wax/oil) | 18.80% | 19.14% |
| Ratio of oil to gelatin | 1.03 | 1.99 |
| Gelatin Type | GLBG | GLBG |
| Oil Type | mineral oil | mineral oil |
| Sphere distribution type | 70/30 w/w 42.7/3.4 micron | 70/30 w/w 42.7/3.4 micron |

Example 6. Preparation of a System Using a Cellulose Textile Impregnated with a Formulation Comprising GLBG, PLGA, and Mineral Oil This example describes the composition and preparation of a fiber reinforced composite device comprising a cellulose hemostat textile as the fibrous component and a compliant formulation as the carrier for active ingredients, wherein the formulation comprises an oil, gelatin binder, and PLGA microspheres, and wherein the formulation is impregnated into the interstitial spaces of the fibrous textile. The cellulose fiber textile in this example was a commercially available hemostat known as SafeGauze® Hemostat™ Topical Hemostatic Dressing (AMD Medicom, Inc.). The SafeGauze cellulosic textile was observed to be a loosely woven mesh-like material, and it was also observed to have ample interstitial space for impregnation and filling with a compliant formulation like Formula #14B as described in Example 5.

In the first step, a single layer of SafeGauze textile was weighed into a tared beaker at 0.1240 g. The textile was determined to have unfolded rectangular dimensions of approximately 3.7 cm×1.7 cm. Next, 0.6 g of Formula #14B was added to one side of the textile to prepare a fiber-reinforced composite. Note that 0.6 g of the mixture is estimated to deliver about 177 mg bupivacaine to the tooth extraction socket as shown in Table 5-1. The mixture was spread with a spatula to form a bilayer comprising rectangular fibrous textile on one side and Formula #14B on the other. The long leg of the rectangular textile was then folded over and onto the Formula #14B mixture, and the assembly was gently kneaded to insure filling of the interstitial spaces of the textile on both sides of the fold. The resulting structure was nearly square (approximately 1.8 cm×1.7 cm), comprising an impregnated textile folded over and onto itself with both sides being cohesively held together by the Formula #14B impregnated therein.

In a separate demonstration, a similar bi-layer assembly was prepared, but this time a second textile layer was placed on top to create a tri-layer comprising an interlayer of the Formula #14B paste surrounded by two fibrous textile outer layers. The rectangular tri-layer was then folded 3 times over to successfully compress the Formula #14B paste into the interstitial spaces of the two textiles.

In another demonstration of the concept, the 1.7 cm×1.8 cm impregnated fiber textile that was prepared with a single SafeGauze textile was folded again a second time upon itself. For comparison, two neat SafeGauze textiles were held together and were then folded twice over one another. This type of folding procedure with two neat textiles was similar to that which would be used by a clinician in preparing the SafeGuaze hemostat for deployment into a tooth extraction socket. Importantly, each of the folded structures qualitatively appeared to occupy similar volumes. Thus, it follows that a single SafeGauze textile, impregnated with 0.6 g of a formulation to form a composite reinforced controlled release delivery system, could be readily deployed to fill a tooth extraction socket. In addition, it was also qualitatively observed that a single layer of the woven textile was more than sufficient to reinforce the Formula #14B formulation. This shows that it is possible to achieve composite-like reinforcement and to maintain mechanical integrity while simultaneously allowing for minimization of occupied volume. In addition, it is conceivable that volume could be further minimized by using lower density woven textiles, or by using random non-woven fibers if so desired. Moreover, improved kneading and pressing procedures could be employed to ensure that all of the non-occupied space within the porous textile becomes completely occupied by the amalgamized formulation.

Example 7. Hydrating a Cellulose Textile Impregnated with a Formulation Comprising GLBG, PLGA, and Mineral Oil The delivery system from Example 6, comprising a single textile impregnated with 0.6 g of Formula #14B, was folded over three times and was kneaded again to insure filling of the interstitial spaces with the Formula #14B mixture. The resulting composite was permitted to age for 1 month under ambient conditions. No changes in relative compliance or compressibility were observed after this period of aging.

In a separate test, a sample of the SafeGauze cellulose textile was observed to be soluble in water, and when it was placed in contact with water, it was noted to immediately consolidate into a sticky mass. Importantly however, the SafeGauze textile material was observed to remain intact within the composite after 1 month of being impregnated with Formula #14B, thereby indicating that the delivery system exhibits good shelf-stability.

In the next step, water was gradually added to hydrate the impregnated formulation, with the total water addition equating to a 2 to 1 ratio by weight of water to the GLBG component within the mixture. When water was initially placed on top of the folded textile, the delivery system did not wet immediately. However, after a short period of time, the entire matrix of textile and Formula #14B was observed to consolidate, and it was easily kneaded into various shapes. The delivery system exhibited high compliance and formability. This suggests that the impregnated textile could be added directly to the tooth extraction socket to hydrate in place, or it could alternatively be hydrated with water first, and then placed into the tooth extraction socket.

These results also show that it should be possible to also create different types of formulations for textile impregnation, including for example, formulas with a low melting wax, formulas with oil/wax blends, or even with lower Tg control-release polymers (e.g., lower than the Tg of the PLGA. Simple pressing processes can be used to pre-consolidate the textile with drug-loaded microspheres under ambient conditions. The ability to process under ambient or near-ambient conditions is particularly advantageous for situations where active ingredients are temperature sensitive.

Optionally, gelatin binder may be omitted from the formulation to thereby allow the cellulose textile component to become the binder for the PLGA microspheres when the delivery system is hydrated. Omission of the gelatin binder would also make more "room" for higher levels of bupivacaine-loaded PLGA microspheres, resulting in higher possible BUP delivery dosages in volume restricted applications.

Example 8. Formulations Comprising Wax, Oil, GLBG, and PLGA for Impregnating into a Cellulose Textile Use of a wax together with the oil can lead to a further way of modulating and controlling the rheological characteristics of a delivery system. Identifying a wax-type, determining the optimum weight ratio of wax to oil, and the optimum level of wax plus oil for textile-impregnation required consideration of several factors, including: 1) the compliance characteristics of the resulting formulation; 2) the cohesive strength of the formulation; 3) the hydration rate of the formulation upon exposure to fluids in vivo; 3) the time-dependent mechanical property characteristics of the formulation during the in vivo hydration process; 4) the conduciveness of the formulation to textile impregnation during manufacturing (e.g., solvent-free, minimal pressure, minimal temperature, textile wettability, etc.); 5) the optional capacity for the formulation to be pre-hydrated with water before insertion into the tooth extraction socket if so desired; and 6) the capacity for the formulation to be delivered with or without a fibrous textile reinforcing component.

The present example describes the preparation of a formulation for delivery as a reinforced composite. Part-1i describes the use of optional waxes as rheology modifiers for an oil carrier. Part-2 describes the first step in preparing formulations where the wax-modified oil carriers from Part-1 are mixed together with gelatin binder to form amalgamated dispersions. Part-3 describes the step of mixing and dispersing PLGA microspheres into the dispersions from Part-2 to yield formulations for either stand-alone deployment via in vivo-hydration, for deployment after hydration, or for use in forming fibrous reinforced composite devices. Part-4 describes the use of the formulation from Part-3 to prepare a reinforced composite delivery system for subsequent deployment. Finally, Part-5 illustrates the optional hydration and mastication of the hydrophobic device from Part-4 with water prior to deployment.

Part-1. Testing Wax/Oil Mixtures (83.33% Mineral Oil+16.67% Wax)

Sample 19-1: 5/1 Mineral Oil to Paraffin Wax 1 g of household paraffin wax (Gulf Wax, distributed by Royal Oak Enterprises, LLC, Roswell, GA) was weighed into an aluminum pan and then 5 g of Aldrich Heavy Weight Mineral Oil (CAS 8020-83-5) was added to yield a 5 to 1 ratio by weight of oil to wax. The mixture was heated on a hot plate for about 10-20 seconds at 175 degrees C. while stirring with a metal spatula until the wax was melted to yield a clear homogeneous solution. At that point, the solution was removed from the hot plate and was allowed to set idle under ambient conditions. Within 10 minutes, the solution became an opaque heterogenous dispersion of uniformly suspended wax crystallites. The mixture had the consistency of a soft spreadable gel.

Sample 19-2: 5/1 Mineral Oil to Beeswax 1 g bees wax (Aldrich, CAS 8012-89-3, cat. #243248, yellow, melt point 61-65 degrees C.) was mixed with 5 g mineral oil. Using the same procedure as described above, the solution forms a gel, but with slightly higher viscosity than Sample 19-1.

Sample 19-3: 5/1 mineral oil to carnauba wax no. 1 yellow 0.75 g carnauba wax (Aldrich, CAS 8015-86-9, cat. #243213, yellow, 82-86 degrees C. melt point) was mixed with 3.75 g mineral oil. Using the same procedure as described above, a gel formed, but with higher viscosity than both Samples 19-1 and 19-2. The Sample 19-3 solution was the fastest to recrystallize.

The viscosities of each of the sample gels can be modulated by changing the ratio of oil to wax. It is also possible to mix the waxes, or alternatively to mix pre-formed oil/wax gels of each type at different ratios. One advantage of mixing different wax-types together is that it can be possible to modulate viscosity with multiple combinations of waxes, while simultaneously maintaining a constant ratio of oil to total wax in the resulting gel. In this way, lower viscosities can be achieved without having to increase the level of oil. In addition, by mixing different wax types together, it can also be possible to minimize the percentage of oil or the percentage of any other type of low molecular weight component that is used in the mixture.

The gels of the types prepared in this example can be used as carrier components for binder materials that are used in preparing formulations analogous to Formula #14B from Example 5. In turn, vehicles incorporating gel carriers can be used in preparing composite reinforced delivery systems like those prepared in Example 6. In the next steps, select gels from Part-1 of the present example will be used to prepare formulations. The gels will be substituted for the equivalent weight of mineral oil that was used in preparing Formula #14B in Example 5.

Part 2. Mixing the Wax/Oil Cakes/Gels with Powdered Great Lakes Bovine Gelatin (GLBG)

Each of the wax/oil mixtures from Part 1 were separately melt-dispersed with GLBG over a hot plate for about 10 seconds (T=175 degrees C.) while stirring with a spatula. The dispersions were removed from heat and allowed to cool and solidify while continuing to stir under ambient conditions. The recrystallization rate was fastest for the highest melting point wax. The final mixed composition was 55.51% by weight MO, 11.10% by weight wax and 33.39% by weight GLBG.

Sample 23-1. 5 g Mineral Oil+1 g Paraffin Wax+3.007 g GLBG

Using the procedure described above, GLBG was added to the 19-1 gel from Part-1 to form sample 23-1. In mixing sample 19-1 with GLBG, the resulting 23-1 amalgam provides the same effective weight ratio of oil-phase to gelatin that was used in creating Formula #14B from Example 5, where 0.2039 g mineral oil was added to 0.1022 g GLBG. The weight ratio of oil phase (wax+oil) to gelatin was 1.995.

Sample 23-2. 5 g Mineral Oil+1 g Beeswax+3.007 g Great Lakes Bovine Gelatin

Using the procedure described above, GLBG was added to the 19-2 gel from Part-1 to form sample 23-2. In mixing sample 19-2 with GLBG, the resulting 23-2 amalgam provides the same effective weight ratio of oil-phase to gelatin that was used in creating Formula #14B from Example 5, where 0.2039 g mineral oil was added to 0.1022 g BG. The weight ratio of oil phase (wax+oil) to gelatin was 1.995.

Sample 23-3. (3.75 g MO+0.75 g Carnauba Wax)+2.255 g Great Lakes Bovine Gelatin.

Using the procedure described above, GLBG was added to the 19-3 gel from Part-1 to form sample 23-3. In mixing sample 19-3 with bovine gelatin, the resulting 23-3 amalgam provides the same effective weight ratio of oil-phase to gelatin that was used in creating Formula #14B from Example 5, where 0.2039 g mineral oil was added to 0.1022 g BG. The ratio of oil phase (wax+oil) to gelatin was 1.995.

Upon cooling, the 23-3 carnauba wax mixture formed a solid cake, whereas the 23-2 beeswax and 23-1 paraffin mixtures formed spreadable gels. The 23-2 beeswax mixture was also higher in viscosity than the 23-1 paraffin mixture.

Part 3. Adding PLGA Microspheres to the Wax/Oil Cakes/Dispersions

The amalgamated dispersions from Part-2 were mixed in a subsequent step with placebo PLGA microspheres to create formulations analogous to Formula #14B as described in Example 5. For the case of Formula #14B, the weight ratio of (wax+oil+gelatin) to PLGA microspheres was 0.573, and 0.6 g of the Formula #14B vehicle was impregnated into a single SafeGauze textile.

In view of Formula #14B, 0.3061 g each of samples of 23-2 and 23-3 were pre-weighed into separate 10 ml beakers. In a separate step, placebo PLGA microsphere mixtures were pre-weighed into two separate 10 ml beakers, with each containing 0.1327 g of 3.4-micron and 0.2990 g of 42.7-micron PLGA microspheres, a weight ratio of large to small microspheres of about 70/30. The pre-weighed microspheres were then added to the 10 ml beakers for mixing. The total weight of each formula when mixed was 0.7378 g, comprising 58.51% by weight of PLGA microspheres and 41.49% by weight of amalgamated dispersion (i.e., the combined wax+oil+GLBG mixtures from Part-2). Said another way, the composition of each formulation included 58.51% by weight PLGA microspheres, 4.61% by weight of wax, 23.03% by weight of mineral oil, and 13.85% by weight of GLBG.

Formula #14C

Sample 23-2, a soft gelatinous dispersion containing beeswax with MO and GLBG, was spatula-stirred and was weighed into a 10 ml beaker. The pre-weighed PLGA powder was added and the mixture was kneaded with a spatula. The resulting mix was a surprisingly tacky & soft, dough-like material, which indicates that the percentage of PLGA and hence the potential BUP dosage level could be increased if so desired. Based on the compliance characteristics of Formula #14C, the formulation could be directly deployed as a drug delivery device to hydrate in vivo, or it could be optionally hydrated for subsequent deployment. Also, based on the relative compliance characteristics of Formula #14C, the level of total wax plus oil could optionally be reduced to allow for an increase in PLGA and BUP dosage levels, or the ratio of mineral oil to beeswax could be reduced if so desired.

Formula #14D

Sample 23-3, a soft cake-like dispersion containing carnauba wax with mineral oil and GLBG, was kneaded into a thick paste, which was qualitatively higher in viscosity than its Sample 23-2 beeswax counterpart. The pre-weighed PLGA powders were added to sample 23-3. More mechanical energy was required to knead the material, and the resultant mixture had more wax-like consistency than Sample 14-C. It was qualitatively higher in relative viscosity, yet it displayed good compressibility. Like its Sample 14C counterpart, the Sample 14D formulation could be optionally deployed for in vivo hydration, or it could be optionally hydrated for subsequent deployment.

Part-4. Impregnating Cellulose Textile with Vehicles from Part-3

There was no qualitative change in the viscosity or hardness of the Samples 14C and 14D after sitting for 24 hours under ambient conditions. Cellulose textiles were separately weighed for each formula mixture (SafeGauze, weight=0.1251 g). Next, 0.625 g of each mixture was separately added to ½ the area of each textile's rectangular surface. Each textile was then folded over its respective vehicle mixture, and the composites were gently kneaded by hand to achieve textile impregnation. Squeeze-out material was removed by cutting with a spatula. Each impregnated textile was then re-opened, and additional vehicle was added for the purpose of exceeding the target-weight of 0.605 g. The total weight of each vehicle at this point was 0.621 g. Each textile was folded over again, and then was gently kneaded for a second time. The excess squeeze-out was cut away with a spatula until the 0.605 g vehicle target weight was achieved. The composites were then stored under ambient conditions for future hydration.

Part-5. Hydration of the Impregnated Cellulose Textiles from Part-4

After a little more than one month of storage under ambient conditions, the textiles that were impregnated with the formulations of Samples 14C and 14D were observed to still be flexible and compliant, and they had remained qualitatively unchanged. The impregnated formulas contained 13.85% by weight of GLBG, which equates to 0.0831 g of GLBG per 0.6 g, where 0.6 g represents the approximate weight of a formula that is impregnated into each of the textiles. Note that the net weight of the impregnated textiles was approximately 0.75 g. In keeping with the addition of water at a 2/1 weight ratio of water to gelatin that was used in the prior hydration of the Formula #14B-impregnated textile in Example 7, 0.1662 g of water was separately added with a syringe to small weighing boats with each boat containing one of the impregnated textiles. The formulations were masticated by hand to yield tacky, highly compliant, dough-like materials. The effective water to device weight ratio was only about 0.2 parts water per unit weight of the device. Neither of these devices exhibited oil-phase exudation as the hydrophobic phase remained emulsified and stable within each of the hydrated devices.

In a second part of the experiment, 0.083 g of additional water was added to the already hydrated Formula #14D impregnated delivery system, bringing the water to gelatin weight ratio to approximately 3/1 (w/w), and the effective water to device weight ratio to approximately 0.33/1 (w/w). The composite was masticated by hand, and the water was successfully entrapped within the composite with no evidence of oil or water phase separation. During mastication, the mixture was tacky and highly compliant, and its compliance characteristics were qualitatively analogous to those of neat Surgifoam when Surgifoam is mixed with 3 parts water by weight to 1 part Surgifoam by weight.

Thus, formulations compromising hydrophobic components can be made to have tactile characteristics that are equivalent to those of other commercially acceptable devices. Moreover, equivalent characteristics can be achieved with significantly less water per unit weight of device. Aside from having the benefit of being usable with less volume-occupying water in an already volume-restricted application, this water-absorbing feature also offers the opportunity for controlled dilution of the formulation, if so desired. For example, if the formulation is manufactured with an upper-limit dosage of active bupivacaine ingredients, it can then be diluted to reduce dosages to the degree necessary for the patient, simply by adding more water to a single type of manufactured unit. Aside from the manufacturing advantages, such as minimizing product types and inventory by manufacturing a single type of formulation, the clinician can simply control dosages by having the choice of either employing maximum dosage via in vivo hydration of the delivery system within the tooth extraction socket, or by diluting the dose via addition to the formulation of volume-occupying water to a prescribed level, followed by masticating and cutting to the necessary weight for reaching the prescribed dosage target, while simultaneously maintaining an adequate volume-fill factor.

In yet another step, the hydrated Formula #14D impregnated device (3/1 sample) was mixed with yet an additional 0.0831 g water, bringing the water to gelatin weight ratio to 4/1 (w/w), and the effective water to delivery system weight ratio to approximately 0.44/1. The formulation was again masticated by hand, and the water was successfully entrapped in the formulation with no evidence of oil or water phase separation. During mastication, the mixture remained tacky and highly compliant.

Thus, formulations compromising hydrophobic components have the surprising capacity to absorb hydrophilic fluids, like water, without undergoing macroscopic phase separation. Moreover, unlike the formulations comprising hydrophilic components as described in Example 2, the formulations shown in this example are erosion-resistant when they are submerged in water under static conditions, as demonstrated in Examples 11 and 12 below.

The serendipitous discovery of formulations that resist erosion while simultaneously allowing for water absorption is both fortuitous and desirable. This dual capability is what facilitates in vivo hydration of the formulation on the one hand, while simultaneously limiting erosion and macroscopic deterioration on the other. The hydration of the formulation allows for the diffusive ingress of water with the simultaneous diffusive egress of molecular-level ingredients, like BUP, to the surrounding tissues. The fact that this happens without macroscopic phase separation and without appreciable erosive-deterioration of the formulation itself is not only unexpected, it is desirable and beneficial from the standpoint that the viability of the device relies on its ability to maintain its long-term in vivo cohesive integrity, and on its ability to simultaneously facilitate the sustained release of active ingredients. This surprising dual capability for water-absorption and static erosion resistance is demonstrated in Examples 12 and 13 below using in-vitro water-soak experiments together with UV spectroscopy.

Example 9. Drug Delivery Devices Comprising Cellulose Materials Impregnated with Formulations Compromising Hydrophobic Components for In Vivo Applications Part-1. Preparation of the Formulation for a Drug Delivery Device Using the procedures outlined in Example 8, a version of the Formula #14C was prepared for textile impregnation studies, and for evaluation during an in vivo porcine study to test the physical and handling efficacy of the delivery device. In this example, the Formula #14C was re-designated as Formula 14C-2 owing to the use of different lots of PLGA particles separately prepared by SWRI and use of light weight mineral oil in place of heavy weight mineral oil.

Materials.

The materials used for the hydrophobic formula preparation included the following:
1. Mineral oil (MO), white, light, Aldrich Chemical, cat. #33,077-9, CAS 8042-47-5;
2. Beeswax (BW), Aldrich, CAS 8012-89-3, cat. #243248, yellow, melt point 61-65° C.;
3. Bovine gelatin (GLBG) powder, Great Lakes Gelatin Company, Grayslake, IL, type B (bovine), unflavored Kosher beef hide, 88-92% protein, US Pharmacopeia consumer grade;
4. Poly(lactic-co-glycolic acid) microspheres (PLGA), Southwest Research Institute (SWRI), Resomer RG504 (Evonik 50/50 grade), spray dried from a solvent solution, sample designation NB:18-0202-015-15 & -16, particle size (D50)=5-micron, surface area 1.36 $m^2/g$;
5. Poly(lactic-co-glycolic acid) microspheres (PLGA), Southwest Research Institute (SWRI), Resomer RG504 (Evonik 50/50 grade), dissolved with solvent into solution, emulsified in a carrier, solvent extracted and dried, sample designation NB:18-0202-015-14 & -17, particle size (D50)= 41-micron, surface area 0.153 $m^2/g$.

Formula 14C-2 Formulation Preparation Procedure and Composition.

Step 1.

The 19-2 MO/BW premix (83.33% by weight mineral oil+16.67% by weight beeswax) as described in Example 8 was prepared. Solid beeswax and liquid mineral oil were weighed and placed together inside of tared aluminum weighing pans. The mixture was heated over a hot plate having a surface temperature of 175° C. while stirring with a metal spatula until the wax was melted to yield a yellowish homogeneous solution. Mix time was about 30 to 45 seconds until the wax was melted. At that point, the solution was removed from the hot plate and was allowed to set idle under ambient conditions. Within 10 minutes, the solution became an opaque heterogenous dispersion of uniformly suspended wax micro-crystallites. The mixture had the consistency of a soft spreadable gel.

Step 2.

The 23-2 MO/BW/GLBG suspension (55.51% by weight MO+11.10% by weight wax+33.39% by weight GLBG), referred to herein as the binder phase, was prepared using procedures similar to those as described in Example 8. GLBG powder was separately weighed and was then spatula-stirred under ambient conditions into an aliquot of the 19-2 gel from step 1. The suspension was then heated over a hot plate in an aluminum pan while spatula stirring for approximately 30 seconds using a hot plate surface temperature of 175° C. until the micro-crystallites of the gel were melted. When the gel phase of the suspension was melted, the pan was removed from the hot plate, and the dispersion was continuously spatula-stirred under ambient conditions until the gel phase (oil+wax) recrystallized to yield a homogeneous suspension of GLBG powder within a continuous gel matrix phase. This became the binder phase vehicle for subsequent dispersion of PLGA microspheres, which were non-drug placebo types in this example.

Step 3.

The Formula 14C-2 formulation was prepared by dispersing placebo PLGA microspheres into the 23-2 gel matrix phase from step 2 using procedures similar to those outlined in Example 8. The target ratio of the two PLGA particle size distributions was approximately 70/30 w/w 41-micron and 5-micron particles. In the first step, the 5-micron particles were weighed into a tared plastic beaker, to which the requisite weight of the 41-micron particles was then added. The two particle size distributions were dry-mixed using a spatula. In the next step, the 23-2 gel matrix phase dispersion from step 2 above was added to the beaker containing the dry PLGA particles, and the mixture was masticated using a spatula until a homogeneous dispersion was created. The final composition contained 41.49% by weight binder (i.e., mineral oil, beeswax, bovine gelatin) and 58.51% by weight of the PLGA microspheres. The entirety of the Formula 14C-2 formulation on a weight % basis is provided in Table 9-1.

TABLE 9-1

| Final 14C-2 Mixture Composition | Wt. % |
|---|---|
| Mineral Oil | 23.03% |
| Beeswax | 4.61% |
| Bovine Gelatin | 13.85% |
| 5 um PLGA microspheres | 17.99% |
| 41 um PLGA microspheres | 40.53% |
| TOTAL | 100.00% |

Part-2. Preparation of Impregnated Fiber-Reinforced Composites for Use as Drug Delivery Devices.

Formulations comprising hydrophobic components, such as the formulation embodied in Formula 14C-2 in Example 9 or others as described in Examples 3 through 8, can be formulated for in vivo use in at least four different ways, including for example: option-1) as a stand-alone device without fibrous reinforcement, where the formulation is masticated with water-based fluids, such as saline solution, plasma, etc., before insertion into a tooth extraction socket; option-2) as a stand-alone device without fibrous reinforcement, where the device is not masticated with a fluid, but instead is allowed to hydrate in vivo via static diffusion processes after being placed within the tooth extraction socket; option-3) as a device wherein the formulation is first reinforced with fibrous material, such as knitted, woven or non-woven cellulose fibers or random cellulose fibers, and then is masticated with water-based fluids before insertion into a tooth extraction socket; and option-4) as a device wherein the formulation is reinforced with fibrous material and is not masticated with a fluid, but instead is allowed to hydrate in vivo via static diffusion processes after being placed within the tooth extraction socket.

Any one of these four options could be used for drug delivery. Option-4 is of particular interest for several reasons pertaining to end use convenience and efficacy. For example, there is a desire among clinicians to have a device that minimizes the need for time-consuming processes such as mastication, or other forms of special handling for deployment. In such an instance, it would be necessary for the device to exhibit sufficient compliance for moldability without having to mix with water-based fluids, while simultaneously having the ability to retain its cohesive properties during handling, during deployment, and during end use after deployment.

A stand-alone option-2 version could be formulated to also achieve this objective since the formulations comprising hydrophobic components can be made sufficiently compliant without the need for mastication with fluids. However, there are several added advantages of using option-4 that not only help to meet the handleability needs of clinicians, but also provide synergistic performance characteristics that satisfy other clinical needs. For example, by reinforcing the formulation with fibrous material, a composite is created wherein the formulation is mechanically reinforced, thus facilitating the optional use of a formulation that is formulated with less binder phase and with more PLGA particles than would otherwise be possible without fiber reinforcement. This helps to satisfy the need for higher drug dosage deployment when so desired, without experiencing the deleterious effects on cohesive strength that would otherwise accompany any diminution in the percentage of binder. The reduction in the binder results in a decrease in cohesive strength, which can be more than compensated for by the use of fiber reinforcement. Fiber reinforcement can also facilitate the use of higher oil levels in the formulation. Hence the use of lower viscosity formulas for ease of manufacturing and for ease of deployment in vivo can be achieved without experiencing the deleterious effects on cohesive strength that would otherwise accompany any reduction in the higher molecular weight components of the binder phase.

With these types of fiber-related factors in mind, four distinctly different cellulose-based hemostats were chosen for comparative use in this example. They were chosen so as to not only demonstrate the flexibility in choice of applicable materials, but to also demonstrate the importance of the impact of the fiber member on handling and efficacy during end use as demonstrated during an in vivo porcine study as described in part-3 of Example 9.

The fibrous products that were used in this example are described in Table 9-2. The sample of SafeGauze was in the form of a rectangular textile and served as a geometric template for fashioning the other comparative fibrous materials. Each of the comparative fibrous materials were purposely pre-cut to have rectangular dimensions similar to those of the SafeGauze product, and then the samples were weighed to determine the relative differences in bulk density among the product types. These data are provided in Table 9-3.

Aside from the differences in bulk densities and stiffness, the commercial hemostats were also chosen for their representative differences in wetting and solubility characteristics. For example, the SafeGauze product is known to dissolve into a gelatinous material when it encounters water or body fluids. By contrast, the Surgicel Original and Nu-Knit products are known to react and transform much more slowly than SafeGauze. This type of difference in solubility, wetting, and diffusion characteristics is known by those skilled in the art to be a function of several chemical and physical factors, including for example, the degree of oxidation of the cellulose material, the molecular weight distribution of the cellulose material, the fiber bundle densities, the knit densities, and the total fiber surface area per unit volume.

These types of differences can be important for the end use in that the mechanical properties and adhesion characteristics can be influenced both during initial deployment of the device, and during protracted use under static conditions in vivo. For example, a more water-soluble fiber might facilitate faster initial wetting of the tissues within the socket cavity, but if the fibrous structure dissolves too quickly, the composite's mechanical properties, such as erosion resistance, might change too quickly as a function of time under static conditions. Conversely, a less soluble fibrous member might help the composite to retain its mechanical characteristics for longer periods of time under static conditions, but possibly at the expense of less than optimal handling characteristics during initial deployment of the device. For example, if the fibrous material is too stiff, owing to a high knit density or to a slow reaction with fluids, the initial handling characteristics and initial cavity wetting characteristics can be less than optimal. If the fibrous member is too slow to react with body fluids, initial adhesion characteristics might also be less than optimal.

As one aspect of this invention, it can be appreciated that the choice of the fibrous member for the composite delivery device is an important one, and that the material can be tuned to the application by controlling the degree of oxidation which affects solubility, by controlling the molecular weight of the cellulose, by controlling the fiber surface area per unit volume, by controlling the fiber bundle density, by controlling the bulk knit density, etc. Aside from these tunable factors, it is also possible to use a mixture of fibrous member types. For example, the fibrous composite could be comprised of both a relatively fast-dissolving type of fiber member, such as SafeGauze, and a relatively slow-dissolving member, such as Surgicel Original. Use of multiple fiber types can impart combinations of desirable characteristics, including faster initial wetting and better initial adhesion during deployment from the more soluble fiber member, and longer term composite integrity from the less soluble fiber member during the in vivo use period associated with dynamic changes in properties owing to inter-diffusion of tooth extraction socket fluids with the device.

With these concepts in mind, the relative differences among the commercial hemostats as qualitatively listed in Table 9-4 were strategically used to conceive of and to create 10 sets of composites for qualitative evaluation during in vivo experiments. The resulting devices and their qualitative characteristics are described in Table 9-5.

TABLE 9-2

Comparative commercial cellulose fiber hemostats.

| Commercial Hemostat Tradename | Source | Form |
|---|---|---|
| SafeGauze ® Hemostat ™ Topical Hemostatic Dressing | AMD Medicom, Inc. | Woven fibrous cellulosic textile comprised from yarns of carboxymethyl cellulose sodium fibers; measured dimensions ca. 1.8 × 3.8 cm. |
| SURGICEL ® Original Absorbable Topical Hemostat | ETHICON ®, division of Johnson and Johnson | Low knit density knitted fibrous cellulosic textile comprised from oxidized regenerated cellulose yarns. |
| SURGICEL ® NU-KNIT ® Absorbable Hemostat | ETHICON ®, division of Johnson and Johnson | High knit density knitted fibrous cellulosic textile comprised from oxidized regenerated cellulose yarns. |
| SURGICEL ® FIBRILLAR ™ Absorbable Hemostat | ETHICON ®, division of Johnson and Johnson | Layered structure of lightweight random fibrous bundles comprised from oxidized regenerated cellulose fibers. |
| SURGICEL ® SNoW ™ Absorbable Hemostat | ETHICON ®, division of Johnson and Johnson | Structured non-woven fabric, needle punched with interlocking fibers comprised from oxidized regenerated cellulose fibers. |

TABLE 9-3

Measured weights of fibrous products that were first pre-cut to dimensions similar to those of the as-received SafeGauze textiles (approximately 1.8 cm × 3.8 cm). These weights are relative indications of the bulk densities of the materials. Note that the relative densities of these reinforcing components scale with the mass of fiber per topical square centimeter, which can be calculated by dividing the average weight by 6.84 $cm^2$.

| Sample | Average Weight (g) | Number of samples measured | Standard Deviation | Mass fiber per topical $cm^2$ | Notes |
|---|---|---|---|---|---|
| SafeGauz as received | 0.115 | 7 | 0.011 | 0.0168 | As received, woven textile |

TABLE 9-3-continued

Measured weights of fibrous products that were first pre-cut to dimensions similar to those of the as-received SafeGauze textiles (approximately 1.8 cm × 3.8 cm). These weights are relative indications of the bulk densities of the materials. Note that the relative densities of these reinforcing components scale with the mass of fiber per topical square centimeter, which can be calculated by dividing the average weight by 6.84 cm$^2$.

| Sample | Average Weight (g) | Number of samples measured | Standard Deviation | Mass fiber per topical cm$^2$ | Notes |
|---|---|---|---|---|---|
| Surgicel Original | 0.047 | 10 | 0.001 | 0.00687 | Knitted textile, pre-cut to the x-y dimensions of as-received SafeGauze. |
| Nu-Knit | 0.124 | 8 | 0.002 | 0.0181 | Knitted textile, pre-cut to the x-y dimensions of as-received SafeGauze. |
| Fibrillar | 0.115 | 9 | 0.009 | 0.0168 | Random non-woven fiber pack, pre-cut to the x-y dimensions of as-received SafeGauze, and then cut approximately in half along the z-axis (thickness) to provide a bulk weight similar to that of SafeGauze. |

20

TABLE 9-4

Summary of relative differences among the fiber types after pre-cutting to the same x-y dimensions of the as-received SafeGauze product.

| Sample | Qualitative differences |
|---|---|
| SafeGauze as-received (SG) | Used as the qualitative standard in these comparisons; exhibits relatively high solubility and gel formation almost immediately upon contact with water (within 5 minutes). |
| Surgicel Original (SO) | Knit structure slightly more open than woven SafeGauze; not as stiff as SafeGauze; approximately ⅓ the bulk density of SafeGauze; significantly less water sensitive than SafeGauze upon initial contact with water. Exhibits slight shrinkage within 5 minutes but does not dissolve. Remains intact for 24 hours when coated with drops of water. |
| Nu-Knit (NK) | Significantly tighter knit structure than Surgicel Original despite its similar bulk density, and higher in stiffness than both SafeGauze and Surgicel Original. The tighter knit structure at similar bulk density to Surgical Original is an indicator of a difference in fiber bundle structure and/or in net surface area per unit volume of sample. The water sensitivity is similar to Surgicel Original (less sensitive than SafeGauze). |
| Fibrillar (FIB) | Non-woven random fiber pack; significantly less contiguous interstitial voids than either of the other woven structures; more resistant to water than SafeGauze (i.e., less susceptible to initial water diffusion than SG), and somewhat more water sensitive than SO and NK. |

TABLE 9-5

Summary of devices that were made, preparation methods, and their qualitative characteristics both during and after their preparation. Except where noted otherwise, textiles were impregnated with the 14C-2 hydrophobic formulation using procedures similar to those outlined in Example 8. Each device had final x-y dimensions of approximately 1.8 × 1.9 cm.

| Sample Set, Device Designation, weights of device members | Description of device construction |
|---|---|
| Set-1<br>1A textile = 0.1214 g.; 14C-2 = 0.6472<br>1B textile = 0.1209 g; 14C-2 = 0.6248 g<br>1C textile = 0.1032 g; 14C-2 = 0.6187 g<br>1D textile = 0.1128 g; 14C-2 = 0.6409 g<br>1E textile = 0.1192 g; 14C-2 = 0.6499 g | SafeGauze rectangular textile (ca. 1.8 × 3.8 cm) folded in half over approximately 0.60 to 0.65 g 14C-2; final x-y dimensions = approximately 1.8 cm × 1.9 cm |
| Set-2<br>2A - textile wt. = 0.4093; 14C-2 = 0.6495 g; 2nd textile wt. = 0.0488 g<br>2B - textile wt. = 0.0474 g; 14C-2 = 0.6408 g; 2nd textile wt. = 0.0487 g<br>2C - textile wt. = 0.0437 g; 14C-2 = 0.6208 g; 2nd textile wt. = 0.0502 g<br>2D - textile wt. = 0.0447 g; 14C-2 = 0.6147 g; 2nd textile wt. = 0.0537 g | Surgicel Original (SO) textile (when cut to same dimensions as SafeGauze and when folded in half over approximately 0.60 to 0.65 g 14C-2) does not have the same interstitial-space capacity to absorb the 14C-2 formula as SafeGauze, nor does it have the same mechanical integrity (the textile is ⅓ the weight with a slightly more open knit structure). For this reason, a second textile was used in the construction of this set. A pre-cut SO |

TABLE 9-5-continued

Summary of devices that were made, preparation methods, and their qualitative characteristics both during and after their preparation. Except where noted otherwise, textiles were impregnated with the 14C-2 hydrophobic formulation using procedures similar to those outlined in Example 8. Each device had final x-y dimensions of approximately 1.8 × 1.9 cm.

| Sample Set, Device Designation, weights of device members | Description of device construction |
|---|---|
| 2E - textile wt. = 0.0443 g; 14C-2 = 0.6603 g; 2nd textile = 0.0485 g | textile was coated, folded on itself, and finger-pressed to get interstitial space impregnation. A second SO textile was then folded over the first folded component members of the construction in the cross orthogonal direction, and the composite was finger-pressed to achieve formula impregnation of the outer SO textile member B, which had then encapsulated the first folded member A. The final folded construction (along the z-axis) = [impregnated SO textile layer B orthogonally positioned to A]/[impregnated SO textile layer A]/[impregnated SO textile layer A]/[impregnated textile layer B orthogonally positioned to A]. Note that the use of two SO textiles still results in a composite with a lower weight percent of fiber than that of set-1 which was made with SG. Despite this difference, the set-2 composites were qualitatively similar in stiffness to the set-1 composites. |
| Set-3<br>3A - textile wt. = 0.1312 g; 14C-2 = 0.6115 g<br>3B - textile wt. = 0.1307 g; 14 C-2 = 0.6551 g<br>3C - textile wt. = 0.1325 g; 14C-2 = 0.06415 g<br>3D - textile wt. = 0.1331 g; 14C-2 = 0.6297 g<br>3E - textile wt. = 0.1328 g; 14C-2 = 0.6336 g | Completely analogous to set 1, but with NuKnit (NK) textile (cut to same dimensions as SG) folded in half and over approximately 0.60 to 0.65 g 14C-2. Note that the rough side of the NK textile was coated before it was folded and impregnated by finger-pressing. This composite was qualitatively higher in stiffness than the comparable composite made with SG (set-1). |
| Set-4<br>4A - fiber wt. = 0.1037 g; 14C-2 = 0.5991 g<br>4B - fiber wt. = 0.1187 g; 14C-2 = 0.6458 g<br>4C - fiber wt. = 0.1168 g; 14C-2 = 0.5990 g<br>4D - textile wt. = 0.1208 g; 14C-2 = 0.6772 g<br>4E - textile wt. = 0.1201 g; 14C-2 = 0.6038 g | Fibrillar random fiber patch was cut to the same x-y dimensions as SafeGauze textile, and it was then cut in the near-center of the z-axis to achieve similar weight. The rectangular slab was folded over onto itself and pressed by hand to impregnate the higher surface area random fibers. This resulted in a less homogeneous macro-structure when compared to the other sets, where the interior of the composite sandwich was higher in 14C-2 concentration, and the exterior of the composite was higher in dry fiber concentration. Thus, although the bulk weight of set-4 was similar to set-1 (also with similar wt. percentages of the device members), set-4 was qualitatively, less malleable, higher in stiffness, and less tacky than set-1. |
| Set-5<br>5A - 0.78 g<br>5B = 0.8077 g<br>5C = 0.8304 g<br>5D = 0.8167 g<br>5E = 0.8593 g | Set-5 was a composite of 14C-2 and Fibrillar cellulose fibers that were homogeneously blended within the 14C-2 hydrophobic formula (ca. 97/3 w/w 14C-2/fiber). In preparing set-5, the first experiment involved taking 0.7067 g 14C-2 + 0.0234 of pre-torn fiber; and masticating it in a plastic weighing boat with a spatula to final wt. = 0.6956 g. The ratio of Fibrillar/14C-2 = 0.0331; and the compliance of this random composite sample was slightly higher than the SafeGauze 1A sample. Thus, a decision was made to use slightly more Fibrillar to achieve higher modulus. In order to accomplish this, 3.215 g of 14C-2 was initially placed into a 15 ml HDPE beaker, and was spatula-masticated with 0.15 g pre-torn Fibrillar fibers (Fibrillar/14C-2 = 0.0466). Mastication of this larger quantity led to a drier blend, so more 14C-2 was added (.5549 g) to bring the ratio of Fibrillar to 14C-2 = 0.03978. With continued mastication, it was still somewhat dry, so an additional 0.971 g of 14C-2 was back-added (4.7409 total), bringing the Fibrillar/14C-2 ratio = 0.0316. The process of stirring with mastication continued to tear the fiber bundles and to produce enough shear to increase fiber surface area, which further increased viscosity. However, as opposed to adding more 14C-2, the composite was cut into approximately 0.8 g aliquots. Each aliquot was |

TABLE 9-5-continued

Summary of devices that were made, preparation methods, and their qualitative characteristics both during and after their preparation. Except where noted otherwise, textiles were impregnated with the 14C-2 hydrophobic formulation using procedures similar to those outlined in Example 8. Each device had final x-y dimensions of approximately 1.8 × 1.9 cm.

| Sample Set, Device Designation, weights of device members | Description of device construction |
|---|---|
| | comprised of approximately 3% fiber, and 87% 14C-2. Thus, a 0.7 to 0.8 g aliquot contained about 0.6 to 0.7 g of 14C-2. |
| Set-6<br>6A - SafeGauze textile wt. = 0.0906 g; 14C-2 = 0.6812 g; NuKnit textile = 0.0518 g<br>6B - SafeGauze textile wt. = 0.1180 g; 14C-2 = 0.6638 g; NuKnit textile = 0.0536 g<br>6C - SafeGauze textile wt. = 0.0902 g; 14C-2 = 0.6423 g; NuKnit textile = 0.0457 g<br>6D - SafeGauze textile wt. = 0.1200 g; 14C-2 = 0.6528 g; NuKnit textile = 0.0511 g<br>6E - SafeGauze textile wt. = 0.1049 g; 14C-2 = 0.6299 g; NuKnit textile = 0.0545 g | In preparing the set-6 composites, the NuKnit rectangular samples, originally cut to the size of SafeGauze rectangles, were purposely cut in half (1.9 cm × 1.8 cm), trimmed, and weighed. SafeGauze rectangular samples were evenly coated with approximately 0.6 to 0.7 g 14C-2. The trimmed NuKnit textile was placed on top of a ½-section of a fully coated SafeGauze textile. The other half of the coated SafeGauze textile was folded over and on top of the NuKnit textile. The sample was compressed lightly by hand to assist in impregnating the members. The resulting construction as dissected through the z-axis = partially impregnated SafeGauze/14C-2/partially impregnated NuKnit/14C-2/partially impregnated SafeGauze. In spite of purposely reducing the relative weight of the NuKnit member, the resulting construction was qualitatively stiffer than sets 1 and 3. This was in part due to the relatively high surface area of the NuKnit member, which resulted in more 14C-2 absorbance by the NuKnit center member than the SafeGauze outer-layer members. Consequently, the z-axis distribution of 14C-2 was more heterogeneous than that of sets 1, 2, and 3. The purpose of this multi-membered composite (like that of set-7) was to provide an outer layer of water-sensitive cellulose for the purpose of imparting fast tissue wetting and tissue adhesion during deployment. The purpose of the less water-sensitive inner member was to provide the device with protracted reinforcement for improved cohesive strength throughout the duration of its static dwelling within the tooth extraction socket cavity. |
| Set-7<br>7A - SafeGauze textile wt. = 0.1039 g; 14C-2 wt. = 0.6568 g; SO textile wt. = 0.0253 g<br>7B - SafeGauze textile wt. = 0.1068 g; 14C-2 wt. = 0.6523 g; SO textile wt. = 0.0267 g<br>7C - SafeGauze textile wt. = 0.1285 g; 14C-2 wt. = 0.6525 g; SO textile wt. = 0.0268 g<br>7D - SafeGauze textile wt. = 0.1200 g; 14C-2 wt. = 0.6625 g; SO textile wt. = 0.0265 g | Surgicel Original (SO) rectangular samples, originally cut to the size of SafeGauze rectangles, were cut in half (squares), and weighed. SafeGauze rectangular samples were evenly coated with approximately 0.6 to 0.7 g 14C-2. The SO textile was placed on top of a ½ section of coated SafeGauze textile. The other half of the coated SafeGauze textile was folded over and on top of the SO textile. The sample was compressed lightly by hand to assist in impregnating the members. The resulting construction as dissected through the z-axis: partially impregnated SafeGauze/14C-2/partially impregnated SO/14C-2/partially impregnated SafeGauze. The more open knit structure of the SO resulted in better 14C-2 homogeneity along the z-axis than that which was achieved in the comparable composite made with NuKnit (set-6). Consequently, this multi-member fibrous composite was less stiff than set-6, and only slightly stiffer than sets 1 and 2. The purpose of this multi-membered composite (like that of set-6) was to provide an outer layer of water-sensitive cellulose for the purpose of imparting fast tissue wetting and adhesion during deployment. The purpose of the less water-sensitive inner member was to provide the device with protracted reinforcement for improved cohesive strength throughout the duration of its static dwelling within the tooth socket cavity. |
| Set-8<br>8A - SafeGauze wt. = 0.0521 g; 14C-2 wt. = 0.6226 g; NuKnit wt. = 0.0611 g<br>8B - SafeGauze wt. = 0.0505 g; 14C-2 wt. = 0.6032 | This construction was a bi-layer with 0.6 g to 0.7 g of 14C-2 interlayer material. Layer-1 was a cut sample of SafeGauze (½ of a SafeGauze rectangle, 1.9 cm × 1.8 cm), and layer-2 was a |

TABLE 9-5-continued

Summary of devices that were made, preparation methods, and their qualitative characteristics both during and after their preparation. Except where noted otherwise, textiles were impregnated with the 14C-2 hydrophobic formulation using procedures similar to those outlined in Example 8. Each device had final x-y dimensions of approximately 1.8 × 1.9 cm.

| Sample Set, Device Designation, weights of device members | Description of device construction |
|---|---|
| g; NuKnit wt. = 0.0558 g<br>8C - SafeGauze wt. = 0.5099 g; 14C-2 wt. = 0.6208 g; NuKnit wt. = 0.0604 g<br>8D - SafeGauze wt. = 0.0517 g; 14C-2 wt. = 0.6678 g; NuKnit wt. = 0.0618 g | NuKnit layer cut to the same dimensions as ½ of the as-received SafeGauze textile. The 14C-2 interlayer was lightly pressed by hand to impregnate the members. During initial evaluation, this construction was targeted to be deployed with the SafeGauze side down towards the tooth extraction socket tissue. The top side (NuKnit) was intended to fold into itself as the device was deployed into the tooth extraction socket. The top side of the device with NuKnit was marked with a black dot. Note that this device could optionally be deployed in the opposite direction. However, the original intent was to provide better initial tissue wetting via use of a more water-sensitive outside member (SG). In this sense, set-8 represents a similar but subtly different manifestation of the set-6 construction. |
| Set-9<br>9A - SafeGauze wt. = 0.0612 g; 14C-2 wt. = 0.06585 g; Surgicel Original wt. = 0.0455 g<br>9B - SafeGauze wt. = 0.0672 g; 14C-2 wt. = 0.6238 g; Surgicel Original wt. = 0.0541 g<br>9C - SafeGauze wt. = 0.0617 g; 14C-2 wt. = 0.6225 g; Surgicel Original wt. = 0.0507 g<br>9D - SafeGauze wt. = 0.0540 g; 14C-2 wt. = 0.6614 g; Surgicel Original wt. = 0.0473 g | This set was completely analogous to set-8 with one exception: Surgicel Original was used as layer-2, and instead of cutting it to the same square shape as ½ the as-received SafeGauze rectangle, a full rectangular piece of SO was used, and it was folded in half to give it the square shape of layer-1 (this was done because SO is only ⅓ the weight of SafeGauze). The final construction as dissected along the z-axis: SafeGauze/14C-2/SO. This construction was intended to be initially evaluated by deploying it with the SafeGauze side down towards the tooth extraction socket tissue. The top side (SO) was thereby intended to fold into itself as the device was deployed into the tooth extraction socket. The top side of the composite with SO was marked with a black dot. Note that this device could optionally be deployed in the opposite direction. However, the original intent was to provide better initial tissue wetting via use of a more water-sensitive outside member (SG). In this sense, set-9 represents a similar but subtly different manifestation of the set-7 construction. |
| Set-10<br>10A- Surgicel Original textile wt. = 0.0490 g; 14C-2 wt. = 0.6072 g<br>10B - Surgicel Original textile wt. = 0.0483 g; 14C-2 wt. = 0.6248 g<br>10C - Surgicel Original textile wt. = 0.0540 g; 14C-2 wt. = 0.6436 g<br>10D- Surgicel Original textile wt. = 0.0515 g; 14C-2 wt. = 0.6115 g | This set was analogous to set-2, which was made with two rectangular members of Surgicel Original. However, in this case (set-10), only one rectangular member of SO was used instead of two. In this sense, set-10 was the analog of sets 1 and 3, each having been prepared with 1 rectangular textile member of SG and NK, respectively. The SO textile was cut to the same rectangular dimensions as SafeGauze, and it was folded in half over approximately 0.60 to 0.65 g 14C-2. Given the lower density of SO, the construction was substantially lower in stiffness than sets 1, 2, and 3 (set-2 having been comprised of two SO rectangular members instead of one). |

Part-3. In Vivo Evaluations of the Impregnated Fibrous Composites for Use as a Drug Delivery Device.

Description of the Test Environment and Experimental Details for the In Vivo Porcine Trial.

The device samples described in Table 9-5 were used for this study. Qualitative notes and observations are provided in Table 9-6. Importantly, although some of the devices have preferable attributes that differentiate them from others, most of the device constructions exhibited acceptable utility for the application, and many of the qualitative differences were consistent with the previously noted qualitative differences among the devices' fibrous members (Tables 9-3 and 9-4) and among the devices themselves (Table 9-5). These results show that despite the identical usage of the Formula 14C-2 formulation, the macrostructural differences associated with the different fiber-types and construction methods led to large differences in performance characteristics. From handling and initial deployment perspectives, set-2 made with SO, set-3 made with NK, and set-7 made with SG and SO mixed textile types exhibited a good overall balance of acceptable performance characteristics. Although the random fiber set-4 performed well after deployment, its initial handling characteristics were found to not be as good as comparable composites that were made with knitted or woven fibrous textiles, thereby providing an illustration of the importance of fiber type. Similarly, although the handleability of set-1 made with water-sensitive SG fibers was deemed to be good, its fast dissolution and resulting lower durometer in the tooth socket made it less desirable under post-deployment static conditions than comparable constructions made with SO and NK of sets 2 and 3 made with less water sensitive fibers.

Devices that were prepared with less water-sensitive fibers, sets 2 and 3 with SO and NK, respectively, tended to form more homogeneous and higher durometer composite structures in vivo than samples made with more water-sensitive fibers such as set-1 with SG. The use of relatively fast-dissolving, water-sensitive fibers resulted in a qualitative deterioration in modulus (durometer) as the device became inter-mixed with cavity fluids under static conditions. This loss in fibrous reinforcement was deterred by the use of the more water-resistant fibers. Thus, even when samples exhibited similar pre-deployment mechanical characteristics as in sets 1 and 2, the difference in fiber-type led to an extreme difference in mechanical behavior during the post-deployment period. This is yet another example of the engineering latitude afforded by the present invention, and the importance of making the correct fiber choice for the end use application.

Another finding was related to the degree to which the fiber-type either facilitated or deterred the formation of a homogeneous in vivo composite under static conditions with fluid components from within the tooth extraction socket. As shown in prior examples, formulations like Formula 14C-2 have the unexpected ability to absorb and emulsify hydrophilic fluids without exhibiting macro phase separation. However, the in vivo observational trends showed that this capability was sometimes deterred by the use of SG fibers and was generally enhanced by the use of SO and NK fibers. Under post-deployment static conditions, the physical probing of the in vivo composites revealed that sets made with SO and NK tended to become more homogeneously infused with blood after short time periods, even within their relatively hydrophobic central regions, indicating that the fibers had facilitated in diffusion-assisted mixing of blood components with the Formula 14C-2 formulation. By contrast, sets that were made with SG as a fibrous member were generally observed to be more heterogeneous during the post-deployment period. Hybrid devices that were made with two fiber types, such as SG and SO, exhibited combined behaviors with macroscopically visible regions where blood had become more homogeneously dispersed than in samples made with SG alone, but also with regions that were more heterogeneous than those observed in samples made with SO or NK alone.

One advantage of diffusion-assisted mixing is that the resulting in vivo composite becomes more homogeneous, and from a mechanical property perspective, this can help to dissipate internal cavity stresses over a larger volume fraction of the socket, thereby helping to minimize surface stresses that could disrupt protective scab formation. In this sense, it also becomes possible for the composite to become an integral component of the protective scab itself, wherein the radial gradient in composition between the tissue surface and the center of the cavity becomes more homogeneous. From a drug elution perspective, this also creates a more homogeneous chemical environment for 2-way diffusion processes, such as free-base BUP diffusion from PLGA, water diffusion into PLGA to cause hydrolysis and molecular weight diminution, diffusion of proton-carriers (i.e., Bronsted acids) toward free-base BUP molecules, etc. Thus, a homogeneous composite environment can have a profound effect on chemical efficacy.

By contrast, when a more heterogeneous environment is enabled to persist for longer periods, the diffusion characteristics and hence the chemical efficacy can be made to vary quite substantially. For example, under heterogenous conditions, the free-base form of BUP may be much slower to protonate, a process which renders it more water soluble, which would have the effect of slowing the bulk rate of release, and thereby the effect of reducing the bio-availability of the drug at any given time.

Mixed environments afforded by use of multiple fiber-types can lead to mixed effects. For example, the more homogeneous regions could be conducive to faster diffusion and bioavailability, whereas the heterogeneous regions might serve to release their active ingredients more slowly, which in essence would render them as storage vesicles for longer-term release. Thus, by controlling the choices of, the ratios of, and the geometric placement of fiber types, it can become possible to impact the global morphology of the device, and hence the global time-release profile of active ingredients. As long as sufficient mechanical integrity can be established and maintained by means of homogeneous infiltration and diffusion of body fluids into some regions of the device, heterogeneous vesicles larger in scale than the micron-sized PLGA particles can be allowed to persist for the purpose of facilitating longer-term release. Depending on the morphology of the resulting composite structure, the heterogeneous vesicles could even be used to impart mechanical benefits like stress dissipation. For example, if the device is engineered to allow for the fast in vivo formation of a homogeneous blood-mixed continuous phase containing a dispersed heterogeneous blood-free phase, the resulting morphology would be analogous to that of many impact-modified materials such as certain polymeric blends (e.g., impact modified polystyrene with a polybutadiene dispersed phase), which benefit from stress-dissipation owing to their dispersed components.

Thus, the choice of fiber type, single types and mixed types, affords surprisingly extreme flexibility for achieving different morphologies and hence varying degrees of control over performance attributes ranging from mechanical properties (e.g., cohesive integrity and resistance to in-use stresses and erosion), to chemical properties (e.g., diffusion rates and time release profiles), and combinations of the two. This type of macro-structural flexibility affords the opportunity to tune the delivery device for various end use needs, and to provide the efficacy characteristics that are desired not only for oral surgery applications, but also for other applications as well.

TABLE 9-6

Summary of clinical observations from the in-vivo porcine study.

| Set # | Placement Location | Placement Time | Device Prep. | Malleability Handling | Device Placement | Stability In vivo | General Comments |
|---|---|---|---|---|---|---|---|
| 1a | Rt. Maxilla, #1 - Molar | 8:19am | Quick, Easy, No Blending | Liked the handling. | Air/Fluid displacement - good, Sticking to socket wall, | T0 - 8:19, Breaking down too quickly, Bleeding coming from edges, | Massive socket, heavy bleeder |

TABLE 9-6-continued

Summary of clinical observations from the in-vivo porcine study.

| Set # | Placement Location | Placement Time | Device Prep. | Malleability Handling | Device Placement | Stability In vivo | General Comments |
|---|---|---|---|---|---|---|---|
| | | | | | Conforms to socket nicely | Appears saturated with blood. T1 - 8:30, Continues to break down, Saturated with blood. T2 - 8:37, Saturated with blood, T3 - 8:49, Semi-Liquid T4 - 9:08, Still in place but mushy T5 - 10:28, becoming displaced | |
| 1b | Lt. Maxilla, #19 - Pre-molar | 9:37am | | Handles very well. | Material gets infused with the blood (rapidly), Good hemostasis, Air/Fluid displacement - good | T0 - 9:37, infuses with blood and melts into the socket. T1 - 10:09, a little mushy, but stays in place with irrigation T2 - 10:27, becoming displaced from socket | Re-test of Set #1 to evaluate within a more nominal socket and bleeding conditions |
| 2a | Rt. Maxilla, #3 - Molar | 8:29am | Minimal effort, no blending Low/No impact to current surgical procedures | More stable - not breaking down as quickly as Set 1 | Air/Fluid displacement was very good, Seemed to achieve hemostasis more rapidly than Set 1, Appears saturated with blood, More solid feeling than Set 1 after placement | T0 - 8:29, more stable during placement than Set 1, seemed solid after placement. T1 - 8:41, Still a solid mass T2 - 8:49, Not breaking down much T3 - 9:07, Some softening noticed T4 - 9:21, Remains intact T5 - 9:53, Solid and in place after irrigation, blood found within center of mass - good sign | One of Dr. Neshat's top 3 favorites. |
| 2b | No tooth extracted created Lt. Maxilla | 10:18am | None. | Easy | Air/Fluid displacement was good, beautiful, Hemostasis was rapidly achieved | T0 - 10:18, T1 - 10:23, Blood thoroughly incorporated deep within device | |
| 2c | Replaced device 9a (No tooth extracted - Lt. Maxilla) | 10:25am | | | Great hemostasis on a big bleeder | | Better stability during and post device placement within an excessively bloody socket, as compared to Set 1. |
| 3a | Rt. Maxilla, #4 - Molar | 8:36am | Minimal effort, no blending Low/No impact to current | Handling was acceptable, Good consistency | Easy insertion, Air/Fluid displacement was very good, Quick | T0 - 8:36, Good placement qualities and rapid hemostasis. T1 - 8:41, Remains | |

TABLE 9-6-continued

Summary of clinical observations from the in-vivo porcine study.

| Set # | Placement Location | Placement Time | Device Prep. | Malleability Handling | Device Placement | Stability In vivo | General Comments |
|---|---|---|---|---|---|---|---|
| | | | surgical procedures | | coagulation | contiguous T2 - 8:50, very solid, very similar to Set #2 T3 - 9:07, most solid T4 - 9:21, Still intact T5 - 9:55, Still in place after irrigation, blood seen throughout, good handling | |
| 3b | | 10:19am | None needed. | | Good incorporation of blood noted. | T0 - 10:19, T1 - 10:30, homogenous the way it reacted with the blood, a little stiffer. | |
| 4a | Rt Maxilla #6 - Pre-molar | 8:47am | None. | Difficult Handling, cannot press well into the socket but does go in. Post-application performed well, handling and placement difficult. | Air/Fluid displacement was acceptable | T0 - 8:47, Performs well in socket T1 - 8:90, Solid, stayed in place T2 - 9:23, Mushy, more break down noted than 7a T3 - 9:55, Still in place after irrigation T4 - 10:01, Good handling, blood within | Heaviest bleeding site, (through nasal) |
| 5a | No tooth extracted created furthest toward nose in the maxilla | 9:06am | None | Very soft, sticks to gloves, | Went in nicely, Air/fluid displacement was acceptable, but not as good as some prior prototypes. Hemostasis was achieved quickly. | T0 - 9:06, Good placement qualities, and rapid hemostasis. T1 - 9:24, Soft T2 - 9:56, Still in there, disrupted some T3 - 10:01, Very soft T4 - 10:05, Broken down more than other prototypes | |
| 6a | No tooth extracted created socket in maxilla | 9:14am | None | Sticks to gloves | Good air/fluid displacement Went into socket well. | T0 - 9:14, Good placement qualities, and good hemostasis T1 - 9:24, Very good, not breaking down, clotting well T2 - 9:56, Good after irrigation T3 - 10:02, Fragmented, not stable | |
| 7a | No tooth extracted created socket in maxilla | 9:19am | none | No tackiness to gloves | Went in nicely, Air/fluid displacement was good, Hemostasis was achieved quickly. | T0 - 9:19, Good placement qualities and good hemostasis. T1 - 9:25, Large socket, doing a good job. T2 - 9:58, Breaking down, did not look like much coagulation. | |
| 7b | Socket reused | 10:04am | None | Very good handling, | Air/fluid displacement | T0 - 10:04, One of the best for | |

TABLE 9-6-continued

Summary of clinical observations from the in-vivo porcine study.

| Set # | Placement Location | Placement Time | Device Prep. | Malleability Handling | Device Placement | Stability In vivo | General Comments |
|---|---|---|---|---|---|---|---|
| | from prototype 6a. | | | "one of the best" | was good, Hemostasis was achieved quickly. | handling and placement. T1 - 10:14, Two phases are obvious, no blood seen inside prototype | |
| 7c | Socket reused from prototype 10a. | 10:22am | None | Great handling | Very good hemostasis | T0 - 10:22, Great placement and hemostasis. T1 - 10:26, Doesn't have blood incorporated as much (as other prototypes) | |
| 8a | No tooth extracted created toward nose within the maxilla | 9:43am | None | Falls apart (while handling) | Air/fluid displacement was good, Hemostasis was achieved, Prototype became firm after placement in socket | T0 - 9:43, Falls apart while forming plug in gloved hands. T1 - 10:10, Top piece falls out | |
| 9a | No tooth extracted created socket in maxilla | 9:47am | None | Nice handling, folded and went into socket well. Feels good. | Air/fluid displacement was very good, Hemostasis was achieved, | T0 - 9:47, Good placement and hemostasis T1 - 10:11, Very mushy throughout, not good, very gel like. | |
| 10a | No tooth extracted created socket in maxilla | 9:50am | Easy | Mushy to start with, really breaking down. | Air/fluid displacement was very good, Hemostasis was achieved, | T0 - 9:50, Prototype was mushy during placement, good hemostasis. T1 - 10:12, Outside had clotting, but no blood was found inside prototype. T2 - 10:21, Not Good | Heavily bleeding site |

Example 10. Devices from Example 9 Prepared with Isopropyl Palmitate and Caprylic Triglyceride in Place of Mineral Oil Using the procedures outlined in Example 9, the Formula 14C-2 formulation provided in Table 1 from Example 9 was used as a guide to prepare two analogous formulations with different oil substitutions for the mineral oil component. In one case, a formulation designated as 12019-23-1 was made using isopropyl palmitate in place of mineral oil (Sigma-Aldrich Cat. # W515604; lot # MKCB9456; >90% isopropyl palmitate; CAS #142-91-6; 298.5 g/mole; melt point reported as 11 to 13 degrees C.; density=0.852 g/ml at 25 degrees C.). In a second case, a formulation designated as 12019-23-2 was made using caprylic triglyceride in place of mineral oil (Croda, Inc.; CAS #65381-09-1; Columbus Circle, Edison, NJ; tradename Crodamol GTCC). Again, apart from the type of oil, the compositions and relative weight percentages of all ingredients were the same as those used in preparing Formula 14C-2.

Both alternative oil-types led to homogeneous compositions with no evidence of macro phase separation or oil exudation. During mixing, the qualitative compliance characteristics were evaluated and ranked from high to low. 12019-23-1 with isopropyl palmitate was kneaded to form a homogeneous dough-like mixture with relative compliance that was qualitatively higher than that of 12019-23-2 with caprylic triglyceride. The compliance ranking from high to low was as follows: Formula 14C-2 was more compliant than 2019-23-1 which was more compliant than 12019-23-2. Interestingly, this result shows that with all other things being equal, the simple substitution of a different type of oil can have a significant impact on the mechanical properties of the drug carrier formulation. In this example, the effect was qualitatively similar to that caused by substitution of a different type of wax, or by the use of a different wax to oil ratio. Thus, this example provides further illustration of the versatility in rheological and mechanical property characteristics that are possible by means of controlling not only composition percentages, but by also controlling the chemical nature of the components. In this example, three different rheological characteristics were achieved by merely changing the nature of the oil type.

The impact of the differences in properties from this simple substitution become more apparent when consideration is given to the manufacturability and to the efficacy of the final composite device when the formula is paired with a fibrous member such as one employed in Example 9. In order to illustrate this, the three comparative formulations in this example were each separately impregnated into pre-cut textiles from the Surgicel Original cellulosic hemostat that was used in Example 9. The textiles were cut to the same approximate dimensions as those used in Example 9, and the three formulations were paired with the textiles using the same approximate weight of carrier formula that was employed in Example 9.

Initially, an attempt was made to create devices like those designated as set-2 and described in Table 9-5 of Example 9 with two SO textiles. As previously noted in Example 9, when the higher compliance Formula 14C-2 was impregnated into a single SO textile, the resulting composite was relatively low in stiffness (see set-10 from Example 9). Moreover, the excess penetration of the Formula 14C-2 into the interstitial spaces of the SO textile necessitated the use of a second textile to achieve better in vivo performance as described in Tables 9-5 and 9-6 of Example 9. By contrast, when attempts were made to create analogous devices with 12019-23-1 and 12019-23-2, the lower relative compliance of these formulas led to less interstitial penetration, and to higher qualitative stiffness characteristics, which thereby negated the need for a second textile component. In essence, the stiffness of devices comprising either 12019-23-1 or 12019-23-2 with one textile was qualitatively similar to the stiffness of devices comprising Formula 14C-2 with two textiles. One advantage of this versatility relates to the efficacy of the final composite device. Specifically, when using a textile with relatively low knit density like SO, a device can be prepared with a lower volume fraction of the cellulosic hemostat component, and with a higher volume fraction of the formulated drug carrier simply by changing the chemical nature of the oil component in the drug carrier formulation. Similar results would also be possible by changing other factors either alone or in combination, including for example, the wax type, the oil to wax weight ratio, and the volume fraction of dispersed solids such as PLGA, and gelatin. Thus, given the volume restrictions associated with the end use application, the ability to control compliance characteristics with these factors can lead to a reduction in the volume % of cellulose textile in the device and consequently to a higher dosages of active ingredients per unit volume if so desired.

In summary, with increasing formula compliance and with lower textile density, excessive formula penetration into the interstitial spaces and a lower net composite stiffness may necessitate the use of a second orthogonal textile to achieve acceptable tactility in terms of stiffness and handleability for certain end use applications. By contrast, lower compliance formulas do not produce the same degree of interstitial impregnation under equivalent pressure, and because they are inherently stiffer, the need for a second textile can be negated. In this example, the lower compliance formulas that have been paired with one SO textile member, analogous to set-10 from Tables 9-5 and 9-6 in Example 9, exhibited qualitatively similar stiffness characteristics to Formula 14C-2 that was made with two SO textile members. Again, one of the advantages of using a lower compliance formula with one low density textile instead of two, particularly when the textile is as low in density as SO, is that the occupied fibrous hemostat volume fraction can be reduced without necessarily compromising the types of tactile characteristics that are important during clinical end use. This can equate to a higher volume fraction of the drug vehicle, and to higher possible drug delivery dosages in certain volume restricted end use applications, as represented by the tooth extraction socket application.

On the other hand, if the hemostat character of the delivery device is of particular functional interest, then the device can be optionally made with higher relative volume fractions of oxidized cellulose if so desired. This type of composite device would necessitate the use of a formulation with higher compliance characteristics. Indeed, this approach was demonstrated previously in Example 9 with the higher compliance Formula 14C-2 made with mineral oil as the liquid carrier. Sample set-2, which was made with two SO textiles, provided better in vivo performance, better diffusion-assisted mixing with body fluids under static conditions and better homogeneity within the oral tooth socket than sample set-10 which was made with only one SO textile.

Example 11—Water Soak Experiment Involving Samples from Example 10

As mentioned previously, a formulation of the vehicle embodiment can be masticated with water to yield a compliant material for placement into a tooth extraction socket during end use either with or without an oxidized cellulose fibrous reinforcement member, or it can be used in its non-hydrated form preferably with a fibrous reinforcement member as illustrated in Example 9. By contrast, the formulation described in Example 2 needs to be masticated with water to yield a compliant dough-like material before it can be deployed during end use.

Figure 1:
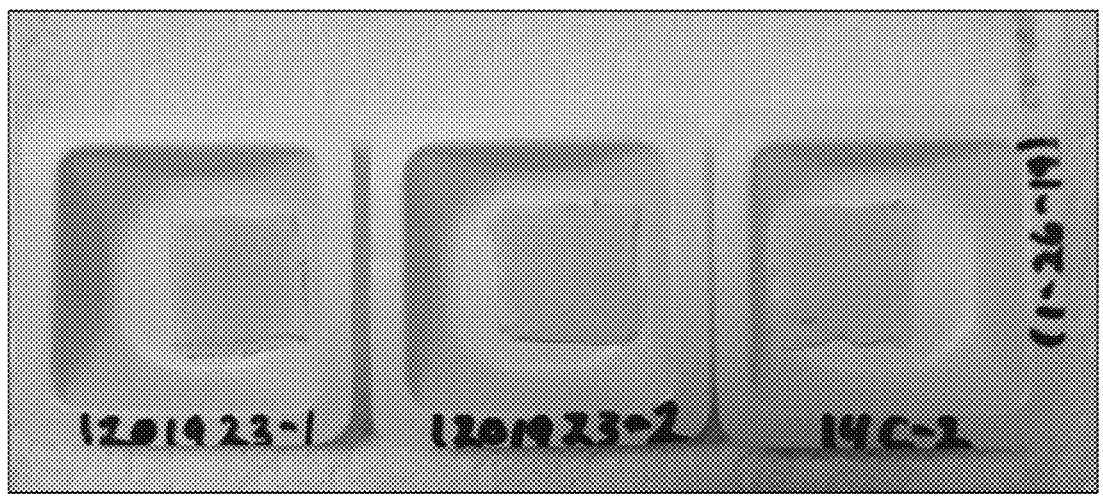
FIG. 1 is a photograph showing formulation mixtures using beeswax with three different types of oils (14C-2 with mineral oil, 12019-23-1 with isopropyl palmitate, and 12019-23-2 with caprylic triglyceride) blended together with powdered bovine gelatin and PLGA particles, and with each impregnating a textile.
Figure 2:
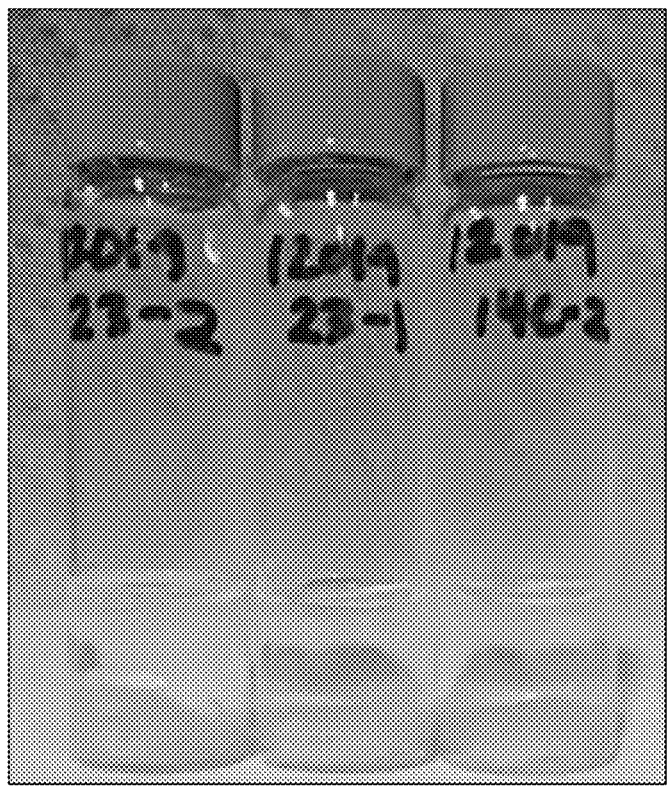
FIG. 2 is a photograph showing three comparative delivery systems from FIG. 1 after placing them into the bottom sections of separate 11 ml glass vials with 2.5 g of added water (representing the t=0 onset of the pH-neutral water soak experiment at approximately 20 degrees C.). Formulations from left to right: 12019-23-2, 12019-23-1, and 14C-2.
Figure 3:
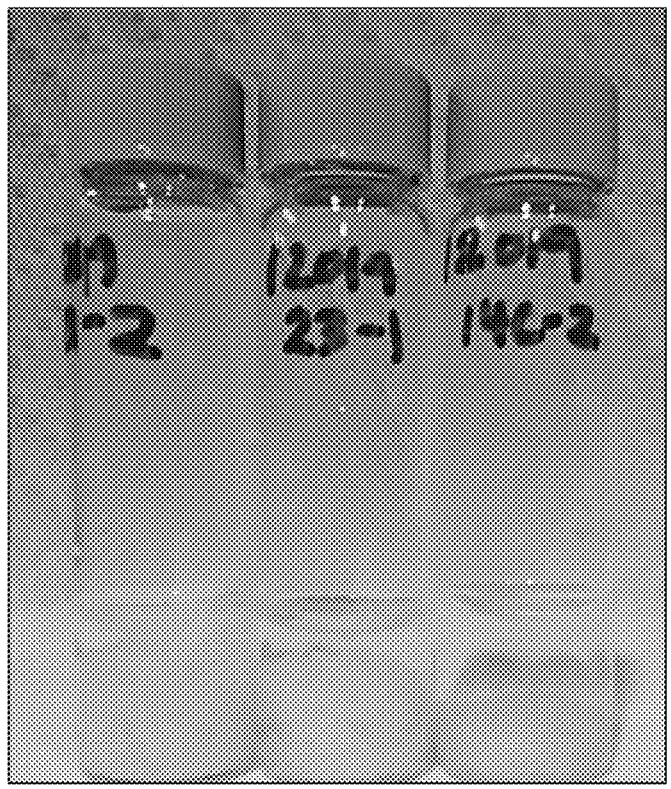
FIG. 3 is a photograph showing three comparative delivery systems from FIG. 1 after placing them into the bottom sections of separate 11 ml glass vials with 2.5 g of added water (representing t=24 hours after the onset of the pH-neutral water soak experiment at approximately 20 degrees C.). Formulations from left to right: 12019-23-2, 12019-23-1, and 14C-2.
Figure 4:
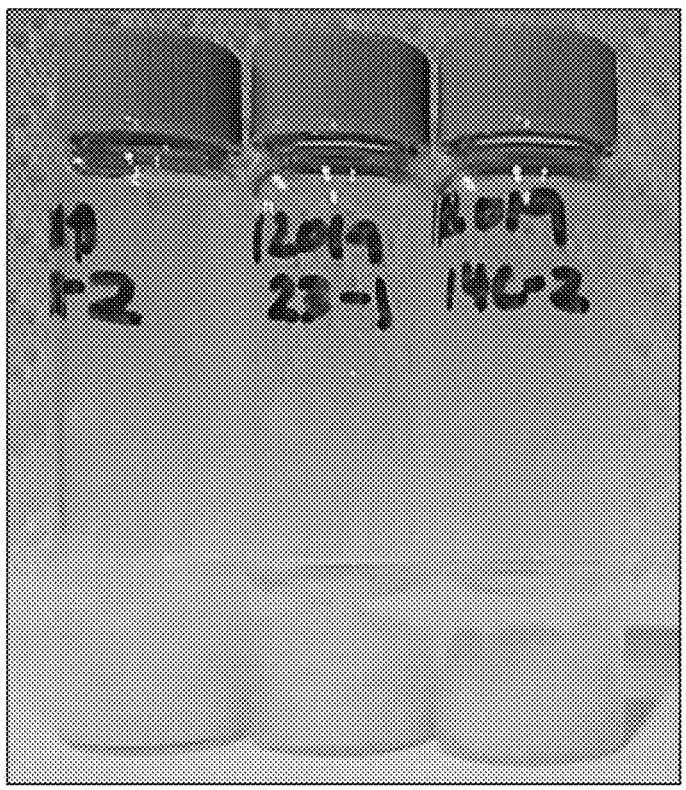
FIG. 4 is a photograph showing three comparative delivery systems from FIG. 1 after placing them into the bottom sections of separate 11 ml glass vials with 2.5 g of added water (representing t=48 hours after the onset of the pH-neutral water soak experiment at approximately 20 degrees C.). Formulations from left to right: 12019-23-2, 12019-23-1, and 14C-2.
Figure 5:
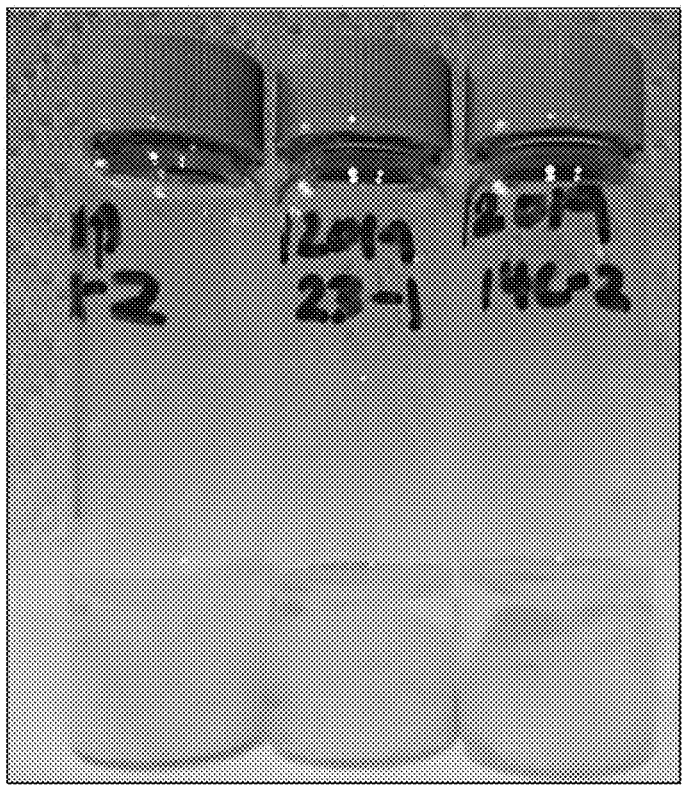
FIG. 5 is a photograph showing three comparative delivery systems from FIG. 1 after placing them into the bottom sections of separate 11 ml glass vials with 2.5 g of added water (representing t=72 hours after the onset of the pH-neutral water soak experiment at approximately 20 degrees C.). Formulations from left to right: 12019-23-2, 12019-23-1, and 14C-2.
Figure 6:
FIG. 6 is a photograph showing three comparative delivery systems from FIG. 1 after placing them into the bottom sections of separate 11 ml glass vials with 2.5 g of added water (representing t=120 hours after the onset of the pH-neutral water soak experiment at approximately 20 degrees C.). Formulations from left to right: 12019-23-2, 12019-23-1, and 14C-2.

Regardless of which embodiment is deployed, it is important that the formulation remain cohesively intact for as long as possible following initial deployment, so as to enable the formulation to 1) absorb fluids from the tooth extraction socket, 2) to gel with the fluids and to build its cohesive strength, and 3) to remain intact as a viable vehicle to facilitate controlled release of active ingredients. A device which begins to erode and disintegrate prior to gelation can lead to lower longevity during use, so it can be appreciated that the best device is one that can maintain its cohesive integrity for as long as possible under end use conditions. In order to qualitatively assess these characteristics, a static water soak test was devised for the purpose of qualitatively testing each device's propensity to swell/expand, or to disintegrate/dissolve under static conditions vs. time. In this example, the three comparative samples from Example 10, Formula 14C-2 with mineral oil, 12019-23-1 with isopropyl palmitate, and 12019-23-2 with caprylic triglyceride, were comparatively tested. The three comparative devices of similar approximate weight are shown in FIG. 1. Each device was placed into separate 11 ml glass vials with lids, and 2.5 g of water (pH neutral distilled water, 20 degrees C.) was added to each as shown in FIG. 2, with formulations from left to right including 12019-23-2, 12019-23-1, and 14C-2. The vial weights, the device weights, and the added water weights were measured as follows: Sample 12019-23-1 vial+lid=9.7394 g, tarred device wt.=0.6155 g, and water weight=2.50 g; Sample 12019-23-2 vial+lid=10.2668 g, tarred device wt.=0.6794 g, water weight=2.50 g; and Sample 12019-14C-2 vial+lid=9.8236 g, tarred device wt.=0.6745 g, and water weight=2.50 g. The samples were then monitored vs. time (FIGS. 3 through 6).

Visual inspection of the samples revealed that the relative degree of swelling and disintegration was mirrored by the qualitative compliance trends as recorded in Example 10. Namely, the formula with higher compliance Formula 14C-2 tended to remain cohesively intact and resisted delamination from its SO textile members through the course of the experiment. By contrast, the least compliant sample, 12019-23-2, exhibited the fastest relative rate of swelling and disintegration, and it also exhibited evidence of delamination from its SO textile member within the first 24 hours of the soak experiment.

These results do not necessarily imply that one type of oil is better than another. Instead, it appears that the compliance and cohesive strength characteristics of the device are important to consider when formulating the device for longevity under static soaking conditions. Based on the teachings of the prior examples, the three oil types in the comparative samples could be formulated in alternative ways to achieve optimum cohesive strength and compliance characteristics. For example, one way to increase compliance would be to increase the oil to wax ratio. Wax type can also have an impact on compliance and cohesive strength. Another way would be to decrease the volume fraction of particulates. Yet another way would be to change the particle size distribution of the PLGA and gelatin particulates. Another way would be to change the knit density of the fibrous textile component in the device.

Thus, when co-optimizing the device formulation and construction for yielding the most desirable set of responses for the end use application, including for example, tactile characteristics during deployment, cohesive integrity, capacity to absorb tooth extraction socket fluids, available concentrations of active ingredients, active ingredient release rates; consideration must be given not only to the chemical nature and ratios of the vehicle components such as oil type, wax type, oil/wax ratio, gelatin type, % of total dispersed solids within the oil/wax phase, gelatin particle size distribution, PLGA particle size distribution, ratio of the gelatin and PLGA dispersed ingredients, but also to the macroscopic nature of the device's construction such as knit density of the fibrous member, volume fraction of fibrous members, surface chemistry of the fibrous members, degree of oxidation of the fibrous members, and the resultant mechanical properties of the fiber reinforced device).

Example 12. Relative Bupivacaine Release Characteristics from Formulations Prepared with Hydrophilic and Hydrophobic Components The main purpose of this example is to illustrate the variance in relative rates of bupivacaine (BUP) release that can be achieved depending upon the hydrophobic or hydrophilic components of the formulation, and on the morphological distribution of the BUP active ingredient. Select versions of embodiments of the formulation as described in Example 2 and the embodiments as described in Examples 9 and 10 were prepared for comparative purposes. Formulations were prepared in two ways: 1) using bupivacaine free base encapsulated within PLGA microspheres; and 2) using BUP free base that had been formulated directly into the delivery device and not encapsulated by PLGA microspheres. Thus, one of the primary differences among samples was the morphological distribution of the BUP active ingredient inside versus outside of the PLGA particles. A second primary difference was the relative hydrophobicity of the formulation. The devices were immersed into mildly acidic water (pH=2 prepared with HCl in deionized water) and were incubated at 37 degrees C. for various lengths of time over a 24-hour interval for the hydrophilic devices, and over a 4-day interval for the hydrophobic devices. Photos of the devices were taken as a function of time to record their relative propensity to either swell, disintegrate & dissolve, or to maintain cohesive integrity under static soaking conditions as a function of time. In addition, UV spectroscopy with specular beam detection was used to follow the relative rate of bupivacaine release as a function of time.

Importantly, the absorbance response from UV spectroscopy in transmission mode with specular beam detection, as employed in this example and in Example 13, is weighted by the presence of molecular-scale components that have become solvated within the liquid medium as opposed to components that have become dispersed through erosion. This is relevant because it implies that soluble components are preferentially detected, while dispersed components are excluded from specular detection and can only be detected and quantified via the use of an integrating sphere because they scatter light diffusely. Thus, in order for one or more soluble components to be detected in the supernatants of samples that have been water-soaked under static conditions, molecular level dissolution is a mandatory precursor. Moreover, in order for dissolution to occur under static conditions, components would have to first become intermixed with water at the molecular level through a process that originates with molecular level diffusion. Molecular level diffusion can occur via one or more of the following pathways in any combination, including for example: 1) water or other fluids entering the mother device; 2) active ingredients or other components dissolving and egressing from the mother device; 3) water diffusing into macro fragments that have been eroded away from the mother device; 4) active ingredients or other components leaching from macro fragments that have been eroded away from the mother device; or 5) components egressing from PLGA microspheres, including, microspheres that remain suspended within the mother device, microspheres contained within macroscopic fragments of the mother device, or microspheres that have become freely dispersed within the supernatant water-phase.

Independent of the originating pathway, each of these molecular-level processes requires translational motion of molecular-scale entities across one or more concentration gradients. By definition, concentration gradients will persist under non-equilibrium conditions until the entire system comes to equilibrium. In a closed system represented by a static water-soak experiment, this implies that ingress and egress of molecules will continue until the entire system reaches its equilibrium end point. Macroscopic erosion is not a mandatory precursor for diffusion and dissolution. However, if macro erosion does occur, it may indeed lead to the faster appearance of molecular level entities that are dissolved in solution, but dissolution is still the necessary precursor for specular beam detection. Thus, when BUP is detected in these experiments with UV spectroscopy, its detection is evidence of its dissolution, which can only occur via diffusion and dissolution from one of the pathways described above. Further, for the case of BUP that originates from the interior of a PLGA particle, it can only be detected if it has become dissolved, necessitating that it must first migrate across one or more concentration gradients represented by 1) the PLGA polymer that constitutes the particle itself, where the interior of the particle initially contains a higher BUP than the external chemical environment; and 2) the matrix phase, which initially constitutes the external chemical environment for a large fraction of the PLGA particles that are dispersed therein.

A detailed accounting of sample compositions, experimental details for sample preparations, measurement procedures, and experimental results are provided below.

Hydrophilic Sample Compositions, Preparations, and Procedures.

Two comparative formulations comprising hydrophilic components were based on compositions as discussed in Example 2. Specifically, the two formulations for the present examples 918-1B and 918-1i were prepared by using a formulation that was analogous to that of formulas #4, #5, and #6 from DOE-DRAFT-6 containing 81% microspheres by weight, 19% GLBG by weight, with GLBG gelatin as the binder. This type of composition was previously observed to provide a high relative BUP-dosage delivery that exhibited acceptable compliance when masticated and hydrated with water. However, for the purposes of the present example, the PLGA particle size distribution was maintained at 100% 3-4 micron PLGA particles as opposed to the distribution comprised of a mixture of small and larger PLGA microspheres as described in DOE DRAFT-6 formula #7, where a 10/90 w/w blend of distributions comprising D50=3.4 micron and D50=42.1 micron particles was employed. Although from a compliance perspective, a mixed PLGA particle size distribution like that from formula #7 is one approach, a single PLGA particle size distribution was employed in this example for facilitating simple relative comparisons of cohesive integrity, release rates, and relative compliance characteristics when comparing the two formulations. The formulations comprising hydrophilic components were prepared with Great Lakes Bovine Gelatin (GLBG), and with PLGA microspheres that were made by SWRI using a solvent-borne Resomer RG504 polymer with a spinning disc atomization drying process. The PLGA microsphere samples had the following specifications: 1) sample ID 18-0202-015-10 having an average particle size of D50=3.5 micron, and containing 20% by weight BUP free base; and 2) sample ID 18-0202-015-7 placebo PLGA, also with an average particle size of D50=3.5 micron, but with no BUP. The dry powder mixtures were prepared using procedures outlined previously in Example 2. For the case of sample 918-1i, BUP free base (Santa Cruz Biotechnology, CAS #38396-39-3) was added directly to the dry powder mixture at a level commensurate to the level used in sample 918-1B. The mixing compositions of the comparative formulations are provided in Table 12-1 for the powders before and after hydration. The two comparative formulations were designed to deliver a maximum dosage of approximately 92 mg BUP per gram of hydrated device. Note that the weight percentage of each ingredient was the same for each device. The only difference was in the morphological distribution of the BUP.

TABLE 12-1

Weight % compositions of hydrophilic devices (dry powders before and after hydration). Calculations also include the weight % concentration of BUP in the devices (before and after hydration), and the effective available BUP concentration for release during the pH-2 water-soak experiments.

| Ingredient | 918-1B dry powder | 918-1B hydrated gel | 918-1i dry powder | 918-1i hydrated gel |
|---|---|---|---|---|
| Great Lakes Bovine Gelatin (GLBG) | 19.14% | 10.93% | 19.14% | 10.93% |
| PLGA from 3.5-micron microspheres loaded with 20% by wt. BUP free base | 64.69% | 36.94% | 0% | 0% |
| Encapsulated BUP from 3.5-micron microspheres loaded with 20% by wt. BUP free base | 16.17% | 9.24% | 0% | 0% |
| PLGA from 3.5-micron placebo microspheres | 0% | 0% | 64.69% | 36.94% |
| BUP free base (non-encapsulated, directly added to the vehicle) | 0% | 0% | 16.17% | 9.24% |
| Water for hydration (pH-2, dilute HCl) | 0% | 42.89% | 0% | 42.89% |
| mg BUP/g device | 162 | 92 | 162 | 92 |
| Ratio of total water to BUP (w/w) in water soak experiment | N/A | 58.3 | N/A | 58.3 |
| Tarred Weight (g) of hydrated device added to 11 ml glass vial | N/A | 1.1532 | N/A | 1.254 |
| Weight of water (g) in hydrated sample | N/A | 0.4946 | N/A | 0.5378 |
| Weight of additional water (g) added to 11 ml vial | N/A | 5.7186 | N/A | 6.2184 |
| Total water used in water soak experiment (sum of water used for hydration + additional water that was added to 11 ml glass vial) | N/A | 6.2132 | N/A | 6.7562 |
| Effective Weight ratio of total device solids to water during the water-soak experiment | N/A | 0.106 | N/A | 0.106 |
| mg of available BUP per ml water | N/A | 17.07 | N/A | 17.07 |

Before initiating the water-soak experiments, the dry powders were first masticated with a fixed weight ratio of water (pH-2, with dilute HCl added to deionized water) to gelatin of 3.92/1 w/w water/GLBG under ambient conditions (20 degrees C.) to yield compliant gel-like mixtures. The samples were mixed with a spatula in 15 ml HDPE beakers using procedures similar to those reported in Example 2. The quantities of powders and water were scaled to achieve a total masticated device weight that was approximately 1.5 g in each case. During the mastication step, the mixtures were initially observed to be creamy and low in viscosity. After mastication, the beakers were covered with aluminum foil, and the foil was removed at various times to check for gelation. Within 30 minutes, the samples had become solid and compliant gel-like materials. At approximately 35 minutes after mixing, the gelled devices were transferred and weighed into zero-tarred 11 ml glass vials with lids. Next, at t=45 minutes after mixing, a specific amount of pH-2 water was added to each vial, such that the total water to BUP weight ratio was 7.0/0.12 w/w, inclusive of water that was used during the mastication step. Thus, the samples were allowed to gel for a total of 45 minutes after mixing prior to the onset of the water soak experiment. Note that a constant water to drug weight ratio of 7.0/0.12 was also used in each of the comparative water-soak experiments for all of the samples, and the same size vials were used to maintain similar surface to volume ratios. For the present samples, this facilitated an equivalent net reservoir of ~17 mg BUP per ml water for potential elution and delivery to the water phase throughout the course of the water soak experiment. The vials were then incubated at 37 degrees C. for the purposes of 1) tracking cohesive integrity vs. time (FIGS. 7a-7d, and 8) tracking the relative eluted drug concentration vs. time via UV spectroscopy.

At t=1.5 hours, the vials were removed from the incubator and a photo was taken. As illustrated in FIGS. 7a through 7d, both samples had already started to swell and to disintegrate, but sample 918-1i had already become noticeably more swollen and had started to disintegrate to a higher degree than sample 918-1B. This was particularly surprising in light of the fact that both samples were formulated to have the same empirical composition (see Table 12-1), with the only difference being in the morphological distribution of the BUP. The relative resistance of 918-1B to erosion is believed to be a result of a synergy between the plasticized polymer matrix phase and the PLGA-encapsulated BUP microparticles that were dispersed therein, where microparticles of this type appear to provide a type of mechanical reinforcement that improves the cohesive integrity of the device.

In the next step, 2 ml of supernatant was removed from each sample for UV analysis. The two glass vials were then closed and were placed back into the incubator, and the two supernatant aliquots were centrifuged at 3000 rpm for 5 minutes. Afterwards, 1 ml of each centrifuged liquid was used for UV absorption spectral analyses. In this way, the relative level of dissolved BUP was monitored as a function of time via UV absorbance intensities. When the UV measurements were completed, the centrifuged aliquots of 2 ml in total for each sample were returned to their respective vials, and the samples were allowed to continue incubating. This sampling procedure was repeated at t=4 hours and again at t=24 hours after the onset of the water-soaking experiment.

UV Absorption Experiments of Samples 918-1i and 918-1B.

As mentioned above, aliquots were manually pipetted from the top portion of the centrifuged supernatants, and 1 mL was loaded into UV/VIS compatible cuvettes having outside dimensions=12 mm×12 mm, and inside path length=10 mm. For the case of samples 918-1i and 918-1B, the net potential availability of BUP for elution into the water phase was therefore approximately 17 mg/ml at maximum for the UV absorption experiments. Poly(methyl methacrylate) cuvettes (Fisher brand) were used to limit cuvette absorption within the range of detection for absorbance measurements on a Tecan Infinite M200 Spectrometer within the range of 2.30-1000 nm. Given the lack of absorbance at higher wavelengths, spectrometer readings were typically measured between 250-350 nm. A wavelength step size of 2 nm with a bandwidth between 5-9 nm was used, and with 25 flashes, which was the number of incident light exposure and detection occurrences that were signal averaged at each wavelength. After each absorbance measurement, the supernatants were collected and added back to the original glass vials, such that the total volume in the elution experiment did not change except for minor loss due to residual supernatant in the pipette or UV cuvette.

Using the same instrument parameters and cuvettes, spectra were also acquired for each individual ingredient in the mixtures for the purpose of determining background contributions to the overall absorbance spectra that were obtained for the fully formulated mixtures. For the purposes of the background experiment, the individual ingredients were either fully dissolved or were fully dispersed in pH-2 water. In this way, the background experiments were representative of the highest degree of spectral background contribution that might be potentially observed for the fully formulated devices if the devices were to completely disintegrate and dissolve during the water-soak experiment.

The concentrations for these individual background experiments were established from the effective ratio of each individual ingredient to water that was used during the pH 2 water-soaking experiment on the fully formulated sample delivery systems themselves. These concentrations, established from ratios of values in Table 12-1, are reported in Table 12-2. The background samples were aged for 24 hours under ambient conditions prior to acquiring the UV spectra shown in FIG. 8. Inspection of these background spectra revealed that the BUP itself was the strongest chromophore in the mixture, and BUP was therefore the most significant contributor to spectral absorption over the wavelength range of interest (250-350 nm). Although the BUP free base has low solubility in water, the mildly acidic conditions insured that the BUP became protonated as the hydrochloride salt (BUP-HCl), rendering it as completely soluble under these conditions. BUP-HCl is known to be a strong chromophore with a documented UV absorption maximum at 262 nm (Corciova, A., Eur. Chem. Bull., 2012, 2(8), 554-557).

Figure 8:
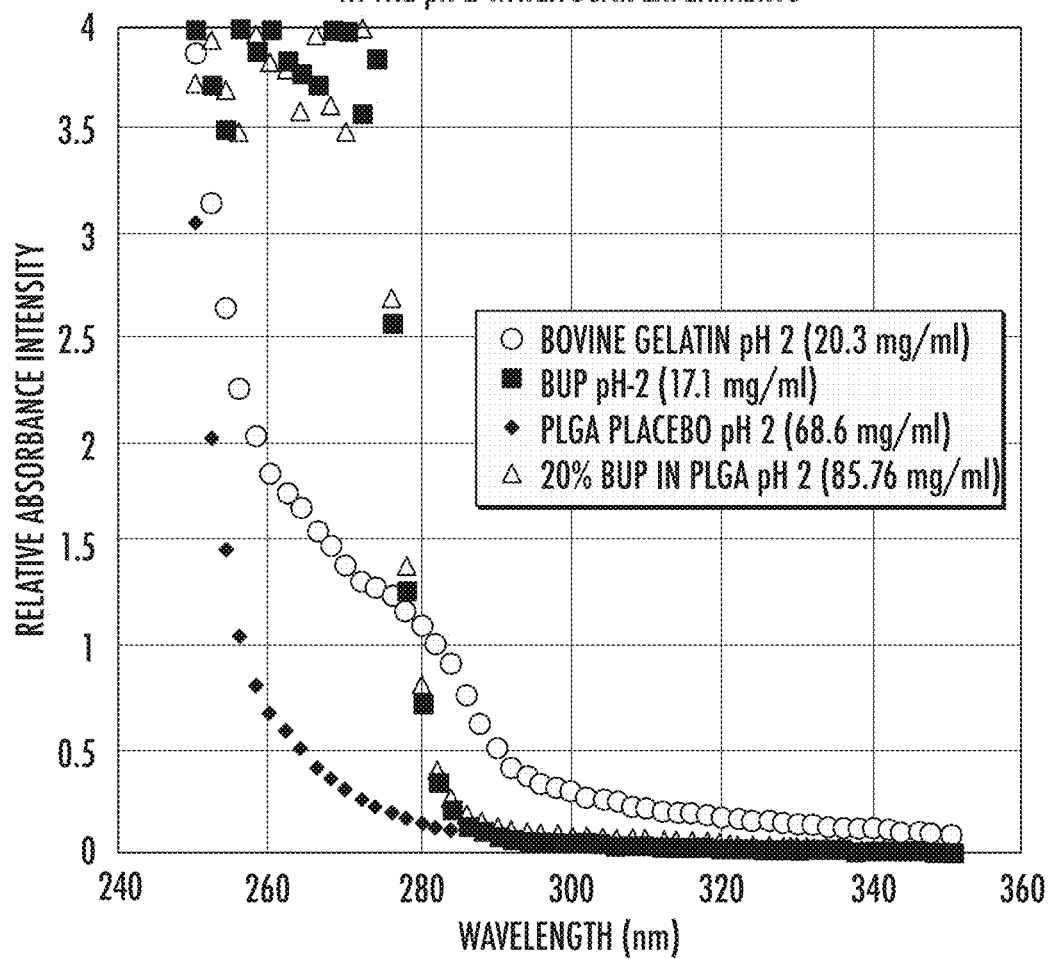
FIG. 8 depicts individual UV absorption spectra of fully dissolved (e.g., GLBG, BUP) and fully dispersed ingredients (e.g., PLGA Placebo, BUP encapsulated by PLGA) in pH 2 water at concentrations that were equivalent to the effective concentrations used in the fully formulated delivery systems.

As shown in FIG. 8, the spectral contributions from PLGA placebo microspheres were negligible. However, a minor absorption contribution was observed for bovine gelatin (GLBG), but this contribution was observed to be minimal over the wavelength range associated with BUP. Also, the PLGA-encapsulated BUP revealed strong absorption after the 24-hour aging period, which was similar in magnitude to that of the freely dissolved BUP itself. Thus, when left unprotected by a matrix phase, the PLGA microspheres can release enough BUP within 24 hours to completely saturate the detector under the experimental conditions that were used in this example. Although the absolute concentration of released BUP was not measured in this experiment, it is important to note that the relative amount that was released from the unprotected microspheres was high enough to saturate the detector under the experimental conditions associated with the water-soak experiment for the fully formulated devices. This is noteworthy because when the BUP encapsulated microspheres were protected by the matrix phase, the net concentration of BUP-release after 24 hours was qualitatively less than that exhibited by the unprotected microspheres. This indicates that the matrix phases also play a substantial role in mitigating diffusion.

Figure 9:
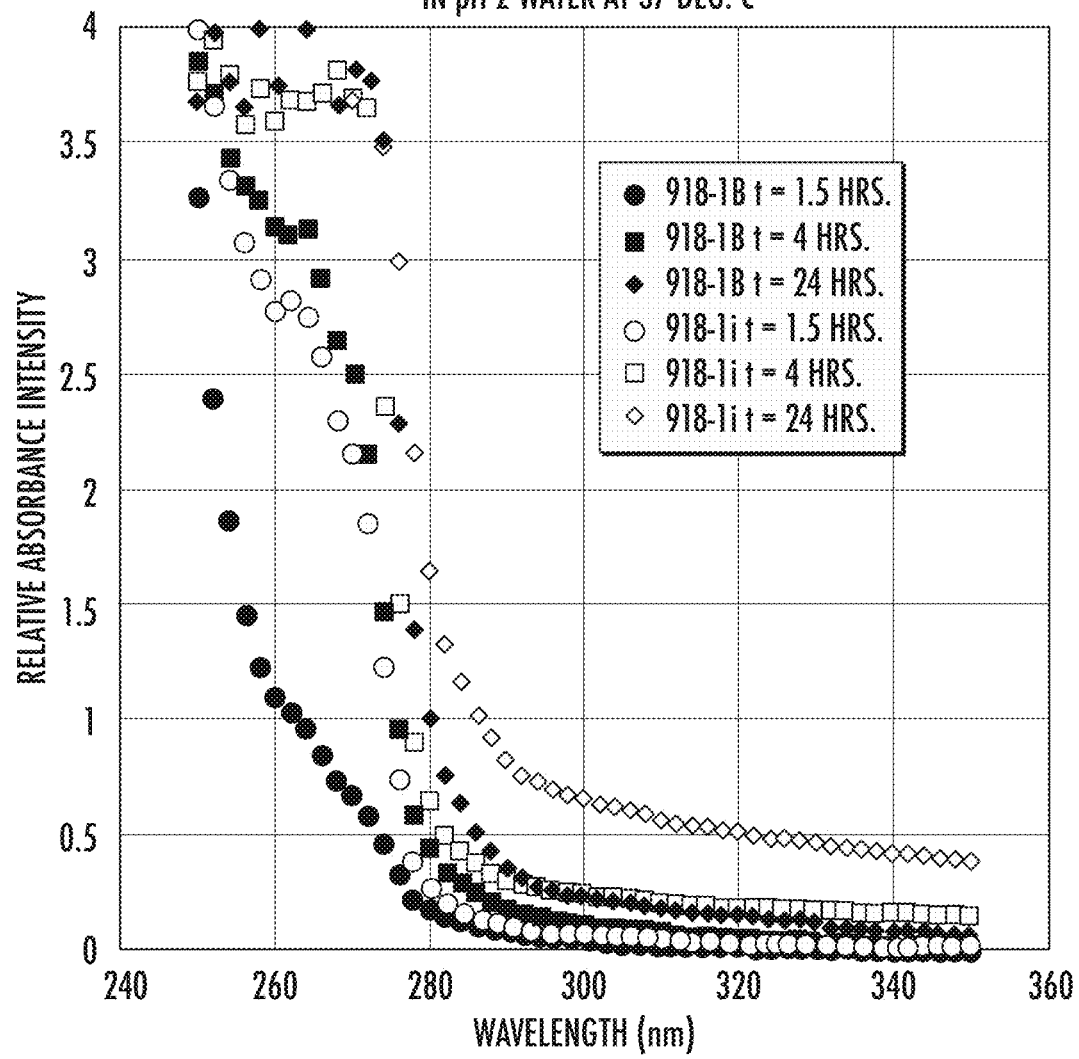
FIG. 9 depicts UV spectra of aliquots removed from the supernatants of delivery systems comprising hydrophilic components while soaking in pH-2 water at 37 degrees C.

The spectra acquired from the supernatants of samples 918-1i and 918-1B are provided in FIG. 9. These results show that the elution of BUP was faster when the BUP was morphologically positioned to be outside of the PLGA microspheres as in sample 918-1i. By contrast, the elution of BUP was deterred by PLGA encapsulation in sample 918-1B. In other words, the system containing BUP that was encapsulated within PLGA microspheres (918-1B) was observed to release BUP more slowly than the system that contained BUP that was directly formulated into the vehicle (91.8-1i). Thus, when PLGA was used to encapsulate the active ingredient, its rate of release into solution was attenuated. Note that a similar trend was observed for analogous delivery made with hydrophobic components, but the release rates were further attenuated by the hydrophobicity of the vehicles (described below).

At t=4 hours, the level of BUP that was released from 918-1i was already at a high enough level to saturate the detector. By contrast, the level of BUP released from 918-1B was lower, and it was still within the range of instrumental detection. However, the amount of BUP that was released from both samples was high enough within 24 hours to saturate the UV detector.

In a separate experiment, a wavelength of 270 nm was chosen for establishing a separate calibration curve for the BUP concentration versus absorbance in pH-2 water. That is, the weight of BUP free base in mg/ml in dilute HCl was plotted versus absorbance at wavelength=270 nm. This calibration equation provided in Table 12-3 was used to roughly estimate the concentration of dissolved BUP as a function of time during the water-soak experiment for the fully formulated samples. Note that since these were single beam acquisitions with no reference cuvette, a separate single beam absorption spectrum from pH-2 water was subtracted from the BUP sample spectra before establishing the correlation.

Before estimating the effective elution concentration of BUP from the fully formulated sample mixtures, the absorbance values at 270 nm were first corrected by subtracting an absorbance contribution from fully dissolved GLBG. This actually represented an overcorrection since the GLBG did not become fully dissolved during the water-soak experiments on the hydrated samples. Thus, whenever this overcorrection resulted in a negative value during early periods of the water-soak experiment, the BUP estimate was equated to zero. For the case of samples 918-1i and 918-1B, the UV absorbance intensity of GLBG that was dissolved in water at a concentration of 0.0203 g per g pH-2 water was used to make this absorbance correction at a concentration equivalent to the net concentration of gelatin that was present and available for complete dissolution during the water-soak experiment on the devices. Note that no correction was made for the presence of PLGA since the separate UV experiments revealed that absorbance contribution of PLGA was negligible within the wavelength range attributable to BUP absorption.

Note also that the detector becomes signal-saturated at absorbance values approaching 4 absorbance units. Through the course of the water-soaking experiments, this saturated detector condition was eventually achieved for each sample. For the purposes of the present example, the [BUP] calibration curve was used to estimate BUP elution concentrations only for cases where the absorbance was <3.9. When the detector saturation level was reached, the estimated BUP elution concentration was reported as equal to or greater than the value calculated from the calibration plot. Note that successive dilutions could be used to bring the absorbance values back within the detection range, but for the purposes of this example, these additional experiments were not necessary to illustrate the important differences among the sample types. In the next step, the estimated BUP elution concentration $[BUP]_t$ was ratioed against the total theoretical concentration $[BUP]_{theoretical}$ to allow for qualitative comparison of relative elution rates among the devices from the present example.

TABLE 12-2

Table entries include concentrations of individual ingredients in pH-2 water (w/w) for acquisitions of individual background UV spectra shown in 8; weights of device mixtures per g of pH-2 water during the water-soak experiment; absorbance contributions of individual ingredients at 270 nm; absorption at 270 nm of supernatants from devices during the water-soak experiment; GLBG overcorrected absorption values; estimated [BUP] at each time interval (from calibration equation in Table 12-3); and the estimated fraction of eluted BUP based on an initial theoretical concentration of BUP that was available from the device (i.e., 17.07 mg/ml for the hydrophilic devices as reported in Table 12-1). Note that when an absorbance overcorrection resulted in a negative value, the value was denoted as zero (marked with an asterisk). When the measured absorbance values were approaching the detector limit, the effective BUP concentration was denoted as equal to or less than the theoretical maximum of ~17 mg/ml (also denoted with an asterisk).

| Ingredient | Weight (g) per gram pH-2 water | Relative Absorbance at 270 nm at t = 1.5 hrs. | Relative Absorbance at 270 nm at t = 4 hrs. | Relative Absorbance at 270 nm at t = 24 hrs. |
| --- | --- | --- | --- | --- |
| pH 2 dilute HCl | 1 | N/A | N/A | 0.2818 |
| PLGA Placebo Microspheres in pH 2 water | 0.0686 | N/A | N/A | 0.3069 (dispersed) |
| GLBG fully dissolved in pH 2 water | 0.0203 | N/A | N/A | 1.3871 (fully dissolved) |
| BUP free base (fully dissolved) | 0.0171 | N/A | N/A | > or = 4 (i.e., saturated signal) |
| 918-1B | 0.106 | 0.6703 | 2.504 | 3.8087 |

TABLE 12-2-continued

Table entries include concentrations of individual ingredients in pH-2 water (w/w) for acquisitions of individual background UV spectra shown in 8; weights of device mixtures per g of pH-2 water during the water-soak experiment; absorbance contributions of individual ingredients at 270 nm; absorption at 270 nm of supernatants from devices during the water-soak experiment; GLBG overcorrected absorption values; estimated [BUP] at each time interval (from calibration equation in Table 12-3); and the estimated fraction of eluted BUP based on an initial theoretical concentration of BUP that was available from the device (i.e., 17.07 mg/ml for the hydrophilic devices as reported in Table 12-1). Note that when an absorbance overcorrection resulted in a negative value, the value was denoted as zero (marked with an asterisk). When the measured absorbance values were approaching the detector limit, the effective BUP concentration was denoted as equal to or less than the theoretical maximum of ~17 mg/ml (also denoted with an asterisk).

| Ingredient | Weight (g) per gram pH-2 water | Relative Absorbance at 270 nm at t = 1.5 hrs. | Relative Absorbance at 270 nm at t = 4 hrs. | Relative Absorbance at 270 nm at t = 24 hrs. |
|---|---|---|---|---|
| 918-1B (corrected for GLBG) | — | ~0* | 1.1169 | 2.4216 |
| 918-1B estimated BUP elution concentration [BUP]t using equation from Table 12-3 (mg/ml) | — | ~0* | 1.4 | *Between 3 and 17.1 |
| 918-1B estimated fraction of BUP elution = [BUP]t/[BUP]theoretical; [BUP]theor. = 17.1 | — | ~0* | 0.08 | > or = 0.17* |
| 918-1i | 0.106 | 2.1606 | 3.7002 | 3.6891 |
| 918-1i (corrected for GLBG) | — | 0.7735 | 2.3131 | 2.3020 |
| 918-1i estimated BUP elution concentration [BUP]t using equation from Table 12-3 (mg/ml) | — | 0.96 | 2.9 | *Between 3 and 17.1 |
| 918-1i estimated fraction of BUP elution = [BUP]t/[BUP]theoretical; [BUP]theor. = 17.1 | — | 0.06 | 0.17 | > or = 0.17* |

TABLE 12-3

BUP calibration equation as obtained from a linear best fit of absorption at 270 nm vs. BUP concentration (mg/ml) in pH-2 water. This table provides the absorbance intensity for BUP free base that was fully dissolved in pH-2 water over the detectable range of [BUP], expressed in mg/ml. Note that the absorbance values as reported below represent corrected values that were obtained by subtracting a single-beam absorbance spectrum of pH-2 water from the single-beam absorbance spectra of the BUP samples.

| [BUP] mg/ml | Relative Absorbance Intensity |
|---|---|
| 2.2364 | 2.7859 |
| 1.2300 | 1.6119 |
| 0.72684 | 0.9195 |
| 0.22364 | 0.2290 |
| 0.022364 | −0.0248 |
| 0.0022364 | −0.0511 |
| 0.00022364 | −0.0394 |
| 0 | 0 |
| $R^2$= | 0.998 |
| Slope= | 1.2787 |
| y-intercept= | −0.0310 |

Hydrophobic Sample Compositions, Preparations, and Procedures.

The comparative formulations comprising hydrophobic components were based on compositions as discussed in Examples 9 and 10. Specifically, three formulations were prepared for this example, 14C-3A, 14C-3B2, and 14C-3A Placebo, by using a formulation that was similar to that of Formula 14C-2 with a few exceptions, including: 1) the 30/70 w/w blend of 5 micron to 41 micron PLGA placebo microspheres were substituted with distributions comprised of 100% of smaller sized PLGA microspheres; 2) 14C-3A was formulated with PLGA microspheres containing 20% BUP free base by weight (SWRI, 20% BUP free base loaded PLGA microspheres based on Resomer RG504, prepared using a using a spinning disc spray-dry atomization process, sample ID 18-0202-015-p21; D50=4.3 microns; photo provided in FIG. 7e); 3) 14C-3B2 was formulated with BUP free base (Santa Cruz Biotechnology, CAS #38396-39-3) that was added directly to the formulation together with PLGA placebo microspheres (SWRI, PLGA placebo microspheres based on Resomer RG504, prepared using a using a spinning disc spray-dry atomization process, sample ID 18-0202-105-15; D50=5 microns); and 4) the compositions of 14C-3B2 and 14C-3A Placebo were subtly modified to achieve compliance characteristics suitable for textile impregnation.

The formulations prior to textile impregnation were prepared using the same materials as those used in Example 9. A gelatinous melt-recrystallized amalgam of mineral oil (MO) and beeswax (BW) was prepared at the same ratio as was used previously for 14C-2 (5/1 w/w oil to wax). In the next step, Great Lakes bovine gelatin (GLBG) was added to the amalgam to form a premix. For the cases of 14C-3A and 14C-3B2, the same weight ratios were used for the premix as reported for 14C-2 from Example 9 (55.10 weight % MO, 11.10 weight % BW, and 33.39 weight % GLBG). For the case of 14C-3A Placebo, a slightly lower level of GLBG was used in the premix for the purpose of adjusting the viscosity.

In the next step, PLGA microspheres were dispersed into the premixtures of MO/BW/GLBG using the same procedures as reported in Example 9. The 14C-3A formulation was made by dispersing the 20% BUP-loaded PLGA microspheres (D50=4.3 microns) into the premixed vehicle under ambient conditions. The resulting dispersion had very similar compliance and viscosity characteristics to sample 14C-2 as was made previously, in spite of the use of the smaller PLGA particle size distribution. The 14C-3B2 formula was similarly prepared, but in the first step, BUP free base was dispersed directly into the premix of MO/BW/GLBG under ambient conditions, and then the PLGA placebo microspheres were added (D50=5 microns). In a first attempt, the 14C-3B2 formula was targeted to have an identical composition to that of 14C-2. However, the total percentage of dispersed solids were initially too high to yield a compliant dispersion and a dry blend was formed instead. For this reason, the total weight % of dispersed solids, predominantly BUP free base and PLGA placebo microspheres in the case of 14C-3B2, were reduced to a level that allowed for the formulation of a dispersion that would be compliant enough to impregnate a fibrous textile. Finally, a third formula, 14C-3A Placebo, was also prepared, analogous to 14C-3A and 14C-3B2, but containing PLGA placebo microspheres (SWRI, PLGA placebo microspheres based on Resomer RG504, prepared using a using a spinning disc spray-dry atomization process, sample ID 18-0202-105-15; D50=5 microns) instead of BUP loaded microspheres. The 14C-3A Placebo formula, like the 14C-3B2 formula, also required a slightly lower weight percent of dispersed solids to achieve compliance characteristics that were suitable for textile impregnation. In this case, the adjustment was made by diluting the vehicle with the 5/1 (w/w) amalgam of melt-recrystallized MO and BW. The three resulting sample formulations exhibited qualitatively similar compliance characteristics to one another, and each was used to prepare cellulose textile-impregnated devices for the purposes of the present example using procedures as reported in Examples 9 and 10. The mixing compositions of the comparative formulations are provided in Table 12-4.

TABLE 12-4

Weight % compositions of hydrophobic vehicles for use in preparing textile-impregnated devices. Calculations also include the net weight % concentration of BUP in each vehicle, the net PLGA polymer weight % (i.e., ~80% of the weight of BUP loaded microspheres, and 100% of placebo microspheres), and the total weight % of dispersed solids.

| Vehicle Mixture Composition | 14C-3A | 14C-3B2 | 14C-3A Placebo |
|---|---|---|---|
| Mineral Oil | 23.03% | 28.39% | 28.12% |
| Beeswax | 4.61% | 5.68% | 5.62% |
| Bovine Gelatin | 13.85% | 17.07% | 12.68% |
| 5 um PLGA Placebo microspheres | 0% | 39.09% | 53.57% |
| 4.3 micron 20% BUP free base loaded PLGA microspheres | 58.51% | 0% | 0% |
| BUP free base (directly added to vehicle) | 0% | 9.77% | 0% |
| TOTAL | 100.00% | 100% | 100% |
| Total BUP in vehicle | 11.70% | 9.77% | 0% |
| Total PLGA polymer in Vehicle | 46.81% | 39.09% | 53.57% |
| Total % dispersed solids in vehicle | 76.97% | 71.61% | 71.88% |

Impregnation of Cellulose Fiber Textiles.

The delivery devices were prepared using procedures as reported in Example 9. The construction used for the devices was like that reported for set-2 in Table 5 of Example 9, with two orthogonal Surgicel Original (SO) textiles having dimensions of approximately 1.8×3.8 cm each. The average single SO textile weight was 0.0470 g (n=35, SD=+/−0.0016 g), resulting in an average cellulose textile weight contribution of 0.094 g per device. The weight of each impregnated vehicle ranged from approximately 0.73 g to 0.75 g per device. The device compositions are reported in Table 12-5. The comparative sample formulations were designed to deliver a maximum BUP concentration of approximately 104 mg BUP per g of the 14C-3A device and 88 mg per g of the 14C-3B2 device.

TABLE 12-5

Weight % compositions of hydrophobic textile-impregnated devices. The vehicle compositions as reported in Table 12-4 were impregnated into two orthogonally oriented SO textiles. The calculations for compositions also include the concentration of BUP, and the effective available BUP concentration for release during the water-soak experiments. Note that when the devices were transferred to 11 ml glass vials, a small amount of vehicle weight was lost. This loss was taken into account to insure that the correct water to BUP weight ratios were employed during the water-soak experiment (i.e., to achieve a BUP reservoir concentration of approximately 17 mg BUP/ml water, which was the same concentration that was used during the water-soak experiments on the comparative devices that were made with hydrophilic components).

| Ingredient | 14C-3A | 14C-3B2 | 14C-3A Placebo |
|---|---|---|---|
| Great Lakes Bovine Gelatin (GLBG) | 12.35% | 15.36% | 11.29% |
| Mineral Oil (MO) | 20.53% | 25.54% | 25.04% |
| Beeswax (BW) | 4.11% | 5.11% | 5.01% |
| PLGA polymer (i.e., representing 80% of the weight of 4.3-micron microspheres loaded with 20% by wt. BUP) | 41.73% | 0% | 0% |
| Encapsulated BUP (i.e., representing 20% by weight of | 10.43% | 0% | 0% |

TABLE 12-5-continued

Weight % compositions of hydrophobic textile-impregnated devices. The vehicle compositions as reported in Table 12-4 were impregnated into two orthogonally oriented SO textiles. The calculations for compositions also include the concentration of BUP, and the effective available BUP concentration for release during the water-soak experiments. Note that when the devices were transferred to 11 ml glass vials, a small amount of vehicle weight was lost. This loss was taken into account to insure that the correct water to BUP weight ratios were employed during the water-soak experiment (i.e., to achieve a BUP reservoir concentration of approximately 17 mg BUP/ml water, which was the same concentration that was used during the water-soak experiments on the comparative devices that were made with hydrophilic components).

| Ingredient | 14C-3A | 14C-3B2 | 14C-3A Placebo |
|---|---|---|---|
| the 4.3-micron microspheres loaded with 20% by wt. BUP) | | | |
| PLGA polymer from 5-micron placebo microspheres | 0% | 35.16% | 47.7% |
| BUP free base (non-encapsulated, directly added to the vehicle) | 0% | 8.79% | 0% |
| SO textiles | 10.84% | 10.05% | 10.96% |
| mg BUP/g device | 104 | 88 | 0 |
| Target ratio of pH 2 water to BUP (w/w) in water soak experiment | 58.33 | 58.33 | N/A |
| Weight of Device as made (g) | 0.8296 | 0.8257 | 0.8457 |
| Weight of Vehicle as made (g) | 0.7372 | 0.7304 | 0.7529 |
| Tarred Weight (g) of device added to 11 ml glass vial | 0.8176 | 0.8250 | 0.8290 |
| Weight of vehicle after transfer to vial (g) | 0.7252 (containing 11.70% BUP) | 0.7297 (containing 9.77% BUP) | 0.7363 |
| Weight of pH 2 water (g) added to 11 ml vial | 4.9522 | 4.1594 | 5.0071 |
| mg of available BUP per ml pH-2 water | 17.13 | 17.13 | 0 |

When the devices comprising the textile-impregnated formulations were transferred to the 11 ml glass vials for the water soak experiment, the level of pH-2 water was adjusted to achieve a net level of approximately 17 mg BUP per ml of water as the theoretical maximum level of available BUP if all of the BUP were to be released and dissolved into the water phase. Note that a constant water to drug weight ratio of 7.0/0.12 was also used in each of the comparative water-soak experiments for the previously described comparative samples that were prepared with hydrophilic components. Thus, independent of the device type, experimental conditions were established to allow for an equivalent net reservoir of 17 mg BUP per ml water for potential elution and delivery to the water phase throughout the course of the water soak experiments. The vials were incubated at 37 degrees C. for the purpose of tracking cohesive integrity vs. time (FIGS. 10a through 10e), and for tracking the relative BUP release concentration versus time via UV spectroscopy (i.e., the relative level of BUP that was released and dissolved in the supernatants).

Figure 10D:
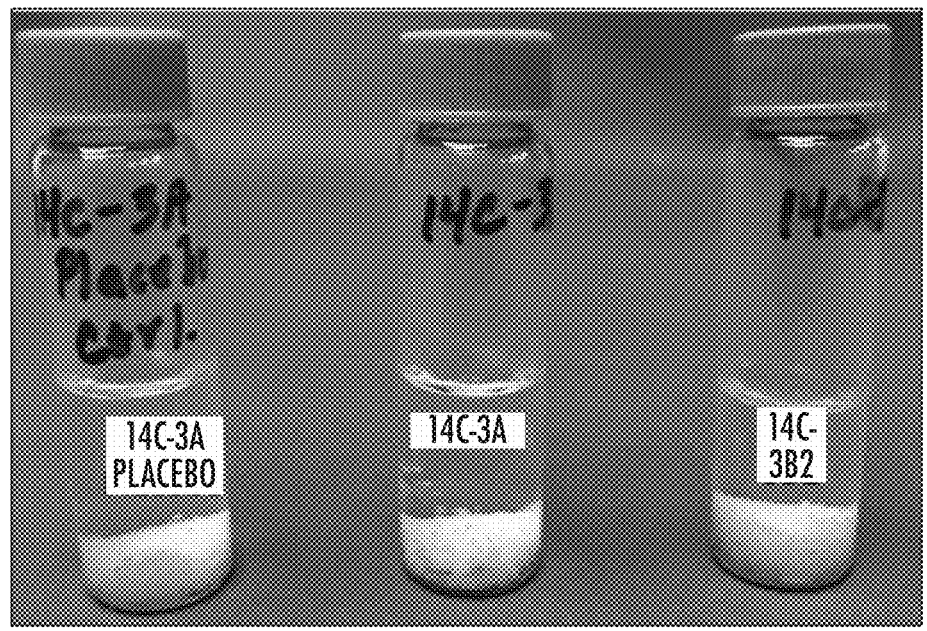
FIG. 10d is a photograph showing the hydrophobic textile-impregnated formulations 14C-3A Placebo, 14C-3A, and 14C-3B2 (from left to right) at t=24 hours during the pH-2 soak experiment at 37 degrees C.
Figure 10E:
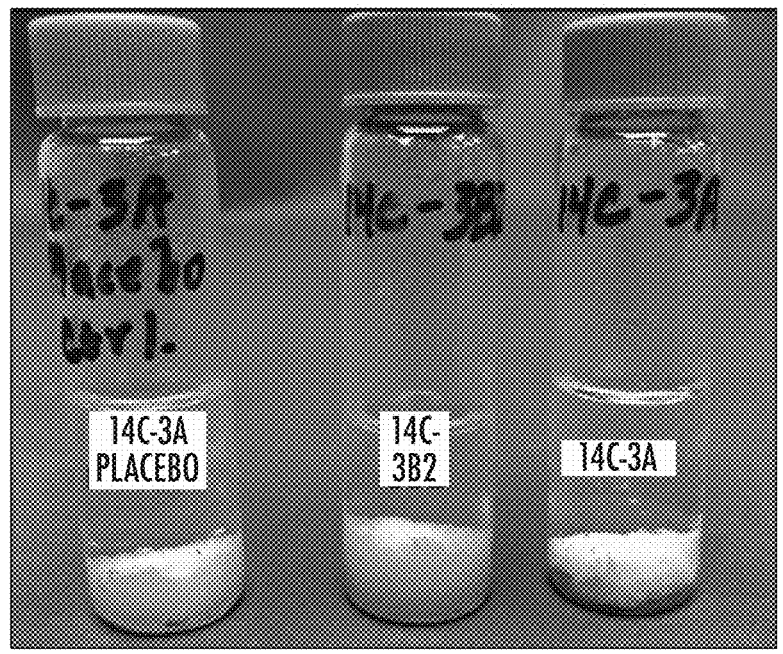
FIG. 10e is a photograph showing the hydrophobic textile-impregnated formulations 14C-3A Placebo, 14C-3A, and 14C-3B2 (from left to right) at t=4 days during the pH-2 soak experiment at 37 degrees C.
Figure 11A:
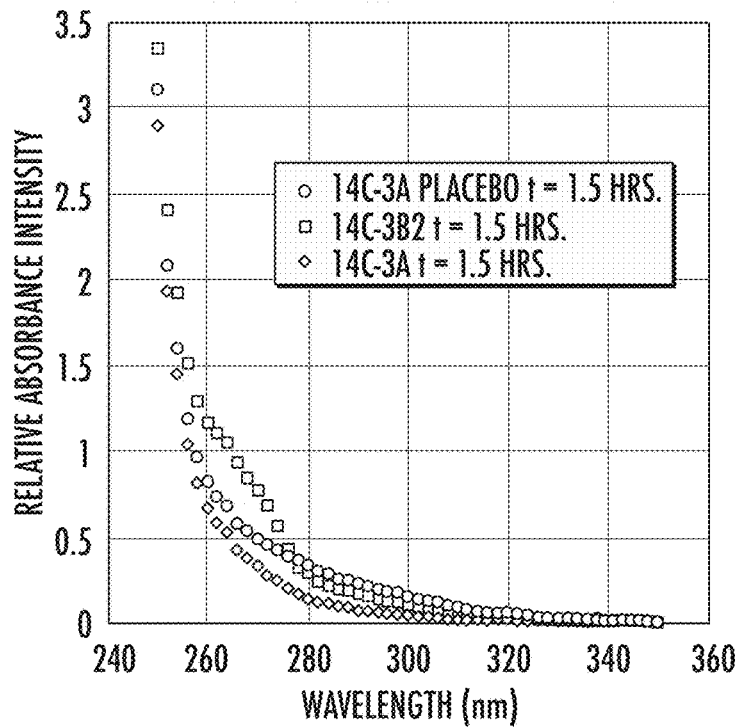
FIG. 11a depicts the relative absorbance vs. wavelength for the hydrophobic delivery system supernatants at t=1.5 hours after the onset of the water soaking experiments in pH-2 water.
Figure 11B:
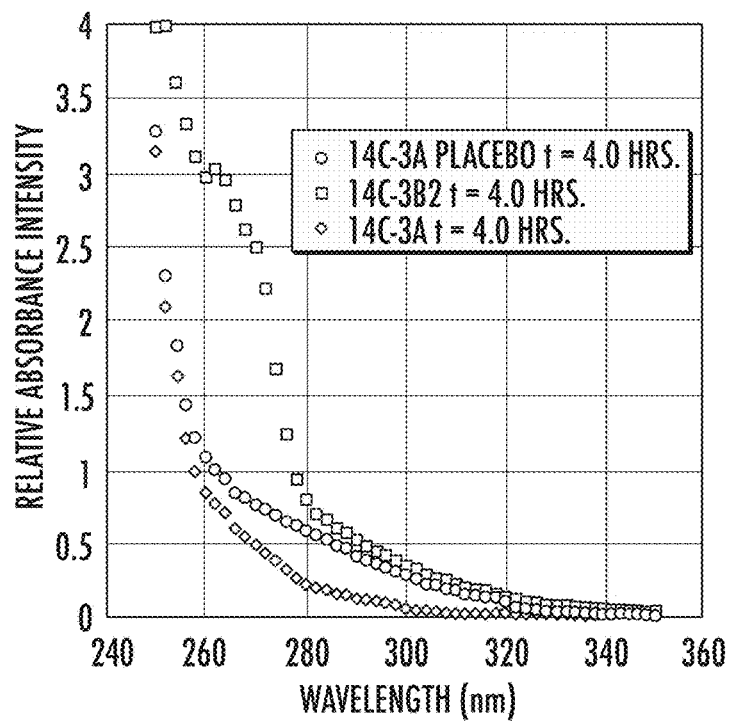
FIG. 11b depicts the relative absorbance vs. wavelength for the hydrophobic delivery system supernatants at t=4 hours after the onset of the water soaking experiments in pH-2 water.
Figure 11C:
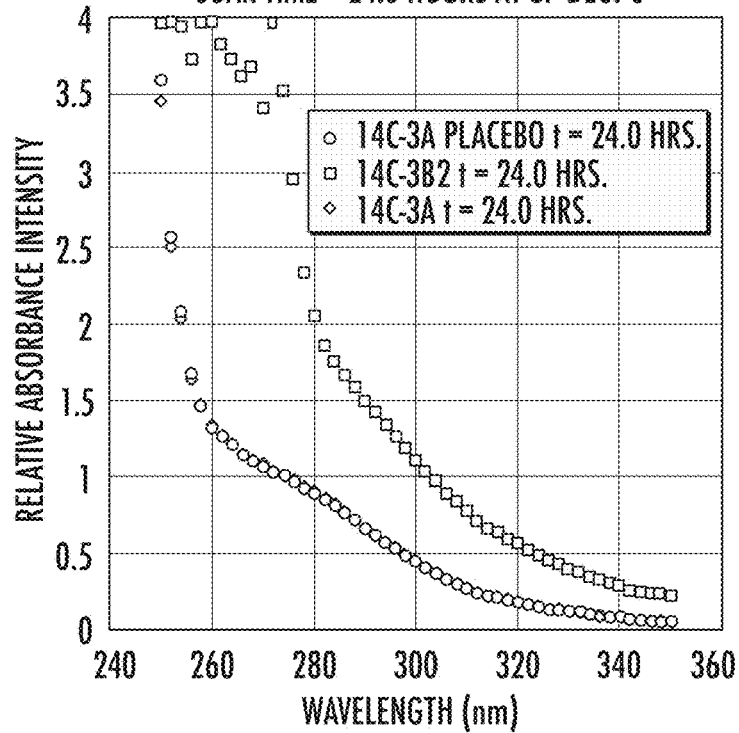
FIG. 11c depicts the relative absorbance vs. wavelength for the hydrophobic delivery system supernatants at t=24 hours after the onset of the water soaking experiments in pH-2 water.
Figure 11D:
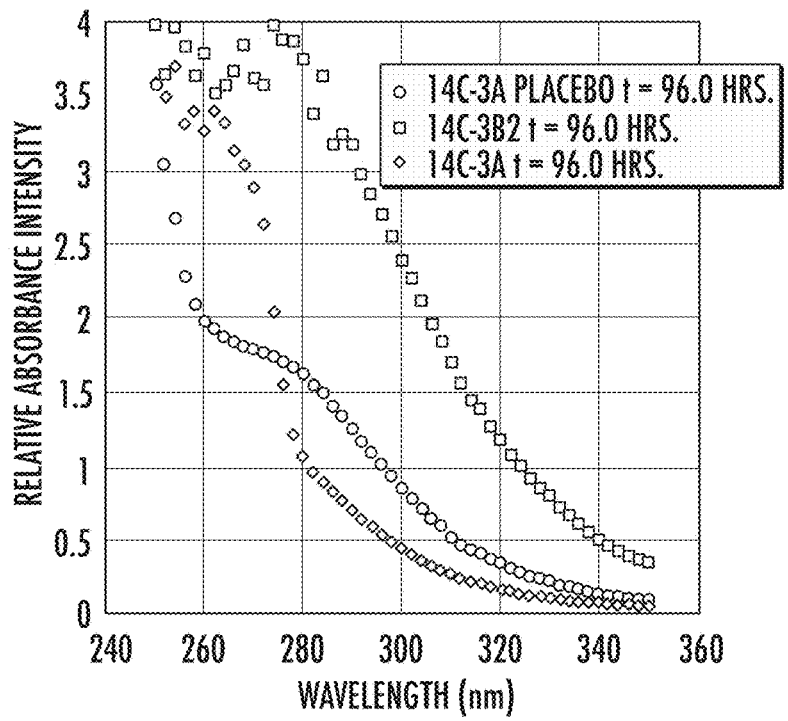
FIG. 11d depicts the relative absorbance vs. wavelength for the hydrophobic delivery system supernatants at t=96 hours after the onset of the water soaking experiments in pH-2 water.

As illustrated in FIGS. 10b, 10c, and 10d, there were no major visual differences among the supernatants of samples at t=1.5 hours, t=4 hours, and at t=24 hours. Unlike the formulations comprising hydrophilic components, there was no evidence of haze in the supernatants from disintegration of the vehicles. This behavior was observed to continue throughout the 4-day course of the water-soak experiment. The behavior was surprising from the standpoint that even in the absence of visual disintegration, measurable relative concentrations of soluble BUP were still released. At t=24 hours, and especially after 4 days, there was a subtle degree of swelling of sample 14C-3B2, but the degree was relatively minimal when compared to the degree of swelling and disintegration that had occurred in both samples 918-1i and 918-1B after only one day.

When the vials were removed from the incubator, 1 ml aliquots of supernatant were removed from each sample for UV analysis. The glass vials were then closed and were placed back into the incubator to continue incubating through the course of time required to complete the UV absorption measurements. Unlike the supernatants from the earlier samples, the supernatant aliquots from the samples comprising hydrophobic components were not centrifuged. This was because no visual erosion and disintegration had occurred among the samples as evidenced by the lack of haze owing to the lack of water-dispersed solids. Again, each of the 1 ml aliquots was used for UV absorption spectral analyses, and the relative levels of dissolved BUP were monitored as a function of time for each of the supernatant samples. When each of the UV measurements was completed, the 1 ml aliquots for each sample were returned to their respective vials, and the samples were returned to continue incubating at 37 degrees C. This sampling procedure was repeated at t=4 hours, t=24 hours, and at t=96 hours after the onset of the water-soaking experiment.

Importantly, the longer duration of the water-soak experiment for samples 14C-3A, 14C-3B2, and 14C-3A Placebo in comparison to samples 918-1i and 918-1B was made possible not only because of slower BUP release rates, but also because of minimal swelling and minimal disintegration among the samples. The samples that were made with hydrophobic components were observed to maintain their mechanical cohesive integrity for significantly longer periods of time while soaking under static conditions than their comparative counterparts that were made with hydrophilic components. The unanticipated benefit of this behavior includes the potential to create formulations for longer term use in the end use application than would otherwise be possible with the comparable formulations.

It is also important to note that the sample formulations comprising hydrophobic components contained a higher weight % of BUP per unit device weight than their hydrated counterpart formulations comprising hydrophilic components. As noted in prior examples, the latter require hydration prior to deployment to form compliant dough-like substances to render them as suitable for clinical use in the end use application. The addition of water during the hydration step results in an unavoidable dilution of the available BUP dosage per unit weight. By contrast, the comparative samples devices do not require hydration because they are formulated to have the necessary compliance needed for clinical use in the end use application. Consequently, the net delivery dosage of BUP per unit weight can be adjusted to higher levels in the formulations with hydrophobic components when compared to the formulations with hydrophilic counterparts. Moreover, the differential in maximum dosage is similar when volume is taken into consideration. In a volume-restricted application, as is the case for an oral tooth socket cavity, the higher active ingredient dosage per unit weight of a formulation with hydrophobic ingredients translates to a higher delivery dosage of BUP per unit volume than would otherwise be possible with a comparable device. This unanticipated benefit provides an expanded opportunity to create formulations with higher net dosage delivery levels for use over protracted periods of time during end use if so desired.

UV Absorption Experiments of Hydrophobic Samples.

Instrument parameters and procedures were the same as those used above, but with one major exception. Namely, as discussed earlier, the 1 ml aliquots were pipetted directly from the supernatants and then were analyzed without centrifuging. The 1 mL aliquots were then loaded into the same types of UV/VIS compatible cuvettes (outside dimensions=12 mm×12 mm, inside path length=10 mm). Again, the net potential availability of BUP for elution into the water phase was approximately 17 mg/ml at maximum for the duration of UV absorption experiments. Spectrometer readings were measured between 250-350 nm. A wavelength step size of 2 nm with a bandwidth between 5-9 nm was used, and with 25 flashes, the number of incident light exposure & detection occurrences that were signal averaged at each wavelength. After each absorbance measurement, the supernatant was collected and was then added back to the original glass vial, such that total volume in the elution experiment did not change except for minor loss due to residual supernatant in the pipette or UV cuvette.

FIGS. 11a through 11d provide four relative absorbance vs. wavelength plots for the supernatants of samples 14C-3A, 14C-3B2 and 14C-3A Placebo with each plot delineating a separate soaking time point, including points at t=1.5 hours, t=4 hours, t=24 hours, and at t=96 hours after the onset of the water soaking experiments in pH 2 water. As was the case for the comparative samples, these plots reveal that BUP was released more slowly when the BUP was encapsulated within PLGA in 14C-3A, and more quickly when the BUP was formulated directly into the formulation as in sample 14C-3B2. All three delivery systems showed evidence of component dissolution as a function of time with the wavelengths between approximately 260-270 nm providing the clearest visual delineation of the absorbance differences among the supernatants at the various time points. Although the partial dissolution of other ingredients may contribute to absorption in this range (as evidenced by the placebo), BUP-HCl is known to be a strong chromophore with a reported UV absorbance maximum of 262 nm (Corciova, A., Eur. Chem. Bull., 2012, 2(8), 554-557). Hence, the evolution of absorption in the 260-270 nm range is strongly influenced by the protonation of BUP and by its subsequent dissolution vs. time. Thus, FIGS. 11a through 11d collectively reveal that BUP was released more slowly from the delivery system when the BUP was encapsulated within PLGA (formulation 14C-3A), and more quickly when the BUP was formulated directly into the hydrophobic vehicle (formulation 14C-3B2).

FIGS. 12a, 12b, and 12c provide an alternative representation of the same data. Specifically, three plots are provided with each plot representing the time evolution of absorption curves for each individual sample. The plot representing the time evolution of the placebo device, 14C-3A Placebo without BUP, illustrates the egress of water-soluble components from the formulation itself as a function of time, components other than BUP, such as GLBG and SO. These types of components would be expected to contribute to the overall background absorption from supernatants of fully formulated samples that contain BUP. Regarding the devices with BUP, the growth in absorption intensity vs. time can be seen over the wavelength range 260-270 nm, with faster growth occurring from the device where BUP was formulated directly into sample 14C-3B2. The increase in absorption intensity from conversion of BUP free base to the soluble amine hydrochloride (BUP-HCl) was paralleled by a measurable increase in the pH of the supernatants for the samples containing BUP. The following pH values were measured after 10 days of soaking in pH-2 water at 37 degrees C.: 14C-3A (BUP free base inside microspheres) =3.51; 14C-3B2 (BUP free base formulated directly into the vehicle and outside of the microspheres)=3.90; and 14C-3A Placebo (no BUP): pH of solution=2.18. The minimal change in pH for the placebo indicates that the other soluble components that contribute to UV absorption in the 260-270 nm range have minimal impact on pH when compared to the effect of the BUP free base itself. Moreover, the highest degree of acid neutralization occurred when the BUP free base was formulated directly into the sample, a result that corroborates with faster release as measured by UV spectroscopy.

Using the reported UV absorbance maximum for BUP-HCl (262 nm), FIG. 13 provides the evolution of the absorbance intensity as a function of time for each of the device types. This plot is presented with a natural log time scale to better illustrate the large differences in the rates of egress among the device types. For illustration purposes, each of the data sets were empirically fit to a simple exponential growth function. The function and best fit parameters are provided in Table 1.2-6. These trends illustrate the relative difference in release rates afforded by 1) the morphological distribution of the BUP, and by 2) the relative hydrophobicity of the formulation. For example, the trends reveal that the relative release rate of BUP increases with the use of hydrophilic components, and then decreases when the BUP is encapsulated by PLGA. Specifically, the relative BUP release rate was observed to trend as follows: 918-1i>918-1B~14C-3B2>14C-3A.

These trends also reveal that independent of the other ingredients, PLGA encapsulation attenuates the relative BUP release rate. Surprisingly however, the initial relative release rate from 14C-3B2 containing BUP that is formulated within the sample without PLGA encapsulation was observed to be approximately the same as that of 918-1B in which the BUP was encapsulated within microspheres. This counterintuitive result reinforces that the present formulation affords the opportunity to control release rates by virtue of employing multiple factors, either alone or in any combination, including the use of BUP encapsulated by PLGA, the use of freely formulated BUP, and the use of formulations with varying degrees of hydrophobic and hydrophilic ingredients. For example, if a short time-duration release profile is desired, 1-3 days, then a formulation with hydrophobic ingredients containing BUP without PLGA encapsulation can be used to achieve similar results to those of a formulation with hydrophilic ingredients containing BUP that is encapsulated within PLGA microspheres.

TABLE 12-6

Exponential growth function along with the adjustable parameters that were used to achieve an iterative best fit of the relative absorbance intensity at 262 nm vs. time data for the supernatants of the hydrophilic and hydrophobic devices while soaking in pH 2 water at 37 degrees C. A plot of the best fit data is provided in FIG. 13. Data were fit to the following functional form: Abs = C1 + C2*[1 − exp(−C3*time)], where Abs = absorbance at 262 nm; C1, C2, and C3 are constants derived from the iterative best fit of the data; and time = soak time in hours. The adjustable parameters are provided below.

| Sample | C1 | C2 | C3 | $R^2$ |
|---|---|---|---|---|
| 918-1i (fastest rate) | −0.53 | 4.29 | 1.01 | .99 |
| 918-18 | −2.68 | 6.44 | 0.57 | .99 |
| 14C-3B2 | −2.22 | 5.90 | 0.55 | .99 |
| 14C-3A | 0.56 | 10.36 | 0.003 | .99 |
| 14C-3A Placebo | 0.80 | 1.36 | 0.019 | .97 |

The [BUP] calibration line from Table 12-3 (i.e., of [BUP] mg/ml vs. relative absorbance intensity at 270 nm) was used to estimate the approximate BUP concentration in the supernatants as a function of time during the pH 2 water soak experiment. However, before estimating the effective elution concentration of BUP from samples 14C-3A and 14C-3B2, the supernatant absorbance values at 270 nm were first corrected by subtracting the absorbance contribution from the 14C-3A Placebo sample, which in essence equates to a mixed contribution of possible absorbances from GLBG, SO, and perhaps even from PLGA, MO, and BW in the absence of BUP. In this way, the corrected absorption values provided an estimate of the relative BUP absorbance contribution, in this case soluble BUP-HCl. These data and calculations are provided in Table 12-7.

The estimates of [BUP] versus time were limited to supernatants with net absorbance values of less than about 3.9, below the detector saturation level. When the detector saturation level was reached, the estimated BUP elution concentration was reported as equal to or greater than the value calculated from the calibration line in Table 12-3, or in other words, greater than or equal to the calculated BUP concentration at an absorbance value approaching 3.9 but less than the maximum value of $[BUP]_{theoretical}$. Note that successive dilutions could have been used to bring the absorbance values back within the detection range, but for the purposes of this example, these additional experiments were not necessary in order to illustrate the important differences among the sample types. In the next step, the estimated BUP elution concentration [BUP]t was ratioed against the total theoretical concentration $[BUP]_{theoretical}$ thereby allowing for comparison of relative BUP elution rates among the various samples.

TABLE 12-7

Relative absorption of supernatants from hydrophobic devices at 270 nm vs. time (hrs.) during the pH 2 water-soak experiment, including the estimated [BUP] at each time interval, and the estimated fraction of eluted BUP based on an initial theoretical concentration of BUP that was available from the device (i.e., 17.13 mg/ml for the hydrophobic devices as reported in Table 12-5). The absorption from the devices containing BUP were corrected for background contributions from non-BUP ingredients that may have dissolved (e.g., SO, GLBG) or dispersed (e.g., PLGA, MO, BW) as a function of time during the soak experiment. These contributions were roughly estimated from the absorbance of the 14C-3A Placebo at 270 nm. Note that when the absorbance correction resulted in a negative value, the correction was denoted as zero (marked with an asterisk). When measured absorbance values were at or approaching the saturation point of the detector, the effective BUP concentration was denoted as greater than the calculated value, but less than the theoretical maximum of ~17 mg/ml (also denoted with an asterisk).

| Device | Weight (g) per ml pH 2 water | 270 nm Abs t = 1.5 hrs. | 270 nm Abs t = 4 hrs. | 270 nm Abs t = 24 hrs. | 270 nm Abs t = 96 hrs. |
|---|---|---|---|---|---|
| 14C-3A Placebo | 0.8290 | 0.4997 | 0.7690 | 1.0712 | 1.7985 |
| 14C-3A | 0.8176 | 0.3296 | 0.4904 | 1.0345 | 2.8987 |
| 14C-3A (corrected for background contributions) | — | ~0* | ~0* | ~0* | 1.1022 |
| 14C-3A estimated BUP elution concentration [BUP]t using equation from Table 12-3 (mg/ml) | — | ~0* | ~0* | ~0* | 1.4 |
| 14C-3A estimated fraction of BUP elution = [BUP]t/ [BUP]theoretical; [BUP]theor. = 17.1 | — | ~0* | ~0* | ~0* | 0.08 |
| 14C-3B2 | 0.8250 | 0.7817 | 2.6323 | 3.4235 | 3.6308 |
| 14C-3B2 (corrected for background contributions) | — | 0.2820 | 1.8633 | 2.3523 | 1.8323 |
| 14C-3B2 estimated BUP elution concentration [BUP]t using equation from Table 12-3 (mg/ml) | — | 0.33 | 2.35 | 2.98 | Between 2.3 and 17.1 |
| 14C-3B2 estimated fraction of BUP elution = [BUP]t/ | — | 0.02 | 0.14 | 0.17 | = or >0.14 |

TABLE 12-7-continued

Relative absorption of supernatants from hydrophobic devices at 270 nm vs. time (hrs.) during the pH 2 water-soak experiment, including the estimated [BUP] at each time interval, and the estimated fraction of eluted BUP based on an initial theoretical concentration of BUP that was available from the device (i.e., 17.13 mg/ml for the hydrophobic devices as reported in Table 12-5). The absorption from the devices containing BUP were corrected for background contributions from non-BUP ingredients that may have dissolved (e.g., SO, GLBG) or dispersed (e.g., PLGA, MO, BW) as a function of time during the soak experiment. These contributions were roughly estimated from the absorbance of the 14C-3A Placebo at 270 nm. Note that when the absorbance correction resulted in a negative value, the correction was denoted as zero (marked with an asterisk). When measured absorbance values were at or approaching the saturation point of the detector, the effective BUP concentration was denoted as greater than the calculated value, but less than the theoretical maximum of ~17 mg/ml (also denoted with an asterisk).

| Device | Weight (g) per ml pH 2 water | 270 nm Abs t = 1.5 hrs. | 270 nm Abs t = 4 hrs. | 270 nm Abs t = 24 hrs. | 270 nm Abs t = 96 hrs. |
|---|---|---|---|---|---|
| [BUP]theoretical; | | | | | |
| [BUP]theor. = 17.1 | | | | | |

Summary of Results.

The cohesive integrity under static soaking conditions, as qualitatively gauged by the relative degrees of visual swelling, device disintegration, and haze in the supernatants from disintegrated material, was qualitatively observed to improve with the use of hydrophobic ingredients. The following trend was observed from lowest to highest relative degree of visual swelling, disintegration, and development of supernatant haze: 14C-3A (hydrophobic vehicle, BUP encapsulated within PLGA microspheres)<14C-3B2 (hydrophobic vehicle, BUP formulated directly into vehicle containing placebo PLGA microspheres)<<918-1B (hydrophilic vehicle, BUP encapsulated within PLGA microspheres) <918-1i (hydrophilic vehicle, BUP formulated directly into vehicle containing placebo PLGA microspheres). The relative release rate of BUP was observed to increase with the use of hydrophilic ingredients, and with BUP that was not encapsulated: 918-1i>918-1B~14C-3B2>14C-3A.

The trends reveal that from the standpoints of mechanical cohesive integrity and relative release rates, the hydrophobic ingredients are best suited for formulations wherein the intention is to achieve longer-term usage in the end application. For example, the more hydrophilic formulations disintegrate more quickly under static conditions, rendering them most useful for shorter-term end use durations. By contrast, the more hydrophobic formulations, particularly with fiber reinforcement, provide longer-term cohesive integrity under static soaking conditions, which render them as well-suited for both short-term and longer-term use. The relative BUP release rates also corroborate with these conclusions. Namely, the hydrophilic formulations afford faster release than the hydrophobic formulations. Thus, one lever that is useful in preparing a formulation with a controlled release profile is the relative hydrophobicity of the formulation, where the more hydrophobic the formulation, the slower the release. A second lever that has proven to be useful for preparing devices with controlled BUP release is PLGA encapsulation of BUP.

Independent of other features of the formulation, PLGA encapsulation was observed to attenuate the relative BUP release rate. Surprisingly however, the relative release rate from a more hydrophobic formulation containing BUP without PLGA encapsulation was observed to be similar to that of a more hydrophilic formulation wherein the BUP was encapsulated within PLGA microspheres. This result reinforces that the present formulation technology affords the opportunity to control release rates by virtue of employing multiple factors, either alone or in combination, including 1) using PLGA to encapsulate BUP; 2) adjusting the degree of hydrophobicity; and 3) incorporating BUP with no PLGA encapsulation. For example, if a short time-duration release profile is desired of 1 to 2 days, then a more hydrophobic formulation containing BUP without PLGA encapsulation can be used to achieve similar results to a more hydrophilic formulation containing BUP that is encapsulated within PLGA microspheres. In another example, microencapsulation of active ingredients can be used in combination with free, non-encapsulated active ingredients, to create devices exhibiting an adjustable range of relative BUP release rates, depending on the ratio of encapsulated BUP to free BUP. Moreover, when a more hydrophobic formulation is employed, even higher net delivery dosages per unit weight device can be achieved if so desired as further demonstrated in Example 13.

Example 13. Formulations Compromising Hydrophobic Ingredients and Containing Mixtures of Encapsulated and Non-Encapsulated Ingredients More hydrophobic formulations like those described in Example 12 were prepared for this example. The objectives were to demonstrate various methods that can be used to control BUP release from a more hydrophobic formulation, to demonstrate methods by which the maximum dosage level of BUP can be raised to even higher levels, and to demonstrate formulation flexibility that allows for the incorporation of additional dispersed ingredients, such as pH modulators, without adversely affecting rheological characteristics and release characteristics.

Factors for this experiment included: 1) use of non-encapsulated BUP-free base; 2) use of PLGA-encapsulated BUP-free base; 3) the use of mixtures of PLGA-encapsulated BUP-free base and non-encapsulated BUP-free base; and 4) the use of pH modulators citric acid (Sigma-Aldrich, cat. #251275, CAS #77-92-9) and dibasic sodium citrate sesquihydrate (Sigma-Aldrich cat. #71635, CAS #6132-05-4, referred to herein as sodium citrate). These experiments demonstrate the use of combinations of encapsulated and non-encapsulated BUP to create devices with even higher possible dosage loadings of BUP or other active ingredients if so desired. Moreover, the experiments demonstrate that a range of release rates are possible depending upon the ratio of the encapsulated to non-encapsulated ingredients.

Using procedures outlined in Example 12, compositions were mixed and were used to impregnate two orthogonally arranged Surgicel Original (SO) textiles for the purpose of forming control-release delivery devices. The compositions of the formulations and devices are provided in Tables 13-1 and 13-2, respectively. The devices were then subjected to pH-2 water-soak testing at 37 degrees C. and, using methodology similar to that which was described in Example 12, UV spectroscopy was used to estimate the relative concentration of BUP that had diffused or eluted into the supernatants as a function of time.

The concentration of BUP at each time increment was estimated by using a two-step procedure. First, the UV absorption values from the supernatants of the pH-2 water-soaked devices were background corrected by subtracting the UV spectra of the supernatant from a water-soaked placebo device which was used to approximate the absorption contributions from non-BUP components, sample 14C-3E Placebo in this example. FIG. 14 displays a relative absorbance vs. time comparison of placebo devices 14C-3E (with citric acid) and 14C-3A (without citric acid). Absorbance vs. time data show that although the devices produced soluble components in the absorbance region overlapping with BUP, there was no significant effect of citric acid under pH-2 soaking conditions. Consequently, to simplify analyses, the 14C-3E absorbance data were used for all pertinent spectral background corrections relating to the spectral absorbance of devices containing BUP.

In the second step, the background-corrected absorption intensities for the devices were used to estimate the [BUP] in each supernatant at each time increment (FIG. 15). This was accomplished by using two separately generated calibration lines of [BUP] vs. absorbance, including one at 270 nm (Table 12-3) and a second at 262 nm (Table 13-3). The two estimates of [BUP] were then averaged, and were then used to assess the relative BUP release rates in mg/ml/hour (Table 13-4 and FIG. 16), and the fraction of BUP elution vs. time based on a theoretical maximum elution of approximately 17 mg/ml for each of the delivery devices (Table 13-5 and FIG. 17).

Note that the raw absorption values from the supernatants of the water-soaked devices were corrected for estimated background contributions from non-BUP components that had become partially dissolved over time. This was accomplished by subtracting the absorbance values from the supernatant of the 14C-3E placebo from those of the other devices at each respective wavelength as a function of time. The data analyses were purposely limited to include only those data time-points that were within the limits of UV detection (i.e., below the saturation limit of the UV detector). The upper time-value limits for each device are reported in Table 13-4. The detector saturation condition was reached more quickly with devices that employed freely dispersed BUP powder (i.e., BUP that was not encapsulated with PLGA). The maximum upper time-limit in these cases was between approximately 12 and 48 hours. The detector saturation condition was reached more slowly with delivery systems that employed PLGA-encapsulated BUP microparticles (i.e., in devices made without the use of freely dispersed BUP). The maximum upper time-limit before detector saturation in these cases was approximately 96 hours (i.e., 4 days). Note that in some cases, the estimates of [BUP] appeared to be slightly negative at short soak times (e.g., at times of less than 8 hours for systems formulated with PLGA-encapsulated BUP). This was an artifact of over-correction from the 14C-3E placebo device, which appeared to provide a slightly higher degree of short-time non-BUP component dissolution than comparable devices that were formulated with PLGA-encapsulated BUP.

FIG. 16 illustrates the relative rates of BUP elution (mg/ml/hour) together with the data ranges used for establishing the best linear fitting parameters. The initial slopes and data ranges for the linear portions are reported in Table 13-4. Note that for the purposes of these analyses, short-time negative absorption values were omitted, a zero-time point was added (i.e., with absorption=0), and the best linear-fit lines were forced through a zero-intercept. Data collection times included the following time points (in hours): 1.5, 4, 8, 12, 24, 48, 72, 96, 120, and 192. However, only the on-scale data were represented because beyond the upper time-point limit, the UV absorption values moved off-scale due to detector saturation. FIG. 16 demonstrates that for devices containing mixtures of freely dispersed BUP and PLGA-encapsulated BUP, the relative BUP elution rate was intermediate between rates for devices containing freely dispersed BUP and for those containing PLGA-encapsulated BUP.

FIG. 17 mirrors the data plot presented in FIG. 16, but with the [BUP] expressed in terms of the fraction of eluted BUP=[BUP]/[BUP]$_{theoretical}$=[BUP]/17.14. This graph reveals that the fastest releasing delivery system eluted 12% of its theoretical [BUP] reservoir within about 12 to 24 hours, whereas the slowest releasing systems released approximately 7 to 8% of their theoretical [BUP] within approximately 4 days. Intermediate devices (i.e., those containing mixtures of freely dispersed BUP and PLGA-encapsulated BUP) had released 8-10% of their theoretical [BUP] within approximately 2 days.

The formulations in each delivery device were formulated to have similar percentages of total dispersed solids, components that were not soluble in mineral oil but instead were dispersed within the formulation matrix. Note that the total percentage of dispersed solids is a factor that affects the rheological and compliance characteristics of both the formulation and the delivery device. These properties not only have an impact on the tactile handleability of the delivery device during deployment, but they also have an impact on the diffusion rates of fluids and active ingredients as they diffuse across concentration gradients, both into and out of the delivery device during its deployment and during subsequent in vivo hydration. Generally, the higher the percentage of dispersed solids, the higher the viscosity and the lower the compliance. Of course, rheo-mechanical properties are also affected by other factors, including for example, the particle size distributions of the dispersed particulates, the total surface to volume ratio of particulates within the formulation matrix and within the delivery device, the weight and volume ratios of the formulation to cellulose fibers in the delivery device, the number and diameters of fibers that constitute a bundled-fiber strand, the knit or weave density of the fibers and fiber bundles that constitute a textile, and the surface wetting characteristics of the fibers. Any one or combination of these factors can be controlled and adjusted to achieve a broad range of rheo-mechanical responses if so desired.

For the purposes of this example, dispersed solids were calculated to include: 1) beeswax micro-crystallites dispersed in mineral oil as a result of the melt-recrystallization process; 2) bovine gelatin powder; 3) PLGA microspheres containing 20% BUP by weight; 4) PLGA placebo microspheres; 5) BUP free base powder; 6) citric acid powder; and 7) di-sodium citrate powder. By maintaining similar levels of total dispersed solids, the resulting vehicles were made to have qualitatively similar rheo-mechanical property characteristics, including relative viscosity and compliance characteristics as qualitatively judged by torque resistance during spatula-mixing, and by compressibility during textile-impregnation.

In one comparison, the relative BUP release rates were compared among three types of formulations: 1) a formulation containing PLGA-encapsulated BUP in a replicate of 14C-3A from Example 12; 2) a formulation containing dispersed BUP free base powder and placebo PLGA microspheres in a replicate of 14C-3B2 from Example 12; and 3) a formulation containing a dispersed mixture of both PLGA-encapsulated BUP and BUP free base (sample 14C-3C). The 14C-3C mixture resulted in a device with a relative BUP release rate that was intermediate between that of 14C-3A with dispersed PLGA-encapsulated BUP and that of 14C-3B2 with dispersed BUP free base, thereby demonstrating one of the methods that can be used to create formulations with controlled release characteristics (Table 13-4 and FIGS. 15, 16, and 17).

The PLGA-encapsulated BUP is reasoned to be slower to diffuse and release because it encounters at least two diffusion barriers, the first being the PLGA polymer itself, and the second being the remainder of the formulation matrix. On the other hand, dispersed BUP free base without PLGA encapsulation is thought to be faster to diffuse and release because it encounters fewer diffusion barriers. By mixing the two types of BUP at various weight ratios, dispersed microspheres of encapsulated BUP mixed with dispersed free base powder, it becomes possible to achieve a range of release rates, any of which can be chosen to achieve a desired control-release profile. Note that the optimum control-release profile will depend upon the clinical needs of the end use application.

It should be understood that this is only one method by which one can achieve a controlled-release profile. Mixtures can be augmented in other ways to include the use of other dispersed or dissolved ingredients that can have an impact on release rates, either alone or in combination with one another, or in combination with the dispersed ingredients mentioned above, and at various weight ratios. Other dispersed ingredients can include, for example, BUP-HCl powder which is more water soluble than BUP, PLGA-encapsulated BUP-HCl, PLGA-encapsulated mixtures of BUP free base and BUP-HCl. Moreover, the same PLGA-encapsulated ingredients can be comprised of larger or smaller PLGA particle size distributions, or mixtures of different PLGA particle size distributions.

Although there were differences in the dispersion characteristics of the various types of solid ingredients due to factors like particle size distribution and surface wetting characteristics, it was still possible to adjust the ratios of ingredients to achieve formulations with nearly equivalent levels of total dispersed solids, while simultaneously maintaining qualitatively similar compliance characteristics. Moreover, as demonstrated by 14C-3C, higher net loadings of BUP were also simultaneously achieved (Table 13-3). For the case of formulation 14C-3C, a higher BUP dosage was achieved by reducing the weight percentage of bovine gelatin, and by then adding an equivalent weight % of BUP free base powder in its place, so as to maintain a similar equivalent percentage of total dispersed solids. Importantly, this is an example of the type of formulation flexibility that can allow for the creation of formulations with the capacity to deliver higher maximum BUP dosages on a unit weight basis than those that would otherwise be possible through the use of PLGA microspheres alone, or more specifically with the 4.3 micron 20% BUP free base loaded PLGA microspheres as used in this example. Moreover, the potential for higher maximum dosages in a formulation with more hydrophobic ingredients will generally exceed what is possible with the more hydrophilic formulation embodiments, partly because the latter require water-dilution for plasticization in order to render them as compliant and useable.

In a second group of comparisons, samples were formulated to contain additional dispersed particulates of either citric acid or di-sodium citrate. The purpose of employing these types of optional pH modulators is to alter the relative acidity or basicity of the local chemical environment during the hydration process. During in vivo deployment, the formulation will absorb and mix with body fluids from the tooth extraction socket (Example 9), and through a process of diffusion, soluble components such as BUP-HCl, citric acid, GLBG, SO, etc., will eventually leach out of the formula and will become actively available to the surrounding tissues. Modulators can serve multiple purposes, including, for example: 1) to reduce or enhance the degree of BUP protonation affecting solubility and chemical activity; 2) to neutralize acid hydrolysis products (e.g., lactic acid that can form via hydrolysis of PLGA); 3) to reduce or enhance the degree of protonation of gelatin-protein amines which can have an impact on rates of gelation and property-build characteristics of gelatin during hydration as demonstrated in earlier examples with citric acid; 4) to form citrate salts that can exchange with and alter the solubility or the chemical activity of conjugate acid-base pairs, such as protonated BUP with Cl as its base-conjugate in exchange with citrate as its base-conjugate; 5) to catalyze the hydrolysis of PLGA, thereby enabling faster release rates of active ingredients if so desired; and 6) to positively impact the tissue healing process during end use, which is a known attribute of acids like citric acid, ascorbic acid, and others. Importantly, modulators that are insoluble in the liquid carrier, like mineral oil, can be directly dispersed within the formulation. These modulators can also be microencapsulated themselves within PLGA or with other polymers and then can be dispersed in the formulation. Of course, the purpose of microencapsulation would be to augment their time-controlled availability to satisfy any of the aforementioned purposes 1 through 6 as stated above.

It can be appreciated that when a modulator has an impact on rheo-mechanical properties via reducing or enhancing the degree of gelatin-protein amine protonation, it will consequently have an impact on rates of diffusion and on the release rates of active ingredients. Similarly, when a modulator has an impact on the solubility of an active ingredient via formation of alternate conjugate base pairs, or via direct protonation or de-protonation, rates of diffusion and rates of release can be similarly affected.

Examples of the use of modulators are represented by samples 14C-3E, 14C-3F, and 14C-3G. Each of these samples demonstrates the formulation flexibility afforded by the more hydrophobic formulation embodiment. Specifically, by using the more hydrophobic formulation impregnated into a cellulose textile, five desirable end use attributes were simultaneously and synergistically demonstrated, including: 1) the ability to achieve specific control-release profiles through the use of mixtures of dispersed ingredients (e.g., PLGA-encapsulated BUP mixed with non-encapsulated BUP); 2) the ability to achieve a wider range of BUP dosage levels; 3) the ability to use mixtures to achieve higher net BUP dosage levels than would otherwise be possible with PLGA-encapsulated BUP alone; 4) the ability to achieve compliance and tactile characteristics commensurate with those desired for the end use application; and 5) the ability to achieve additional end use functionality via the incorporation of dispersed pH modulators, without negatively impacting the rheo-mechanical properties or the efficacy of the device.

TABLE 13-1

Weight % compositions of hydrophobic vehicles for use in preparing textile-impregnated devices. Calculations also include the net weight % concentration of BUP in each vehicle, the net PLGA polymer weight % (i.e., ~80% of the weight of BUP loaded microspheres, and 100% of placebo microspheres), and the total weight % of dispersed solids.

| Vehicle Mixture Composition | 14C-3A Replicate | 14C-3B2 Replicate | 14C-3C | 14C-3E | 14C-3G | 14C-3F | 14C-3E Placebo |
|---|---|---|---|---|---|---|---|
| Mineral Oil | 23.03% | 28.39% | 23.03% | 23.03% | 23.03% | 23.03% | 28.12% |
| Beeswax | 4.61% | 5.68% | 4.61% | 4.61% | 4.61% | 4.61% | 5.62% |
| Bovine Gelatin | 13.85% | 17.07% | 9.24% | 11.55% | 6.94% | 11.55% | 10.57% |
| 5 um PLGA Placebo microspheres (dispersed) | 0% | 39.09% | 0% | 0% | 0% | 0% | 53.58% |
| 4.3 micron 20% BUP free base loaded PLGA microspheres (dispersed) | 58.51% | 0% | 58.51% | 58.51% | 58.51% | 58.51% | 0% |
| BUP free base (directly dispersed in vehicle) | 0% | 9.77% | 4.61% | 0% | 4.61% | 0% | 0% |
| citric acid (dispersed) | 0% | 0% | 0% | 2.30% | 2.30% | 0% | 2.11% |
| di-sodium citrate (dispersed) | 0% | 0% | 0% | 0% | 0% | 2.30% | 0% |
| TOTAL | 100.00% | 100% | 100% | 100% | 100% | 100% | 100% |
| Total BUP in vehicle | 11.70% | 9.77% | 16.31% | 11.70% | 16.31% | 11.70% | 0% |
| Total PLGA polymer in Vehicle | 46.81% | 39.09% | 46.81% | 46.81% | 46.81% | 46.81% | 53.58% |
| Total % dispersed solids in vehicle | 76.97% | 71.61% | 76.97% | 76.97% | 76.97% | 76.97% | 71.88% |

TABLE 13-2

Weight % compositions of hydrophobic textile-impregnated devices. The vehicle compositions as reported in Table 13-1 were impregnated into two orthogonally oriented SO textiles. The calculations for compositions also include the concentration of BUP per unit weight of device, and the effective available BUP concentration for release during the water-soak experiments. Note that when the devices were transferred to 11 ml glass vials, a small amount of vehicle weight was lost. This loss was taken into account to insure that the correct water to BUP weight ratios were employed during the water-soak experiment (i.e., to achieve a BUP reservoir concentration of approximately 17 mg BUP/ml water, which was the same concentration that was used during the water-soak experiments in Example 12).

| Ingredient | 14C-3A Replicate | 14C-3B2 Replicate | 14C-3C | 14C-3E | 14C-3G | 14C-3F | 14C-3E Placebo |
|---|---|---|---|---|---|---|---|
| Great Lakes Bovine Gelatin (GLBG) | 12.35% | 15.36% | 8.24% | 10.35% | 6.13% | 10.28% | 9.39% |
| Mineral Oil (MO) | 20.53% | 25.54% | 20.54% | 20.63% | 20.33% | 20.51% | 24.96% |
| Beeswax (BW) | 4.11% | 5.11% | 4.11% | 4.13% | 4.07% | 4.10% | 4.99% |
| PLGA polymer (i.e., representing 80% of the weight of 4.3-micron microspheres loaded with 20% by wt. BUP) | 41.73% | 0% | 41.74% | 41.94% | 41.31% | 41.69% | 0% |
| Encapsulated BUP (i.e., representing 20% by weight of the 4.3-micron microspheres loaded with 20% by wt. BUP) | 10.43% | 0% | 10.43% | 10.48% | 10.33% | 10.42% | 0% |
| PLGA polymer from 5-micron placebo microspheres | 0% | 35.16% | 0% | 0% | 0% | 0% | 47.56% |
| BUP free base (non-encapsulated, directly added to the vehicle) | 0% | 8.79% | 4.11% | 0% | 4.07% | 0% | 0% |
| Citric Acid | 0% | 0% | 0% | 2.06% | 2.03% | 0% | 1.87% |
| di-Sodium Citrate | 0% | 0% | 0% | 0% | 0% | 2.05% | 0% |
| SO textiles | 10.84% | 10.05% | 10.83% | 10.41% | 11.74% | 10.94% | 11.24% |
| mg BUP/g device | 104 | 88 | 145 | 104 | 145 | 104 | 0 |
| Target ratio of pH 2 water to BUP (w/w) in water soak experiment | 58.33 | 58.33 | 58.33 | 58.33 | 58.33 | 58.33 | Water/device (w/w) ~14C-3A |

TABLE 13-2-continued

Weight % compositions of hydrophobic textile-impregnated devices. The vehicle compositions as reported in Table 13-1 were impregnated into two orthogonally oriented SO textiles. The calculations for compositions also include the concentration of BUP per unit weight of device, and the effective available BUP concentration for release during the water-soak experiments. Note that when the devices were transferred to 11 ml glass vials, a small amount of vehicle weight was lost. This loss was taken into account to insure that the correct water to BUP weight ratios were employed during the water-soak experiment (i.e., to achieve a BUP reservoir concentration of approximately 17 mg BUP/ml water, which was the same concentration that was used during the water-soak experiments in Example 12).

| Ingredient | 14C-3A Replicate | 14C-3B2 Replicate | 14C-3C | 14C-3E | 14C-3G | 14C-3F | 14C-3E Placebo |
|---|---|---|---|---|---|---|---|
| Weight of Device as made (g) | 0.8134 | 0.8688 | 0.8483 | 0.8543 | 0.8064 | 0.8334 | 0.8222 |
| Weight of Vehicle as made (g) | 0.7252 | 0.7815 | 0.7564 | 0.7654 | 0.7117 | 0.7422 | 0.7298 |
| Tarred Weight (g) of device added to 11 ml glass vial | 0.8037 | 0.8533 | 0.8409 | 0.8438 | 0.7953 | 0.8234 | 0.8105 |
| Weight of vehicle after transfer to vial (g) | 0.7155 (containing 11.70% BUP) | 0.7660 (containing 9.77% BUP) | 0.7490 (16.31% BUP) | 0.7549 (11.70% BUP) | 0.7006 (16.31% BUP) | 0.7322 (11.70% BUP) | 0.7181 (0% BUP) |
| Weight of pH 2 water (g) added to 11 ml vial | 4.884 | 4.365 | 7.125 | 5.153 | 6.665 | 4.998 | 4.880 |
| mg of available BUP per ml pH-2 water (i.e., $[BUP]_{theoretical}$) | 17.14 | 17.14 | 17.14 | 17.14 | 17.14 | 17.14 | 0 |

TABLE 13-3

BUP calibration equation as obtained from a linear best fit of absorption at 262 nm vs. BUP concentration (mg/ml) in pH-2 water. This table provides the absorbance intensity for BUP free base that was fully dissolved in pH-2 water over the detectable range of [BUP], expressed in mg/ml. Note that the absorbance values as reported below represent corrected values that were obtained by subtracting a single-beam absorbance spectrum of pH-2 water from the single-beam absorbance spectra of the BUP samples. This calibration was used together with the calibration at 270 nm (Table 12-3) to estimate the [BUP] in supernatants from pH-2 water-soaked devices for the present example.

| [BUP] mg/ml | Relative Absorbance Intensity |
|---|---|
| 2.2364 | 3.0275 |
| 1.2300 | 2.0130 |
| 0.72684 | 1.1347 |
| 0.22364 | 0.2393 |
| 0.022364 | −0.0681 |
| 0.0022364 | −0.1004 |
| 0.00022364 | −0.0825 |
| 0 | 0 |
| $R^2$= | 0.987 |
| Slope= | 1.4482 |
| y-intercept= | −0.0336 |

TABLE 13-4

Relative rates of BUP elution (mg/ml/hour) established from the slopes of the linear portions of each elution curve in FIG. 16. Note that for the purposes of these analyses, short-time negative absorption values were omitted, a zero-time point was added (i.e., with absorption = 0), and the best linear fit lines were forced through a zero-intercept. This table also includes the linear ranges that were used to obtain the best linear fits, as well as the upper time limits that were used for presentation of the data in FIG. 16. Data collection times included the following time points (in hours): 1.5, 4, 8, 12, 24, 48, 72, 96, 120, and 192. For times above the upper-time limit, the UV absorption values were off-scale due to detector saturation. Note that for devices containing mixtures of freely dispersed BUP and PLGA-encapsulated BUP, the measured rate (e.g., 14C-3C~0.06 mg/ml/hour) was observed to be in reasonable agreement with a calculated rate that was based on weight fractions of freely dispersed BUP and PLGA-encapsulated BUP multiplied by the rates associated with devices that were formulated exclusively with PLGA-encapsulated BUP, and exclusively with dispersed BUP (e.g., 0.28 × (rate for 14C-3B2) + 0.72 × (rate for 14C-3A)~0.08 mg/ml/hour).

| Sample | Relative Rate of BUP elution from FIG. 16 (mg/ml/hour) | Calculated Rate based on weight fractions of freely dispersed BUP and PLGA-encapsulated BUP | Linear best-fit time region | Upper time limit for data presentation in FIG. 16 (i.e., UV detection on-scale) |
|---|---|---|---|---|
| 14C-3A replicate with BUP encapsulated by PLGA | 0.0137 | NA | 0 to 96 hours | 96 hours |

TABLE 13-4-continued

Relative rates of BUP elution (mg/ml/hour) established from the slopes of the linear portions of each elution curve in FIG. 16. Note that for the purposes of these analyses, short-time negative absorption values were omitted, a zero-time point was added (i.e., with absorption = 0), and the best linear fit lines were forced through a zero-intercept. This table also includes the linear ranges that were used to obtain the best linear fits, as well as the upper time limits that were used for presentation of the data in FIG. 16. Data collection times included the following time points (in hours): 1.5, 4, 8, 12, 24, 48, 72, 96, 120, and 192. For times above the upper-time limit, the UV absorption values were off-scale due to detector saturation. Note that for devices containing mixtures of freely dispersed BUP and PLGA-encapsulated BUP, the measured rate (e.g., 14C-3C~0.06 mg/ml/hour) was observed to be in reasonable agreement with a calculated rate that was based on weight fractions of freely dispersed BUP and PLGA-encapsulated BUP multiplied by the rates associated with devices that were formulated exclusively with PLGA-encapsulated BUP, and exclusively with dispersed BUP (e.g., 0.28 × (rate for 14C-3B2) + 0.72 × (rate for 14C-3A)~0.08 mg/ml/hour).

| Sample | Relative Rate of BUP elution from FIG. 16 (mg/ml/hour) | Calculated Rate based on weight fractions of freely dispersed BUP and PLGA-encapsulated BUP | Linear best-fit time region | Upper time limit for data presentation in FIG. 16 (i.e., UV detection on-scale) |
|---|---|---|---|---|
| 14C-3B2 replicate with freely dispersed BUP | 0.2533 | NA | 0 to 8 hours | 12 hours |
| 14C-3C with a ~28/72 blend (w/w) of BUP that was freely dispersed together with BUP that was encapsulated with PLGA | 0.0564 | 0.08 = 0.28(14C-3B2) + 0.72(14C-3A) | 0 to 24 hours | 48 hours |
| 14C-3E with BUP encapsulated by PLGA; and with dispersed citric acid | 0.0121 | NA | 0 to 96 hours | 96 hours |
| 14C-3G with a ~28/72 blend (w/w) of BUP that was freely dispersed together with BUP that was encapsulated with PLGA; and with dispersed citric acid | 0.0523 | 0.08 = 0.28(14C-3B2) + 0.72(14C-3E) | 0 to 24 hours | 48 hours |
| 14C-3F with BUP encapsulated by PLGA; and with dispersed sodium citrate | 0.0164 | NA | 0 to 72 hours | 96 hours |

TABLE 13-5

The devices were allowed to continue soaking in pH-2 water beyond the upper time limit that was reported in Table 13-5, and an estimate of the fraction of BUP released at t = 192 hours (8 days) was performed. At t = 192 hours, the supernatants of all samples, including the 14C-3E placebo were sampled, and were then subjected to a 10-fold dilution with pH-2 water. The dilution of the supernatants enabled the acquisition of on-scale UV absorption spectra. The resulting absorbance values at 262 nm and at 270 nm were background corrected by using the 10-fold diluted UV spectrum of the comparable 14C-3E placebo. The corrected absorption values were then used to estimate the BUP concentrations that had eluted into the closed systems at t = 8 days. The averages of the values calculated from the 262 nm and 270 nm wavelengths (using the calibration lines from Tables 12-3 and 13-3) are presented below, together with the weight fractions that had eluted after 8 days of soaking in pH-2 water.

| Sample | Estimated [BUP] released after t = 8 days (mg/ml) | Estimated fraction of BUP released after t = 8 days = [BUP]/[BUP]$_{theoretical}$ = [BUP]/17.14 |
|---|---|---|
| 14C-3A replicate with BUP encapsulated by PLGA | 4.85 | 0.28 |
| 14C-3B2 replicate with freely dispersed BUP | 15.98 | 0.93 |
| 14C-3C with a ~28/72 blend (w/w) of BUP that was freely dispersed, together with BUP encapsulated with PLGA | 7.65 | 0.45 |
| 14C-3E with BUP encapsulated by PLGA, together with dispersed citric acid | 3.89 | 0.23 |
| 14C-3G with a ~28/72 blend (w/w) of BUP that was freely dispersed and BUP | 8.22 | 0.48 |

TABLE 13-5-continued

The devices were allowed to continue soaking in pH-2 water beyond the upper time limit that was reported in Table 13-5, and an estimate of the fraction of BUP released at t = 192 hours (8 days) was performed. At t = 192 hours, the supernatants of all samples, including the 14C-3E placebo were sampled, and were then subjected to a 10-fold dilution with pH-2 water. The dilution of the supernatants enabled the acquisition of on-scale UV absorption spectra. The resulting absorbance values at 262 nm and at 270 nm were background corrected by using the 10-fold diluted UV spectrum of the comparable 14C-3E placebo. The corrected absorption values were then used to estimate the BUP concentrations that had eluted into the closed systems at t = 8 days. The averages of the values calculated from the 262 nm and 270 nm wavelengths (using the calibration lines from Tables 12-3 and 13-3) are presented below, together with the weight fractions that had eluted after 8 days of soaking in pH-2 water.

| Sample | Estimated [BUP] released after t = 8 days (mg/ml) | Estimated fraction of BUP released after t = 8 days = [BUP]/[BUP]$_{theoretical}$ = [BUP]/17.14 |
|---|---|---|
| encapsulated with PLGA, plus dispersed citric acid | | |
| 14C-3F with BUP encapsulated by PLGA, together with dispersed sodium citrate | 9.12 | 0.53 |

Example 14. Suspension Test for Choosing Liquid Components Suitable for Use in Preparing Hydrophobic and Hydrophilic Formulations As noted previously, hydrophobic formulations and delivery devices can be desirable from the standpoint that they can be formulated to yield dough-like materials with compliance characteristics that are conducive to end use deployment, without having to rely upon pre-deployment swelling and gelation of the gelatin particulates. Thus, hydrophobic formulations and delivery devices are ones whereby the gelatin particulates remain intact during manufacture and during storage, and do not yield macroscopic chain-entangled gelled networks until they become exposed to the tooth extraction socket and its fluids after deployment, unless the option of pre-deployment hydration is exercised.

It is important to note that each of the embodiments of the formulation will eventually become hydrated with fluids from the tooth extraction socket after deployment. This is predominantly due to the presence of hygroscopic, water-absorbing network-forming polymers like gelatin or to the presence of other water-absorbing materials such as cellulose fibers. However, in order to render the devices as compliant and conformable prior to their deployment, it is desirable that they be properly formulated in advance of deployment so that the clinician does not have to spend time meticulously measuring and premixing materials before they can be used. In other words, it is desirable to have a device that is already a compliant solid without having to be premixed with fluids like saline solutions or water.

In previous examples pertaining to the more hydrophilic embodiment of the present formulation, water was used as a plasticizer to pre-hydrate and to masticate blends of powdered ingredients to yield compliant dough-like mixtures, including water and bovine gelatin with PLGA-encapsulated BUP as described in Example 12. In these cases, water was the primary liquid ingredient in the formulation, and the mechanical integrity of the device was achieved by virtue of gelation and network formation prior to the deployment of the device. The compliance and conformability of these formulations were controlled by the weight ratio of water to gelatin with consideration also given to the total weight % solids in the plasticized mixture. Importantly, water was used as a liquid plasticizer for the gelatin polymer.

A plasticizer is generally a liquid (sometimes a solid) that when blended with a polymer increases the fraction of free volume, which in turn lowers the polymer glass transition temperature and consequently the elastic modulus and increases the compliance. Plasticizers are known to be at least partially miscible with the polymers that they plasticize.

By contrast, in examples pertaining to the more hydrophobic embodiment of the present formulation, oils with optional waxes were used as liquid carriers to suspend hygroscopic, water-absorbing network-forming polymers such as gelatin powders together with other dispersed ingredients, including PLGA-encapsulated BUP, free BUP, and citric acid, to name a few. These devices achieved their pre-deployment conformability and compliance characteristics not by plasticization of a polymeric continuous phase, but instead by virtue of other interactive factors that impact the rheological properties of suspensions, including the ratio of hydrophobic liquid to wax, which controls the viscosity of the liquid carrier and affects the viscosity of the resulting vehicle, the particle size distributions of dispersed ingredients, and the total percentage of dispersed solids in the vehicle, to name a few. In these cases, the mechanical integrity of the pre-deployed device was not achieved by virtue of gelling a polymer with a plasticizer to yield a reinforcing polymer network, but instead it was achieved by virtue of fiber reinforcement by impregnating knitted or woven cellulose textiles, or non-woven fibers with non-gelled suspensions to yield fiber-reinforced composite-like structures.

Thus, one of the primary distinctions between the hydrophilic and hydrophobic devices relates to pre-deployment morphology. By design, a hydrophilic device is comprised of a water-miscible hygroscopic polymer network that is homogenously gelled and pre-plasticized with a polar, hydrogen bonding liquid such as water, glycerin, honey, polyethylene glycols, polypropylene glycols, etc.; while by contrast, the hydrophobic device contains inter-dispersed fibrous components and suspended particulates of water-miscible and hygroscopic network-forming polymers like gelatin that have the latent potential to form gelled networks once exposed to water (i.e., after deployment), but in their pre-deployment state, they are made to persist as morphologically discrete entities suspended within and wetted by a hydrophobic vehicle. By design, these devices do not rely on gelatin plasticization and network formation (gelation) to achieve their pre-deployment properties. However, after deployment, they are morphologically designed to accept water through diffusion, which allows for post-deployment polymer network formation, analogous to what occurs in the pre-deployment stage with a hydrophilic device. At that point (i.e., after the deployment), the development of a gelled polymer network from water-ingress can have the added benefit of providing an additional mechanism of mechanical reinforcement, augmenting that which is already provided by the inter-dispersed cellulose fibers.

With these morphological considerations in mind, the differences between a more hydrophilic and a more hydrophobic device can be further reduced to another important design-controlling distinction, namely, the nature of the liquid component that is used in formulating the vehicle for the device. Generally, a liquid that leads to pre-deployment gelation is best suited and preferred for use in preparing the more hydrophilic formulations. A liquid that does not lead to pre-deployment gelation, at least little to no gelation for a period of time after manufacture that coincides with the desired shelf-life of the device prior to its deployment, is best suited and preferred for use in preparing the more hydrophobic formulations. The delineation between a liquid that leads to gelation and one that does not lead to gelation can be defined by a suspension test as demonstrated in the present example.

The miscibility of a liquid carrier with gelatin and hence the propensity for gelation can be gauged with a simple suspension test, where gelatin particulates are first blended with the liquid at weight ratios sufficient to form pourable suspensions, for example 2/1, 3/1, 4/1 or even higher weight ratios of liquid to gelatin, including 10/1, 25/1 or more. The suspensions are then qualitatively monitored as a function of time for physical changes, such as the onset of gelation, by using any one of a variety of possible qualitative or quantitative techniques. Note that other liquid to gelatin ratios can also be employed, including ratios that are intended for use in various end-applications. The ratio that was used in the present example, 2/1 w/w liquid to GLBG, was meant only to illustrate the phenomenon and to provide a general rubric for making an educated choice pertaining to liquid carrier.

Monitoring times of suspensions can include various time points after the suspensions are mixed, including for example, 5 minutes after mixing, 0.5 hours after mixing, 1 hour after mixing, 5 hours after mixing, 24 hours after mixing, 48 hours after mixing, 1 week after mixing, 1 month after mixing, 6 months after mixing, 1 year after mixing, and even 2 to 5 years after mixing.

Qualitative techniques for monitoring suspensions for time-dependent changes that pertain to gelation or the lack thereof can include, for example: 1) monitoring the suspensions for relative time-dependent changes in viscosity by means of hand-stirring the suspensions with a spatula (spatula test-1); 2) determining whether the suspensions can still be poured from their containers after various periods of aging (pour test); 3) shaking the suspensions by hand to determine if they remain as liquid dispersions after various periods of aging (shake test); 4) using an optical microscope to determine if discrete particulates of gelatin remain intact and suspended within the liquid over time (microscope test); or 5) qualitatively viewing the elastic recovery response of the suspension when it is perturbed by hand using either a spatula or a similar object to see if a plasticized and gelled polymer network begins to develop, as evidenced by being able to lift the plasticized polymer from its container with a spatula (spatula test 2). Of course, quantitative measurements can also be employed if so desired (e.g., Brookfield viscosity, parallel plate dynamic mechanical techniques, etc.). The tests should be performed at a temperature that is above the melting point of the liquid so that the resulting suspension is initially one that is characterized as having particulates dispersed in a liquid as opposed to particulates dispersed in a solid.

Using any one of these qualitative techniques, candidate liquids for a more hydrophobic device are those that when mixed with gelatin-particulates form suspensions that exhibit one or more of the following responses within a preferred monitoring time window: 1) minimal to no change in relative viscosity (spatula test-1); 2) retention of pourability (pour test); 3) retention of liquid dispersion/suspension state characteristics (shake test); 4) maximum retention of discrete gelatin particulates within the liquid continuous phase (microscope test); and 5) minimal to no elastic recovery (spatula test-2). In general, if there are no signs of gelation as gauged by one or more of these responses within a preferred monitoring time window, then these liquids are considered to be candidates for use in preparing a more hydrophobic device. Mineral oil, caprylic triglyceride, isopropyl palmitate, and coconut oil are such liquids as illustrated by the results in Table 14-3.

Conversely, if there are signs of gelation, including for example, any one or more of the following responses before the end of the monitoring time window: 1) development of elastic recovery; 2) visualization of permanent coalescence of gelatin particulates; or 3) solid network formation with loss of pourability, then these liquids are by definition excluded as candidates for use in more hydrophobic formulations, and are instead considered as candidate liquids for use in preparing more hydrophilic formulations. Thus, liquids that are observed to lead to gelation of gelatin within the preferred time monitoring window are considered to be good candidates for use in preparing a more hydrophilic formulation. Glycerin and water are such liquids as shown in Table 14-3.

For the purposes of this example, the preferred monitoring time windows for the suspension test are 0-24 hours and 0-48 hours. For preparing a more hydrophobic formulation with optimal storage stability, the preferred monitoring time is more preferably 0-3 months or 0-6 months, and even more preferably, 0-12 months.

If the particulates of a water-miscible and hygroscopic network-forming polymer do not gel for at least a time period of 24 hours after being separately suspended within one or more hydrophobic components, or more preferably for at least a time period of less than 3 to 12 months after being separately suspended within one or more hydrophobic components, then the one or more hydrophobic components are deemed suitable for preparation of a hydrophobic sustained release system or formulation. Conversely, if the particulates of a water-miscible and hygroscopic network-forming polymer form a gel within a time period of 24 hours after being separately suspended within one or more of the components, then the one or more components are deemed suitable for preparation of a hydrophilic sustained release system or formulation. Importantly, if the hydrophilic sustained release system is intended to be reinforced with a fibrous member such as a cellulose textile, then it is preferable that the particulates of the water-miscible and hygroscopic network-forming polymer do not gel for at least a time period of 2 hours, and more preferably for a time period of at least 4 to 8 hours after being separately suspended within one or more hydrophilic components. In this way, the delivery system can be more readily manufactured within a manageable work-time window, wherein the viscosity of the formulation remains sufficiently low enough to facilitate impregnation of the reinforcing member.

For desirable embodiments where particulates of a water-miscible and hygroscopic network-forming polymer do gel in at least a time period of 24 hours after being separately suspended within one or more hydrophobic components, two component, mix-on-demand such as two part syringes would be considered to realize these desirable embodiments.

Note that similar tests can be employed to test the miscibility of carrier liquids with other dispersed ingredients, including for example, microspheres of PLGA-encapsulated BUP, freely dispersed BUP, freely dispersed BUP-HCl, citric acid, ascorbic acid, citrates, etc. The liquid carrier can also be modified in advance of the test via incorporation of optional waxes or surfactants if so desired.

Importantly, the suspension test is not necessarily limited to gelatin protein. Instead, it can be used to test the suitability of a liquid for use in preparing hydrophobic or hydrophilic formulations wherein the formulation comprises other, alternative water-miscible and hygroscopic network-forming polymer components besides gelatin. Thus, in its most general sense, it is intended to test the suitability of a liquid for preparing hydrophilic or hydrophobic formulations whereby the formulation contains a hygroscopic, water-absorbing network-forming polymer component, such as a protein polymer like gelatin, or other alternative hygroscopic network-forming polymer components, including natural gums from a variety of plant sources, such as tree exudates of which arabic, ghatti, karaya, and tragacanth are examples, seaweed colloids of which agar, Irish moss, carrageenin, and alginates are examples, seed extracts of which locust bean, locust kernel, and quince seed gums are examples, manufactured and modified dextrins, British gums, and water-dispersible or soluble derivatives of cellulose to name a few. A more thorough account of these and similar materials can be found in *The Water Soluble Gums*, C. L. Mantell, Reinhold Publishing Corporation, New York, 1947. Thus, independent of which hygroscopic, water-absorbing network-forming polymer is chosen, particulates of the polymer are dispersed in a test-liquid, and the suspension test is conducted using the same procedures as those outlined for gelatin in the present example.

In this example, suspension tests were conducted using candidate liquid carriers as described in Table 14-1. 0.50 g aliquots of GLBG with general information provided in Table 14-2 were weighed into 11 ml glass vials with lids. Next, a 1 g aliquot of a candidate test liquid was weighed into an individual vial containing the GLBG to achieve a 2/1 liquid/GLBG weight ratio. A spatula was used to stir the ingredients to create a suspension. The suspensions were then allowed to set under static conditions and were qualitatively monitored as a function of time. Results at t=5 minutes after mixing, t=0.5 hours after mixing, t=5 hours after mixing, t=24 hours after mixing, and at t=48 hours after mixing were reported. The tests were conducted at 20 degrees C. with one exception, one of the tests was conducted at 27 degrees C. to ensure that the carrier was above its melt point and in its liquid state. For cases where sedimentation was observed to occur, which happened over time with liquids that did not lead to gelation, the spatula and shake tests were used to facilitate redispersion of the gelatin particulates so that pourability could also be evaluated. Results are provided in Table 14-3.

TABLE 14-1

Liquids used for suspension tests.
Liquid

Distilled water
Glycerin; USP grade, 99.9% anhydrous; Rite-Aid; CAS # 56-81-5
caprylic triglyceride; Croda, Inc.; CAS # 65381-09-1 (see Example 10)
isopropyl palmitate; Sigma-Aldrich; CAS # 142-91-6 (see Example 10)
coconut oil (virgin); Nutiva; cold-pressed unrefined; UPC 692752200052; CAS# 8001-31-8; melt point 76 deg. F.
mineral oil; Aldrich; CAS 8042-47-5 (see Example 9)

TABLE 14-2

Analytical data and specifications for the Great Lakes brand of bovine gelatin (GLBG) that was used in the suspension tests. Manufacture: Bovine gelatin powder, Great Lakes Gelatin Company, Grayslake, IL, type B (bovine, alkali process), unflavored Kosher beef hide, 88-92% protein, Kosher, Gluten Free, US Pharmacopeia consumer grade General Analysis:

PROTEIN 88-92%
Bloom 225 g
Viscosity mp 34-40
pH 4.1-5.5
Moisture <12%
Ash <2%
Sodium 100 mg/100 g
Carbohydrates 0%
Fat 0%
Heavy Metals <0.005%
Bacteria Test USP/NF
Calories per ounce 103.0
Maximum Amino Acid Content:

Alanine 11.0%/1,210 mg
Arginine 9.3%/1,023 mg
Aspartic Acid 6.7%/737 mg
Cystine 0.1%/11 mg
Glutamic Acid 11.4%/1,254 mg
Glycine 29.0%/3,190 mg
Histidine 1.0%/110 mg
Hydroxyproline 14.5%/1,595 mg
Hydroxylysine 1.2%/132 mg
Isoleucine 1.8%/198 mg
Leucine 3.4%/374 mg
Lysine 4.6%/506 mg
Methionine 1.0%/110 mg
Phenylalanine 2.6%/286 mg
Proline 17.6%/1,936 mg
Serine 3.8%/418 mg
Threonine 2.2%/242 mg
Tryptophane 0.0%/0 mg
Tyrosine 1.0%/110 mg
Valine 3.3%/363 mg

TABLE 14-3

Suspension test results. Each suspension existed as a liquid dispersion at t = 0. Results at either t = 5 minutes after mixing, t = 0.5 hours after mixing, t = 5 hours after mixing, t = 24 hours after mixing, or t = 48 hours after mixing are reported.

| Liquid | T of Test (deg. C.) | Spatula test-1 | Pour test & Shake test | Spatula test-2 | Suitable for use in a hydrophobic device | Suitable for use in a hydrophilic device |
|---|---|---|---|---|---|---|
| Water | 20 | High viscosity at t = 5 minutes | Neither pourable nor shakable at t = 5 minutes | Elastic network at t = 5 minutes | No | Yes |
| Glycerin | 20 | No change at 5 min.; waxy dispersion at 5 hours | Pourable and shakable at 5 minutes but not at 5 hours | Elastic network at 24 hours | No | Yes |

TABLE 14-3-continued

Suspension test results. Each suspension existed as a liquid dispersion at t = 0. Results at either t = 5 minutes after mixing, t = 0.5 hours after mixing, t = 5 hours after mixing, t = 24 hours after mixing, or t = 48 hours after mixing are reported.

| Liquid | T of Test (deg. C.) | Spatula test-1 | Pour test & Shake test | Spatula test-2 | Suitable for use in a hydrophobic device | Suitable for use in a hydrophilic device |
|---|---|---|---|---|---|---|
| caprylic triglyceride | 20 | No change, a liquid dispersion from 0-48 hours | No change, pourable and shakable dispersion from 0-48 hours | No elastic network formation from 0-48 hours | Yes | No |
| isopropyl palmitate | 20 | No change, a liquid dispersion from 0-48 hours | No change, pourable and shakable dispersion from 0-48 hours | No elastic network formation from 0-48 hours | Yes | No |
| coconut oil | 27 | No change, a liquid dispersion from 0-48 hours | No change, pourable and shakable dispersion from 0-48 hours | No elastic network formation from 0-48 hours | Yes | No |
| mineral oil | 20 | No change, a liquid dispersion from 0-48 hours | No change, pourable and shakable dispersion from 0-48 hours | No elastic network formation from 0-48 hours | Yes | No |

In some circumstances, the degree of hydrophilicity and hydrophobicity of a liquid can also be gauged by parameters that pertain to molecular-level properties such as polarity (e.g., dipole moment forces from permanent dipoles), dispersion forces (e.g., non-permanent dipoles or van der Waals forces), and hydrogen bonding forces. Indices such as the Hildebrand Solubility Parameter (HSP) or Hansen Solubility Parameter (HAN) of liquids and polymers (J. Brandrup and E. H. Immergut, *Polymer Handbook*, Third Edition, John Wiley & Sons, New York, 1989, pp. 519-559), as well as Hoy solubility parameters (HOY), have been developed in attempts to better quantify what is meant by "hydrophilicity" and "hydrophobicity." Hoy solubility parameters (HOY), like Hansen Solubility parameters (HAN) are based on chemical group methods of calculating energetic contributions from dispersion forces, polar forces, and hydrogen bonding forces. These contributions are summed to yield the total solubility parameter by taking the square root of the sum of the squares. Generally, although the estimation methods differ for the HAN and HOY terms, the sums of the contributions from HAN and HOY parameters produce similar total solubility parameter estimates, which are also considered to be equivalent to HSP values (i.e., HSP~ $HAN_{total}$~$HOY_{total}$).

It is generally understood by those skilled in the art that polymers and liquids tend to be more miscible when their solubility parameters are similar in magnitude to one another. Conversely, polymer/solvent pairs become less miscible as their solubility parameters diverge from one another.

Various solubility parameter values as reported in the literature for components like those found in the present formulations are provided in Table 14-4.

For the purposes of the present description, the most hydrophobic liquids can be defined as those with either a small or no permanent dipole moment, and with a low capacity to participate in hydrogen bonding. These types of liquids have been observed to be the least compatible with highly polar and water-soluble protein-based polymers like gelatin, which explains why the gelatin particulates remain dispersed and stable over time when suspended (i.e., not gelled) in formulations comprising such liquid carriers. These types of liquids would also be expected to have limited compatibility with other polar molecules such as water and BUP-HCl, thus rendering them as relative deterrents to both molecular-level and macro-level diffusion during the end use application as has been illustrated in Example 12. This behavior renders such liquids as useful levers in quests aimed at achieving specific control over time-release profiles. An example of an extreme version of this type of liquid is represented by a paraffinic hydrocarbon like mineral oil.

On the other side of the spectrum, liquids with permanent dipoles and with higher capacities for hydrogen bonding can be classified as being less hydrophobic and more hydrophilic. In the present description, this type of liquid is represented by water in one extreme (HSP=approximately 48 $MPa^{1/2}$). These types of liquids are highly compatible with hygroscopic polymers like gelatin, which explains why the dispersed gelatin particulates do not persist in formulations containing water, but instead become swollen through diffusion and plasticization, leading to the coalescence of the particulates through polymer chain entanglement and leading ultimately to gelation and to solid network formation prior to deployment of the device.

Note that for the case of a more hydrophobic formulation that is prepared with hydrophobic components like oils or waxes, the more hygroscopic components like gelatin particles and cellulose fibers remain discrete and intact prior to hydration, either as dispersed, non-gelled particulates, or as intermeshed fibrous entities. In these cases, the oils and waxes that constitute the continuous phase of the formulation serve to facilitate the dispersion of other ingredients like gelatin, PLGA microparticles, BUP, and citric acid. Note that optional surfactants can also be added to assist in stabilizing such dispersions.

In a pre-deployment morphological state, the mechanical integrity of the more hydrophobic formulation is predominantly derived from its reinforcement with cellulose fibers. Importantly, the morphology of the hydrophobic formulation has been designed to adsorb polar liquids like water as demonstrated in Examples 5 and 7. Thus, when a polar liquid, such as water, glycerin, polyethylene glycol, mixtures thereof, or fluids from the tooth extraction socket, etc., is intermixed with a more hydrophobic formulation, the morphology of the formulation and of the delivery device accommodate the adsorption of the polar liquid without producing the side effect of macroscopic phase separation of other components. This behavior is consistent with a morphological change that occurs when polar liquids are mixed with the device, whereby the more hygroscopic components like gelatin or cellulose begin to absorb the polar liquid becoming plasticized, and then begin to coalesce into a gelled network matrix such that the new continuous phase contains the gelled network matrix (i.e., polar liquid+gelatin+cellulose), inter-dispersed together with the hydrophobic components, the oils and waxes that previously constituted the continuous phase prior to hydration. At this stage, other dispersed ingredients like PLGA, BUP, BUP-HCl, citric acid, etc., that were previously dispersed in the oil-based continuous phase, either remain dispersed within the oil-phase components that themselves become inter-dispersed within the gelled matrix, or they become directly dissolved in the water that diffuses into the newly-formed continuous phase of the gelled matrix). Importantly, the plasticization, the chain-entanglement, the ensuing gelation, and the ultimate network formation that accompanies this adsorption process are desirable attributes for the more hydrophobic formulation. Most importantly, and by design, this morphological change is made to occur in vivo and does not have to occur during the pre-deployment stage or during the storage period for the formulation.

The latent capacity for a hydrophobic device to adsorb a polar H-bonding liquid like water is not only a desirable and surprising attribute that arises from the synergistic interactions among the component ingredients of the formulation, it is a measurable attribute that can be used to specify a distinguishing characteristic of a more hydrophobic formulation. Namely, a more hydrophobic device is one that after being mixed via physical mastication with water at a minimum ratio of water to device=0.2/1 w/w, or more preferably 0.33/1 w/w, or even more preferably 0.44/1 w/w or higher, does not exhibit macroscopic phase separation under static conditions for a period of at least 1 hour, and preferably for 2 or more hours, and more preferably for 24 hours or more. It further retains the added water for said period of time under static conditions without exhibiting visual indications of macro phase separation of water or other components. Indeed, this behavior was exemplified by fibrous textile-reinforced hydrophobic delivery devices that were demonstrated in Examples 5 and 7.

As stated previously, if the end-product objective is to minimize active-ingredient dilution in the formulation while simultaneously achieving mechanical compliance characteristics that are desirable for deployment, then gelation of gelatin or other macromolecular hygroscopic components would be most desirable if it were made to occur after deployment of the formulation and not before. Thus, the formulation of a more hydrophobic formulation with a hydrophobic liquid like mineral oil or others as shown in Table 14-3 represents an approach towards achieving this objective.

On the other hand, when compared to hydrophobic liquids like mineral oil, hydrophilic liquids like water and glycerin are more compatible and more miscible with polar molecules like BUP-HCl, a fact which is consistent with the observation of faster diffusion rates exhibited by formulations that are pre-plasticized with water as opposed to those prepared with mineral oil as the liquid vehicle carrier as in Example 12. Hence, if the end-product objective is to maximize the release rates of water-soluble active-ingredients while simultaneously achieving mechanical compliance characteristics that are desirable for deployment, then pre-gelation of gelatin or other hygroscopic components with hydrophilic liquids like water and glycerin could be a desirable approach wherein gelation is made to occur before deployment of the device. Thus, the formulation of a more hydrophilic formulation represents a method of approach towards achieving this objective, but only if the resulting dilution of active ingredients can be tolerated in the end use application.

Again, in the absence of gelation, the more hydrophobic formulas achieve their initial mechanical cohesive integrity through a mechanism that is independent of gelled network formation. Specifically, if the formulation is formulated to have the compliance characteristics of a cream, it can then be used to disperse active ingredients, and it can then be impregnated into a fibrous textile which serves as a reinforcing scaffold for the formulation before its deployment. The reinforced delivery device is therefore made to have cohesive integrity and compliance which renders it as sufficiently acceptable for use by the clinician during its deployment. It is only later, after deployment, that the gelatin particulates dispersed within the formulation and cellulose fibers begin to swell with liquids from the tooth extraction socket, leading to their chain entanglement and ultimately to their network formation and to an accompanying change in morphology. The gelled network then becomes a type of reinforcing scaffold for the device in vivo, serving to enhance its cohesive strength which enhances its mechanical integrity after deployment and not before.

Other liquids besides mineral oil, such as caprylic triglyceride and isopropyl palmitate as demonstrated in Example 10, are more polar than mineral oil, and they have at least some capacity for hydrogen bonding. However, their polarity and H-bonding characteristics are insufficient to cause gelation of the gelatin particulates that are suspended within them. Thus, although these types of liquids have permanent dipoles and therefore have some capacity for hydrogen bonding, they are poor plasticizers for gelatin. For the purposes of the present description, formulations comprised of such liquids are also classified as more hydrophobic formulations and delivery devices. These more hydrophobic formulations and the delivery devices containing them have a distinguishing attribute in common, the liquid carriers that serve to suspend and bind the ingredients within the vehicle do not promote the gelation of the gelatin particulates, and they are either immiscible with gelatin or have limited miscibility under ambient conditions. Consequently, macromolecular chain entanglement and gelation do not occur when the particulates are suspended in such liquids.

Liquids that are deemed as being suitable for use in a more hydrophobic formulation via the suspension test can also perform other functions when included in the formulation. For example, the HAN of isopropyl palmitate is reported as 15.3 MPa$^{1/2}$. Although these types of liquids are recognized as being more polar than mineral oil, for the purposes of the present description they are still classified as being relatively hydrophobic in that they do not diffuse and swell gelatin particulates in the way that water does. Instead, the gelatin protein particulates persist in such formulations until they are subjected to hydration during end use. Nevertheless, the permanent dipole moments of these liquids would be anticipated to render them as more amenable to facilitating molecular-scale diffusion of small polar molecules than would mineral oil. Thus, liquids of these types can be useful to modulate diffusion rates of active ingredients, thereby providing an additional lever to achieve intermediate controlled-release time profiles. In addition, hydrophobic liquids with higher polarity than mineral oil can also serve the secondary purpose of lowering the Tg of PLGA via plasticization. This would result in a faster rate of diffusion of encapsulated ingredients because a lower Tg will equate to a higher fraction of free volume, which in turn would translate to lower potential energy barriers for diffusion of small molecules across the PLGA polymer gradient from within the PLGA particle and into the binder matrix.

TABLE 14-4

Hildebrand Solubility Parameters (HSP), Hansen Solubility Parameters (HAN), and Hoy Solubility Parameters (HOY), as reported or estimated from J. Brandrup and E. H. Immergut, *Polymer Handbook*, Third Edition, John Wiley & Sons, New York, 1989, pp. 519-559; or as referenced from other footnoted sources. Note that the total solubility parameter for the purposes of the present invention is taken as any one of the following values: HSP~HAN~HOY.

| Material | HSP MPa$^{1/2}$ | HAN$_{total}$ (or HOY$_{total}$ if so noted) MPa$^{1/2}$ | HAN $\delta_{Dispersion}$ (or HOY if so noted) MPa$^{1/2}$ | HAN $\delta_{Polar}$ (or HOY if so noted) MPa$^{1/2}$ | HAN $\delta_{H\text{-}bonding}$ (or HOY if so noted) MPa$^{1/2}$ |
|---|---|---|---|---|---|
| Mineral oil[c] | 15-18 (estimated) | 16-18 (estimated) | 16-18 (estimated) | 0 (estimated) | 0 (estimated) |
| isopropyl palmitate | — | 15.3 | 14.3 | 3.9 | 3.7 |
| Caprylic triglyceride[a] | — | 17.0 | 16.2 | 3.4 | 4 |
| Glycerol | 33.8 | 36.2 | 17.4 | 12.1 | 29.3 |
| Water | 47.9 | 47.9 | 15.5 | 16.0 | 42.4 |
| water[d] | — | 48.0 | 12.2 | 22.8 | 20.4 |
| Coconut Oil[a] | — | 16.6 | 16.2 | 2.5 | 2.8 |
| PLGA (lactide/glycolide = 100/0)[b] | — | 21.7 | 17.4 | 7.6 | 10.5 |
| PLGA (lactide/glycolide = 85/15)[b] | — | 21.7 | 17.4 | 8.3 | 9.9 |
| PLGA (lactide/glycolide = 75/25)[b] | — | 21.7 | 17.4 | 8.3 | 9.9 |
| PLGA (lactide/glycolide = 50/50)[b] | — | 22.3 | 17.4 | 9.1 | 10.5 |
| Denatured Dry Collagen (gelatin)[d] | — | 22.5 | 11.7 | 12.1 | 14.8 |
| Denatured Wet Collagen (gelatin)[d] | — | 30.1 | 11.8 | 15.3 | 22.5 |

[a]Anaid De La Peña-Gil, Jorge F. Toro-Vazquez, and Michael A. Rogers, Food Biophysics, Springer Science+Business Media, New York 2016.
[b]Schenderlein, S., Luck, M., Muller, B. W., International Journal of Pharmaceutics 286 (2004) 19-26.
[c]estimated from ranges attributed to other long chain hydrocarbons as reported in J. Brandrup and E. H. Immergut, *Polymer Handbook*, Third Edition, John Wiley & Sons, New York, 1989, pp. 519-559.
[d]Hoy solubility parameters as reported by Pashley, David H., et al., American Journal of Dentistry, 20 (1), 2007, p. 9.

Example 15. Preparation of a Fibrous Reinforced Delivery Device with Glycerin as the Liquid Component There are occasions when the use of a formulation comprising a hydrophilic liquid would be desirable for end use. For example, a formulation that is pre-mixed with water can be useful in achieving relatively fast time-release profiles of water-soluble ingredients as demonstrated in Example 12. The present description provides for creating a formulation that is first premixed and pre-plasticized with water, glycerin, polyethylene glycols, other polyhydric alcohols, or mixtures thereof. These types of formulations are analogous to the more hydrophobic formulations, but they are made with a polar H-bonding liquid as the primary liquid ingredient instead of oils and waxes, and they are designed to gel prior to deployment instead of afterwards. Thus, as long as they are shelf-stable, these types of formulations can be used for controlled-release delivery on their own without fiber reinforcement. However, they can also be optionally reinforced with a fibrous cellulose hemostat to form a composite structure. The purpose of this example is to demonstrate this aspect of the formulation.

As noted by Jaymin C. Shah and Manoj Maniar in *Journal of Controlled Release*, 23 (1993) 261-270, control release of active ingredients like BUP from polymeric matrices, such as biodegradable polyanhydride polymers, can occur via diffusion, dissolution or erosion of the polymer. The authors note that erosion or diffusion processes are generally assumed to control the rate of drug release. Hence, if the drug and its conjugate salt have low water solubility, then it is anticipated that the dissolution rate of the drug could have significant effect on the release-kinetics of the drug.

It should also be realized that diffusion and erosion are interactive processes, and that diffusion involves not just the egress of active ingredients from a delivery device, but ingress of water and fluids from the chemical environment where the device is deployed. As fluids diffuse into the device via both macro and molecular-level pathways, the matrix polymer can become more susceptible to erosion, either through dissolution of volume elements from the exposed surfaces of the delivery device, from the macro separation of particulates near the surfaces of the device, or through a combination of the two.

As noted earlier, one advantage of using fibrous reinforcement for a delivery device is that it can improve the cohesive integrity of the device, and thereby render it to be more erosion resistant. When a delivery device erodes during end use, internal cohesive failures of the matrix can cause particulates of the device to become macroscopically separated from the original structure. During end use, fluids can permeate into the matrix phase of the device through a combination of macroscopic and microscopic diffusion mechanisms. Macroscopic diffusion can occur through permeable boundaries that are present from defects like void elements arising from entrapped air between partially bonded matrix polymer particulates, such as gelatin particulates, or from matrix polymer that is partially delaminated from the surfaces of weakly bonded elements or components that are dispersed within the matrix.

If the matrix contains a polymer that is hygroscopic, as it is in a more hydrophilic formulation, molecular level diffusion of hydrous liquids can occur along every frontal boundary that becomes available to the fluid. When the fluid macroscopically diffuses into the matrix along a frontal boundary, it also can begin to permeate into the matrix polymer through a process of molecular-level diffusion. As a volume element of a matrix polymer begins to expand from the ingress of lower molecular weight fluids, it can become plasticized by the fluid, leading to an increase in the fraction of free volume within the matrix polymer phase and to a subsequent further increase in the rate of molecular level diffusion, both into and out of the matrix polymer network.

An increase in free volume at the molecular level also leads to a number of additional physical changes in the matrix polymer phase, including a decrease in the glass transition temperature, an accompanying decrease in modulus, a decrease in ultimate stress to failure resulting in lower strength, and to an accompanying acceleration in the rate of molecular level diffusion of molecules both into and out of the matrix polymer phase. The macro volume expansion of the liquid-occupied volume element, that is the polymer volume element that has become diffusion-permeated and plasticized by fluids, leads to the development of localized stresses that tend to accumulate at weak boundaries, such as at frontal boundaries that separate swollen volume elements from other volume elements that have not yet been permeated and are not yet swollen. Defects sites near these boundary regions become particularly susceptible to localized stress-induced tensile and shear types of failures. The ensuing number of internal cohesive failure events can begin to increase and even to accelerate from excessive strains at weak junctures at cell walls of macroscopic voids, at the interfaces of weakly bonded particulates, etc. The cycle continues as more macroscopic pathways develop for the macroscopic ingress of even more fluids, leading to a further increase in the number of pathways for molecular level diffusion, which then leads to an increase in the number of swollen volume elements, which then leads to the further development of more localized stresses. Hence, the cascade continues, culminating in an acceleration in the rate of occurrence of ultimate failure events.

The interconnected processes of erosion and diffusion can also affect the efficacy of a delivery device. Clearly, as erosion occurs, the total amount of surface area simultaneously increases. This will affect one of the primary functions of the device—to achieve and maintain a specific time-controlled release profile of one or more active ingredients during end use. An increase in the total surface area from erosion leads to an acceleration of molecular-scale diffusion of active ingredients across the growing number of concentration gradients that are provided by the growing number of interfacial boundaries. This process will not only impact the molecular level diffusion rates through the matrix polymer, it can impact the molecular level diffusion rates through other types of secondary diffusion barriers that have been purposely put into place, the diffusion barrier created by a PLGA polymer which serves to impede the molecular-level diffusion rate of its encapsulated active ingredients like BUP or BUP-HCl.

Any process that leads to an increase in free volume of a polymer will subsequently lead to an increase in the number of molecular pathways that are available for molecular level diffusion. Importantly, diffusion of small molecules will occur across passive boundaries where a concentration gradient is in existence (i.e., Fickian diffusion). Aside from relative polarity considerations, the rate of diffusion depends on the fraction of free volume within the materials on both sides of the frontal boundary, as well as the relative concentration of the diffusing species on both sides. Thus, as fluids begin to have access to the surfaces of PLGA particles within the delivery device, they can permeate the surfaces of the particles and thereby increase free volume, and then increase the rate of diffusion of small molecules that are encapsulated and contained within them. To add even more complexity to this scenario, if the fluid contains water, PLGA can hydrolyze. The hydrolysis process leads to a decrease in molecular weight, to the production of more chain ends, and thus to a further increase in free volume which further enhances the rate of diffusion. A gelatin matrix polymer with polypeptide sequences will also be susceptible to the same type of hydrolysis-initiated acceleration of free volume. Thus, each molecular level diffusion barrier that is purposely set in place to control the release of drugs and the like can become altered and affected by a cascade of macroscopic and molecular-level events. These events will collectively affect the global time release profile of the device.

It is understood that, when harnessed for the purpose of achieving specific control-release profiles over sustained periods of time, these mechanisms can be useful. On the other hand, if these processes occur too quickly, it may become difficult if not impossible to achieve longer-term sustained release. As shown in Example 12, this is most particularly the case for a more hydrophilic delivery device.

Importantly, composite structures can be used to reduce the rate of occurrence of internal cohesive failure events of the types described above. In a composite-like structure, the matrix can be reinforced with fibers or with particulates, which serve as scaffolds that can help to hold a mechanically weaker matrix phase in place by reducing the probability of crack growth and propagation along any one single boundary via distributing stresses from swelling over larger volume elements and hence over multiple boundaries within the structure, thereby reducing the magnitudes of localized stresses and strains, and hence reducing the number and frequency of catastrophic failure events. Lower levels of localized stresses will translate to lower localized strains, which in turn, depending on the geometric structure of the defect site, can lead to sustained mechanical and cohesive integrity of the delivery device over longer periods of time.

The more hydrophobic formulations lend themselves well to the creation of fiber-reinforced composites primarily because, by design, the formulations that are used to impregnate the fibers are not pre-gelled into macro polymeric networks. Instead, these formulations, with their hydrophobic liquid carriers, remain compliant and moldable for long periods of time. The gelatin particulates suspended therein do not begin to gel and swell until they are exposed to fluids within the tooth extraction socket. Even then, the rate of water ingress is diminished owing to the hydrophobic nature of the formulation. All of this translates to an extended work-time for accomplishing the manufacturing steps that are required to make a composite device, including the time needed to complete multiple process steps, such as mixing, metering, impregnating, conveying, cutting, and packaging.

On the other hand, the creation of a composite reinforced delivery device that is more hydrophilic poses a different set of challenges. Importantly, from a process manufacture perspective, if fiber reinforcement is to be employed, then it is preferable to intermix and to pre-wet the cellulose fibrous components with a hydrophilic formulation prior to the onset of appreciable gelation. This is because the fibers can be more easily wetted and intermeshed with the formulation when the formulation exhibits low viscosity and minimal elastic recovery as it would prior to gelation. In order to accomplish this process step, there needs to be ample work time prior to gelation to facilitate the total time requirements for vehicle mixing, metering, wetting, and infiltration/impregnation of the fibrous material.

As illustrated in Example 14, the work time window prior to gelation is significantly shortened for formulations comprising hydrophilic liquids. For example, when water is mixed with GLBG at a 2/1 (w/w) ratio, gelation and elastic network formation was observed to begin almost immediately.

However, for the case of glycerin, the work time window prior to the onset of gelation was observed to be significantly longer, thereby making glycerin a more practical choice as a liquid for creating more hydrophilic hemostatic fiber-reinforced delivery devices. It is understood by those skilled in the art that within some time period after mixing liquids like water or glycerin with gelatin, gelation will begin to occur, and the initial suspension of discrete gelatin particulates will become transformed into an elastic gelled network of surface-bonded, aggregated gelatin particulates. In the present example, the time-period preceding gelation, herein referred to as the "work-time") defines the window of time that enables the product to be made through the process of impregnating a fibrous substrate. As long as the process is initiated during the work-time prior to gelation, the viscosity and elasticity of the vehicle will be low enough to enable facile impregnation of fibrous substrates with high expediency. Thus, it is desirable that the gelation process be made to occur after the fibrous textile is impregnated with the formulation, and not before.

For the purposes of creating a more hydrophilic fiber-reinforced delivery device, it is desirable that the liquid component be miscible enough with the hygroscopic network-forming component, including gums like gelatin, gum arabic, ghatti, karaya, tragacanth, agar, Irish moss, carrageenin, alginates, seed extracts of which include locust bean, locust kernel, and quince seed gums as examples, manufactured and modified dextrins and British gums, water-dispersible or soluble derivatives of cellulose, etc., to lead to gelation and to the formation of a plasticized polymer network. It is further desirable that the work-time prior to gelation be long enough to facilitate all of the process steps that are required for product formation, such as vehicle mixing, metering, conveying, wetting, pressing, etc. The work-time window for textile impregnation can be determined from the suspension test as defined in Example 14. If a continuous or semi-continuous process is used to meter and convey the formulation onto a web of fibrous material, then the web could be optionally conveyed through a forced air or infrared heated oven to facilitate faster gelation. Regardless of the use of ovens, once the gelation process is complete, the resulting impregnated composite can be cut to achieve the desired geometric size for the application, and then the resulting delivery device can be packaged for storage prior to deployment.

Regarding storage, it is further desirable that the liquid be biostable, either on its own, or through the incorporation of preservatives that guard against bacterial growth during periods of product manufacturing, packaging and storage. It is also desirable that the liquid lead to formation of a gelled polymer network after textile impregnation and not before. One example of a liquid that meets both criteria is glycerin. Other liquids can be used, including for example, propylene glycol, polyethylene glycols and polypropylene glycols of various molecular weights, water-based natural products like honey, polyhydric alcohols and derivatives of the same, as well as mixtures of any of these types.

It is also important that the fibrous components of the composite delivery device be resistant to deterioration, swelling, or dissolution by a hydrophilic liquid. Surgicel Original (SO) textiles were determined to be resistant to glycerin. In a separate experiment, pre-cut SO textiles ((1.8×3.8 cm) were separately drop-coated with glycerin and water. After 24 hours, the glycerin-coated textile was observed to retain its meshed structure with no noticeable evidence of dissolution or physical changes, including no shrinkage or swelling. In a similar test, the SO textile was also observed to be more resistant to water than its SafeGauze counterpart. SafeGauze dissolved upon exposure to water as shown in Example 5, whereas SO showed no apparent signs of dissolution within a 24-hour window of testing, only shrinkage.

Regardless of whether a delivery device is designed to be more hydrophobic or hydrophilic, the resistance of the fibrous material to water dissolution or to degradation can be an important and desirable attribute, particularly after deployment of the delivery device. Although it is desirable that the fibrous material eventually degrade and become bio-absorbed, it is still desirable that the fibrous material maintain integrity for a period of time during the post-deployment lifetime of the device, mainly because the retention of a composite structure with fibrous reinforcement is conducive to maximizing macroscopic erosion resistance, which is another desirable attribute for longer-term durability if the delivery device is deployed in an oral tooth socket application.

In the present example, the following steps were taken to prepare two composite-reinforced delivery devices with glycerin as the liquid component in the formulation. Samples 15A and 15B with compositions are provided in Tables 15-1 and 15-2.

Sample 15A.
- Step-1: a segment of Surgicel Original (SO) oxidized cellulose textile was cut (1.8×3.8 cm) and weighed at 0.0475 g;
- Step-2: 0.3061 g of PLGA-encapsulated BUP (SWRI; sample 18-0202-015-21; 20% w/w BUP loaded; Resomer RG 504; D50=4.3 microns) was pre-weighed into a 15 ml HDPE beaker;
- Step-3: a premixed suspension of Great Lakes bovine gelatin (GLBG) and glycerin was prepared using 1.8 g GLBG+3.6 g glycerin, and the mix was allowed to set for 10 minutes;
- Step-4: 0.4317 g of the premixed suspension from step 3 was added to the beaker with the pre-weighed PLGA-encapsulated microspheres, and the resulting vehicle was mixed by hand for approximately 5 minutes with a spatula until it formed a homogeneous cream;
- Step-5: using a spatula, 0.6189 g of the cream from step-5 was coated and spread over the entire length of a single pre-weighed textile from step-1, and then the textile was folded once in its center, over and onto itself before being subjected to light pressing with the spatula to achieve impregnation;
- Step-6: The square shaped impregnated device was weighed to a final weight of textile+vehicle=0.5852 g, equating to a final weight after transfer loss=0.5377 g;
- Step-7: the delivery device was then allowed to set and gel under ambient conditions (20 degrees C.), and then was qualitatively monitored over time.

Initially, the more hydrophilic 15A formulation as prepared in step-4 was noted to be qualitatively similar in viscosity and in compliance to the comparable, but more hydrophobic formulation of 14C-3A that was prepared in Example 12. After textile impregnation was completed in step-6, the device was also noted to be qualitatively similar in stiffness and in compliance to the analogous delivery device that was prepared in Example 12.

After approximately 2 hours, the delivery device was still cohesively intact, but it had become noticeably more stiff owing to the onset of gelation. Note that the 2/1 glycerin/

GLBG (w/w) mixture that was retained from step-3 had become waxy and higher in viscosity at this stage. After 15 hours, the 2/1 glycerin/GLBG (w/w) mixture that was retained from step-3 had become a solid elastic network. The device itself exhibited internal cohesive failure as it had opened along its fold to reveal a powdery and friable surface of cohesively failed formulation. The stress of the fold in the textile coupled with swelling stresses from the glycerin-infused gelatin particles was substantial enough to cause cohesive failure of the gelled mixture.

Thus, unlike the comparable composite reinforced delivery device 14C-3A from Example 12, the more hydrophilic delivery device of sample 15A was unable to retain enough cohesive strength after gelation to resist swelling stresses and to remain cohesively intact, thereby illustrating one of the difficulties in manufacturing a more hydrophilic composite reinforced delivery device which is gelled prior to deployment. This result serves to demonstrate one of the limitations of a more hydrophilic delivery device that does not occur with comparable hydrophobic devices. Specifically, higher total binder levels (e.g., water+GLBG or glycerin+GLBG) are required for devices where the binder is designed to be gelled prior to deployment. This is necessary not only to provide adequate compliance for deployment, but to also provide mechanical properties that are commensurate with those needed to manufacture and store a textile-impregnated delivery device. Thus, like its water-gelled counterparts as described earlier in 618-1B from Example 12, this indicates that one of at least three things would have to be done to create a viable composition: 1) increase the total binder level (gelatin+glycerin); 2) increase the glycerin/gelatin weight ratio to be more akin to what was used in more hydrophilic delivery devices with water to about 4/1 (w/w) instead of 2/1 (w/w); or 3) exercise some combination of both.

However, it must be borne in mind that one consequence of these approaches is that the delivery device and its active ingredients will become diluted. Of course, the ramifications of this are dependent on the end use application requirements, and on the net dosage-level requirements of active ingredients that are needed for the end use application.

In accordance with this thinking, sample 15B was prepared using a 3.92/1 w/w ratio of glycerin to GLBG instead of 2/1 w/w, and a total vehicle binder level (glycerin+gelatin) of 62% by weight instead of 58.51% by weight. The steps used in preparing 15B are provided below.

Sample 15B.
- Step-1: a segment of Surgicel Original (SO) oxidized cellulose textile was cut (1.8×3.8 cm) and weighed at 0.0489 g;
- Step-2: 0.3064 g of PLGA-encapsulated BUP (SWRI; sample 18-0202-015-21; 20% w/w BUP loaded; Resomer RG 504; D50=4.3 microns) was pre-weighed into a 15 ml HDPE beaker;
- Step-3: a premixed suspension of Great Lakes bovine gelatin (GLBG) and glycerin was prepared using 1.0 g GLBG+3.92 g glycerin, and then the mix was allowed to set for approximately 20 minutes;
- Step-4: 0.5 g of the premixed suspension from step 3 was added to the beaker with the pre-weighed PLGA-encapsulated microspheres, and the resulting vehicle was mixed by hand with a spatula for approximately 10 minutes until it formed a homogeneous cream;
- Step-5: using a spatula, 0.6119 g of the vehicle cream from step-5 was coated and spread over the entire length of a single pre-weighed textile from step-1, and then the textile was folded once in its center, over and onto itself before being subjected to light pressing with the spatula to achieve impregnation;
- Step-6: The square shaped impregnated device was weighed to a final weight of textile+vehicle=0.5859 g, equating to a final vehicle weight after transfer loss=0.5370 g;
- Step-7: the delivery device was then allowed to set and gel under ambient conditions (20 degrees C.), and it was qualitatively monitored over time.

Initially, the 15B formulation as prepared in step-4 was noted to be qualitatively similar in viscosity to sample 15A at the same stage of the process. After textile impregnation was completed in step-6, the delivery device was also noted to be qualitatively similar in stiffness and in compliance to 15A, and to the analogous more hydrophobic delivery device that was prepared in Example 12.

After approximately 2 hours, the delivery device of 15B was still cohesively intact, but unlike 15A, there was no noticeable qualitative change in the compliance of the device. Also, unlike the 15A premix of glycerin and gelatin that had become waxy at this stage, the 3.92/1 (w/w) premix for 15B was still a pourable liquid.

After approximately 15 hours, the 15B delivery device had become noticeably more stiff owing to the onset of gelation, but it was cohesively intact. At this stage, its stiffness was qualitatively similar to that of 15A at time=2 hours. Similarly, the 3.92/1 (w/w) premix from 15B was waxy, much like the 15A premix had appeared after only two hours. By contrast, the 2/1 (w/w) 15A premix had become an elastic network at t=15 hours.

After approximately 24 hours, the 15B device did not exhibit a noticeable change, and it was still cohesively intact. In addition, the 3.92/1 (w/w) premix from 15B had become noticeably more elastic.

The 15B delivery device continued to remain mechanically stable and unchanged throughout the duration of the experiment of 48 hours.

The compositions of the 15A and 15B vehicles are provided in Table 15-1, and the final device compositions are provided in Table 15-2. Note that the level of dispersed solids is expressed for two different physical states of the formulations—before gelation, while glycerin is the continuous phase for dispersed particulates of gelatin and PLGA), and after gelation when plasticized gelatin becomes the continuous phase for the dispersion of PLGA.

TABLE 15-1

Weight % compositions of hydrophilic vehicles for use in preparing textile-impregnated devices made with glycerin as the liquid carrier for the vehicle. Calculations also include the net weight % concentration of BUP in each vehicle, the net PLGA polymer weight % (i.e., ~80% of the weight of BUP loaded microspheres), the total weight % of dispersed solids in the vehicle prior to gelation, and the total weight % of dispersed solids in the matrix after gelation (the continuous phase is glycerin prior to gelation, and plasticized glycerin after gelation).

| Vehicle Mixture Composition | 15A | 15B |
|---|---|---|
| glycerin | 39.01% | 49.4% |
| Bovine Gelatin | 19.50% | 12.6% |
| 5 um PLGA Placebo microspheres | 0% | 0% |
| 4.3 micron 20% BUP free base loaded PLGA microspheres | 41.49% | 38.0% |
| BUP free base (directly added to vehicle) | 0% | 0% |
| TOTAL | 100.00% | 100% |
| Total BUP in vehicle | 8.30% | 7.6% |
| Total PLGA polymer in Vehicle | 33.19% | 30.4% |

TABLE 15-1-continued

Weight % compositions of hydrophilic vehicles for use in preparing textile-impregnated devices made with glycerin as the liquid carrier for the vehicle. Calculations also include the net weight % concentration of BUP in each vehicle, the net PLGA polymer weight % (i.e., ~80% of the weight of BUP loaded microspheres), the total weight % of dispersed solids in the vehicle prior to gelation, and the total weight % of dispersed solids in the matrix after gelation (the continuous phase is glycerin prior to gelation, and plasticized glycerin after gelation).

| Vehicle Mixture Composition | 15A | 15B |
|---|---|---|
| Total % dispersed solids in liquid vehicle prior to gelation = 100 × (PLGA-BUP + GLBG)/(glycerin + GLBG + PLGA-BUP) | 60.99% | 50.6% |
| Total % dispersed solids in gelled vehicle matrix phase = 100 × (PLGA-BUP)/(glycerin + GLBG + PLGA-BUP) | 41.49% | 38% |

TABLE 15-2

Weight % compositions of hydrophilic textile-impregnated devices made with glycerin as the liquid carrier for the vehicle. The vehicle compositions as reported in Table 15-1 were separately impregnated into individual SO textiles. The calculations for compositions also include the weight % concentration of BUP, and the effective available BUP concentration for release on a unit weight of device basis (mg/g).

| Ingredient | 15A | 15B |
|---|---|---|
| Great Lakes Bovine Gelatin (GLBG) | 17.92% | 11.55% |
| glycerin | 35.84% | 45.28% |
| PLGA polymer (i.e., representing 80% of the weight of 4.3-micron microspheres loaded with 20% by wt. BUP) | 30.50% | 27.86% |
| Encapsulated BUP (i.e., representing 20% by weight of the 4.3-micron microspheres loaded with 20% by wt. BUP) | 7.62% | 6.96% |
| PLGA polymer from 5-micron placebo microspheres | 0% | 0% |
| BUP free base (non-encapsulated, directly added to the vehicle) | 0% | 0% |
| SO textile | 8.12% | 8.35% |
| mg BUP/g device | 76 | 70 |
| Weight of Device as made (g) | 0.5852 | 0.5859 |
| Weight of Vehicle as made (g) | 0.5377 | 0.5370 |

Example 16. Preparation of a Temperature Activated Hydrophobic Device with Coconut Oil as the Liquid Component A delivery device analogous to 14C-3A from Example 12 was prepared using coconut oil (CO) as the liquid carrier in place of mineral oil. The CO as discussed in Example 14 was deemed to be suitable for use as a liquid carrier in preparing a more hydrophobic device. The compositions of the vehicle and the device are provided in Tables 16-1 and 16-2. The formulation and textile impregnated delivery devices were prepared using procedures outlined in Examples 9, 12 and 13. However, while preparing both the premix of gelatin with CO and the formulation with added PLGA, the temperature was maintained at 27 degrees C., which is above the melt point of the CO. The CO/gelatin premix was observed to solidify upon cooling to 20 degrees C. This process of solidification and melting was observed to be reversible for both the premix, and for the resulting formulation. While in its liquid dispersion state, the formulation was coated onto a precut SO textile. Initially, at 27 degrees C., it was a compliant device, qualitatively similar in compliance characteristics to the analogous device prepared with mineral oil in Example 12 (14C-3A). When the device was allowed to cool to 20 degrees C., it became noticeably stiffer. Upon re-heating to 27 degrees C., it became noticeably compliant again like its 14C-3A counterpart. This process was observed to be reversible over multiple cycles.

CO is a complex mixture of symmetric and asymmetric triglycerides. Some of the components within the CO have melt points that render the mixture as having the capability of exhibiting solid-like characteristics at 20 degrees C. and liquid characteristics at 27 degrees C. Importantly, it is possible to formulate any oil that is deemed to be suitable for use in a more hydrophobic device with waxes, fatty acid esters, or mixtures thereof at appropriate weight ratios to create carriers with melt points that can be tuned to any temperature, including body temperature. In so doing, a temperature activated device can be made to soften and or to harden at specific temperatures, thereby changing its mechanical characteristics or time-release characteristics.

By using these teachings, a delivery device can be made to soften at or above 37 degrees C. (body temperature) and to freeze or harden when it becomes cooled. The advantage is that through pre-heating the device, it can be made conformable for optimal placement into the tooth extraction socket. Upon cooling to body temperature, the delivery device can then be made to harden via recrystallization of components that have been formulated into the vehicle.

Conversely, a delivery device can be made to soften upon deployment. This can be accomplished by tuning the melt point of the vehicle to be near or below body temperature.

Either of these approaches can have an impact on end use characteristics. For example, a softer and more compliant delivery device is easier to conform to the geometric shape of a cavity. A delivery device with higher modulus can exhibit better resistance to erosion. For example, a delivery device that remains soft and conformable after deployment could be made to temporarily harden if the patient consumes a cold liquid. This can result in improved erosion resistance on-demand upon exposure to the cooler liquid as it flows across an exposed surface of the delivery device.

Release rates and fluid influx rates will also be affected by the compliance of the delivery device, with diffusion being slower through a more rigid matrix medium than through a softer medium.

TABLE 16-1

Weight % compositions of a hydrophobic vehicle for use in preparing textile-impregnated devices using coconut oil as the liquid carrier for the vehicle. Calculations also include the net weight % concentration of BUP in each vehicle, the net PLGA polymer weight % (i.e., ~80% of the weight of BUP loaded microspheres), and the total weight % of dispersed solids.

| Vehicle Mixture Composition | 16A |
|---|---|
| Coconut Oil | 39.01% |
| Beeswax | 0% |
| Bovine Gelatin | 19.50% |
| 5 um PLGA Placebo microspheres | 0% |
| 4.3 micron 20% BUP free base loaded PLGA microspheres | 41.49% |
| BUP free base (directly added to vehicle) | 0% |
| TOTAL | 100.00% |
| Total BUP in vehicle | 8.30% |
| Total PLGA polymer in Vehicle | 33.19% |
| Total % dispersed solids in vehicle | 60.99% |

TABLE 16-2

Weight % composition of a hydrophobic textile-impregnated device made with coconut oil. The vehicle composition as reported in Table 16-1 was impregnated into a single SO textile to yield the empirical composition as presented below. The calculations also include the weight % concentration of BUP, and the effective available BUP concentration for release per unit weight of device (mg/g).

| Ingredient | 16A |
|---|---|
| Great Lakes Bovine Gelatin (GLBG) | 15.32% |
| Coconut Oil (CO) | 30.63% |
| Beeswax (BW) | 0% |
| PLGA polymer (i.e., representing 80% of the weight of 4.3-micron microspheres loaded with 20% by wt. BUP) | 36.76% |
| Encapsulated BUP (i.e., representing 20% by weight of the 4.3-micron microspheres loaded with 20% by wt. BUP) | 9.19% |
| PLGA polymer from 5-micron placebo microspheres | 0% |
| BUP free base (non-encapsulated, directly added to the vehicle) | 0% |
| SO textile | 8.10% |
| mg BUP/g device | 92 |
| Weight of Device as made (g) | 0.6048 |
| Weight of Vehicle as made (g) | 0.5558 |

We claim:

1. A non-hydrated compliant composite for sustained release of a pharmaceutical formulation for pain management following deployment in vivo, the composite comprising:
    4% to 15% by weight of particulates of free bupivacaine;
    5% to 25% by weight of particulates of gelatin having the capacity to become plasticized in vivo by body fluids and to undergo gelation over time to yield a macroscopic macromolecular chain-entangled gelled network;
    16% to 26% by weight of caprylic triglyceride forming a hydrophobic fluid continuous phase medium, wherein the particulates of bupivacaine and the particulates of gelatin are co-dispersed within the hydrophobic fluid continuous phase medium to form a dispersion, such that the dispersed particulates of bupivacaine and gelatin are discrete and the dispersed particulates of gelatin are neither plasticized nor gelled by the hydrophobic fluid continuous phase medium; and
    3% to 27% by weight of a water-soluble and bioresorbable fibrous reinforcing member comprising a cellulose hemostatic material having interstitial spaces capable of being impregnated by the dispersion for imparting mechanical reinforcement to the dispersion,
    wherein the dispersion is impregnated into the interstitial spaces of the reinforcing component to form the non-hydrated compliant composite, and
    wherein the non-hydrated compliant composite delivers at least 50 mg to 100 mg of the bupivacaine per cc of the composite and resists cohesive failure during handling and resists swelling and erosion for a period of time following deployment in vivo while simultaneously allowing uniform oral body fluid ingress for gelation of the network-forming material and the sustained release of the bupivacaine.

2. The pharmaceutical formulation as recited in claim 1, further comprising an encapsulating material comprising poly (lactic-co-glycolic acid) encapsulating the free bupivacaine particulates.

3. The pharmaceutical formulation as recited in claim 2, wherein the encapsulated free bupivacaine particulates are prepared using a spinning disk or spray dry atomization process, or an emulsion, solvent extraction process.

4. The pharmaceutical formulation as recited in claim 1, wherein the gelatin comprises a thermoformable non-crosslinked gelatin having a Bloom value of 50 to 325.

5. The pharmaceutical formulation as recited in claim 1, further comprising a pH modulator.

6. A non-hydrated compliant composite for sustained release of a pharmaceutical formulation for pain management following deployment in vivo, the composite comprising:
    4% to 15% by weight of particulates of free bupivacaine;
    5% to 32% by weight of particulates of gelatin having the post-deployment capacity to become plasticized in vivo by body fluids and to undergo gelation over time to yield a macroscopic macromolecular chain-entangled gelled network, wherein the particulates of the active ingredient are dispersed within the particulates of the network-forming material to form a first dispersion; and
    16% to 30% by weight of caprylic triglyceride forming a hydrophobic fluid carrier medium, wherein the particulates of the first dispersion are dispersed within the hydrophobic fluid carrier continuous phase medium to form a second dispersion, and wherein the particulates of the first dispersion are discrete and the particulates of the gelatin are discrete and neither plasticized nor gelled by the hydrophobic fluid carrier medium; and
    3% to 27% by weight of a water-soluble and bioresorbable fibrous reinforcing member comprising a cellulose hemostatic material having interstitial spaces capable of being impregnated by the dispersion for imparting mechanical reinforcement to the dispersion,
    wherein the second dispersion is impregnated into the interstitial spaces of the reinforcing member to form the non-hydrated compliant composite, and
    wherein the non-hydrated compliant composite delivers at least 50 mg to 100 mg of the bupivacaine per cc of the composite and resists cohesive failure during handling and resists swelling and erosion for a period of time following deployment in vivo while simultaneously allowing for uniform body fluid ingress for gelation of the network-forming material and the sustained release of the bupivacaine.

7. The pharmaceutical formulation as recited in claim 6, further comprising an encapsulating material comprising poly (lactic-co-glycolic acid) encapsulating the free bupivacaine particulates.

8. The pharmaceutical formulation as recited in claim 7, wherein the encapsulated free bupivacaine particulates are prepared using a spinning disk or spray dry atomization process, or an emulsion, solvent extraction process.

9. The pharmaceutical formulation as recited in claim 6, wherein the gelatin is not crosslinked and has a Bloom value of 50 to 325.

10. The pharmaceutical formulation as recited in claim 6, further comprising a pH modulator.

* * * * *